US012648946B2

(12) United States Patent
Harada et al.

(10) Patent No.: US 12,648,946 B2
(45) Date of Patent: Jun. 9, 2026

(54) COMBINATION OF ANTIBODY-PYRROLOBENZODIAZEPINE DERIVATIVE CONJUGATE AND PARP INHIBITOR

(71) Applicant: DAIICHI SANKYO COMPANY, LIMITED, Tokyo (JP)

(72) Inventors: Naoya Harada, Tokyo (JP); Michiko Kitamura, Tokyo (JP)

(73) Assignee: DAIICHI SANKYO COMPANY, LIMITED, Tokyo (JP)

( * ) Notice: Subject to any disclaimer, the term of this patent is extended or adjusted under 35 U.S.C. 154(b) by 1222 days.

(21) Appl. No.: 17/442,608

(22) PCT Filed: Mar. 26, 2020

(86) PCT No.: PCT/JP2020/013555

§ 371 (c)(1),
(2) Date: Sep. 23, 2021

(87) PCT Pub. No.: WO2020/196712

PCT Pub. Date: Oct. 1, 2020

(65) Prior Publication Data

US 2022/0168438 A1 Jun. 2, 2022

(30) Foreign Application Priority Data

Mar. 27, 2019 (JP) ................................ 2019-061761

(51) Int. Cl.

| | |
|---|---|
| ***A61K 47/68*** | (2017.01) |
| ***A61K 31/454*** | (2006.01) |
| ***A61K 31/502*** | (2006.01) |
| ***A61K 31/5025*** | (2006.01) |
| ***A61K 31/5517*** | (2006.01) |
| ***A61K 45/06*** | (2006.01) |
| ***A61P 35/00*** | (2006.01) |
| ***C07K 16/30*** | (2006.01) |
| ***C07K 16/46*** | (2006.01) |

(52) U.S. Cl.

CPC .......... *A61K 31/502* (2013.01); *A61K 31/454* (2013.01); *A61K 31/5025* (2013.01); *A61K 31/5517* (2013.01); *A61K 45/06* (2013.01); *A61K 47/68035* (2023.08); *A61K 47/6855* (2017.08); *A61K 47/6877* (2017.08); *A61K 47/6889* (2017.08); *A61P 35/00* (2018.01); *C07K 16/30* (2013.01); *C07K 16/46* (2013.01)

(58) Field of Classification Search

None

See application file for complete search history.

(56) References Cited

U.S. PATENT DOCUMENTS

| | | | | |
|---|---|---|---|---|
| 7,449,464 | B2 * | 11/2008 | Martin .................. | A61K 31/00 514/218 |
| 2006/0270661 | A1 | 11/2006 | Liu et al. | |
| 2007/0072846 | A1 | 3/2007 | Vishnuvajjala et al. | |
| 2007/0265324 | A1 | 11/2007 | Wernet et al. | |
| 2008/0039448 | A1 | 2/2008 | Liu et al. | |
| 2008/0146638 | A1 | 6/2008 | Giranda et al. | |
| 2008/0280867 | A1 | 11/2008 | Giranda et al. | |
| 2008/0293795 | A1 | 11/2008 | Donawho et al. | |
| 2009/0029966 | A1 | 1/2009 | Donawho et al. | |
| 2009/0149449 | A1 | 6/2009 | Liu et al. | |
| 2011/0151023 | A1 | 6/2011 | Wernet et al. | |
| 2011/0152336 | A1 | 6/2011 | Wernet et al. | |
| 2012/0045524 | A1 | 2/2012 | Wernet et al. | |
| 2012/0190720 | A1 | 7/2012 | Giranda et al. | |
| 2012/0264795 | A1 | 10/2012 | Donawho et al. | |
| 2013/0028919 | A1 | 1/2013 | Howard et al. | |
| 2013/0225647 | A1 | 8/2013 | Donawho et al. | |
| 2013/0309223 | A1 | 11/2013 | Sutherland et al. | |
| 2015/0005354 | A1 | 1/2015 | Giranda et al. | |
| 2015/0005355 | A1 | 1/2015 | Donawho et al. | |
| 2015/0147316 | A1 | 5/2015 | Sutherland et al. | |
| 2015/0258210 | A1 | 9/2015 | Van Delft et al. | |
| 2015/0320882 | A1 | 11/2015 | Van Delft et al. | |
| 2016/0015828 | A1 | 1/2016 | Torgov et al. | |
| 2016/0045615 | A1 | 2/2016 | Li et al. | |
| 2016/0082114 | A1 | 3/2016 | Chari et al. | |
| 2016/0106863 | A1 | 4/2016 | Chari et al. | |
| 2016/0129013 | A1 | 5/2016 | Howard et al. | |
| 2016/0175460 | A1 | 6/2016 | Arathoon et al. | |
| 2016/0176964 | A1 | 6/2016 | Arathoon et al. | |
| 2016/0199510 | A1 | 7/2016 | Mcdonald et al. | |
| 2016/0200742 | A1 | 7/2016 | Zhang et al. | |
| 2016/0250344 | A1 | 9/2016 | Howard et al. | |
| 2016/0250345 | A1 | 9/2016 | Howard et al. | |

(Continued)

FOREIGN PATENT DOCUMENTS

| | | | |
|---|---|---|---|
| CN | 101370497 | A | 2/2009 |
| CN | 106604927 | A | 4/2017 |

(Continued)

OTHER PUBLICATIONS

MacCallum et al. (1996). J. Mol. Biol. 262:732-745.*
De Pascalis et al. (2002). Journal of Immunology. 169:3076-3084.*
Casset et al. (2003). Biochemical and Biophysical Research Communications. 307:198-205.*
Chen et al. (1999). J. Mol. biol. 293:865-881.*
Wu et al. (1999). J. Mol. Biol. 294:151-162.*
Rudikoff et al. (1982). PNAS. 79:1979-1983.*
Vikas et al. (2010). Frontiers in Oncology. 10:570; 10 pages.*
Wei et al. (2024). Journal of Hematology & Oncology. 17(1):1; 32 pages.*

(Continued)

*Primary Examiner* — Christine J Saoud
*Assistant Examiner* — Jon M Lockard
(74) *Attorney, Agent, or Firm* — Foley & Lardner LLP

(57) ABSTRACT

A pharmaceutical composition for treatment of cancer or a method for treating cancer, wherein an antibody-pyrrolobenzodiazepine derivative conjugate and a PARP inhibitor are administered in combination.

58 Claims, 34 Drawing Sheets

Specification includes a Sequence Listing.

(56) References Cited

U.S. PATENT DOCUMENTS

| | | | |
|---|---|---|---|
| 2016/0250346 | A1 | 9/2016 | Howard et al. |
| 2016/0256561 | A1 | 9/2016 | Howard et al. |
| 2016/0263239 | A1 | 9/2016 | Howard et al. |
| 2016/0263242 | A1 | 9/2016 | Howard et al. |
| 2016/0287720 | A1 | 10/2016 | Liu et al. |
| 2016/0310611 | A1 | 10/2016 | Flygare et al. |
| 2016/0324829 | A1 | 11/2016 | Donawho et al. |
| 2016/0367698 | A1 | 12/2016 | Chari et al. |
| 2017/0014522 | A1 | 1/2017 | Yoder et al. |
| 2017/0057959 | A1 | 3/2017 | Mcdonald et al. |
| 2017/0073357 | A1 | 3/2017 | Zhang et al. |
| 2017/0095570 | A1 | 4/2017 | Dragovich et al. |
| 2017/0143846 | A1 | 5/2017 | Howard et al. |
| 2017/0204180 | A1 | 7/2017 | Sutherland et al. |
| 2017/0232112 | A1 | 8/2017 | Li et al. |
| 2017/0233392 | A1 | 8/2017 | Mcdonald et al. |
| 2017/0233436 | A1 | 8/2017 | Zhang et al. |
| 2017/0274092 | A1 | 9/2017 | Chen et al. |
| 2017/0340748 | A1 | 11/2017 | Chari et al. |
| 2017/0340749 | A1 | 11/2017 | Chari et al. |
| 2018/0037581 | A1 | 2/2018 | Mcdonald et al. |
| 2018/0079781 | A1 | 3/2018 | Zhang et al. |
| 2018/0169257 | A1 | 6/2018 | Lewis et al. |
| 2018/0185486 | A1 | 7/2018 | Dragovich et al. |
| 2018/0228916 | A1 | 8/2018 | Howard et al. |
| 2018/0318441 | A1 | 11/2018 | Torgov et al. |
| 2018/0326062 | A1 | 11/2018 | Dragovich et al. |
| 2018/0346565 | A1 | 12/2018 | Arathoon et al. |
| 2018/0369408 | A1 | 12/2018 | Li et al. |
| 2019/0015524 | A1 | 1/2019 | Feingold et al. |
| 2019/0022241 | A1 | 1/2019 | Liu et al. |
| 2019/0169293 | A1 | 6/2019 | Iwamoto et al. |
| 2019/0269786 | A1 | 9/2019 | Chari et al. |
| 2019/0336614 | A1 | 11/2019 | Howard et al. |
| 2020/0085840 | A1 | 3/2020 | Chen et al. |
| 2020/0157240 | A1 | 5/2020 | Flygare et al. |
| 2020/0261594 | A1 | 8/2020 | Toda et al. |
| 2020/0405870 | A1 | 12/2020 | Chari et al. |
| 2020/0405873 | A1 | 12/2020 | Feingold et al. |
| 2021/0047404 | A1 | 2/2021 | Sutherland et al. |
| 2021/0085800 | A1 | 3/2021 | Yoder et al. |
| 2021/0163623 | A1 | 6/2021 | Van Delft et al. |
| 2022/0016257 | A1 | 1/2022 | Saito et al. |
| 2022/0125943 | A1 | 4/2022 | Toda et al. |
| 2022/0168440 | A1 | 6/2022 | Toda et al. |
| 2022/0177601 | A1 | 6/2022 | Harada et al. |
| 2022/0395579 | A1 | 12/2022 | Toda et al. |
| 2023/0084707 | A1 | 3/2023 | Toda et al. |
| 2023/0233697 | A1 | 7/2023 | Chari et al. |

FOREIGN PATENT DOCUMENTS

| | | | |
|---|---|---|---|
| CN | 107124870 | A | 9/2017 |
| CN | 108391422 | A | 8/2018 |
| JP | 2015-534996 | A | 12/2015 |
| JP | 2016-512540 | A | 4/2016 |
| TW | 201922788 | A | 6/2019 |
| WO | WO-2005/040170 | A2 | 5/2005 |
| WO | WO-2011/130613 | A1 | 10/2011 |
| WO | WO-2013/173496 | A2 | 11/2013 |
| WO | WO-2014/130879 | A2 | 8/2014 |
| WO | WO-2015/031693 | A1 | 3/2015 |
| WO | WO-2015/052321 | A1 | 4/2015 |
| WO | WO-2015/052322 | A1 | 4/2015 |
| WO | WO-2015/052534 | A1 | 4/2015 |
| WO | WO-2015/095124 | A1 | 6/2015 |
| WO | WO-2016/036804 | A1 | 3/2016 |
| WO | WO-2016/115191 | A1 | 7/2016 |
| WO | WO-2017/004025 | A1 | 1/2017 |
| WO | WO-2017/004330 | A1 | 1/2017 |
| WO | WO-2017/020972 | A1 | 2/2017 |
| WO | WO-2017/137556 | A1 | 8/2017 |
| WO | WO-2018/003983 | A1 | 1/2018 |
| WO | WO-2018/102212 | A1 | 6/2018 |
| WO | WO-2019/065964 | A1 | 4/2019 |
| WO | WO-2020/100954 | A1 | 5/2020 |
| WO | WO-2020/196474 | A1 | 10/2020 |
| WO | WO-2020/196475 | A1 | 10/2020 |

OTHER PUBLICATIONS

Dziadkowiec Karolina N. et al: "PARP inhibitors: review of mechanisms of action and BRCA½mutation targeting", Przeglad Menopauzalny/Menopause Review, vol. 4, Jan. 1, 2016, pp. 215-219, XP055967602, PL ISSN: 1643-8876, DOI: 10.5114/pm.2016.65667 Retrieved from the Internet: URL:http://dx.doi.org/10.5114/pm.2016.65667>.

Extended European Search Report issued in corresponding European Patent Application No. 20778479.4, dated Oct. 18, 2022.

Office Action issued in corresponding Chinese Patent Application No. 202080024555.3 dated Aug. 18, 2023 (17 pages).

Office Action issued in corresponding Taiwanese Patent Application No. 109110172 dated Oct. 13, 2023 (14 pages).

Antonow, et al., "Synthesis of DNA-Interactive Pyrrolo[2,1-c][1,4]benzodiazepines (PBDs)", Chemical Reviews, vol. 111, pp. 2815-2864 (2011).

Benafif, et al., "An update on PARP inhibitors for the treatment of cancer", Onco. Targets Ther. vol. 8, pp. 519-528 (2015).

Fong, et al., "Inhibition of Poly(ADP-Ribose) Polymerase in Tumors from BRCA Mutation Carriers", N. Engl. J. Med., vol. 361, pp. 123-134 (2009).

Fong, et al., "Poly(ADP)-Ribose Polymerase Inhibition: Frequent Durable Responses in BRCA Carrier Ovarian Cancer Correlating With Platinum-Free Interval", J. Clin. Oncol., vol. 28, pp. 2512-2519 (2010).

Gelman, et al., "Olaparib in patients with recurrent high-grade serous or poorly differentiated ovarian carcinoma or triple-negative breast cancer: a phase 2, multicentre, open-label, non-randomised study", Lancet Oncol., vol. 12, pp. 852-861 (2011).

Gillmore, et al., "Multkilogram Scale-up of a Reductive Alkylation Route to a Novel PARP Inhibitor", Org. Process Res. Dev., vol. 16, pp. 1897-1904 (2012).

Hurley, "Covalent Binding of Antitumor Antibiotics in the Minor Groove of DNA. Mechanism of Action of CC-1065 and the Pyrrole (1,4) benzodiazepines", Acc. Chem. Res., vol. 19, pp. 230-237 (1986).

International Search Report and Written Opinion issued in International Patent Application No. PCT/JP2020/013555 dated Jun. 23, 2020 (20 pages).

Jones, et al., "Discovery of 2-{4-[(3S)-Piperidin-3-yl]phenyl}-2H-indazole-7-carboxamide (MK-4827): a Novel Oral Poly(ADP-ribose)polymerase (PARP) Inhibitor Efficacious in BRCA-1 and -2 Mutant Tumors", J. Med. Chem., vol. 52, pp. 7170-7185 (2009).

Kohn, "Anthramycin", In Antibiotics III. Springer Verlag, New York, pp. 3-11 (1975).

Lord, et al., "The DNA damage response and cancer therapy", Nature, vol. 481, pp. 287-294 (2012).

Mantaj, et al., "From Anthramycin to Pyrrolobenzodiazepine (PBD)-Containing Antibody-drug Conjugates (ADCs)", Angew. Chem. Int. Ed., vol. 55, pp. 2-29 (2016).

Menear, et al., "4-[3-(4-Cyclopropanecarbonylpiperazine-1-carbonyl)-4-fluorobenzyl]-2H-phthalazin-1-one: a Novel Bioavailable Inhibitor of Poly(ADP-ribose) Polymerase-1", J. Med. Chem., vol. 51, pp. 6581-6591 (2008).

Shen, et al., "BMN 673, a Novel and Highly Potent PARP½Inhibitor for the Treatment of Human Cancers with DNA Repair Deficiency", Clin. Cancer Res., vol. 19(18), pp. 5003-5015 (2013).

Subhas Bose, et al., "Rational Design of a Highly Efficient Irreversible DNA Interstrand Cross-Linking Agent Based on the Pyrrolobenzodiazepine Ring System", J. Am. Chem. Soc., vol. 114, pp. 4939-4941 (1992).

Thurston, et al., "Synthesis of Sequence-Selective C8-Linked Pyrrolo[2,1-c][1,4]benzodiazepine DNA Interstrand Cross-Linking Agents", J. Org. Chem., vol. 61, pp. 8141-8147 (1996).

Zhong, et al., "Improved Therapeutic Window 1-73 in BRCA-mutant Tumors with Antibody-linked Pyrrolobenzodiazepine Dimers with and without PARP Inhibition", Molecular Cancer Therapeutics, vol. 18, No. 1, pp. 89-99 (2018).

(56) References Cited

OTHER PUBLICATIONS

Office Action issued in corresponding Canadian Patent Application No. 3139180 dated Oct. 16, 2023 (6 pages).

* cited by examiner

[Figure 1]
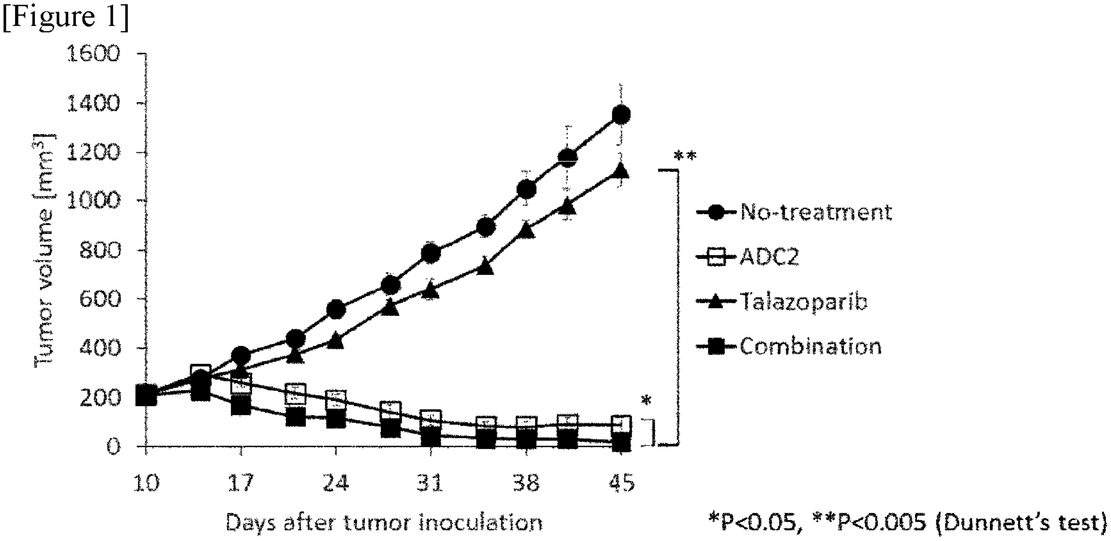
*P<0.05, **P<0.005 (Dunnett's test)
[Figure 2]
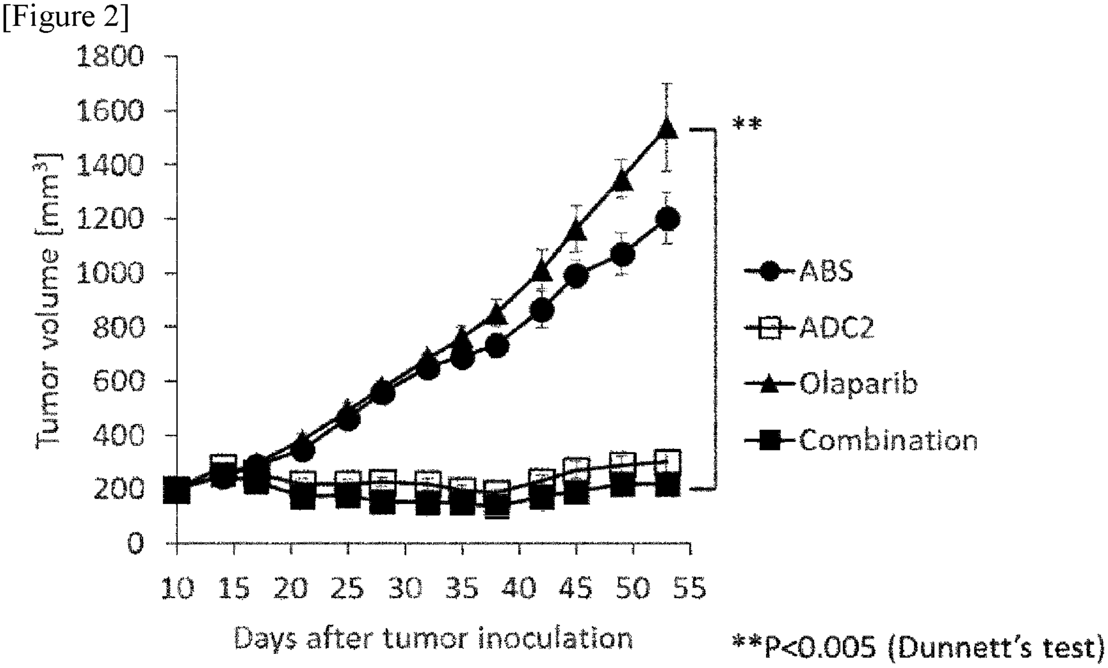
**P<0.005 (Dunnett's test)

[Figure 3]
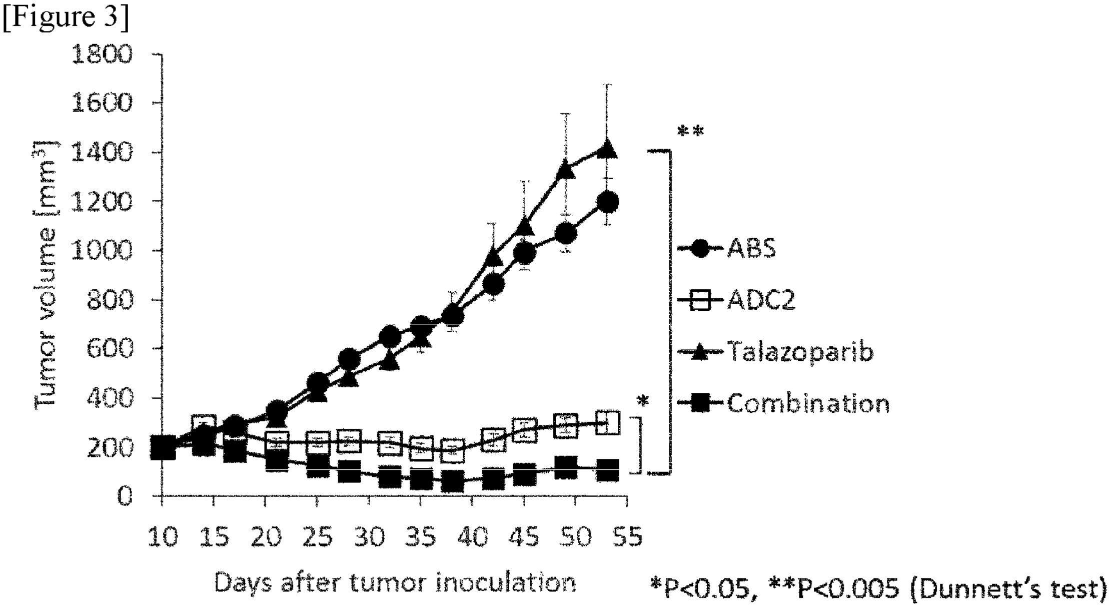
[Figure 4]
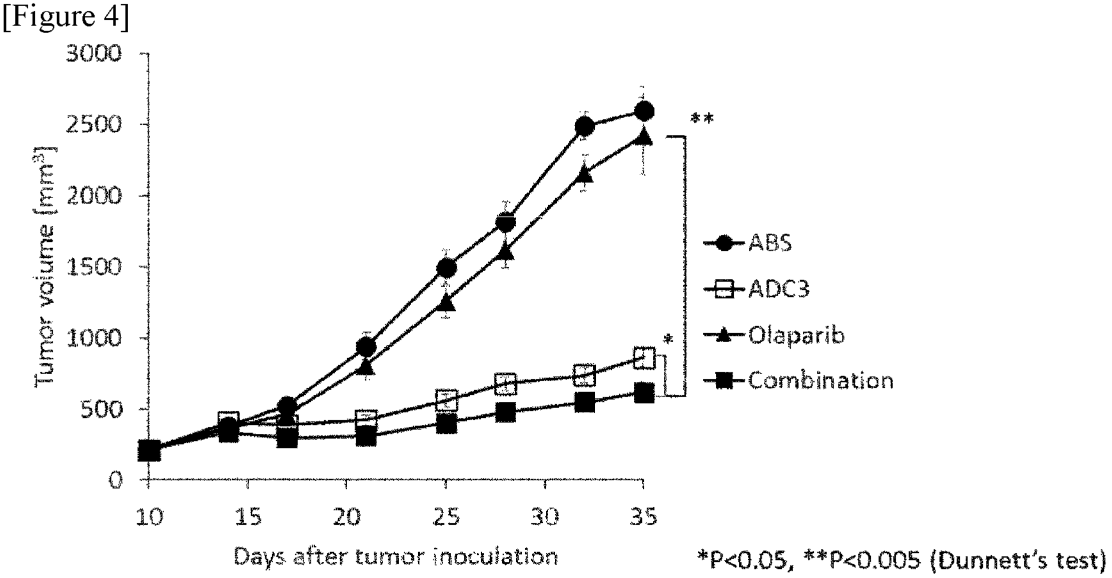

[Figure 5]

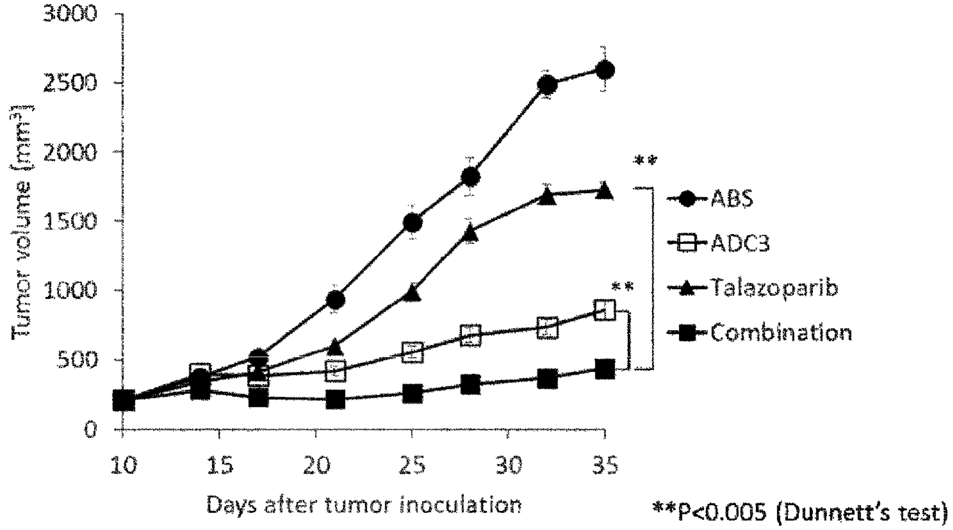

[Figure 6]

Full-length amino acid sequence of human CLDN6 (SEQ ID NO: 1)

MASAGMQILGVVLTLLGWVNGLVSCALPMWKVTAFIGNSIVVAQVVWEGLWMSCVVQSTGQMQCKVYDSL
LALPQDLQAARALCVIALLVALFGLLVYLAGAKCTTCVEEKDSKARLVLTSGIVFVISGVLTLIPVCWTA
HAIIRDFYNPLVAEAQKRELGASLYLGWAASGLLLLGGGLLCCTCPSGGSQGPSHYMARYSTSAPAISRG
PSEYPTKNYV

Nucleotide sequence of full-length cDNA for human CLDN6 (SEQ ID NO: 2)

atggcctctgccggaatgcagatcctgggagtcgtcctgacactgctgggctgggtgaatggcctggtct
cctgtgccctgcccatgtggaaggtgaccgctttcatcggcaacagcatcgtggtggcccaggtggtgtg
ggagggcctgtggatgtcctgcgtggtgcagagcaccggccagatgcagtgcaaggtgtacgactcactg
ctggcgctgccacaggacctgcaggctgcacgtgccctctgtgtcatcgccctccttgtggccctgttcg
gcttgctggtctaccttgctggggccaagtgtaccacctgtgtggaggagaaggattccaaggcccgcct
ggtgctcacctctgggattgtctttgtcatctcaggggtcctgacgctaatccccgtgtgctggacggcg
catgccatcatccgggacttctataaccccctggtggctgaggcccaaaagcgggagctgggggcctccc
tctacttgggctgggcggcctcaggccttttgttgctgggtgggggggttgctgtgctgcacttgcccctc
gggggggtcccagggccccagccattacatggcccgctactcaacatctgcccctgccatctctcggggg
ccctctgagtaccctaccaagaattacgtctga

[Figure 7]

Full-length amino acid sequence of human CLDN9 (SEQ ID NO: 3)

MASTGLELLGMTLAVLGWLGTLVSCALPLWKVTAFIGNSIVVAQVVWEGLWMSCVVQSTGQMQCKVY
DSLLALPQDLQAARALCVIALLLALLGLLVAITGAQCTTCVEDEGAKARIVLTAGVILLLAGILVLI
PVCWTAHAIIQDFYNPLVAEALKRELGASLYLGWAAAALLMLGGGLLCCTCPPPQVERPRGPRLGYS
IPSRSGASGLDKRDYV

Nucleotide sequence of full-length cDNA for human CLDN9 (SEQ ID NO: 4)

atggcttcgaccggcttagaactgctgggcatgaccctggctgtgctgggctggctggggaccctgg
tgtcctgcgccctgcccctgtggaaggtgaccgccttcatcggcaacagcatcgtggtggcccaggt
ggtgtgggagggcctgtggatgtcctgcgtggtgcagagcacgggccagatgcagtgcaaggtgtac
gactcactgctggctctgccgcaggacctgcaggccgcacgtgccctctgtgtcattgccctcctgc
tggccctgcttggcctcctggtggccatcacaggtgcccagtgtaccacgtgtgtggaggacgaagg
tgccaaggcccgtatcgtgctcaccgcgggggtcatcctcctcctcgccggcatcctggtgctcatc
cctgtgtgctggacggcgcacgccatcatccaggacttctacaacccccctggtggctgaggccctca
agcgggagctgggggcctccctctacctgggctgggcggcggctgcactgcttatgctgggcggggg
gctcctctgctgcacgtgccccccgccccaggtcgagcggccccgcggacctcggctgggctactcc
atcccctcccgctcgggtgcatctggactggacaagagggactacgtgtga

[Figure 8]

Amino acid sequence of CDRL1 of B1 antibody light chain (SEQ ID NO: 5)

RASQDINNYLN

Amino acid sequence of CDRL2 of B1 antibody light chain (SEQ ID NO: 6)

FTSRLHS

Amino acid sequence of CDRL3 of B1 antibody light chain (SEQ ID NO: 7)

QQGYPLPWT

[Figure 9]

Amino acid sequence of CDRL3 of humanized B1 antibody light chain L4 (SEQ ID NO: 8)

QQGNTLPWT

[Figure 10]

Amino acid sequence of CDRH1 of B1 antibody heavy chain (SEQ ID NO: 9)

GYTFTEYTMH

Amino acid sequence of CDRH2 of B1 antibody heavy chain (SEQ ID NO: 10)

GVNPNSGDTS

Amino acid sequence of CDRH3 of B1 antibody heavy chain (SEQ ID NO: 11)

PGGYDVGYYAMDY

[Figure 11]

Amino acid sequence of CDRL1 of C7 antibody light chain (SEQ ID NO: 12)

RASQDINNYLN

Amino acid sequence of CDRL2 of C7 antibody light chain (SEQ ID NO: 13)

STSRLHS

Amino acid sequence of CDRL3 of C7 antibody light chain (SEQ ID NO: 14)

QQGYPLPWT

[Figure 12]

Amino acid sequence of CDRH1 of C7 antibody heavy chain (SEQ ID NO: 15)

GYTFTEYTMH

Amino acid sequence of CDRH2 of C7 antibody heavy chain (SEQ ID NO: 16)

GVNPNSGDTS

Amino acid sequence of CDRH3 of C7 antibody heavy chain (SEQ ID NO: 17)

PGGYDVGYYAMDY

[Figure 13]

Nucleotide sequence of cDNA encoding variable region of B1 antibody light chain (SEQ ID NO: 18)

GATATCCAGATGACACAGACTGCATCCTCCCTGTCTGCCTCTCTTGGAGACAGAGTCACCATCAGTT

GCAGGGCAAGTCAGGACATTAACAATTATTTAAACTGGTATCAGCAGAAACCAGATGGAACTGTTAA

ACTCCTGATCTACTTCACATCAAGATTACACTCAGGAGTCCCATCAAGGTTCAGTGGCAGTGGGTCT

GGAACACATTATTCTCTCACCATTACTAACCTGGAACAAGAAGATATTGCCACTTACTTTTGCCAAC

AGGGTTATCCGCTTCCGTGGACGTTCGGTGGAGGCACCAAACTGGAAATCAAA

Amino acid sequence of variable region of B1 antibody light chain (SEQ ID NO: 19)

DIQMTQTASSLSASLGDRVTISCRASQDINNYLNWYQQKPDGTVKLLIYFTSRLHSGVPSRFSGSGS

GTHYSLTITNLEQEDIATYFCQQGYPLPWTFGGGTKLEIK

[Figure 14]

Nucleotide sequence of cDNA encoding variable region of B1 antibody heavy chain (SEQ ID NO: 20)

GAGGTCCAGCTTCAACAGTCTGGACCTGAACTGGTGAAGCCTGGGGCTTCAGTGAAGATATCCTGCA
AGACTTCTGGATACACATTCACTGAATACACCATGCACTGGGTGCAGCAGAGCCATGGAAAGAGCCT
TGAGTGGATTGGAGGTGTTAATCCTAATAGTGGTGATACTAGCTACAACCAGAAGTTCAAGGGCAAG
GCCACATTGACTGTTGACAAGTCCTCCAGCACAGCCTACATGGAGCTCCGCAGCCTGACATCTGAGG
ATTCTGCAGTCTATTACTGTGCAAGACCCGGGGGGTACGACGTGGGTTACTATGCTATGGACTACTG
GGGTCAAGGAACCTCAGTCACCGTCTCCTCA

Amino acid sequence of variable region of B1 antibody heavy chain (SEQ ID NO: 21)

EVQLQQSGPELVKPGASVKISCKTSGYTFTEYTMHWVQQSHGKSLEWIGGVNPNSGDTSYNQKFKGK
ATLTVDKSSSTAYMELRSLTSEDSAVYYCARPGGYDVGYYAMDYWGQGTSVTVSS

[Figure 15]

Nucleotide sequence of cDNA encoding variable region of C7 antibody light chain (SEQ ID NO: 22)

GATATCCAGATGACACAGACTGCATCCTCCCTGTCTGCCTCTCTTGGAGACAGAGTCACCATCAGTT
GCAGGGCAAGTCAGGACATTAACAATTATTTAAACTGGTATCAGCAGAAACCAGATGGAACTGTTAA
ACTCCTGATCTACTCCACATCAAGATTACACTCAGGAGTCCCATCAAGGTTCAGTGGCAGTGGGTCT
GGAACACATTATTCTCTCACCATTACTCACCTGGAACAAGAAGATATTGCCACTTACTTTTGCCAAC
AGGGTTATCCGCTTCCGTGGACGTTCGGTGGAGGCACCAAACTGGAAATCAAA

Amino acid sequence of variable region of C7 antibody light chain (SEQ ID NO: 23)

DIQMTQTASSLSASLGDRVTISCRASQDINNYLNWYQQKPDGTVKLLIYSTSRLHSGVPSRFSGSGS
GTHYSLTITHLEQEDIATYFCQQGYPLPWTFGGGTKLEIK

[Figure 16]

Nucleotide sequence of cDNA encoding variable region of C7 antibody heavy chain (SEQ ID NO: 24)

GAGGTCCAGCTTCAACAGTCTGGACCTGAACTGGTGAAGCCTGGGGCTTCAGTGAAGATATCCTGCA
AGACTTCTGGATACACATTCACTGAATACACCATGCACTGGGTGCAGCAGAGCCATGGAAAGAGCCT
TGAGTGGATTGGAGGTGTTAATCCTAATAGTGGTGATACTAGCTACAACCAGAAGTTCAAGGGCAAG
GCCACATTGACTGTTGACAAGTCCTCCAGCACAGCCTACATGGAGCTCCGCAGCCTGACATCTGAGG
ATTCTGCAGTCTATTACTGTGCAAGACCCGGGGGGTACGACGTGGGTTACTATGCTATGGACTACTG
GGGTCAAGGAACCTCAGTCACCGTCTCCTCA

Amino acid sequence of variable region of C7 antibody heavy chain (SEQ ID NO: 25)

EVQLQQSGPELVKPGASVKISCKTSGYTFTEYTMHWVQQSHGKSLEWIGGVNPNSGDTSYNQKFKGK
ATLTVDKSSSTAYMELRSLTSEDSAVYYCARPGGYDVGYYAMDYWGQGTSVTVSS

[Figure 17]

Amino acid sequence of chB1 light chain (SEQ ID NO: 28)

MVLQTQVFISLLLWISGAYGDIQMTQTASSLSASLGDRVTISCRASQDINNYLNWYQQKPDGTVKLL
IYFTSRLHSGVPSRFSGSGSGTHYSLTITNLEQEDIATYFCQQGYPLPWTFGGGTKLEIKRAVAAPS
VFIFPPSDEQLKSGTASVVCLLNNFYPREAKVQWKVDNALQSGNSQESVTEQDSKDSTYSLSSTLTL
SKADYEKHKVYACEVTHQGLSSPVTKSFNRGEC

Signal sequence (1 - 20), Light chain variable region (21 - 127), Light chain constant region (128 - 234)

DNA fragment including DNA sequence encoding amino acid sequence of chB1 light chain (SEQ ID NO: 29)

ccagcctccggactctagagccaccATGGTGCTGCAGACCCAGGTGTTCATCAGCCTGCTGCTGTGG
ATCAGCGGCGCCTACGGCGACATCCAGATGACCCAGACAGCCAGCAGCCTGAGCGCCAGCCTGGGCG
ATAGAGTGACCATCAGCTGCAGAGCCAGCCAGGACATCAACAACTACCTGAACTGGTATCAGCAGAA
ACCCGACGGCACCGTGAAGCTGCTGATCTACTTCACCAGCAGACTGCACAGCGGCGTGCCCAGCAGA
TTTTCTGGCAGCGGCTCTGGCACCCACTACAGCCTGACCATCACCAACCTGGAACAGGAAGATATCG
CTACCTACTTCTGTCAGCAAGGCTACCCCCTGCCCTGGACCTTTGGCGGCGGAACAAAGCTGGAAAT
CAAGCGGGCCGTGGCCGCTCCCTCCGTGTTCATCTTTCCACCCAGCGACGAGCAGCTGAAGTCCGGC
ACAGCTAGCGTCGTGTGCCTGCTGAACAACTTCTACCCCCGCGAGGCCAAGGTGCAGTGGAAGGTGG
ACAATGCCCTGCAGAGCGGCAACAGCCAGGAAAGCGTGACCGAGCAGGACAGCAAGGACTCCACCTA
CTCCCTGAGCAGCACCCTGACCCTGAGCAAGGCCGACTACGAGAAGCACAAGGTGTACGCCTGCGAA
GTGACCCACCAGGGCCTGTCTAGCCCCGTGACCAAGAGCTTCAACCGGGGCGAGTGTtgagtttaaa
cgggggaggctaact

Signal sequence (26 - 85), Light chain variable region (86 - 406), Light chain constant region (407 - 727)

[Figure 18]

Amino acid sequence of variable region of chB1 light chain (SEQ ID NO: 30)

DIQMTQTASSLSASLGDRVTISCRASQDINNYLNWYQQKPDGTVKLLIYFTSRLHSGVPSRFSGSGS
GTHYSLTITNLEQEDIATYFCQQGYPLPWTFGGGTKLEIK

Nucleotide sequence encoding chB1 light chain variable region (SEQ ID NO: 31)

GACATCCAGATGACCCAGACAGCCAGCAGCCTGAGCGCCAGCCTGGGCGATAGAGTGACCATCAGCT
GCAGAGCCAGCCAGGACATCAACAACTACCTGAACTGGTATCAGCAGAAACCCGACGGCACCGTGAA
GCTGCTGATCTACTTCACCAGCAGACTGCACAGCGGCGTGCCCAGCAGATTTTCTGGCAGCGGCTCT
GGCACCCACTACAGCCTGACCATCACCAACCTGGAACAGGAAGATATCGCTACCTACTTCTGTCAGC
AAGGCTACCCCCTGCCCTGGACCTTTGGCGGCGGAACAAAGCTGGAAATCAAG

[Figure 19]

Amino acid sequence of chB1 heavy chain (SEQ ID NO: 32)

MKHLWFFLLLVAAPRWVLSEVQLQQSGPELVKPGASVKISCKTSGYTFTEYTMHWVQQSHGKSLEWI
GGVNPNSGDTSYNQKFKGKATLTVDKSSSTAYMELRSLTSEDSAVYYCARPGGYDVGYYAMDYWGQG
TSVTVSSASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKRVEPKSCDKTHTCPPCPAPEAAGGPSVFLFP
PKPKDTLMISRTPEVTCVVVDVSHEDPEVKFNWYVDGVEVHNAKTKPREEQYNSTYRVVSVLTVLHQ
DWLNGKEYKCKVSNKALPAPIEKTISKAKGQPREPQVYTLPPSREEMTKNQVSLTCLVKGFYPSDIA
VEWESNGQPENNYKTTPPVLDSDGSFFLYSKLTVDKSRWQQGNVFSCSVMHEALHNHYTQKSLSLSP
GK

Signal sequence (1 - 19), Heavy chain variable region (20 - 141), Heavy chain constant region (142 - 471)

Nucleotide sequence encoding chB1 heavy chain (SEQ ID NO: 33

ATGAAACACCTGTGGTTCTTCCTCCTGCTGGTGGCAGCTCCCAGATGGGTGCTGAGCGAAGTGCAGC
TGCAGCAGTCTGGCCCCGAGCTCGTGAAACCTGGCGCCTCCGTGAAGATCAGCTGCAAGACCAGCGG
CTACACCTTCACCGAGTACACCATGCACTGGGTGCAGCAGAGCCACGGCAAGAGCCTGGAATGGATC
GGCGGCGTGAACCCCAACAGCGGCGACACCAGCTACAACCAGAAGTTCAAGGGCAAGGCCACCCTGA
CCGTGGACAAGAGCAGCAGCACCGCCTACATGGAACTGCGGAGCCTGACCAGCGAGGACAGCGCCGT
GTACTACTGTGCCAGACCTGGCGGCTACGACGTGGGCTACTACGCCATGGATTACTGGGGCCAGGGC
ACCAGCGTGACCGTCAGCTCAGCCTCCACCAAGGGCCCAAGCGTCTTCCCCCTGGCACCCTCCTCCA
AGAGCACCTCTGGCGGCACAGCCGCCCTGGGCTGCCTGGTCAAGGACTACTTCCCCGAACCCGTGAC
CGTGAGCTGGAACTCAGGCGCCCTGACCAGCGGCGTGCACACCTTCCCCGCTGTCCTGCAGTCCTCA
GGACTCTACTCCCTCAGCAGCGTGGTGACCGTGCCCTCCAGCAGCTTGGGCACCCAGACCTACATCT
GCAACGTGAATCACAAGCCCAGCAACACCAAGGTGGACAAGAGAGTTGAGCCCAAATCTTGTGACAA
AACTCACACATGCCCACCCTGCCCAGCACCTGAAGCCGCGGGGGGACCCTCAGTCTTCCTCTTCCCC
CCAAAACCCAAGGACACCCTCATGATCTCCCGGACCCCTGAGGTCACATGCGTGGTGGTGGACGTGA
GCCACGAAGACCCTGAGGTCAAGTTCAACTGGTACGTGGACGGCGTGGAGGTGCATAATGCCAAGAC
AAAGCCCCGGGAGGAGCAGTACAACAGCACGTACCGGGTGGTCAGCGTCCTCACCGTCCTGCACCAG
GACTGGCTGAATGGCAAGGAGTACAAGTGCAAGGTCTCCAACAAAGCCCTCCCAGCCCCCATCGAGA
AAACCATCTCCAAAGCCAAAGGCCAGCCCCGGGAACCACAGGTGTACACCCTGCCCCCATCCCGGGA
GGAGATGACCAAGAACCAGGTCAGCCTGACCTGCCTGGTCAAAGGCTTCTATCCCAGCGACATCGCC
GTGGAGTGGGAGAGCAATGGCCAGCCCGAGAACAACTACAAGACCACCCCTCCCGTGCTGGACTCCG
ACGGCTCCTTCTTCCTCTACAGCAAGCTCACCGTGGACAAGAGCAGGTGGCAGCAGGGCAACGTCTT
CTCATGCTCCGTGATGCATGAGGCTCTGCACAACCACTACACCCAGAAGAGCCTCTCCCTGTCTCCC
GGCAAA

Signal sequence (1 - 57), Heavy chain variable region (58 - 423), Heavy chain constant region (424 - 1413)

[Figure 20]

Amino acid sequence of variable region of chB1 heavy chain (SEQ ID NO: 34)

EVQLQQSGPELVKPGASVKISCKTSGYTFTEYTMHWVQQSHGKSLEWIGGVNPNSGDTSYNQKFKGK

ATLTVDKSSSTAYMELRSLTSEDSAVYYCARPGGYDVGYYAMDYWGQGTSVTVSS

Nucleotide sequence encoding variable region of chB1 heavy chain (SEQ ID NO: 35)

GAAGTGCAGCTGCAGCAGTCTGGCCCCGAGCTCGTGAAACCTGGCGCCTCCGTGAAGATCAGCTGCA

AGACCAGCGGCTACACCTTCACCGAGTACACCATGCACTGGGTGCAGCAGAGCCACGGCAAGAGCCT

GGAATGGATCGGCGGCGTGAACCCCAACAGCGGCGACACCAGCTACAACCAGAAGTTCAAGGGCAAG

GCCACCCTGACCGTGGACAAGAGCAGCAGCACCGCCTACATGGAACTGCGGAGCCTGACCAGCGAGG

ACAGCGCCGTGTACTACTGTGCCAGACCTGGCGGCTACGACGTGGGCTACTACGCCATGGATTACTG

GGGCCAGGGCACCAGCGTGACCGTCAGCTCA

[Figure 21]

Amino acid sequence of humanized antibody light chain hL1 (SEQ ID NO: 36)

MVLQTQVFISLLLWISGAYGDIQMTQSPSSLSASVGDRVTITCRASQDINNYLNWYQQKPGKAPKLL

IYFTSRLHSGVPSRFSGSGSGTDYTLTISSLQPEDFATYYCQQGYPLPWTFGQGTKVEIKRTVAAPS

VFIFPPSDEQLKSGTASVVCLLNNFYPREAKVQWKVDNALQSGNSQESVTEQDSKDSTYSLSSTLTL

SKADYEKHKVYACEVTHQGLSSPVTKSFNRGEC

Signal sequence (1 - 20), Light chain variable region (21 - 127), Light chain constant region (128 - 234)

Nucleotide sequence encoding humanized antibody light chain hL1 (SEQ ID NO: 37)

ATGGTGCTGCAGACCCAGGTGTTCATCTCCCTGCTGCTGTGGATCTCCGGCGCGTACGGCGACATCC

AGATGACCCAGAGCCCTAGCAGCCTGAGCGCCAGCGTGGGCGACAGAGTGACCATCACCTGTAGAGC

CAGCCAGGACATCAACAACTACCTGAACTGGTATCAGCAGAAGCCCGGCAAGGCCCCCAAGCTGCTG

ATCTACTTCACCAGCAGACTGCACAGCGGCGTGCCCAGCAGATTTTCTGGCAGCGGCTCCGGCACCG

ACTACACCCTGACAATCAGCAGCCTGCAGCCCGAGGACTTCGCCACCTACTACTGCCAGCAGGGCTA

CCCCCTGCCTTGGACATTTGGCCAGGGCACCAAGGTGGAAATCAAGCGTACGGTGGCCGCCCCCTCC

GTGTTCATCTTCCCCCCCTCCGACGAGCAGCTGAAGTCCGGCACCGCCTCCGTGGTGTGCCTGCTGA

ATAACTTCTACCCCAGAGAGGCCAAGGTGCAGTGGAAGGTGGACAACGCCCTGCAGTCCGGGAACTC

CCAGGAGAGCGTGACCGAGCAGGACAGCAAGGACAGCACCTACAGCCTGAGCAGCACCCTGACCCTG

AGCAAAGCCGACTACGAGAAGCACAAGGTGTACGCCTGCGAGGTGACCCACCAGGGCCTGAGCTCCC

CCGTCACCAAGAGCTTCAACAGGGGGGAGTGT

Signal sequence (1 - 60), Light chain variable region (61 - 381), Light chain constant region (382 - 702)

[Figure 22]

Amino acid sequence of variable region of humanized antibody light chain hL1 (SEQ ID NO: 38)

DIQMTQSPSSLSASVGDRVTITCRASQDINNYLNWYQQKPGKAPKLLIYFTSRLHSGVPSRFSGSGS

GTDYTLTISSLQPEDFATYYCQQGYPLPWTFGQGTKVEIK

Nucleotide sequence encoding variable region of humanized antibody light chain hL1 (SEQ ID NO: 39)

GACATCCAGATGACCCAGAGCCCTAGCAGCCTGAGCGCCAGCGTGGGCGACAGAGTGACCATCACCT

GTAGAGCCAGCCAGGACATCAACAACTACCTGAACTGGTATCAGCAGAAGCCCGGCAAGGCCCCCAA

GCTGCTGATCTACTTCACCAGCAGACTGCACAGCGGCGTGCCCAGCAGATTTTCTGGCAGCGGCTCC

GGCACCGACTACACCCTGACAATCAGCAGCCTGCAGCCCGAGGACTTCGCCACCTACTACTGCCAGC

AGGGCTACCCCCTGCCTTGGACATTTGGCCAGGGCACCAAGGTGGAAATCAAG

[Figure 23]

Amino acid sequence of humanized antibody light chain hL2 (SEQ ID NO: 40)

MVLQTQVFISLLLWISGAYGDIQMTQSPSSLSASVGDRVTITCRASQDINNYLNWYQQKPGKAVKLL

IYFTSRLHSGVPSRFSGSGSGTHYTLTISSLQPEDFATYYCQQGYPLPWTFGQGTKVEIKRTVAAPS

VFIFPPSDEQLKSGTASVVCLLNNFYPREAKVQWKVDNALQSGNSQESVTEQDSKDSTYSLSSTLTL

SKADYEKHKVYACEVTHQGLSSPVTKSFNRGEC

Signal sequence (1 - 20), Light chain variable region (21 - 127), Light chain constant region (128 - 234)

Nucleotide sequence encoding humanized antibody light chain hL2 (SEQ ID NO: 41)

ATGGTGCTGCAGACCCAGGTGTTCATCTCCCTGCTGCTGTGGATCTCCGGCGCGTACGGCGACATCC

AGATGACCCAGAGCCCTAGCAGCCTGAGCGCCAGCGTGGGCGACAGAGTGACCATCACCTGTAGAGC

CAGCCAGGACATCAACAACTACCTGAACTGGTATCAGCAGAAACCCGGCAAGGCCGTGAAGCTGCTG

ATCTACTTCACCAGCAGACTGCACAGCGGCGTGCCCAGCAGATTTTCTGGCAGCGGCTCTGGCACCC

ACTACACCCTGACAATCAGCAGCCTGCAGCCCGAGGACTTCGCCACCTACTACTGCCAGCAGGGCTA

CCCCCTGCCTTGGACATTTGGCCAGGGCACCAAGGTGGAAATCAAGCGTACGGTGGCCGCCCCCTCC

GTGTTCATCTTCCCCCCCTCCGACGAGCAGCTGAAGTCCGGCACCGCCTCCGTGGTGTGCCTGCTGA

ATAACTTCTACCCCAGAGAGGCCAAGGTGCAGTGGAAGGTGGACAACGCCCTGCAGTCCGGGAACTC

CCAGGAGAGCGTGACCGAGCAGGACAGCAAGGACAGCACCTACAGCCTGAGCAGCACCCTGACCCTG

AGCAAAGCCGACTACGAGAAGCACAAGGTGTACGCCTGCGAGGTGACCCACCAGGGCCTGAGCTCCC

CCGTCACCAAGAGCTTCAACAGGGGGGAGTGT

Signal sequence (1 - 60), Light chain variable region (61 - 381), Light chain constant region (382 - 702)

[Figure 24]

Amino acid sequence of variable region of humanized antibody light chain hL2 (SEQ ID NO: 42)

DIQMTQSPSSLSASVGDRVTITCRASQDINNYLNWYQQKPGKAVKLLIYFTSRLHSGVPSRFSGSGS

GTHYTLTISSLQPEDFATYYCQQGYPLPWTFGQGTKVEIK

Nucleotide sequence encoding variable region of humanized antibody light chain hL2 (SEQ ID NO: 43)

GACATCCAGATGACCCAGAGCCCTAGCAGCCTGAGCGCCAGCGTGGGCGACAGAGTGACCATCACCT

GTAGAGCCAGCCAGGACATCAACAACTACCTGAACTGGTATCAGCAGAAACCCGGCAAGGCCGTGAA

GCTGCTGATCTACTTCACCAGCAGACTGCACAGCGGCGTGCCCAGCAGATTTTCTGGCAGCGGCTCT

GGCACCCACTACACCCTGACAATCAGCAGCCTGCAGCCCGAGGACTTCGCCACCTACTACTGCCAGC

AGGGCTACCCCCTGCCTTGGACATTTGGCCAGGGCACCAAGGTGGAAATCAAG

[Figure 25]

Amino acid sequence of humanized antibody light chain hL3 (SEQ ID NO: 44)

MVLQTQVFISLLLWISGAYGDIQMTQSPSSLSASVGDRVTITCRASQDINNYLNWYQQKPGGAVKLL

IYFTSRLHSGVPSRFSGSGSGTDYTLTISSLQPEDFATYYCQQGYPLPWTFGGGTKVEIKRTVAAPS

VFIFPPSDEQLKSGTASVVCLLNNFYPREAKVQWKVDNALQSGNSQESVTEQDSKDSTYSLSSTLTL

SKADYEKHKVYACEVTHQGLSSPVTKSFNRGEC

Signal sequence (1 - 20), Light chain variable region (21 - 127), Light chain constant region (128 - 234)

Nucleotide sequence encoding humanized antibody light chain hL3 (SEQ ID NO: 45)

ATGGTGCTGCAGACCCAGGTGTTCATCTCCCTGCTGCTGTGGATCTCCGGCGCGTACGGCGACATCC

AGATGACCCAGAGCCCTAGCAGCCTGAGCGCCAGCGTGGGCGACAGAGTGACCATCACCTGTAGAGC

CAGCCAGGACATCAACAACTACCTGAACTGGTATCAGCAGAAACCCGGCGGAGCCGTGAAGCTGCTG

ATCTACTTCACCAGCAGACTGCACAGCGGCGTGCCCAGCAGATTTTCTGGCAGCGGCTCCGGCACCG

ACTACACCCTGACAATCAGCAGCCTGCAGCCCGAGGACTTCGCCACCTACTACTGCCAGCAGGGCTA

CCCCCTGCCCTGGACATTTGGCGGCGGAACAAAGGTGGAAATCAAGCGTACGGTGGCCGCCCCCTCC

GTGTTCATCTTCCCCCCCTCCGACGAGCAGCTGAAGTCCGGCACCGCCTCCGTGGTGTGCCTGCTGA

ATAACTTCTACCCCAGAGAGGCCAAGGTGCAGTGGAAGGTGGACAACGCCCTGCAGTCCGGGAACTC

CCAGGAGAGCGTGACCGAGCAGGACAGCAAGGACAGCACCTACAGCCTGAGCAGCACCCTGACCCTG

AGCAAAGCCGACTACGAGAAGCACAAGGTGTACGCCTGCGAGGTGACCCACCAGGGCCTGAGCTCCC

CCGTCACCAAGAGCTTCAACAGGGGGGAGTGT

Signal sequence (1 - 60), Light chain variable region (61 - 381), Light chain constant region (382 - 702)

[Figure 26]

Amino acid sequence of variable region of humanized antibody light chain hL3 (SEQ ID NO: 46)

DIQMTQSPSSLSASVGDRVTITCRASQDINNYLNWYQQKPGGAVKLLIYFTSRLHSGVPSRFSGSGS

GTDYTLTISSLQPEDFATYYCQQGYPLPWTFGGGTKVEIK

Nucleotide sequence encoding variable region of humanized antibody light chain hL3 (SEQ ID NO: 47)

GACATCCAGATGACCCAGAGCCCTAGCAGCCTGAGCGCCAGCGTGGGCGACAGAGTGACCATCACCT

GTAGAGCCAGCCAGGACATCAACAACTACCTGAACTGGTATCAGCAGAAACCCGGCGGAGCCGTGAA

GCTGCTGATCTACTTCACCAGCAGACTGCACAGCGGCGTGCCCAGCAGATTTTCTGGCAGCGGCTCC

GGCACCGACTACACCCTGACAATCAGCAGCCTGCAGCCCGAGGACTTCGCCACCTACTACTGCCAGC

AGGGCTACCCCCTGCCCTGGACATTTGGCGGCGGAACAAAGGTGGAAATCAAG

[Figure 27]

Amino acid sequence of humanized antibody light chain hL4 (SEQ ID NO: 48)

MVLQTQVFISLLLWISGAYGDIQMTQSPSSLSASVGDRVTITCRASQDINNYLNWYQQKPGGAVKLL

IYFTSRLHSGVPSRFSGSGSGTDYTLTISSLQPEDFATYYCQQGNTLPWTFGGGTKVEIKRTVAAPS

VFIFPPSDEQLKSGTASVVCLLNNFYPREAKVQWKVDNALQSGNSQESVTEQDSKDSTYSLSSTLTL

SKADYEKHKVYACEVTHQGLSSPVTKSFNRGEC

Signal sequence (1 - 20), Light chain variable region (21 - 127), Light chain constant region (128 - 234)

Nucleotide sequence encoding humanized antibody light chain hL4 (SEQ ID NO: 49)

ATGGTGCTGCAGACCCAGGTGTTCATCTCCCTGCTGCTGTGGATCTCCGGCGCGTACGGCGACATCC

AGATGACCCAGAGCCCTAGCAGCCTGAGCGCCAGCGTGGGCGACAGAGTGACCATCACCTGTAGAGC

CAGCCAGGACATCAACAACTACCTGAACTGGTATCAGCAGAAACCCGGCGGAGCCGTGAAGCTGCTG

ATCTACTTCACCAGCAGACTGCACAGCGGCGTGCCCAGCAGATTTTCTGGCAGCGGCTCCGGCACCG

ACTACACCCTGACAATCAGCAGCCTGCAGCCCGAGGACTTCGCCACCTACTACTGCCAGCAGGGCAA

CACCCTGCCCTGGACATTTGGCGGAGGCACCAAGGTGGAAATCAAGCGTACGGTGGCCGCCCCCTCC

GTGTTCATCTTCCCCCCCTCCGACGAGCAGCTGAAGTCCGGCACCGCCTCCGTGGTGTGCCTGCTGA

ATAACTTCTACCCCAGAGAGGCCAAGGTGCAGTGGAAGGTGGACAACGCCCTGCAGTCCGGGAACTC

CCAGGAGAGCGTGACCGAGCAGGACAGCAAGGACAGCACCTACAGCCTGAGCAGCACCCTGACCCTG

AGCAAAGCCGACTACGAGAAGCACAAGGTGTACGCCTGCGAGGTGACCCACCAGGGCCTGAGCTCCC

CCGTCACCAAGAGCTTCAACAGGGGGGAGTGT

Signal sequence (1 - 60), Light chain variable region (61 - 381), Light chain constant region (382 - 702)

[Figure 28]

Amino acid sequence of variable region of humanized antibody light chain hL4 (SEQ ID NO: 50)

DIQMTQSPSSLSASVGDRVTITCRASQDINNYLNWYQQKPGGAVKLLIYFTSRLHSGVPSRFSGSGS

GTDYTLTISSLQPEDFATYYCQQGNTLPWTFGGGTKVEIK

Nucleotide sequence encoding variable region of humanized antibody light chain hL4 (SEQ ID NO: 51)

GACATCCAGATGACCCAGAGCCCTAGCAGCCTGAGCGCCAGCGTGGGCGACAGAGTGACCATCACCT

GTAGAGCCAGCCAGGACATCAACAACTACCTGAACTGGTATCAGCAGAAACCCGGCGGAGCCGTGAA

GCTGCTGATCTACTTCACCAGCAGACTGCACAGCGGCGTGCCCAGCAGATTTTCTGGCAGCGGCTCC

GGCACCGACTACACCCTGACAATCAGCAGCCTGCAGCCCGAGGACTTCGCCACCTACTACTGCCAGC

AGGGCAACACCCTGCCCTGGACATTTGCCGGAGGCACCAAGGTGGAAATCAAG

[Figure 29]

Amino acid sequence of humanized antibody heavy chain hH1 (SEQ ID NO: 52)

MKHLWFFLLLVAAPRWVLSQVQLVQSGAEVKKPGASVKVSCKASGYTFTEYTMHWVRQAPGQGLEWM
GGVNPNSGDTSYAQKFQGRVTITADTSTSTAYMELSSLRSEDTAVYYCARPGGYDVGYYAMDYWGQG
TLVTVSSASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKRVEPKSCDKTHTCPPCPAPEAAGGPSVFLFP
PKPKDTLMISRTPEVTCVVVDVSHEDPEVKFNWYVDGVEVHNAKTKPREEQYNSTYRVVSVLTVLHQ
DWLNGKEYKCKVSNKALPAPIEKTISKAKGQPREPQVYTLPPSREEMTKNQVSLTCLVKGFYPSDIA
VEWESNGQPENNYKTTPPVLDSDGSFFLYSKLTVDKSRWQQGNVFSCSVMHEALHNHYTQKSLSLSP
GK

Signal sequence (1 - 19), Heavy chain variable region (20 - 141), Heavy chain constant region (142 - 471)

Nucleotide sequence encoding humanized antibody heavy chain hH1 (SEQ ID NO: 53)

ATGAAACACCTGTGGTTCTTCCTCCTGCTGGTGGCAGCTCCCAGATGGGTGCTGAGCCAGGTGCAGC
TGGTGCAGTCTGGCGCCGAAGTGAAGAAACCAGGCGCCAGCGTGAAGGTGTCCTGCAAGGCCAGCGG
CTACACCTTTACCGAGTACACCATGCACTGGGTGCGCCAGGCTCCAGGCCAGGGACTGGAATGGATG
GGCGGCGTGAACCCCAACAGCGGCGATACAAGCTACGCCCAGAAATTCCAGGGCAGAGTGACCATCA
CCGCCGACACCAGCACCTCCACCGCCTACATGGAACTGAGCAGCCTGCGGAGCGAGGACACCGCCGT
GTACTACTGTGCTAGACCTGGCGGCTACGACGTGGGCTACTACGCCATGGATTACTGGGGCCAGGGC
ACCCTCGTGACCGTCAGCTCAGCCTCCACCAAGGGCCCAAGCGTCTTCCCCCTGGCACCCTCCTCCA
AGAGCACCTCTGGCGGCACAGCCGCCCTGGGCTGCCTGGTCAAGGACTACTTCCCCGAACCCGTGAC
CGTGAGCTGGAACTCAGGCGCCCTGACCAGCGGCGTGCACACCTTCCCCGCTGTCCTGCAGTCCTCA
GGACTCTACTCCCTCAGCAGCGTGGTGACCGTGCCCTCCAGCAGCTTGGGCACCCAGACCTACATCT
GCAACGTGAATCACAAGCCCAGCAACACCAAGGTGGACAAGAGAGTTGAGCCCAAATCTTGTGACAA
AACTCACACATGCCCACCCTGCCCAGCACCTGAAGCCGCGGGGGGACCCTCAGTCTTCCTCTTCCCC
CCAAAACCCAAGGACACCCTCATGATCTCCCGGACCCCTGAGGTCACATGCGTGGTGGTGGACGTGA
GCCACGAAGACCCTGAGGTCAAGTTCAACTGGTACGTGGACGGCGTGGAGGTGCATAATGCCAAGAC
AAAGCCCCGGGAGGAGCAGTACAACAGCACGTACCGGGTGGTCAGCGTCCTCACCGTCCTGCACCAG
GACTGGCTGAATGGCAAGGAGTACAAGTGCAAGGTCTCCAACAAAGCCCTCCCAGCCCCCATCGAGA
AAACCATCTCCAAAGCCAAAGGCCAGCCCCGGGAACCACAGGTGTACACCCTGCCCCCATCCCGGGA
GGAGATGACCAAGAACCAGGTCAGCCTGACCTGCCTGGTCAAAGGCTTCTATCCCAGCGACATCGCC
GTGGAGTGGGAGAGCAATGGCCAGCCCGAGAACAACTACAAGACCACCCCTCCCGTGCTGGACTCCG
ACGGCTCCTTCTTCCTCTACAGCAAGCTCACCGTGGACAAGAGCAGGTGGCAGCAGGGCAACGTCTT
CTCATGCTCCGTGATGCATGAGGCTCTGCACAACCACTACACCCAGAAGAGCCTCTCCCTGTCTCCC
GGCAAA

Signal sequence (1 - 57), Heavy chain variable region (58 - 423), Heavy chain constant region (424 - 1413)

[Figure 30]

Amino acid sequence of variable region of humanized antibody heavy chain hH1 (SEQ ID NO: 54)

QVQLVQSGAEVKKPGASVKVSCKASGYTFTEYTMHWVRQAPGQGLEWMGGVNPNSGDTSYAQKFQGR

VTITADTSTSTAYMELSSLRSEDTAVYYCARPGGYDVGYYAMDYWGQGTLVTVSS

Nucleotide sequence encoding variable region of humanized antibody heavy chain hH1 (SEQ ID NO: 55)

CAGGTGCAGCTGGTGCAGTCTGGCGCCGAAGTGAAGAAACCAGGCGCCAGCGTGAAGGTGTCCTGCA

AGGCCAGCGGCTACACCTTTACCGAGTACACCATGCACTGGGTGCGCCAGGCTCCAGGCCAGGGACT

GGAATGGATGGGCGGCGTGAACCCCAACAGCGGCGATACAAGCTACGCCCAGAAATTCCAGGGCAGA

GTGACCATCACCGCCGACACCAGCACCTCCACCGCCTACATGGAACTGAGCAGCCTGCGGAGCGAGG

ACACCGCCGTGTACTACTGTGCTAGACCTGGCGGCTACGACGTGGGCTACTACGCCATGGATTACTG

GGGCCAGGGCACCCTCGTGACCGTCAGCTCA

[Figure 31]

Amino acid sequence of humanized antibody heavy chain hH2 (SEQ ID NO: 56)

MKHLWFFLLLVAAPRWVLSEVQLVQSGAEVKKPGASVKVSCKTSGYTFTEYTMHWVRQAPGKSLEWM
GGVNPNSGDTSYAQKFQGRVTITADTSTSTAYMELSSLRSEDTAVYYCARPGGYDVGYYAMDYWGQG
TLVTVSSASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKRVEPKSCDKTHTCPPCPAPEAAGGPSVFLFP
PKPKDTLMISRTPEVTCVVVDVSHEDPEVKFNWYVDGVEVHNAKTKPREEQYNSTYRVVSVLTVLHQ
DWLNGKEYKCKVSNKALPAPIEKTISKAKGQPREPQVYTLPPSREEMTKNQVSLTCLVKGFYPSDIA
VEWESNGQPENNYKTTPPVLDSDGSFFLYSKLTVDKSRWQQGNVFSCSVMHEALHNHYTQKSLSLSP
GK

Signal sequence (1 - 19), Heavy chain variable region (20 - 141), Heavy chain constant region (142 - 471)

Nucleotide sequence encoding humanized antibody heavy chain hH2 (SEQ ID NO: 57)

ATGAAACACCTGTGGTTCTTCCTCCTGCTGGTGGCAGCTCCCAGATGGGTGCTGAGCGAAGTGCAGC
TGGTGCAGTCTGGCGCCGAAGTGAAGAAACCAGGCGCCAGCGTGAAGGTGTCCTGCAAGACCAGCGG
CTACACCTTTACCGAGTACACCATGCACTGGGTGCGCCAGGCCCCTGGCAAGAGCCTGGAATGGATG
GGCGGCGTGAACCCCAACAGCGGCGATACAAGCTACGCCCAGAAATTCCAGGGCAGAGTGACCATCA
CCGCCGACACCAGCACCTCCACCGCCTACATGGAACTGAGCAGCCTGCGGAGCGAGGACACCGCCGT
GTACTACTGTGCTAGACCTGGCGGCTACGACGTGGGCTACTACGCCATGGATTACTGGGGCCAGGGC
ACCCTCGTGACCGTCAGCTCAGCCTCCACCAAGGGCCCAAGCGTCTTCCCCCTGGCACCCTCCTCCA
AGAGCACCTCTGGCGGCACAGCCGCCCTGGGCTGCCTGGTCAAGGACTACTTCCCCGAACCCGTGAC
CGTGAGCTGGAACTCAGGCGCCCTGACCAGCGGCGTGCACACCTTCCCCGCTGTCCTGCAGTCCTCA
GGACTCTACTCCCTCAGCAGCGTGGTGACCGTGCCCTCCAGCAGCTTGGGCACCCAGACCTACATCT
GCAACGTGAATCACAAGCCCAGCAACACCAAGGTGGACAAGAGAGTTGAGCCCAAATCTTGTGACAA
AACTCACACATGCCCACCCTGCCCAGCACCTGAAGCCGCGGGGGGACCCTCAGTCTTCCTCTTCCCC
CCAAAACCCAAGGACACCCTCATGATCTCCCGGACCCCTGAGGTCACATGCGTGGTGGTGGACGTGA
GCCACGAAGACCCTGAGGTCAAGTTCAACTGGTACGTGGACGGCGTGGAGGTGCATAATGCCAAGAC
AAAGCCCCGGGAGGAGCAGTACAACAGCACGTACCGGGTGGTCAGCGTCCTCACCGTCCTGCACCAG
GACTGGCTGAATGGCAAGGAGTACAAGTGCAAGGTCTCCAACAAAGCCCTCCCAGCCCCCATCGAGA
AAACCATCTCCAAAGCCAAAGGCCAGCCCCGGGAACCACAGGTGTACACCCTGCCCCCATCCCGGGA
GGAGATGACCAAGAACCAGGTCAGCCTGACCTGCCTGGTCAAAGGCTTCTATCCCAGCGACATCGCC
GTGGAGTGGGAGAGCAATGGCCAGCCCGAGAACAACTACAAGACCACCCCTCCCGTGCTGGACTCCG
ACGGCTCCTTCTTCCTCTACAGCAAGCTCACCGTGGACAAGAGCAGGTGGCAGCAGGGCAACGTCTT
CTCATGCTCCGTGATGCATGAGGCTCTGCACAACCACTACACCCAGAAGAGCCTCTCCCTGTCTCCC
GGCAAA

Signal sequence (1 - 57), Heavy chain variable region (58 - 423), Heavy chain constant region (424 - 1413)

[Figure 32]

Amino acid sequence of variable region of humanized antibody heavy chain hH2 (SEQ ID NO: 58)

EVQLVQSGAEVKKPGASVKVSCKTSGYTFTEYTMHWVRQAPGKSLEWMGGVNPNSGDTSYAQKFQGR

VTITADTSTSTAYMELSSLRSEDTAVYYCARPGGYDVGYYAMDYWGQGTLVTVSS

Nucleotide sequence encoding variable region of humanized antibody heavy chain hH2 (SEQ ID NO: 59)

GAAGTGCAGCTGGTGCAGTCTGGCGCCGAAGTGAAGAAACCAGGCGCCAGCGTGAAGGTGTCCTGCA

AGACCAGCGGCTACACCTTTACCGAGTACACCATGCACTGGGTGCGCCAGGCCCCTGGCAAGAGCCT

GGAATGGATGGGCGGCGTGAACCCCAACAGCGGCGATACAAGCTACGCCCAGAAATTCCAGGGCAGA

GTGACCATCACCGCCGACACCAGCACCTCCACCGCCTACATGGAACTGAGCAGCCTGCGGAGCGAGG

ACACCGCCGTGTACTACTGTGCTAGACCTGGCGGCTACGACGTGGGCTACTACGCCATGGATTACTG

GGGCCAGGGCACCCTCGTGACCGTCAGCTCA

[Figure 33]

Amino acid sequence of humanized antibody heavy chain hH3 (SEQ ID NO: 60)

MKHLWFFLLLVAAPRWVLSEVQLVQSGAEVKKPGASVKVSCKTSGYTFTEYTMHWVRQAPGQGLEWM
GGVNPNSGDTSYAQKFQGRVTLTVDKSTSTAYMELSSLRSEDTAVYYCARPGGYDVGYYAMDYWGQG
TLVTVSSASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKRVEPKSCDKTHTCPPCPAPEAAGGPSVFLFP
PKPKDTLMISRTPEVTCVVVDVSHEDPEVKFNWYVDGVEVHNAKTKPREEQYNSTYRVVSVLTVLHQ
DWLNGKEYKCKVSNKALPAPIEKTISKAKGQPREPQVYTLPPSREEMTKNQVSLTCLVKGFYPSDIA
VEWESNGQPENNYKTTPPVLDSDGSFFLYSKLTVDKSRWQQGNVFSCSVMHEALHNHYTQKSLSLSP
GK

Signal sequence (1 - 19), Heavy chain variable region (20 - 141), Heavy chain constant region (142 - 471)

Nucleotide sequence encoding humanized antibody heavy chain hH3 (SEQ ID NO: 61)

ATGAAACACCTGTGGTTCTTCCTCCTGCTGGTGGCAGCTCCCAGATGGGTGCTGAGCGAAGTGCAGC
TGGTGCAGTCTGGCGCCGAAGTGAAGAAACCAGGCGCCAGCGTGAAGGTGTCCTGCAAGACCAGCGG
CTACACCTTTACCGAGTACACCATGCACTGGGTGCGCCAGGCTCCAGGCCAGGGACTGGAATGGATG
GGCGGCGTGAACCCCAACAGCGGCGATACAAGCTACGCCCAGAAATTCCAGGGCAGAGTGACCCTGA
CCGTGGACAAGAGCACCAGCACCGCCTACATGGAACTGAGCAGCCTGCGGAGCGAGGACACCGCCGT
GTACTACTGTGCTAGACCTGGCGGCTACGACGTGGGCTACTACGCCATGGATTACTGGGGCCAGGGC
ACCCTCGTGACCGTCAGCTCAGCCTCCACCAAGGGCCCAAGCGTCTTCCCCCTGGCACCCTCCTCCA
AGAGCACCTCTGGCGGCACAGCCGCCCTGGGCTGCCTGGTCAAGGACTACTTCCCCGAACCCGTGAC
CGTGAGCTGGAACTCAGGCGCCCTGACCAGCGGCGTGCACACCTTCCCCGCTGTCCTGCAGTCCTCA
GGACTCTACTCCCTCAGCAGCGTGGTGACCGTGCCCTCCAGCAGCTTGGGCACCCAGACCTACATCT
GCAACGTGAATCACAAGCCCAGCAACACCAAGGTGGACAAGAGAGTTGAGCCCAAATCTTGTGACAA
AACTCACACATGCCCACCCTGCCCAGCACCTGAAGCCGCGGGGGGACCCTCAGTCTTCCTCTTCCCC
CCAAAACCCAAGGACACCCTCATGATCTCCCGGACCCCTGAGGTCACATGCGTGGTGGTGGACGTGA
GCCACGAAGACCCTGAGGTCAAGTTCAACTGGTACGTGGACGGCGTGGAGGTGCATAATGCCAAGAC
AAAGCCCCGGGAGGAGCAGTACAACAGCACGTACCGGGTGGTCAGCGTCCTCACCGTCCTGCACCAG
GACTGGCTGAATGGCAAGGAGTACAAGTGCAAGGTCTCCAACAAAGCCCTCCCAGCCCCCATCGAGA
AAACCATCTCCAAAGCCAAAGGCCAGCCCCGGGAACCACAGGTGTACACCCTGCCCCCATCCCGGGA
GGAGATGACCAAGAACCAGGTCAGCCTGACCTGCCTGGTCAAAGGCTTCTATCCCAGCGACATCGCC
GTGGAGTGGGAGAGCAATGGCCAGCCCGAGAACAACTACAAGACCACCCCTCCCGTGCTGGACTCCG
ACGGCTCCTTCTTCCTCTACAGCAAGCTCACCGTGGACAAGAGCAGGTGGCAGCAGGGCAACGTCTT
CTCATGCTCCGTGATGCATGAGGCTCTGCACAACCACTACACCCAGAAGAGCCTCTCCCTGTCTCCC
GGCAAA

Signal sequence (1 - 57), Heavy chain variable region (58 - 423), Heavy chain constant region (424 - 1413)

[Figure 34]

Amino acid sequence of variable region of humanized antibody heavy chain hH3 (SEQ ID NO: 62)

EVQLVQSGAEVKKPGASVKVSCKTSGYTFTEYTMHWVRQAPGQGLEWMGGVNPNSGDTSYAQKFQGR

VTLTVDKSTSTAYMELSSLRSEDTAVYYCARPGGYDVGYYAMDYWGQGTLVTVSS

Nucleotide sequence encoding variable region of humanized antibody heavy chain hH3 (SEQ ID NO: 63)

GAAGTGCAGCTGGTGCAGTCTGGCGCCGAAGTGAAGAAACCAGGCGCCAGCGTGAAGGTGTCCTGCA

AGACCAGCGGCTACACCTTTACCGAGTACACCATGCACTGGGTGCGCCAGGCTCCAGGCCAGGGACT

GGAATGGATGGGCGGCGTGAACCCCAACAGCGGCGATACAAGCTACGCCCAGAAATTCCAGGGCAGA

GTGACCCTGACCGTGGACAAGAGCACCAGCACCGCCTACATGGAACTGAGCAGCCTGCGGAGCGAGG

ACACCGCCGTGTACTACTGTGCTAGACCTGGCGGCTACGACGTGGGCTACTACGCCATGGATTACTG

GGGCCAGGGCACCCTCGTGACCGTCAGCTCA

[Figure 35]
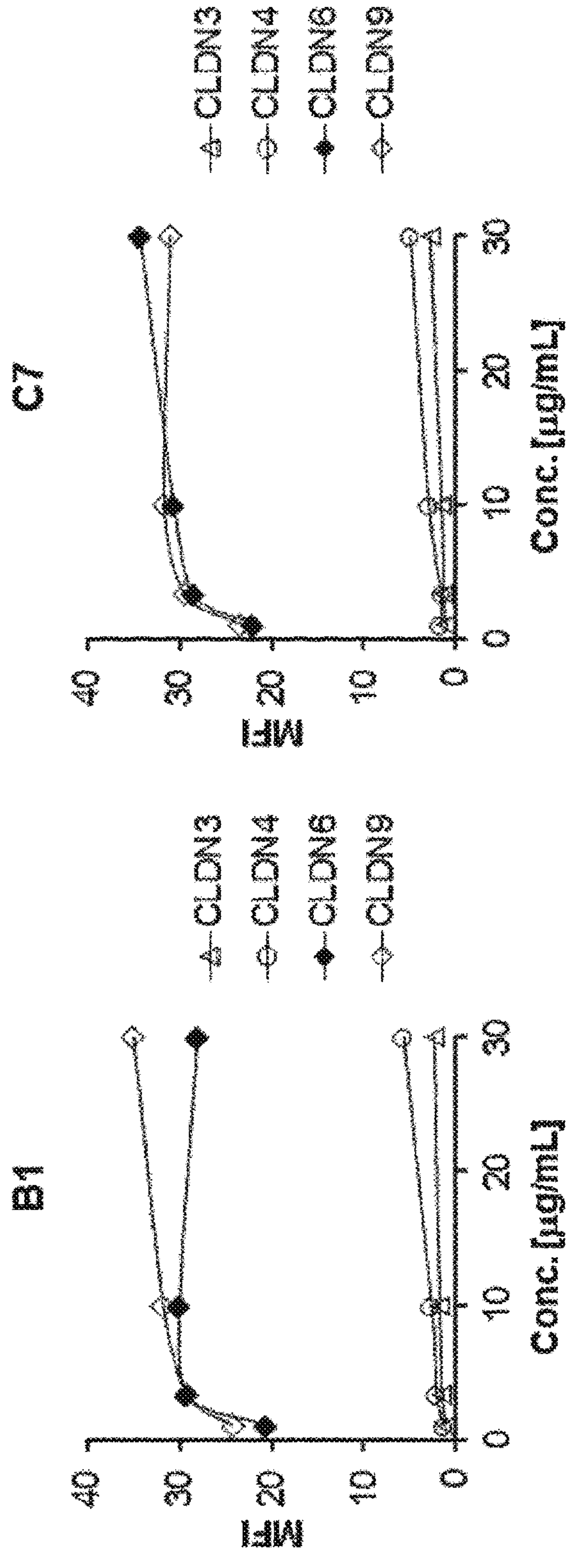

[Figure 36]
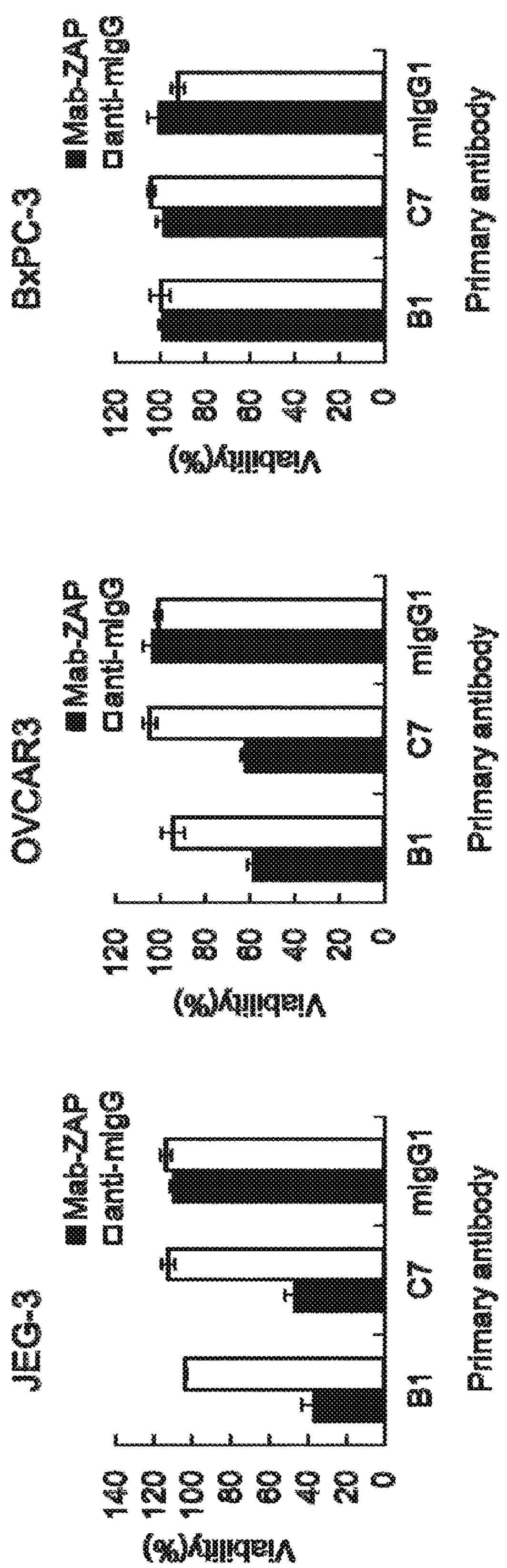

[Figure 37]
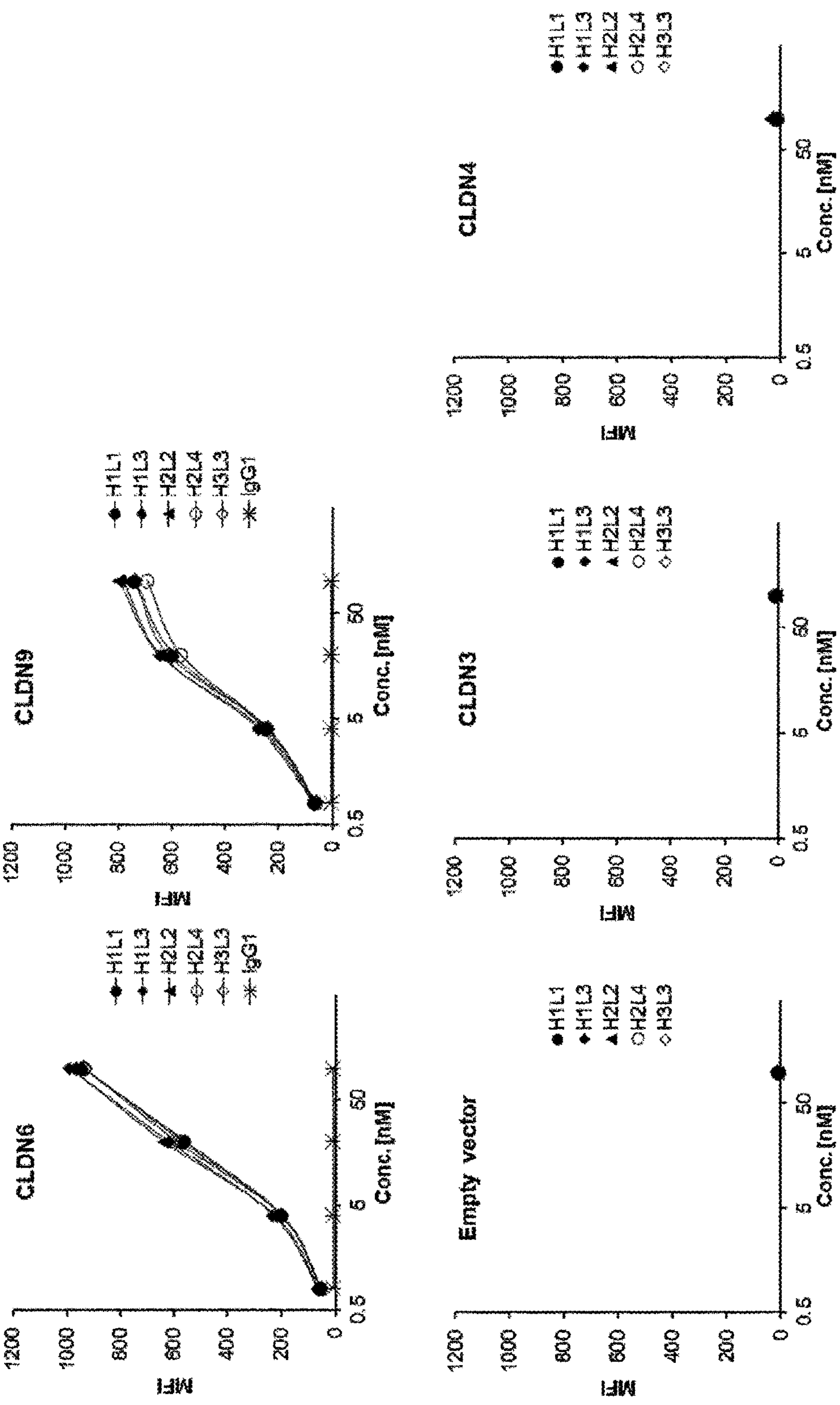

[Figure 38]

Amino acid sequence of trastuzumab light chain (SEQ ID NO: 64)

DIQMTQSPSSLSASVGDRVTITCRASQDVNTAVAWYQQKPGKAPKLLIYSASFLYSGVPSRFSGSRS

GTDFTLTISSLQPEDFATYYCQQHYTTPPTFGQGTKVEIKRTVAAPSVFIFPPSDEQLKSGTASVVC

LLNNFYPREAKVQWKVDNALQSGNSQESVTEQDSKDSTYSLSSTLTLSKADYEKHKVYACEVTHQGL

SSPVTKSFNRGEC

Amino acid sequence of trastuzumab heavy chain (SEQ ID NO: 65)

EVQLVESGGGLVQPGGSLRLSCAASGFNIKDTYIHWVRQAPGKGLEWVARIYPTNGYTRYADSVKGR

FTISADTSKNTAYLQMNSLRAEDTAVYYCSRWGGDGFYAMDYWGQGTLVTVSSASTKGPSVFPLAPS

SKSTSGGTAALGCLVKDYFPEPVTVSWNSGALTSGVHTFPAVLQSSGLYSLSSVVTVPSSSLGTQTY

ICNVNHKPSNTKVDKKVEPKSCDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLNGKEYKCKVSNKALPAPI

EKTISKAKGQPREPQVYTLPPSREEMTKNQVSLTCLVKGFYPSDIAVEWESNGQPENNYKTTPPVLD

SDGSFFLYSKLTVDKSRWQQGNVFSCSVMHEALHNHYTQKSLSLSPGK

[Figure 39]

Amino acid sequence of trastuzumab variant light chain (SEQ ID NO: 73)

MVLQTQVFISLLLWISGAYGDIQMTQSPSSLSASVGDRVTITCRASQDVNTAVAWYQQKPGKAPKLLIYSAS

FLYSGVPSRFSGSRSGTDFTLTISSLQPEDFATYYCQQHYTTPPTFGQGTKVEIKRTVAAPSVFIFPPSDEQ

LKSGTASVVCLLNNFYPREAKVQWKVDNALQSGNSQESVTEQDSKDSTYSLSSTLTLSKADYEKHKVYACEV

THQGLSSPVTKSFNRGEC

Signal sequence (1 - 20), Light chain variable region (21 - 127), Light chain constant region (128 - 234)

Amino acid sequence of trastuzumab variant heavy chain (SEQ ID NO: 75)

MKHLWFFLLLVAAPRWVLSEVQLVESGGGLVQPGGSLRLSCAASGFNIKDTYIHWVRQAPGKGLEWVARIYP

TNGYTRYADSVKGRFTISADTSKNTAYLQMNSLRAEDTAVYYCSRWGGDGFYAMDYWGQGTLVTVSSASTKG

PSVFPLAPSSKSTSGGTAALGCLVKDYFPEPVTVSWNSGALTSGVHTFPAVLQSSGLYSLSSVVTVPSSSLG

TQTYICNVNHKPSNTKVDKRVEPKSCDKTHTCPPCPAPEAAGGPSVFLFPPKPKDTLMISRTPEVTCVVVDV

SHEDPEVKFNWYVDGVEVHNAKTKPREEQYNSTYRVVSVLTVLHQDWLNGKEYKCKVSNKALPAPIEKTISK

AKGQPREPQVYTLPPSREEMTKNQVSLTCLVKGFYPSDIAVEWESNGQPENNYKTTPPVLDSDGSFFLYSKL

TVDKSRWQQGNVFSCSVMHEALHNHYTQKSLSLSPGK

Signal sequence (1 - 19), Heavy chain variable region (20 - 139), Heavy chain constant region (140 - 469)

[Figure 40]

```
chB1_H   1 EVQLQQSGPELVKPGASVKISCKTSGYTFTEYTMHWVQQSHGKSLEWIGGVNPNSGDTSYNQKFKGKATL 70
hH1      1 Q...V...A.VK.......V...A.............R.AP.QG...M............A...Q.RV.I 70
hH2      1 ....V...A.VK.......V.................R.AP......M............A...Q.RV.I 70
hH3      1 ....V...A.VK.......V.................R.AP.QG...M............A...Q.RV.. 70

chB1_H  71 TVDKSSSTAYMELRSLTSEDSAVYYCARPGGYDVGYYAMDYWGQGTSVTVSS                   122
hH1     71 .A.T.T.......S..R...T.........................L.....                   122
hH2     71 .A.T.T.......S..R...T.........................L.....                   122
hH3     71 .....T.......S..R...T.........................L.....                   122
```

[Figure 41]

```
chB1_L  1 DIQMTQTASSLSASLGDRVTISCRASQDINNYLNWYQQKPDGTVKLLIYFTSRLHSGVPS 60
hL1     1 ......SP......V......T..................GKAP................ 60
hL2     1 ......SP......V......T..................GKA................. 60
hL3     1 ......SP......V......T..................G.A................. 60
hL4     1 ......SP......V......T..................G.A................. 60

chB1_L 61 RFSGSGSGTHYSLTITNLEQEDIATYFCQQGYPLPWTFGGGTKLEIK              107
hL1    61 .........D.T...SS.QP..F...Y............Q...V...              107
hL2    61 ...........T...SS.QP..F...Y............Q...V...              107
hL3    61 .........D.T...SS.QP..F...Y................V...              107
hL4    61 .........D.T...SS.QP..F...Y...NT...........V...              107
```

[Figure 42]
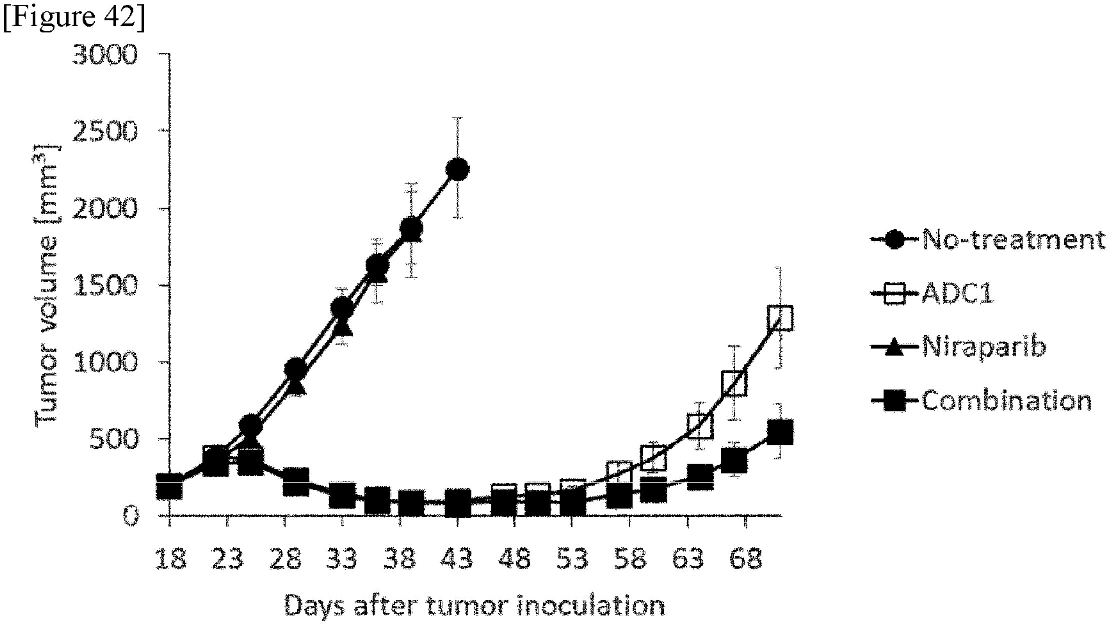

[Figure 43]
[Formula 52]
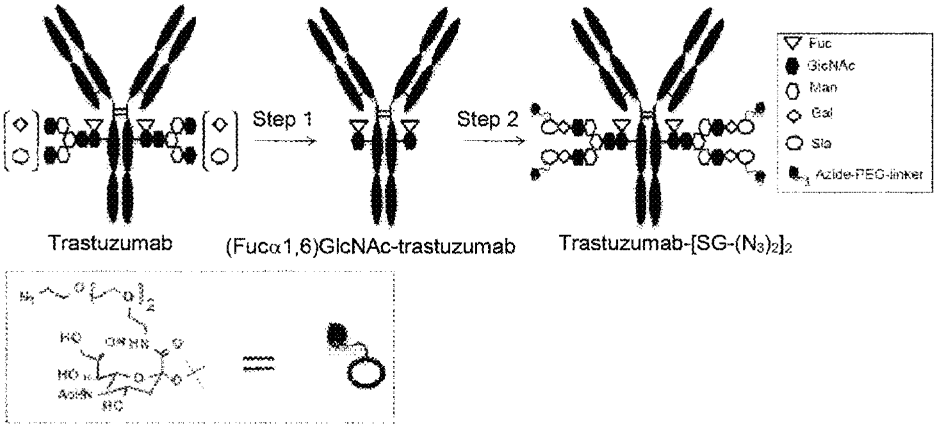
[Figure 44]
[Formula 53]
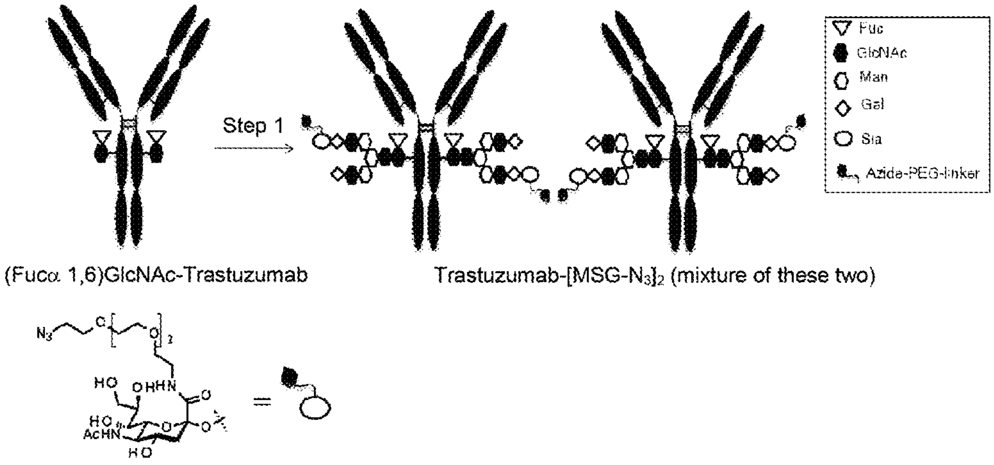

[Figure 45]
[Formula 54]
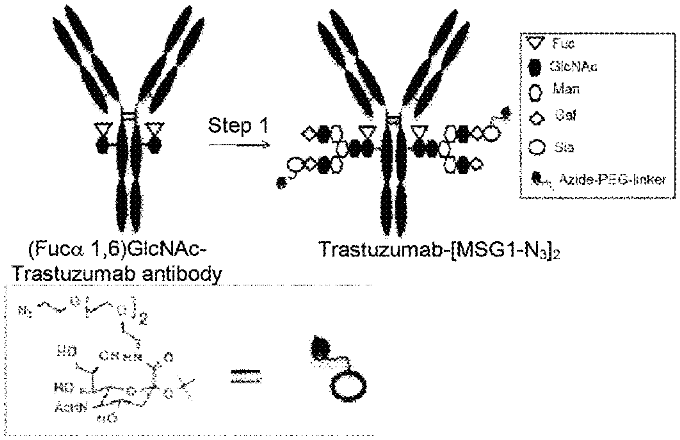
[Figure 46]
[Formula 55]
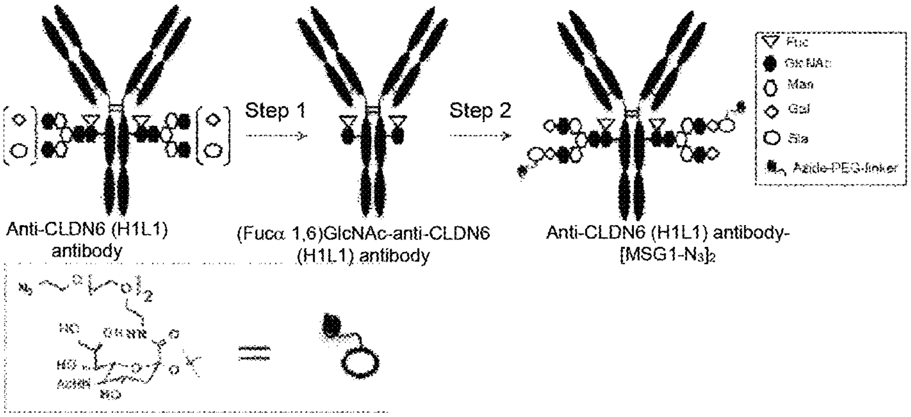

[Figure 47]
[Formula 56]
R =
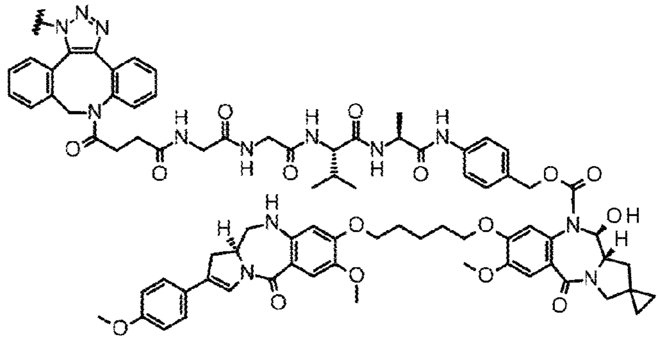
or
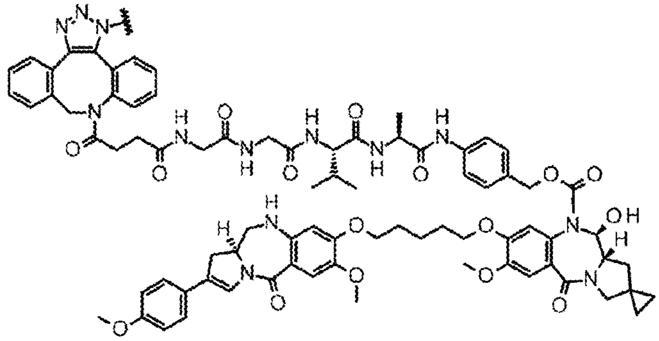

[Figure 48]
[Formula 57]
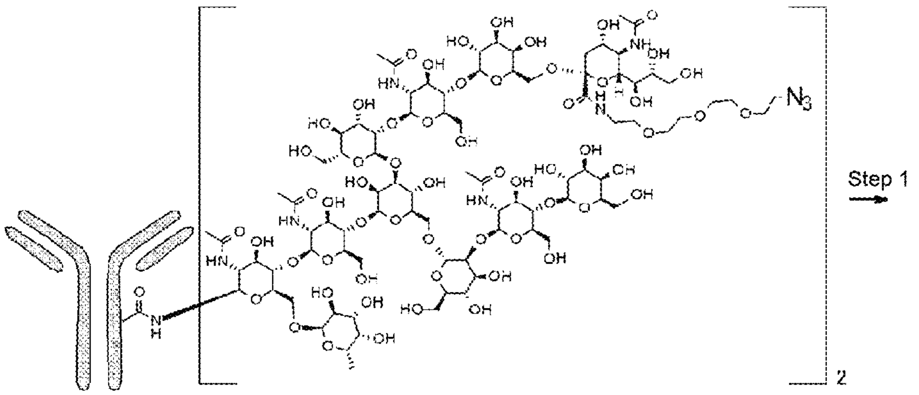
Anti-CLDN6 (H1L1)-(MSG1-$N_3$)$_2$
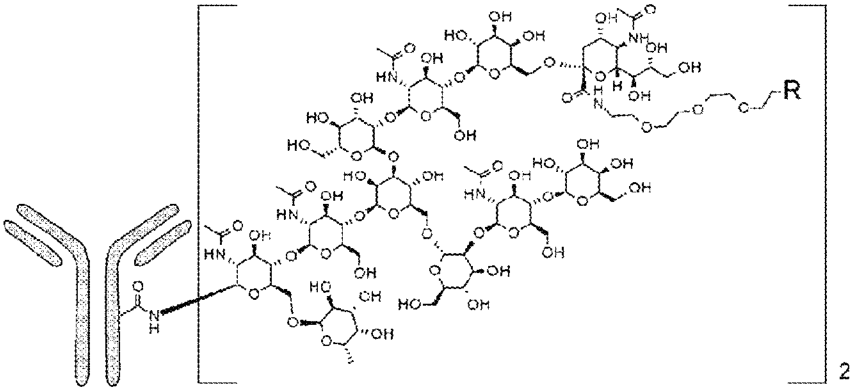

[Figure 49]
[Formula 58]
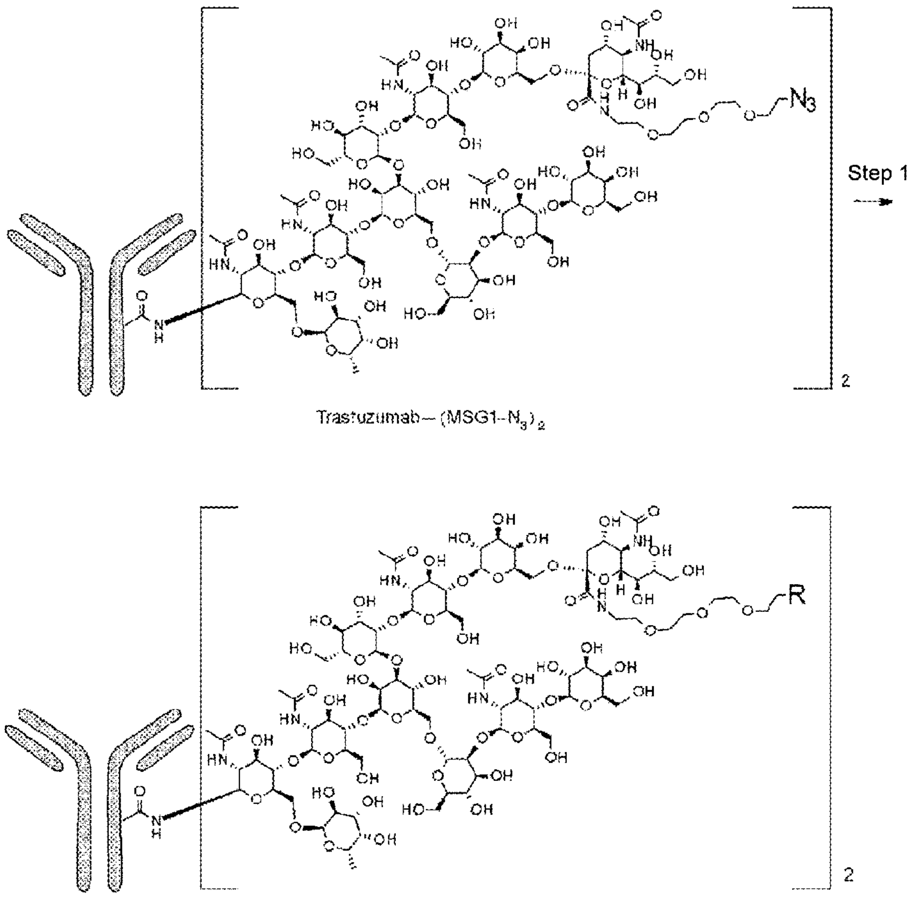
Trastuzumab—(MSG1-$N_3$)$_2$

[Figure 50]
[Formula 59]
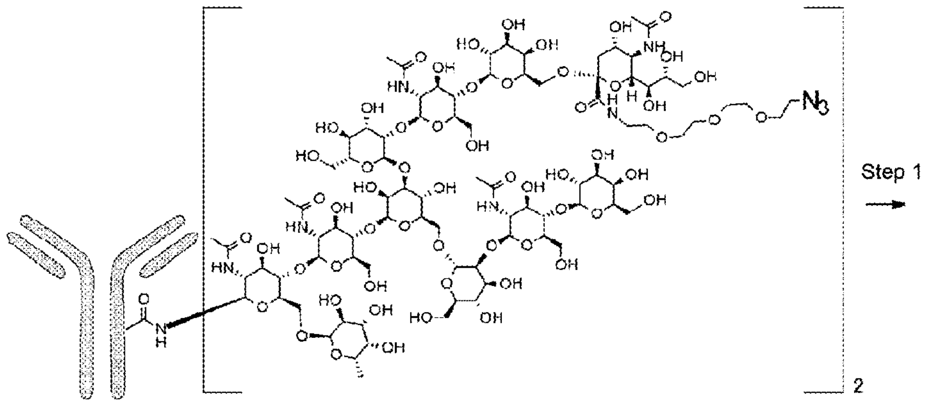
Anti-Trop2-(MSG1-$N_3$)$_2$
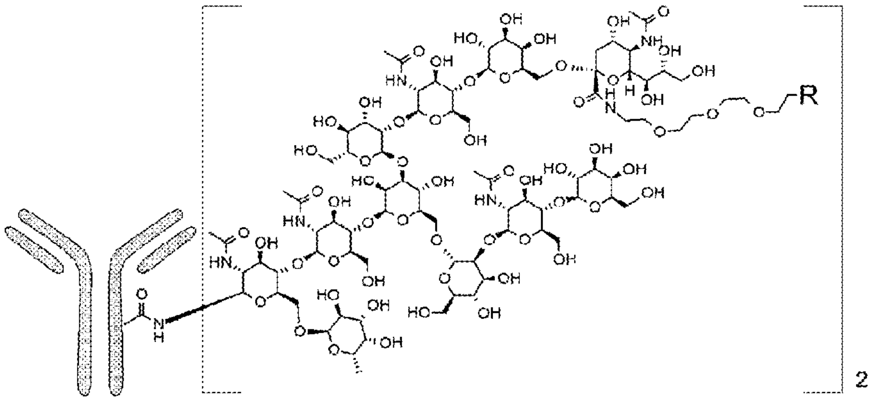

[Figure 51]
[Formula 60]
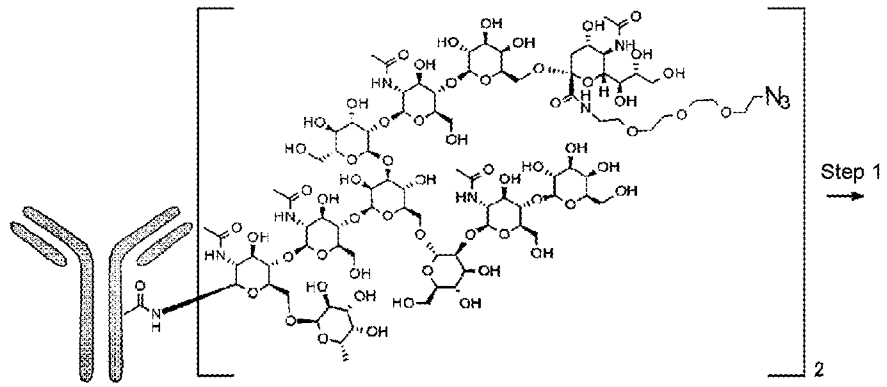
Anti-CLDN6 (H2L2)-(MSG1-$N_3$)$_2$
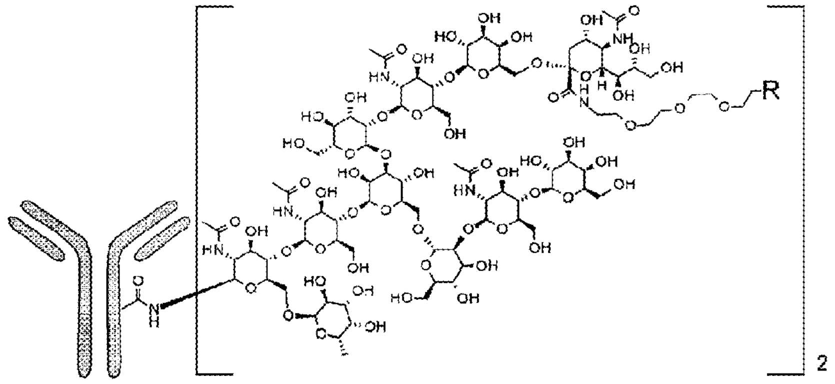

[Figure 52]
[Formula 61]
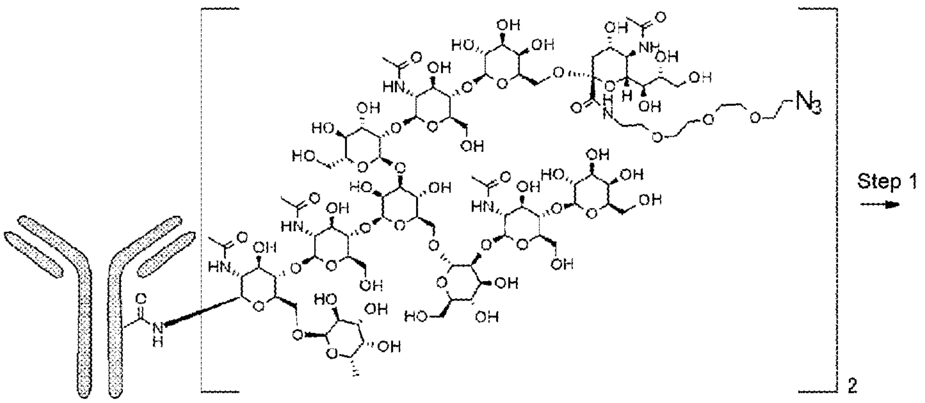
Anti-CLDN6 (H1L3)-(MSG1-$N_3$)$_2$
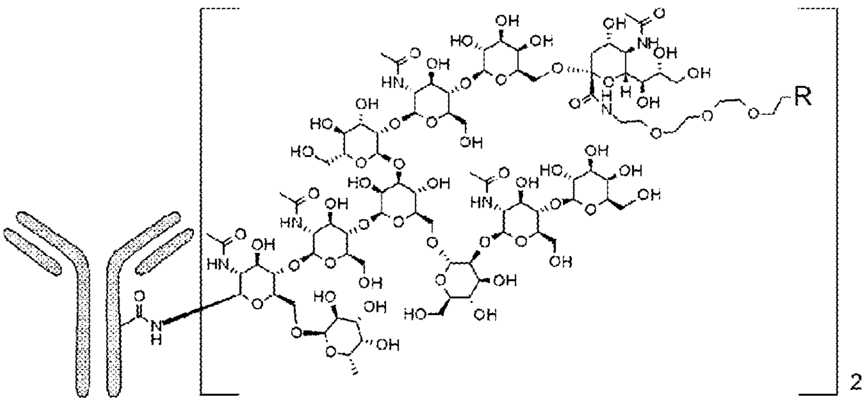

COMBINATION OF ANTIBODY-PYRROLOBENZODIAZEPINE DERIVATIVE CONJUGATE AND PARP INHIBITOR

CROSS-REFERENCE TO RELATED APPLICATIONS

The present application claims priority under 35 U.S.C. § 371 to International Patent Application No. PCT/JP2020/013555, filed Mar. 26, 2020, which claims priority to and the benefit of Japanese Patent Application No. 2019-061761, filed on Mar. 27, 2019. The contents of these applications are hereby incorporated by reference in their entireties.

SEQUENCE LISTING

The instant application contains a Sequence Listing which has been submitted in ASCII format via EFS-Web and is hereby incorporated by reference in its entirety. Said ASCII copy, is named 122763-0105_SL.txt and is 120,887 bytes in size.

TECHNICAL FIELD

The present invention relates to a pharmaceutical composition for treatment of cancer and a method for treating cancer, wherein a specific antibody-drug conjugate and PARP inhibitor are administered in combination.

BACKGROUND ART

Antibody-drug conjugates (ADCs), which are used for treatment of cancer and so on, have a drug with cytotoxic activity conjugated to an antibody, for example, that binds to an antigen expressed on the surface of cancer cells and is capable of cellular internalization of the antigen through the binding. ADCs can effectively deliver the drug to cancer cells, and are thus expected to cause accumulation of the drug within the cancer cells and to kill the cancer cells.

A useful example of drugs to be used for ADCs is pyrrolobenzodiazepine (PBD). PBD exhibits cytotoxicity by binding to, for example, the PuGPu sequence in the DNA minor groove. Anthramycin, a naturally-occurring PBD, was first discovered in 1965, and since this discovery various naturally-occurring PBDs and analog PBDs thereof have been discovered (Non Patent Literatures 1 to 4).

The general structural formula of PBDs is represented by the following formula:

[Formula 1]

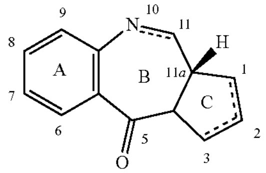

Known are PBDs different in the number of, types of, and sites of substituents in the A and C ring parts, and those different in degree of unsaturation in the Band C ring parts.

PBDs are known to come to have dramatically enhanced cytotoxicity through formation of a dimer structure (Non Patent Literatures 5, 6), and various ADCs with a dimer PBD have been reported (Patent Literatures 1 to 15). However, a PBD having a spiro ring at its C2-position and an ADC form thereof have not known.

A poly(ADP-ribose) polymerase (PARP) inhibitor is an agent having a function to interfere with repair of single-strand breaks by inhibiting PARP (in particular, PARP-1 and PARP-2). It is known that some cancers such as breast cancer and ovarian cancer involve abnormality in repair of double-strand breaks, and PARP inhibitors have been found to have antitumor effect on these cancers through synthetic lethality (Non Patent Literatures 7 to 11).

Known examples of PARP inhibitors include olaparib (Non Patent Literature 12), rucaparib (Non Patent Literature 13), niraparib (Non Patent Literature 14), and talazoparib (Non Patent Literature 15).

Use of a PARP inhibitor and an ADC using a PBD in combination is known to provide an effect similar to synthetic lethality. For example, a combined effect of olaparib and an ADC has been found in a xenograft model of BRCA2-knockout DLD1 cells, where PARP inhibitors exhibit efficacy for BRCA2. However, no combined effect was found in a xenograft model of DLD1 cells, the parent strain (Non Patent Literature 16). In addition, no combined effect with a PARP inhibitor has been known for the above PBD having a spiro ring and antibody-drug conjugates therewith.

CITATION LIST

Patent Literature

Patent Literature 1: WO 2013/173496
Patent Literature 2: WO 2014/130879
Patent Literature 3: WO 2017/004330
Patent Literature 4: WO 2017/004025
Patent Literature 5: WO 2017/020972
Patent Literature 6: WO 2016/036804
Patent Literature 7: WO 2015/095124
Patent Literature 8: WO 2015/052322
Patent Literature 9: WO 2015/052534
Patent Literature 10: WO 2016/115191
Patent Literature 11: WO 2015/052321
Patent Literature 12: WO 2015/031693
Patent Literature 13: WO 2011/130613
Patent Literature 14: WO 2005/040170
Patent Literature 15: WO 2017/137556

Non Patent Literature

Non Patent Literature 1: Angewandte Chemie International Edition 2016, 55, 2-29
Non Patent Literature 2: Chemical Reviews 2010, 111, 2815-2864
Non Patent Literature 3: In Antibiotics III. Springer Verlag, New York, pp. 3-11
Non Patent Literature 4: Accounts of Chemical Research 1986, 19, 230
Non Patent Literature 5: Journal of the American Chemical Society 1992, 114, 4939
Non Patent Literature 6: Journal of Organic Chemistry 1996, 61, 8141
Non Patent Literature 7: Lord C J, et al., Nature (2012) 481, 287-294.
Non Patent Literature 8: Benafif S, et al., Onco. Targets Ther. (2015) 8, 519-528.
Non Patent Literature 9: Fong P C, et al., N. Engl. J. Med. (2009) 361, 123-134.

Non Patent Literature 10: Fong P C, et al., J. Clin. Oncol. (2010) 28, 2512-2519.
Non Patent Literature 11: Gelmon K A, et al., Lancet Oncol. (2011) 12, 852-861.
Non Patent Literature 12: Menear K A, et al., J. Med. Chem. (2008) 51, 6581-6591.
Non Patent Literature 13: Gillmore A T, et al., Org. Process Res. Dev. (2012) 16, 1897-1904.
Non Patent Literature 14: Jones P, et al., J. Med. Chem. (2009) 52, 7170-7185.
Non Patent Literature 15: Shen Y, et al., Clin. Cancer Res. (2013) 19 (18), 5003-5015.
Non Patent Literature 16: Zhong H, et al., Mol Cancer Ther. (2019) 18 (1), 89-99.

SUMMARY OF INVENTION

Problems to be Resolved by the Invention

The present invention provides a medicine for treatment of cancer, wherein an antibody-pyrrolobenzodiazepine derivative conjugate and a PARP inhibitor are administered in combination, and a method for treating cancer, wherein an antibody-pyrrolobenzodiazepine derivative conjugate and a PARP inhibitor are administered in combination.

Means of Solving the Problems

The present inventors diligently examined to solve the above problems to find that administration of an antibody-pyrrolobenzodiazepine derivative conjugate and a PARP inhibitor in combination provided excellent antitumor effect. Further, the conjugate exhibited excellent antitumor effect through being administered in combination with a PARP inhibitor, even for cell lines and xenograft tumors to which PARP inhibitors exhibit no sensitivity. The present invention was completed on the basis of the findings.

Specifically, the present invention relates to the following.

[1] A pharmaceutical composition for treatment of cancer, the pharmaceutical composition comprising an antibody-pyrrolobenzodiazepine derivative conjugate and/or a PARP inhibitor, wherein the antibody-pyrrolobenzodiazepine derivative conjugate and the PARP inhibitor are administered in combination, and the conjugate is represented by the following formula:

[Formula 2]

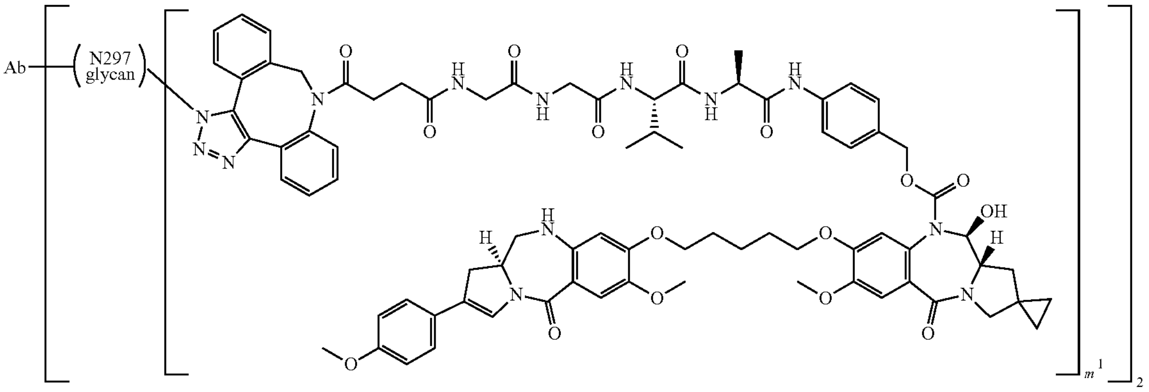

or

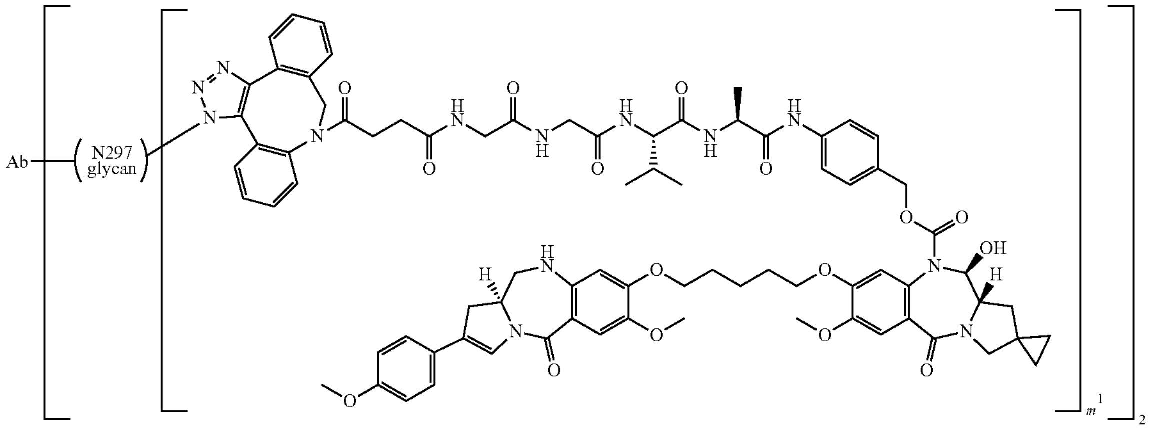

-continued
[Formula 3]
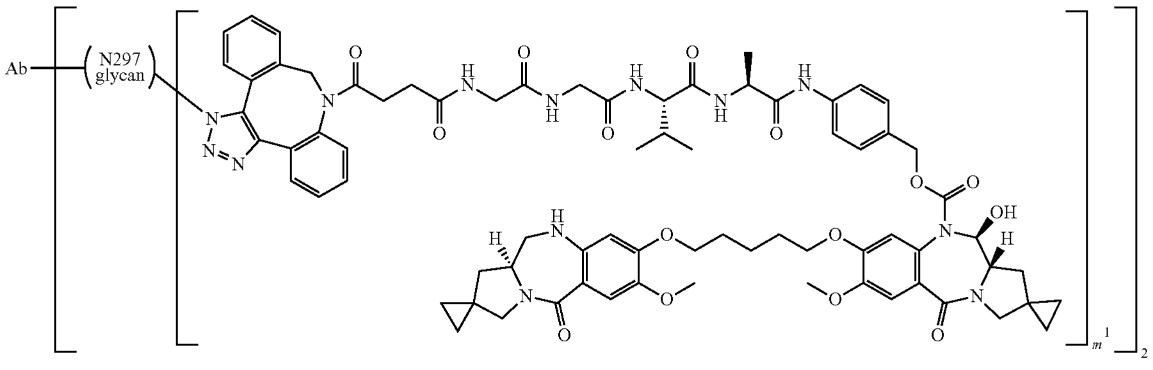
or
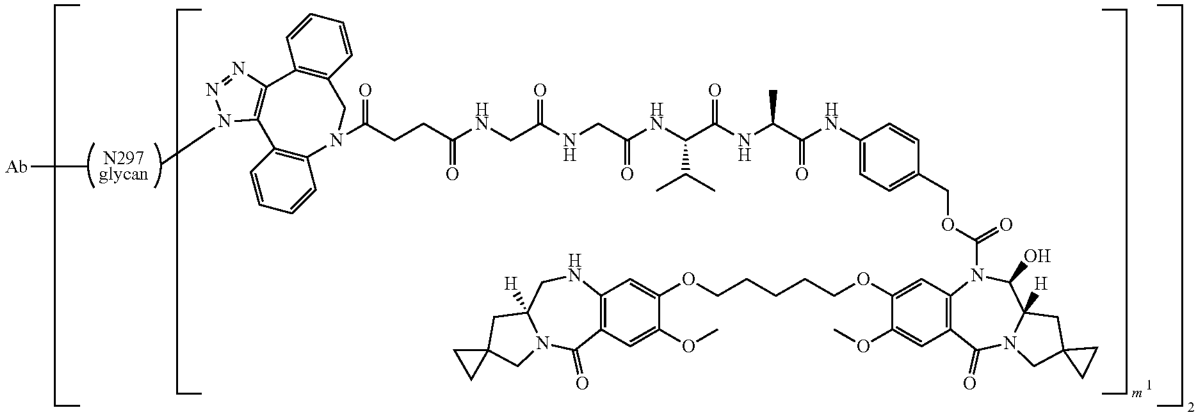
[Formula 4]
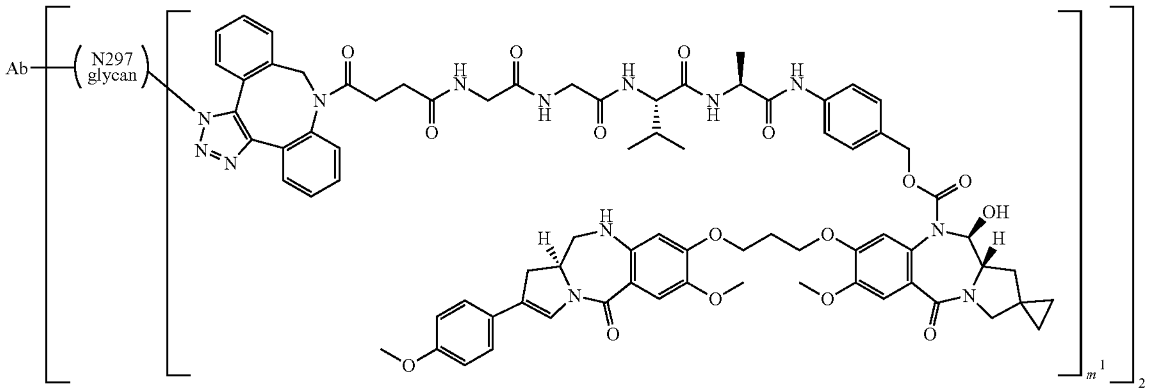
or
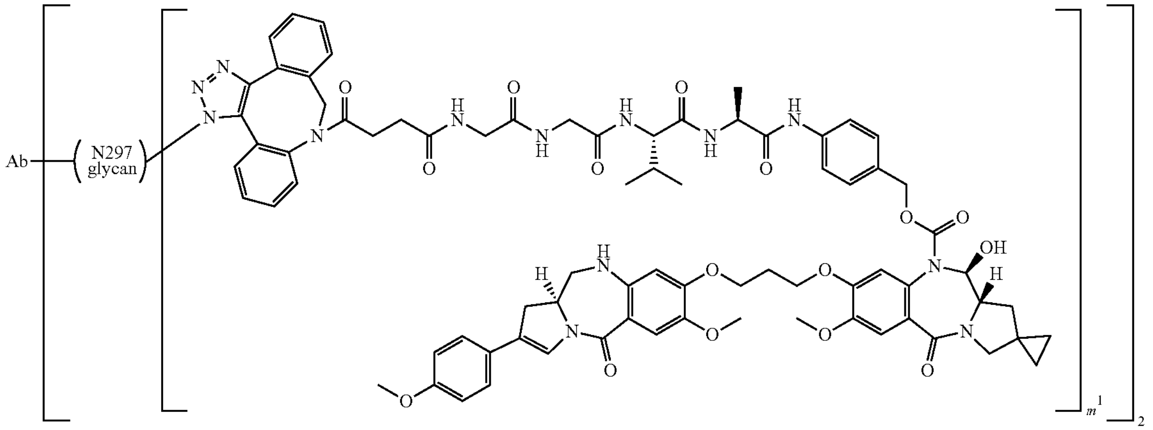
or, -continued

[Formula 5]

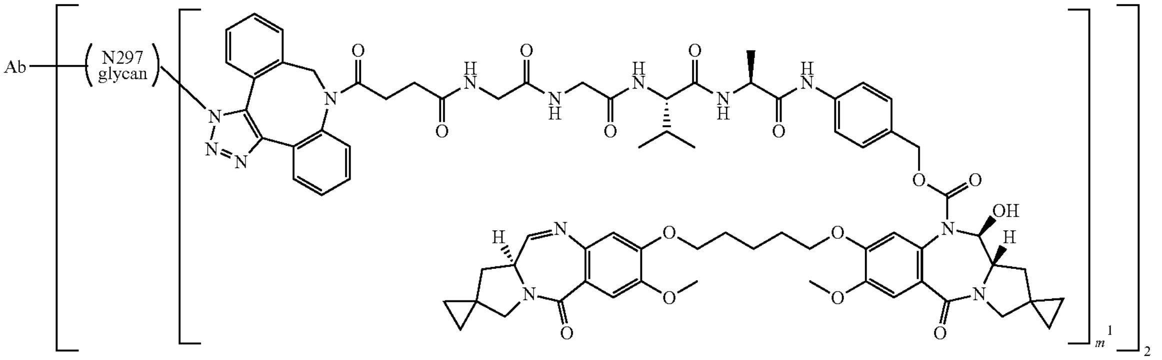

or

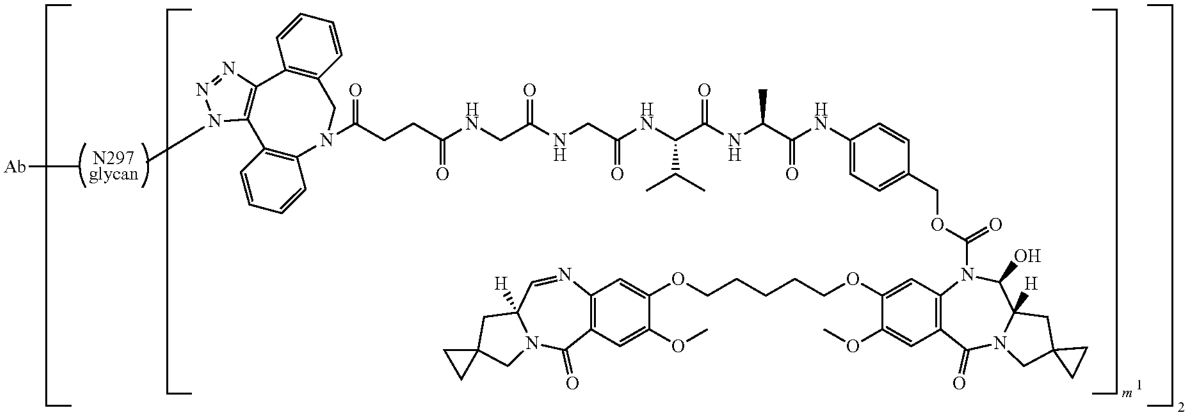

wherein, in each structural formula shown above, $m^1$ is an integer of 1 or 2;

Ab is an antibody or a functional fragment of the antibody;

the N297 glycan is any one of N297-(Fuc)MSG1, N297-(Fuc)MSG2, and a mixture thereof, and N297-(Fuc)SG, with N297-(Fuc)MSG1, N297-(Fuc)MSG2, and N297-(Fuc)SG having structures represented by the following formulas:

[Formula 6]

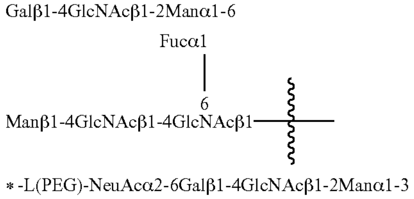

[N297-(Fuc)MSG1]

[Formula 7]

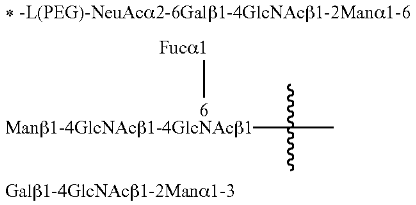

[N297-(Fuc)MSG2]

-continued

[Formula 8]

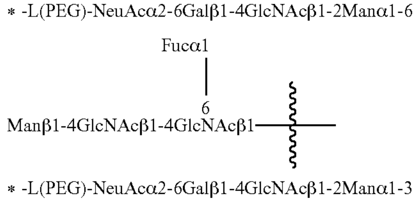

[N297-(Fuc)SG]

wherein each wavy line represents bonding to Asn297 of the antibody,

L(PEG) in the N297 glycan represents *—$(CH_2CH_2—O)_3—CH_2CH_2—NH—$, wherein the amino group at the right end is bound via an amide bond to carboxylic acid at the 2-position of a sialic acid at the non-reducing terminal in each or either one of the 1-3 and 1-6 branched chains of β-Man in the N297 glycan, and the asterisk * at the left end represents bonding to a nitrogen atom at the 1- or 3-position of the triazole ring in the corresponding structural formula.

[2] The pharmaceutical composition according to [1], wherein the antibody binds to an antigen expressed on a tumor cell and is incorporated and internalized in the tumor cell.

[3] The pharmaceutical composition according to [1] or [2], wherein the antibody has antitumor effect.

[4] The pharmaceutical composition according to any one of [1] to [3], wherein the antibody is an anti-CLDN6 antibody, an anti-CLDN9 antibody, an anti-CLDN6/CLDN9 antibody, an anti-HER2 antibody, an anti-HER3 antibody, an anti-DLL3 antibody, an anti-FAP antibody, an anti-CDH11 antibody, an anti-A33 antibody, an anti-CanAg antibody, an anti-CD19 antibody, an anti-CD20 antibody, an anti-CD22 antibody, an anti-CD25 antibody, an anti-CD30 antibody, an anti-CD33 antibody, an anti-CD37 antibody, an anti-CD56 antibody, an anti-CD70 antibody, an anti-CD98 antibody, an anti-B7-H3 antibody, an anti-TROP2 antibody, an anti-CEA antibody, an anti-Cripto antibody, an anti-EphA2 antibody, an anti-FGFR2 antibody, an anti-G250 antibody, an anti-MUC1 antibody, an anti-GPNMB antibody, an anti-Integrin antibody, an anti-PSMA antibody, an anti-Tenascin-C antibody, an anti-SLC44A4 antibody, an anti-Mesothelin antibody, an anti-EGFR antibody, an anti-5T4 antibody, an anti-LRRC15 antibody, an anti-DR5 antibody, an anti-CDH3 antibody, an anti-PDPN antibody, or an anti-CD123 antibody.

[5] The pharmaceutical composition according to any one of [1] to [4], wherein the antibody specifically binds to CLDN6 and/or CLDN9.

[6] The pharmaceutical composition according to [5], the antibody comprising a heavy chain comprising CDRH1, CDRH2, and CDRH3 and a light chain comprising CDRL1, CDRL2, and CDRL3 as described in any one of the following (a) and (b):

(a) CDRH1 consisting of an amino acid sequence represented by SEQ ID NO: 9, CDRH2 consisting of an amino acid sequence represented by SEQ ID NO: 10, and CDRH3 consisting of an amino acid sequence represented by SEQ ID NO: 11, and CDRL1 consisting of an amino acid sequence represented by SEQ ID NO: 5, CDRL2 consisting of an amino acid sequence represented by SEQ ID NO: 6, and CDRL3 consisting of an amino acid sequence represented by SEQ ID NO: 7 or an amino acid sequence having one or two amino acid substitutions in the amino acid sequence represented by SEQ ID NO: 7; and (b) CDRH1 consisting of an amino acid sequence represented by SEQ ID NO: 15, CDRH2 consisting of an amino acid sequence represented by SEQ ID NO: 16, and CDRH3 consisting of an amino acid sequence represented by SEQ ID NO: 17, and CDRL1 consisting of an amino acid sequence represented by SEQ ID NO: 12, CDRL2 consisting of an amino acid sequence represented by SEQ ID NO: 13, and CDRL3 consisting of an amino acid sequence represented by SEQ ID NO: 14.

[7] A pharmaceutical composition according to [6], the antibody comprising a heavy chain comprising CDRH1, CDRH2, and CDRH3 and a light chain comprising CDRL1, CDRL2, and CDRL3 as described in any one of the following (a) and (b):

(a) CDRH1 consisting of an amino acid sequence represented by SEQ ID NO: 9, CDRH2 consisting of an amino acid sequence represented by SEQ ID NO: 10, and CDRH3 consisting of an amino acid sequence represented by SEQ ID NO: 11, and CDRL1 consisting of an amino acid sequence represented by SEQ ID NO: 5, CDRL2 consisting of an amino acid sequence represented by SEQ ID NO: 6, and CDRL3 consisting of an amino acid sequence represented by SEQ ID NO: 7 or an amino acid sequence represented by SEQ ID NO: 8; and (b) CDRH1 consisting of an amino acid sequence represented by SEQ ID NO: 15, CDRH2 consisting of an amino acid sequence represented by SEQ ID NO: 16, and CDRH3 consisting of an amino acid sequence represented by SEQ ID NO: 17, and CDRL1 consisting of an amino acid sequence represented by SEQ ID NO: 12, CDRL2 consisting of an amino acid sequence represented by SEQ ID NO: 13, and CDRL3 consisting of an amino acid sequence represented by SEQ ID NO: 14.

[8] The pharmaceutical composition according to any one of [5] to [7], the antibody comprising a heavy chain variable region and a light chain variable region as described in any one of the following (a) and (b):

(a) a heavy chain variable region consisting of an amino acid sequence represented by SEQ ID NO: 21 and a light chain variable region consisting of an amino acid sequence represented by SEQ ID NO: 19; or (b) a heavy chain variable region consisting of an amino acid sequence represented by SEQ ID NO: 25 and a light chain variable region consisting of an amino acid sequence represented by SEQ ID NO: 23.

[9] The pharmaceutical composition according to any one of [5] to [8], the antibody comprising a heavy chain variable region consisting of an amino acid sequence selected from the group consisting of the following (a) to (e) and a light chain variable region consisting of an amino acid sequence selected from the group consisting of the following (f) to (k):

(a) an amino acid sequence represented by SEQ ID NO: 54;

(b) an amino acid sequence represented by SEQ ID NO: 58;

(c) an amino acid sequence represented by SEQ ID NO: 62;

(d) an amino acid sequence with a homology of at least 95% or higher to a sequence of a framework region excluding CDR sequences in any of the sequences (a) to (c);

(e) an amino acid sequence having one to several amino acid deletions, substitutions, or additions in a sequence of a framework region excluding CDR sequences in any of the sequences (a) to (c);

(f) an amino acid sequence represented by SEQ ID NO: 38;

(g) an amino acid sequence represented by SEQ ID NO: 42;

(h) an amino acid sequence represented by SEQ ID NO: 46;

(i) an amino acid sequence represented by SEQ ID NO: 50;

(j) an amino acid sequence with a homology of at least 95% or higher to a sequence of a framework region excluding CDR sequences in any of the sequences (f) to (i); and (k) an amino acid sequence having one to several amino acid deletions, substitutions, or additions in a sequence of a framework region excluding CDR sequences in any of the sequences (f) to (i).

[10] The pharmaceutical composition according to [9], the antibody comprising a heavy chain variable region and a light chain variable region selected from the group consisting of the following (a) to (e):

(a) a heavy chain variable region consisting of an amino acid sequence represented by SEQ ID NO: 54 and a light chain variable region consisting of an amino acid sequence represented by SEQ ID NO: 38;

(b) a heavy chain variable region consisting of an amino acid sequence represented by SEQ ID NO: 58 and a light chain variable region consisting of an amino acid sequence represented by SEQ ID NO: 42;

(c) a heavy chain variable region consisting of an amino acid sequence represented by SEQ ID NO: 54 and a light chain variable region consisting of an amino acid sequence represented by SEQ ID NO: 46;

(d) a heavy chain variable region consisting of an amino acid sequence represented by SEQ ID NO: 58 and a light chain variable region consisting of a light chain variable region consisting of an amino acid sequence represented by SEQ ID NO: 50; and (e) a heavy chain variable region consisting of an amino acid sequence represented by SEQ ID NO: 62 and a light chain variable region consisting of an amino acid sequence represented by SEQ ID NO: 46.

[11] The pharmaceutical composition according to any one of [5] to [10], wherein the antibody is a chimeric antibody.

[12] The pharmaceutical composition according to any one of [5] to [10], wherein the antibody is a humanized antibody.

[13] The pharmaceutical composition according to any one of [5] to [12], wherein the antibody comprises a heavy chain constant region of human IgG1, human IgG2, or human IgG4.

[14] The pharmaceutical composition according to [12] or [13], comprising a heavy chain and a light chain selected from the group consisting of the following (a) to (e):

(a) a heavy chain consisting of an amino acid sequence consisting of amino acid residues 20 to 471 of SEQ ID NO: 52 and a light chain consisting of an amino acid sequence consisting of amino acid residues 21 to 234 of SEQ ID NO: 36;

(b) a heavy chain consisting of an amino acid sequence consisting of amino acid residues 20 to 471 of SEQ ID NO: 56 and a light chain consisting of an amino acid sequence consisting of amino acid residues 21 to 234 of SEQ ID NO: 40;

(c) a heavy chain consisting of an amino acid sequence consisting of amino acid residues 20 to 471 of SEQ ID NO: 52 and a light chain consisting of an amino acid sequence consisting of amino acid residues 21 to 234 of SEQ ID NO: 44;

(d) a heavy chain consisting of an amino acid sequence consisting of amino acid residues 20 to 471 of SEQ ID NO: 56 and a light chain consisting of an amino acid sequence consisting of amino acid residues 21 to 234 of SEQ ID NO: 48; and (e) a heavy chain consisting of an amino acid sequence consisting of amino acid residues 20 to 471 of SEQ ID NO: 60 and a light chain consisting of an amino acid sequence consisting of amino acid residues 21 to 234 of SEQ ID NO: 44.

[15] The pharmaceutical composition according to [5], wherein the antibody competes with the antibody according to any one of [6] to [10] and [14] for binding to CLDN6 and/or CLDN9, or binds to a site of CLDN6 and/or CLDN9 recognizable to the antibody according to any one of [6] to [10] and [14].

[16] The pharmaceutical composition according to any one of [1] to [4], wherein the antibody specifically binds to HER2.

[17] The pharmaceutical composition according to [16], having activities or activity of antibody-dependent cellular cytotoxicity (ADCC) and/or complement-dependent cytotoxicity (CDC).

[18] The pharmaceutical composition according to [16], wherein the heavy chain constant region of the antibody is a heavy chain constant region of human IgG1, and comprises a mutation that causes lowering of activities or activity of ADCC and/or CDC.

[19] The pharmaceutical composition according to [18], wherein the heavy chain constant region of the antibody is a heavy chain constant region of human IgG1, and leucine at the 234- and 235-positions specified by EU Index numbering in the heavy chain constant region is substituted with alanine.

[20] The pharmaceutical composition according to [16] or [17], being an antibody comprising a heavy chain consisting of an amino acid sequence represented by SEQ ID NO: 65 and a light chain consisting of an amino acid sequence represented by SEQ ID NO: 64. [21] The pharmaceutical composition according to any one of [16], [18], and [19], being an antibody comprising a heavy chain variable region consisting of an amino acid sequence consisting of amino acid residues 20 to 139 of SEQ ID NO: 75 and a light chain variable region consisting of an amino acid sequence consisting of amino acid residues 21 to 127 of SEQ ID NO: 73.

[22] The pharmaceutical composition according to any one of [16], [18], [19], and [21], wherein the antibody comprises a heavy chain consisting of an amino acid sequence consisting of amino acid residues 20 to 469 of SEQ ID NO: 75 and a light chain consisting of an amino acid sequence consisting of amino acid residues 21 to 234 of SEQ ID NO: 73.

[23] The pharmaceutical composition according to any one of [16], [18], [19], and [21], wherein the antibody comprises a heavy chain consisting of an amino acid sequence consisting of amino acid residues 20 to 469 of SEQ ID NO: 77 and a light chain consisting of an amino acid sequence consisting of amino acid residues 21 to 234 of SEQ ID NO: 76.

[24] The pharmaceutical composition according to any one of [5] to [23], wherein the antibody comprises one or two or more modifications selected from the group consisting of N-linked glycosylation, O-linked glycosylation, N-terminal processing, C-terminal processing, deamidation, isomerization of aspartic acid, oxidation of methionine, addition of a methionine residue at an N terminus, amidation of a proline residue, and deletion of one or two amino acid residues at the carboxyl terminus of a heavy chain.

[25] The pharmaceutical composition according to [24], wherein one or several amino acid residues are deleted at the carboxyl terminus of a heavy chain of the antibody.

[26] The pharmaceutical composition according to [24] or [25], wherein one amino acid residue is deleted at the carboxyl terminus of each of the two heavy chains of the antibody.

[27] The pharmaceutical composition according to any one of [24] to [26], wherein a proline residue at the carboxyl terminus of a heavy chain of the antibody is further amidated.

[28] The pharmaceutical composition according to any one of [1] to [27], wherein the N297 glycan is N297-(Fuc) MSG1.

[29] The pharmaceutical composition according to any one of [1] to [28], wherein $m^1$ is an integer of 1.

[30] The pharmaceutical composition according to any one of [1] to [29], wherein the average number of conjugated drug molecules per antibody molecule in the antibody-pyrrolobenzodiazepine derivative conjugate is 1 to 3 or 3 to 5.

[31] The pharmaceutical composition according to any one of [1] to [30], wherein the PARP inhibitor is olaparib, rucaparib, niraparib, or talazoparib, or a pharmacologically acceptable salt thereof.

[32] The pharmaceutical composition according to any one of [1] to [31], wherein the antibody-drug conjugate and the PARP inhibitor are individually contained as an active ingredient in separate formulations and administered simultaneously or at different times.

[33] The pharmaceutical composition according to any one of [1] to [32], for treatment of at least one cancer selected from the group consisting of lung cancer (e.g., non-small cell lung cancer, small cell lung cancer), kidney cancer, urothelial cancer, colorectal cancer, prostate cancer, glioblastoma multiforme, ovarian cancer (e.g., surface epithelial tumor, stromal tumor, germ cell tumor), pancreatic cancer, breast cancer, melanoma, liver cancer, bladder cancer, gastric cancer, esophageal cancer, endometrial cancer, testicular cancer (seminoma, non-seminoma), uterine cervix cancer, placental choriocarcinoma, brain tumor, and head-and-neck cancer, and metastatic forms of them.

[34] A method for treating cancer, wherein an antibody-pyrrolobenzodiazepine derivative conjugate and a PARP inhibitor are administered in combination, and the conjugate is represented by the following formula:

[Formula 9]

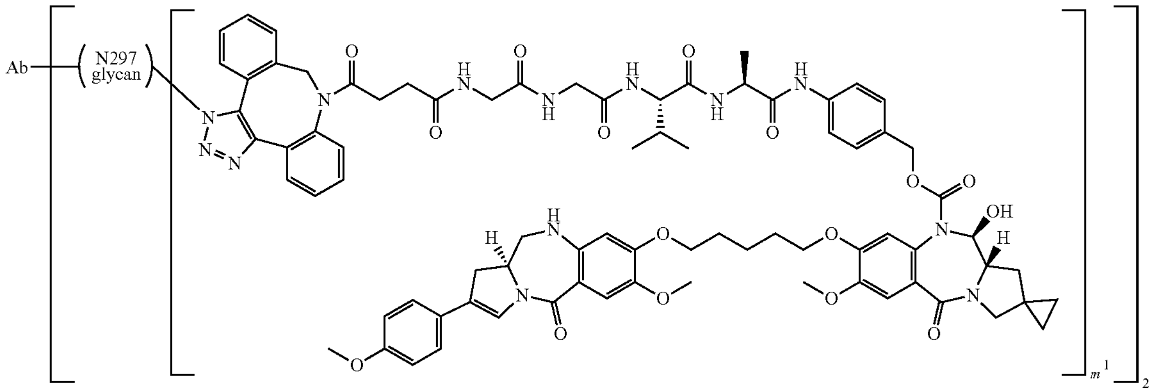

or

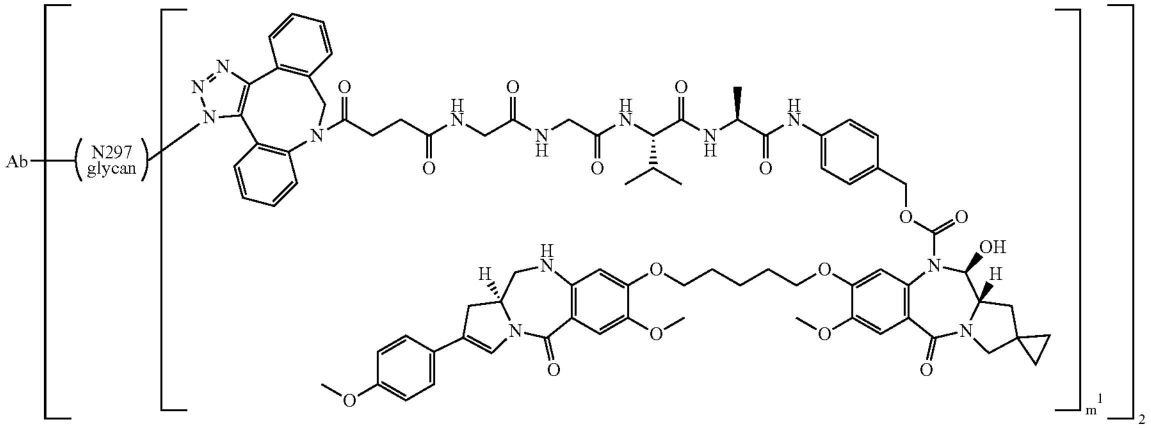

[Formula 10]

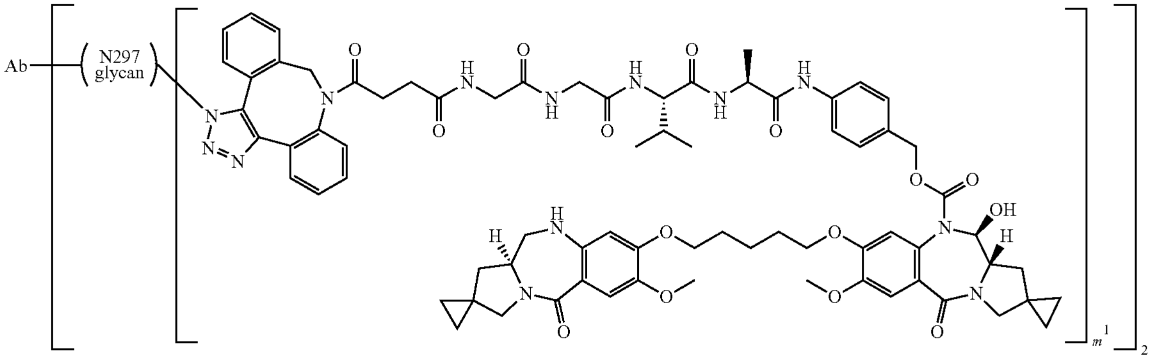

or

-continued
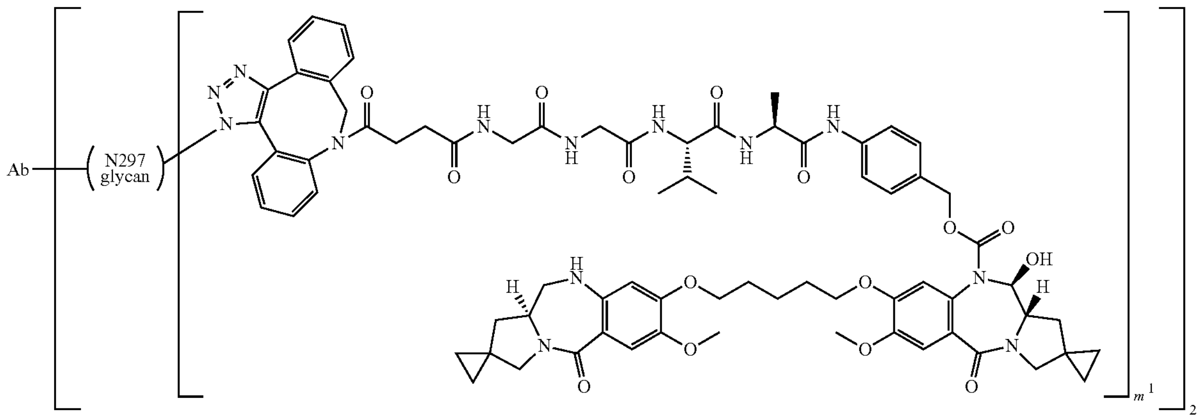
[Formula 11]
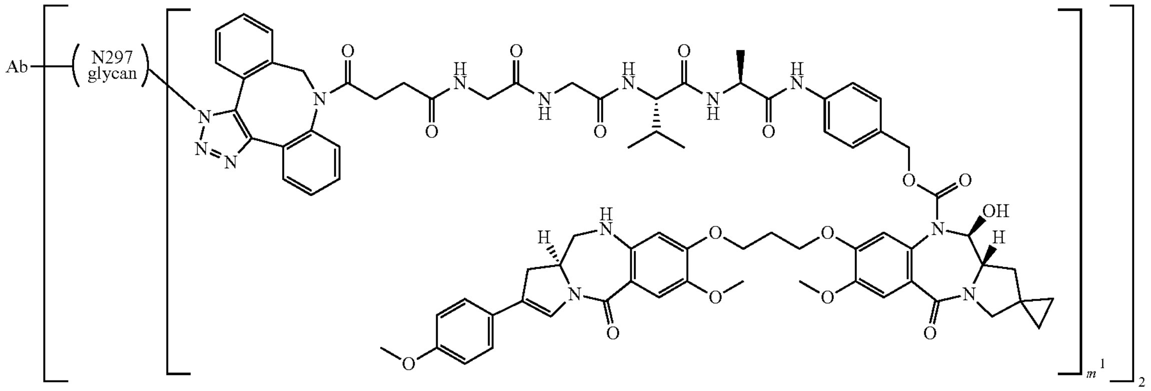
or
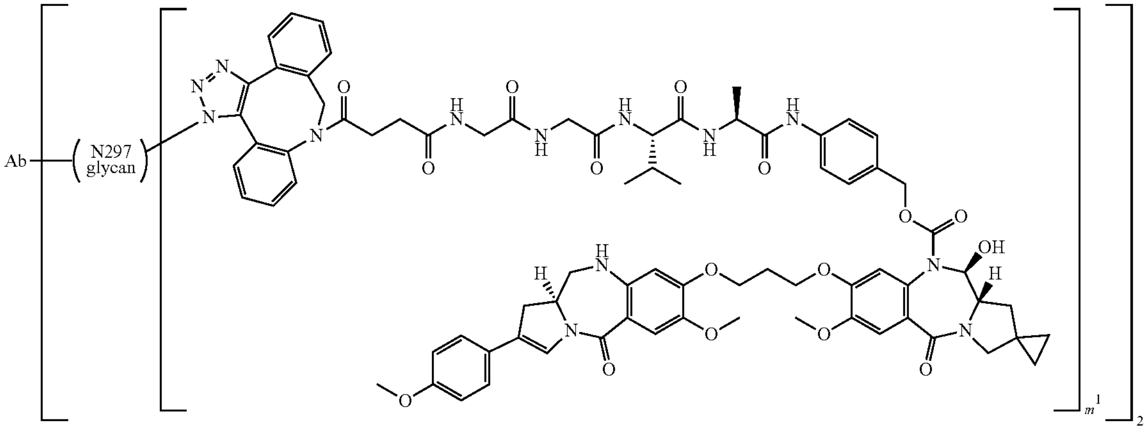
or,
[Formula 12]
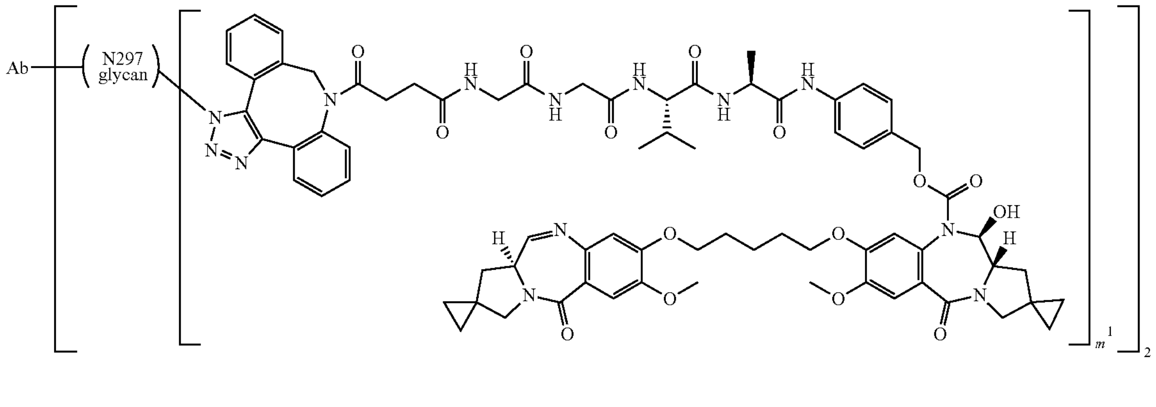
or -continued

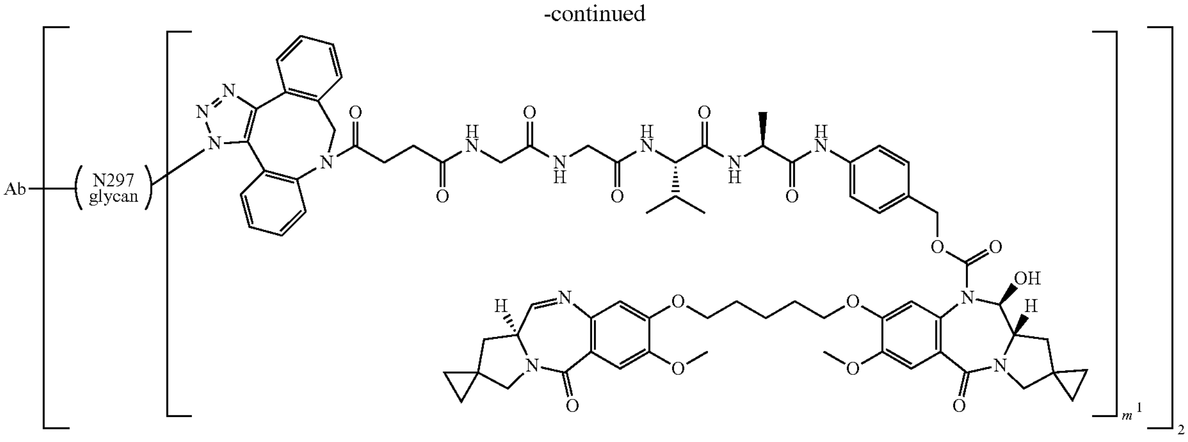

wherein, in each structural formula shown above, $m^1$ is an integer of 1 or 2;

Ab is an antibody or a functional fragment of the antibody;

the N297 glycan is any one of N297-(Fuc)MSG1, N297-(Fuc)MSG2, and a mixture thereof, and N297-(Fuc)SG, with N297-(Fuc)MSG1, N297-(Fuc) MSG2, and N297-(Fuc)SG having structures represented by the following formulas:

[Formula 13]

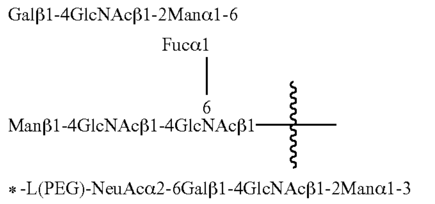

[N297-(Fuc)MSG1]

[Formula 14]

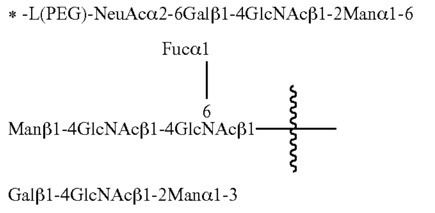

[N297-(Fuc)MSG2]

[Formula 15]

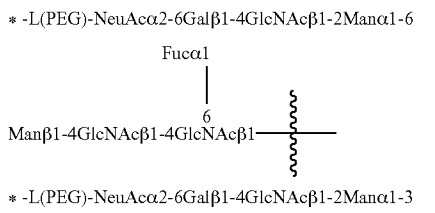

[N297-(Fuc)SG]

wherein each wavy line represents bonding to Asn297 of the antibody,

L(PEG) in the N297 glycan represents *—$(CH_2CH_2—O)_3$—$CH_2CH_2$—NH—, wherein the amino group at the right end is bound via an amide bond to carboxylic acid at the 2-position of a sialic acid at the non-reducing terminal in each or either one of the 1-3 and 1-6 branched chains of β-Man in the N297 glycan, and the asterisk * at the left end represents bonding to a nitrogen atom at the 1- or 3-position of the triazole ring in the corresponding structural formula.

[35] The method according to [34], wherein the antibody binds to an antigen expressed on a tumor cell and is incorporated and internalized in the tumor cell.

[36] The method according to [34] or [35], wherein the antibody has antitumor effect.

[37] The method according to any one of [34] to [36], wherein the antibody is an anti-CLDN6 antibody, an anti-CLDN9 antibody, an anti-CLDN6/CLDN9 antibody, an anti-HER2 antibody, an anti-HER3 antibody, an anti-DLL3 antibody, an anti-FAP antibody, an anti-CDH11 antibody, an anti-A33 antibody, an anti-CanAg antibody, an anti-CD19 antibody, an anti-CD20 antibody, an anti-CD22 antibody, an anti-CD25 antibody, an anti-CD30 antibody, an anti-CD33 antibody, an anti-CD37 antibody, an anti-CD56 antibody, an anti-CD70 antibody, an anti-CD98 antibody, an anti-B7-H3 antibody, an anti-TROP2 antibody, an anti-CEA antibody, an anti-Cripto antibody, an anti-EphA2 antibody, an anti-FGFR2 antibody, an anti-G250 antibody, an anti-MUC1 antibody, an anti-GPNMB antibody, an anti-Integrin antibody, an antibody PSMA antibody, an anti-Tenascin-C antibody, an anti-SLC44A4 antibody, an anti-Mesothelin antibody, an anti-EGFR antibody, an anti-5T4 antibody, an anti-LRRC15 antibody, an anti-DR5 antibody, an anti-CDH3 antibody, an anti-PDPN antibody, or an anti-CD123 antibody.

[38] The method according to any one of [34] to [37], wherein the antibody specifically binds to CLDN6 and/or CLDN9.

[39] The method according to [38], the antibody comprising a heavy chain comprising CDRH1, CDRH2, and CDRH3 and a light chain comprising CDRL1, CDRL2, and CDRL3 as described in any one of the following (a) and (b):

(a) CDRH1 consisting of an amino acid sequence represented by SEQ ID NO: 9, CDRH2 consisting of an amino acid sequence represented by SEQ ID NO: 10, and CDRH3 consisting of an amino acid sequence represented by SEQ ID NO: 11, and CDRL1 consisting of an amino acid sequence represented by SEQ ID NO:

5, CDRL2 consisting of an amino acid sequence represented by SEQ ID NO: 6, and CDRL3 consisting of an amino acid sequence represented by SEQ ID NO: 7 or an amino acid sequence having one or two amino acid substitutions in the amino acid sequence represented by SEQ ID NO: 7; and (b) CDRH1 consisting of an amino acid sequence represented by SEQ ID NO: 15, CDRH2 consisting of an amino acid sequence represented by SEQ ID NO: 16, and CDRH3 consisting of an amino acid sequence represented by SEQ ID NO: 17, and CDRL1 consisting of an amino acid sequence represented by SEQ ID NO: 12, CDRL2 consisting of an amino acid sequence represented by SEQ ID NO: 13, and CDRL3 consisting of an amino acid sequence represented by SEQ ID NO: 14.

[40] The method according to [39], wherein the antibody comprises a heavy chain comprising CDRH1, CDRH2, and CDRH3 and a light chain comprising CDRL1, CDRL2, and CDRL3 as described in any one of the following (a) and (b):

(a) CDRH1 consisting of an amino acid sequence represented by SEQ ID NO: 9, CDRH2 consisting of an amino acid sequence represented by SEQ ID NO: 10, and CDRH3 consisting of an amino acid sequence represented by SEQ ID NO: 11, and CDRL1 consisting of an amino acid sequence represented by SEQ ID NO: 5, CDRL2 consisting of an amino acid sequence represented by SEQ ID NO: 6, and CDRL3 consisting of an amino acid sequence represented by SEQ ID NO: 7 or an amino acid sequence represented by SEQ ID NO: 8; and (b) CDRH1 consisting of an amino acid sequence represented by SEQ ID NO: 15, CDRH2 consisting of an amino acid sequence represented by SEQ ID NO: 16, and CDRH3 consisting of an amino acid sequence represented by SEQ ID NO: 17, and CDRL1 consisting of an amino acid sequence represented by SEQ ID NO: 12, CDRL2 consisting of an amino acid sequence represented by SEQ ID NO: 13, and CDRL3 consisting of an amino acid sequence represented by SEQ ID NO: 14.

[41] The method according to any one of [38] to [40], wherein the antibody comprises a heavy chain variable region and a light chain variable region as described in any one of the following (a) and (b):

(a) a heavy chain variable region consisting of an amino acid sequence represented by SEQ ID NO: 21 and a light chain variable region consisting of an amino acid sequence represented by SEQ ID NO: 19; and (b) a heavy chain variable region consisting of an amino acid sequence represented by SEQ ID NO: 25 and a light chain variable region consisting of an amino acid sequence represented by SEQ ID NO: 23.

[42] The method according to any one of [38] to [41], the antibody comprising a heavy chain variable region consisting of an amino acid sequence selected from the group consisting of the following (a) to (e) and a light chain variable region consisting of an amino acid sequence selected from the group consisting of the following (f) to (k):

(a) an amino acid sequence represented by SEQ ID NO: 54;

(b) an amino acid sequence represented by SEQ ID NO: 58;

(c) an amino acid sequence represented by SEQ ID NO: 62;

(d) an amino acid sequence with a homology of at least 95% or higher to a sequence of a framework region excluding CDR sequences in any of the sequences (a) to (c);

(e) an amino acid sequence having one to several amino acid deletions, substitutions, or additions in a sequence of a framework region excluding CDR sequences in any of the sequences (a) to (c);

(f) an amino acid sequence represented by SEQ ID NO: 38;

(g) an amino acid sequence represented by SEQ ID NO: 42;

(h) an amino acid sequence represented by SEQ ID NO: 46;

(i) an amino acid sequence represented by SEQ ID NO: 50;

(j) an amino acid sequence with a homology of at least 95% or higher to a sequence of a framework region excluding CDR sequences in any of the sequences (f) to (i); and (k) an amino acid sequence having one to several amino acid deletions, substitutions, or additions in a sequence of a framework region excluding CDR sequences in any of the sequences (f) to (i).

[43] The method according to [42], the antibody comprising a heavy chain variable region and a light chain variable region selected from the group consisting of the following (a) to (e):

(a) a heavy chain variable region consisting of an amino acid sequence represented by SEQ ID NO: 54 and a light chain variable region consisting of an amino acid sequence represented by SEQ ID NO: 38;

(b) a heavy chain variable region consisting of an amino acid sequence represented by SEQ ID NO: 58 and a light chain variable region consisting of an amino acid sequence represented by SEQ ID NO: 42;

(c) a heavy chain variable region consisting of an amino acid sequence represented by SEQ ID NO: 54 and a light chain variable region consisting of an amino acid sequence represented by SEQ ID NO: 46;

(d) a heavy chain variable region consisting of an amino acid sequence represented by SEQ ID NO: 58 and a light chain variable region consisting of a light chain variable region consisting of an amino acid sequence represented by SEQ ID NO: 50; and (e) a heavy chain variable region consisting of an amino acid sequence represented by SEQ ID NO: 62 and a light chain variable region consisting of an amino acid sequence represented by SEQ ID NO: 46.

[44] The method according to any one of [38] to [43], wherein the antibody is a chimeric antibody.

[45] The method according to any one of [38] to [43], wherein the antibody is a humanized antibody.

[46] The method according to any one of [38] to [45], wherein the antibody comprises a heavy chain constant region of human IgG1, human IgG2, or human IgG4.

[47] The method according to [45] or [46], comprising a heavy chain and a light chain selected from the group consisting of the following (a) to (e):

(a) a heavy chain consisting of an amino acid sequence consisting of amino acid residues 20 to 471 of SEQ ID NO: 52 and a light chain consisting of an amino acid sequence consisting of amino acid residues 21 to 234 of SEQ ID NO: 36;

(b) a heavy chain consisting of an amino acid sequence consisting of amino acid residues 20 to 471 of SEQ ID NO: 56 and a light chain consisting of an amino acid sequence consisting of amino acid residues 21 to 234 of SEQ ID NO: 40;

(c) a heavy chain consisting of an amino acid sequence consisting of amino acid residues 20 to 471 of SEQ ID NO: 52 and a light chain consisting of an amino acid sequence consisting of amino acid residues 21 to 234 of SEQ ID NO: 44;

(d) a heavy chain consisting of an amino acid sequence consisting of amino acid residues 20 to 471 of SEQ ID NO: 56 and a light chain consisting of an amino acid sequence consisting of amino acid residues 21 to 234 of SEQ ID NO: 48; and (e) a heavy chain consisting of an amino acid sequence consisting of amino acid residues 20 to 471 of SEQ ID NO: 60 and a light chain consisting of an amino acid sequence consisting of amino acid residues 21 to 234 of SEQ ID NO: 44.

[48] The method according to [38], wherein the antibody competes with the antibody according to any one of [39] to [43] and [47] for binding to CLDN6 and/or CLDN9, or binds to a site of CLDN6 and/or CLDN9 recognizable to the antibody according to any one of [39] to [43] and [47].

[49] The method according to any one of [34] to [37], wherein the antibody specifically binds to HER2.

[50] The method according to [49], having activities or activity of antibody-dependent cellular cytotoxicity (ADCC) and/or complement-dependent cytotoxicity (CDC).

[51] The method according to [49], wherein the heavy chain constant region of the antibody is a heavy chain constant region of human IgG1, and comprises a mutation that causes lowering of activities or activity of ADCC and/or CDC.

[52] The method according to [51], wherein the heavy chain constant region of the antibody is a heavy chain constant region of human IgG1, and leucine at the 234- and 235-positions specified by EU Index numbering in the heavy chain constant region is substituted with alanine.

[53] The method according to [49] or [50], wherein the antibody is an antibody comprising a heavy chain consisting of an amino acid sequence represented by SEQ ID NO: 65 and a light chain consisting of an amino acid sequence represented by SEQ ID NO: 64.

[54] The method according to any one of [49], [51], and [52], wherein the antibody is an antibody comprising a heavy chain variable region consisting of an amino acid sequence consisting of amino acid residues 20 to 139 of SEQ ID NO: 75 and a light chain variable region consisting of an amino acid sequence consisting of amino acid residues 21 to 127 of SEQ ID NO: 73.

[55] The method according to any one of [49], [51], [52], and [54], wherein the antibody is an antibody comprising a heavy chain consisting of an amino acid sequence consisting of amino acid residues 20 to 469 of SEQ ID NO: 75 and a light chain consisting of an amino acid sequence consisting of amino acid residues 21 to 234 of SEQ ID NO: 73.

[56] The method according to any one of [49], [51], [52], and [54], wherein the antibody is an antibody comprising a heavy chain consisting of an amino acid sequence consisting of amino acid residues 20 to 469 of SEQ ID NO: 77 and a light chain consisting of an amino acid sequence consisting of amino acid residues 21 to 234 of SEQ ID NO: 76.

[57] The method according to any one of [38] to [56], wherein the antibody comprises one or two or more modifications selected from the group consisting of N-linked glycosylation, O-linked glycosylation, N-terminal processing, C-terminal processing, deamidation, isomerization of aspartic acid, oxidation of methionine, addition of a methionine residue at an N terminus, amidation of a proline residue, and deletion of one or two amino acid residues at the carboxyl terminus of a heavy chain.

[58] The method according to [57], wherein one or several amino acid residues are deleted at the carboxyl terminus of a heavy chain of the antibody.

[59] The method according to [57] or [58], wherein one amino acid residue is deleted at the carboxyl terminus of each of the two heavy chains of the antibody.

[60] The method according to any one of [57] to [59], wherein a proline residue at the carboxyl terminus of a heavy chain of the antibody is further amidated.

[61] The method according to any one of [34] to [60], wherein the N297 glycan is N297-(Fuc)MSG1.

[62] The method according to any one of [34] to [61], wherein $m^1$ is an integer of 1.

[63] The method according to any one of [34] to [62], wherein the average number of conjugated drug molecules per antibody molecule in the antibody-pyrrolobenzodiazepine derivative conjugate is 1 to 3 or 3 to 5.

[64] The method according to any one of [34] to [63], wherein the PARP inhibitor is olaparib, rucaparib, niraparib, or talazoparib, or a pharmacologically acceptable salt thereof.

[65] The method according to any one of [34] to [64], for treatment of at least one cancer selected from the group consisting of lung cancer (e.g., non-small cell lung cancer, small cell lung cancer), kidney cancer, urothelial cancer, colorectal cancer, prostate cancer, glioblastoma multiforme, ovarian cancer (e.g., surface epithelial tumor, stromal tumor, germ cell tumor), pancreatic cancer, breast cancer, melanoma, liver cancer, bladder cancer, gastric cancer, esophageal cancer, endometrial cancer, testicular cancer (seminoma, non-seminoma), uterine cervix cancer, placental choriocarcinoma, brain tumor, and head-and-neck cancer, and metastatic forms of them.

[66] A pharmaceutical composition comprising the antibody-pyrrolobenzodiazepine derivative conjugate according to [1] for use in combination with a PARP inhibitor.

[67] A pharmaceutical composition comprising a PARP inhibitor, wherein by using in combination with the antibody-pyrrolobenzodiazepine derivative conjugate according to

[1], the pharmaceutical composition elevates the effect of the conjugate.

[68] A pharmaceutical composition comprising a PARP inhibitor for use in combination with the antibody-pyrrolobenzodiazepine derivative conjugate according to

[1].

[69] A pharmaceutical composition comprising the antibody-pyrrolobenzodiazepine derivative conjugate according to [1], wherein by using in combination with a PARP inhibitor, the pharmaceutical composition elevates the effect of the PARP inhibitor.

[70] The pharmaceutical composition according to [1], wherein the pyrrolobenzodiazepine derivative does not form any crosslink in minor grooves of DNA.

[71] The pharmaceutical composition according to [1], wherein the cancer is insensitive to the PARP inhibitor.

[72] The pharmaceutical composition according to [1], wherein the cancer is independent of a homologous recombination (HR)-dependent DNA double-strand break (DSB) repair pathway.

[73] The method according to any one of [34] to [64], wherein the antibody-drug conjugate and PARP inhibitor according to [1] are individually contained as an active ingredient in separate formulations and administered simultaneously or at different times.

Advantageous Effects of Invention

The present invention is useful as a method for treating cancer and/or an anti-cancer agent.

BRIEF DESCRIPTION OF DRAWINGS

FIG. 1 shows a diagram representing tumor growth-suppressing effect for a single administration group with the anti-HER2 antibody-drug conjugate ADC2, that for a single administration group with talazoparib, and that for a combined administration group with the HER2 antibody-drug conjugate ADC2 and talazoparib in mice having subcutaneously transplanted CFPAC-1 cells, a human pancreatic cancer cell line.

FIG. 2 shows a diagram representing tumor growth-suppressing effect for a single administration group with the anti-HER2 antibody-drug conjugate ADC2, that for a single administration group with olaparib, and that for a combined administration group with the HER2 antibody-drug conjugate ADC2 and olaparib in mice having subcutaneously transplanted JIMT-1 cells, a human breast cancer cell line.

FIG. 3 shows a diagram representing tumor growth-suppressing effect for a single administration group with the anti-HER2 antibody-drug conjugate ADC2, that for a single administration group with talazoparib, and that for a combined administration group with the anti-HER2 antibody-drug conjugate ADC2 and talazoparib in mice having subcutaneously transplanted JIMT-1 cells, a human breast cancer cell line.

FIG. 4 shows a diagram representing tumor growth-suppressing effect for a single administration group with the anti-TROP2 antibody-drug conjugate ADC3, that for a single administration group with olaparib, and that for a combined administration group with the anti-TROP2 antibody-drug conjugate ADC3 and olaparib in mice having subcutaneously transplanted FaDu, a human pharyngeal cancer cell line.

FIG. 5 shows a diagram representing tumor growth-suppressing effect for a single administration group with the anti-TROP2 antibody-drug conjugate ADC3, that for a single administration group with talazoparib, and that for a combined administration group with the anti-TROP2 antibody-drug conjugate ADC3 and talazoparib in mice having subcutaneously transplanted FaDu, a human pharyngeal cancer cell line.

FIG. 6 shows the full-length amino acid sequence of human CLDN6 (SEQ ID NO: 1) and the nucleotide sequence of full-length cDNA for human CLDN6 (SEQ ID NO: 2).

FIG. 7 shows the full-length amino acid sequence of human CLDN9 (SEQ ID NO: 3) and the nucleotide sequence of full-length cDNA for human CLDN9 (SEQ ID NO: 4).

FIG. 8 shows the amino acid sequences of CDRL1 to 3 of a B1 antibody light chain (SEQ ID NOs: 5 to 7).

FIG. 9 shows the amino acid sequence of CDRL3 of the humanized B1 antibody light chain L4 (SEQ ID NO: 8).

FIG. 10 shows the amino acid sequences of CDRH1 to 3 of a B1 antibody heavy chain (SEQ ID NOs: 9 to 11).

FIG. 11 shows the amino acid sequences of CDRL1 to 3 of a C7 antibody light chain (SEQ ID NOs: 12 to 14).

FIG. 12 shows the amino acid sequences of CDRH1 to 3 of a C7 antibody heavy chain (SEQ ID NOs: 15 to 17).

FIG. 13 shows the nucleotide sequence of cDNA encoding the variable region of a B1 antibody light chain (SEQ ID NO: 18) and the amino acid sequence of the variable region of a B1 antibody light chain (SEQ ID NO: 19). Each underline in the amino acid sequence indicates a CDR sequence.

FIG. 14 shows the nucleotide sequence of cDNA encoding the variable region of a B1 antibody heavy chain (SEQ ID NO: 20) and the amino acid sequence of the variable region of a B1 antibody heavy chain (SEQ ID NO: 21). Each underline in the amino acid sequence indicates a CDR sequence.

FIG. 15 shows the nucleotide sequence of cDNA encoding the variable region of a C7 antibody light chain (SEQ ID NO: 22) and the amino acid sequence of the variable region of a C7 antibody light chain (SEQ ID NO: 23). Each underline in the amino acid sequence indicates a CDR sequence.

FIG. 16 shows the nucleotide sequence of cDNA encoding the variable region of a C7 antibody heavy chain (SEQ ID NO: 24) and the amino acid sequence of the variable region of a C7 antibody heavy chain (SEQ ID NO: 25). Each underline in the amino acid sequence indicates a CDR sequence.

FIG. 17 shows the amino acid sequence of a chB1 light chain (SEQ ID NO: 28) and a DNA fragment including a DNA sequence encoding the amino acid sequence of a chB1 light chain (SEQ ID NO: 29). Each underline in the amino acid sequence indicates a CDR sequence.

FIG. 18 shows the amino acid sequence of the variable region of a chB1 light chain (SEQ ID NO: 30) and the nucleotide sequence encoding a chB1 light chain variable region (SEQ ID NO: 31). Each underline in the amino acid sequence indicates a CDR sequence.

FIG. 19 shows the amino acid sequence of a chB1 heavy chain (SEQ ID NO: 32) and the nucleotide sequence encoding a chB1 heavy chain (SEQ ID NO: 33). Each underline in the amino acid sequence indicates a CDR sequence.

FIG. 20 shows the amino acid sequence of the variable region of a chB1 heavy chain (SEQ ID NO: 34) and the nucleotide sequence encoding a variable region of a chB1 heavy chain (SEQ ID NO: 35). Each underline in the amino acid sequence indicates a CDR sequence.

FIG. 21 shows the amino acid sequence of the humanized antibody light chain hL1 (SEQ ID NO: 36) and the nucleotide sequence encoding the humanized antibody light chain hL1 (SEQ ID NO: 37). Each underline in the amino acid sequence indicates a CDR sequence.

FIG. 22 shows the amino acid sequence of the variable region of the humanized antibody light chain hL1 (SEQ ID NO: 38) and the nucleotide sequence encoding the variable region of the humanized antibody light chain hL1 (SEQ ID NO: 39). Each underline in the amino acid sequence indicates a CDR sequence.

FIG. 23 shows the amino acid sequence of the humanized antibody light chain hL2 (SEQ ID NO: 40) and the nucleotide sequence encoding the humanized antibody light chain hL2 (SEQ ID NO: 41). Each underline in the amino acid sequence indicates a CDR sequence.

FIG. 24 shows the amino acid sequence of the variable region of the humanized antibody light chain hL2 (SEQ ID NO: 42) and the nucleotide sequence encoding the variable region of the humanized antibody light chain hL2 (SEQ ID NO: 43).

FIG. 25 shows the amino acid sequence of the humanized antibody light chain hL3 (SEQ ID NO: 44) and the nucleotide sequence encoding the humanized antibody light chain hL3 (SEQ ID NO: 45). Each underline in the amino acid sequence indicates a CDR sequence.

FIG. 26 shows the amino acid sequence of the variable region of the humanized antibody light chain hL3 (SEQ ID NO: 46) and the nucleotide sequence encoding the variable region of the humanized antibody light chain hL3 (SEQ ID NO: 47) . . . . Each underline in the amino acid sequence indicates a CDR sequence.

FIG. 27 shows the amino acid sequence of the humanized antibody light chain hL4 (SEQ ID NO: 48) and the nucleotide sequence encoding the humanized antibody light chain hL4 (SEQ ID NO: 49). Each underline in the amino acid sequence indicates a CDR sequence.

FIG. 28 shows the amino acid sequence of the variable region of the humanized antibody light chain hL4 (SEQ ID NO: 50) and the nucleotide sequence encoding the variable region of the humanized antibody light chain hL4 (SEQ ID NO: 51). Each underline in the amino acid sequence indicates a CDR sequence.

FIG. 29 shows the amino acid sequence of the humanized antibody heavy chain hH1 (SEQ ID NO: 52) and the nucleotide sequence encoding the humanized antibody heavy chain hH1 (SEQ ID NO: 53). Each underline in the amino acid sequence indicates a CDR sequence.

FIG. 30 shows the amino acid sequence of the variable region of the humanized antibody heavy chain hH1 (SEQ ID NO: 54) and the nucleotide sequence encoding the variable region of the humanized antibody heavy chain hH1 (SEQ ID NO: 55). Each underline in the amino acid sequence indicates a CDR sequence.

FIG. 31 shows the amino acid sequence of the humanized antibody heavy chain hH2 (SEQ ID NO: 56) and the nucleotide sequence encoding the humanized antibody heavy chain hH2 (SEQ ID NO: 57). Each underline in the amino acid sequence indicates a CDR sequence.

FIG. 32 shows the amino acid sequence of the variable region of the humanized antibody heavy chain hH2 (SEQ ID NO: 58) and the nucleotide sequence encoding the variable region of the humanized antibody heavy chain hH2 (SEQ ID NO: 59).

FIG. 33 shows the amino acid sequence of the humanized antibody heavy chain hH3 (SEQ ID NO: 60) and the nucleotide sequence encoding the humanized antibody heavy chain hH3 (SEQ ID NO: 61). Each underline in the amino acid sequence indicates a CDR sequence.

FIG. 34 shows the amino acid sequence of the variable region of the humanized antibody heavy chain hH3 (SEQ ID NO: 62) and the nucleotide sequence encoding the variable region of the humanized antibody heavy chain hH3 (SEQ ID NO: 63). Each underline in the amino acid sequence indicates a CDR sequence.

FIG. 35 shows the binding abilities of a B1 antibody and a C7 antibody to human CLDN6 and the family molecules CLDN3, CLDN4, and CLDN9 measured by flow cytometry.

FIG. 36 shows the antibody internalization activities of a B1 antibody and C7 antibody measured by Mab-ZAP.

FIG. 37 shows the binding abilities of the humanized anti-CLDN6 antibodies H1L1, H2L2, H1L3, H2L4, and H3L3 to CLDN6 and the family molecules measured by flow cytometry.

FIG. 38 shows the amino acid sequence of the trastuzumab light chain (SEQ ID NO: 64) and the amino acid sequence of the trastuzumab heavy chain (SEQ ID NO: 65).

FIG. 39 shows the amino acid sequence of a light chain of a trastuzumab variant (SEQ ID NO: 73) and the amino acid sequence of a heavy chain of a trastuzumab variant (SEQ ID NO: 75).

FIG. 40 shows comparison of the amino acid sequences of chB1_H, which is a heavy chain of the chimerized human anti-CLDN6 antibody chB1, and the humanized antibody heavy chains hH1, hH2, and hH3. The symbol "." indicates an amino acid residue identical to the corresponding amino acid residue of chB1_H, and each position with a symbol of an amino acid residue indicates a substituted amino acid residue.

FIG. 41 shows comparison of the amino acid sequences of chB1_L, which is a light chain of the chimerized human anti-CLDN6 antibody chB1, and the humanized antibody light chains hL1, hL2, hL3, and hL4. The symbol "." indicates an amino acid residue identical to the corresponding amino acid residue of chB1_L, and each position with symbol of an amino acid residue indicates a substituted amino acid residue.

FIG. 42 shows a diagram representing tumor growth-suppressing effect for a single administration group with the anti-CLDN6 antibody-drug conjugate ADC1, that for a single administration group with niraparib, and that for a combined administration group with the anti-CLDN6 antibody-drug conjugate ADC1 and niraparib in mice having subcutaneously transplanted OV-90, a human ovarian cancer cell line.

FIG. 43 shows Formula 52, which is a preparation of glycan remodelling antibodies as represented by Example 12: Sugar chain remodeling 1 (T-SG).

FIG. 44 shows Formula 53 as represented by Example 13: Sugar chain remodeling 2 (T-MSG).

FIG. 45 shows Formula 54 as represented by Example 14: Sugar chain remodeling 3 (T-MSG1).

FIG. 46 shows Formula 55 as represented by Example 15: Sugar chain remodeling 4 (CLDN6-MSG1 (H1L1)).

FIG. 47 shows Formula 56, which is a Synthesis of ADC, as represented by Examples 19 to 23 show preparation methods for ADC1 to ADC6. Each of the R groups in the reaction formulas in Examples 19 to 23 is represented by Formula 56.

FIG. 48 shows Formula 57 as represented by Example 19: ADC1.

FIG. 49 shows Formula 58 as represented by Example 20: ADC2.

FIG. 50 shows Formula 59 as represented by Example 21: ADC3.

FIG. 51 shows Formula 60 as represented by Example 22: ADC4.

FIG. 52 shows Formula 61 as represented by Example 23: ADC5.

DESCRIPTION OF EMBODIMENTS

1. Antibody-Drug Conjugate

The antibody-drug conjugate to be used in the present invention is an antitumor drug having an antitumor compound conjugated via a linker moiety to an antibody capable of recognizing an antigen expressed on tumor cells or binding to the antigen.

The conjugate of the present invention is preferably represented by the following formula:

[Formula 16]

$$Ab-\left[(N297\ glycan)-\left[L-D\right]_{m^1}\right]_2$$

wherein $m^1$ is an integer of 1 or 2 (preferably, 1), D represents a drug, L represents a linker linking the N297 glycan and D, Ab represents an antibody or a functional fragment of the antibody, and the N297 glycan represents a glycan bonding to the side chain of Asn297 of the antibody. The N297 glycan may be a remodeled glycan.

<Drug>

Drug D of the present invention is preferably an antitumor compound. The antitumor compound develops antitumor effect, when a part or the entire of the linker of the antibody-drug conjugate of the present invention is cleaved in a tumor cell and the antitumor compound moiety is released. Examples of drug D of the present invention may include, but are not limited to, a PBD derivative including a structure represented by the following formula:

[Formula 17]

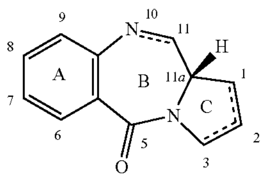

Examples of drug D of the present invention may include, but are not limited to, PBD derivatives that do not form any crosslink in minor grooves of DNA.

The drug in the antibody-drug conjugate of the present invention, that is, the PBD derivative is preferably any one selected from the following group:

[Formula 18]

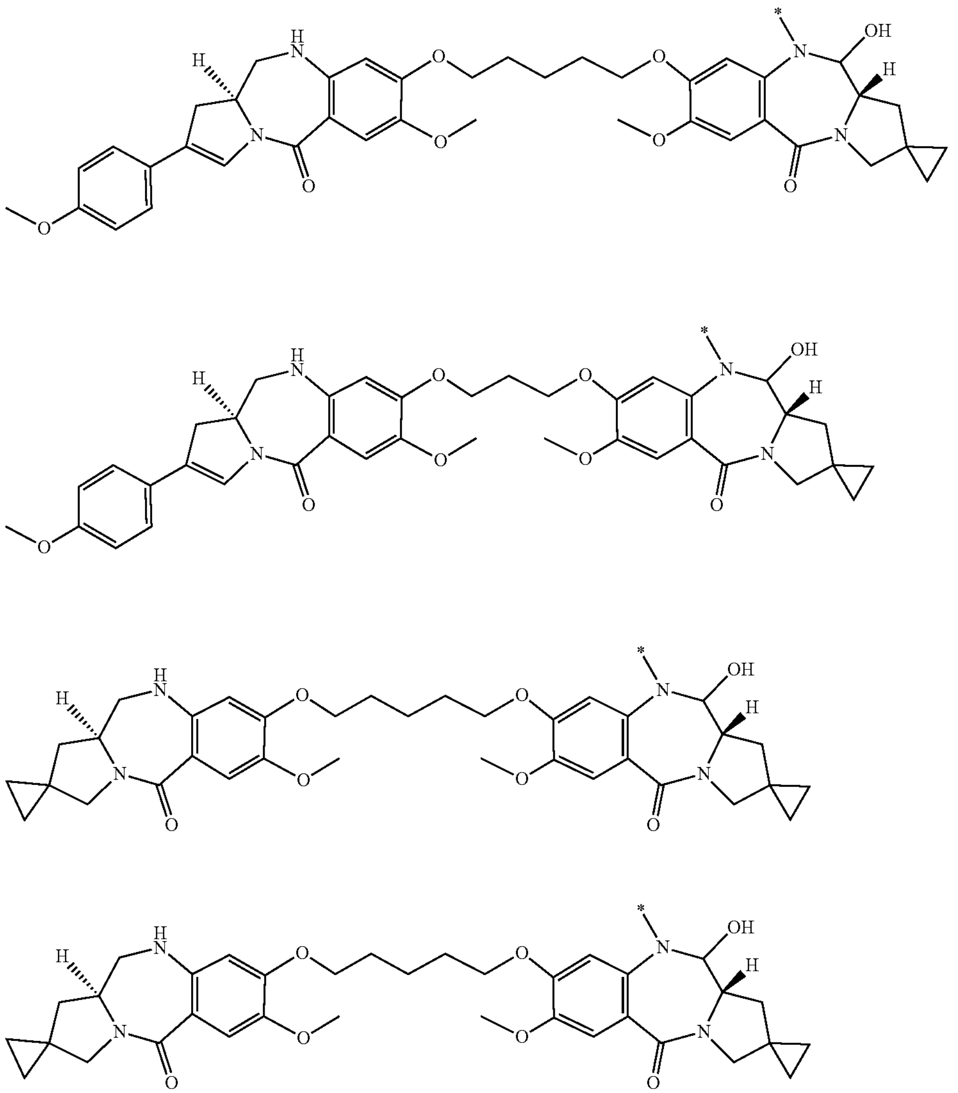

wherein the asterisk * represents bonding to L.

As shown in partial structures I(a) or I(b) below, the PBD derivative of the present invention has an asymmetric carbon at the 11'-position, and thus there exist optical isomers.

[Formula 19]

I(a)

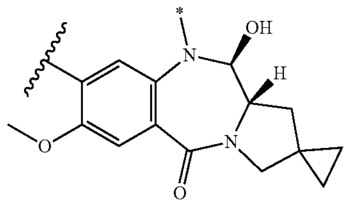

I(b)

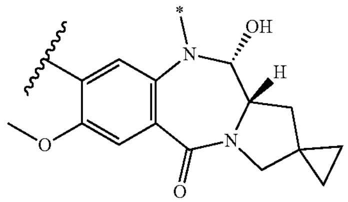

Accordingly, the PBD derivative of the present invention in each case includes the optical isomers and mixtures of the optical isomers at any ratio. The absolute steric configuration at the 11'-position of the PBD derivative can be determined through X-ray crystal structure analysis or NMR such as a Mosher method for its crystalline product or intermediate, or a derivative thereof. Then, the absolute steric configuration may be determined by using a crystalline product or intermediate derivatized with a reagent having an asymmetric center whose steric configuration is known. As desired, stereoisomers of the synthesized compound according to the present invention may be obtained by isolating with a common optical resolution method or separation method.

There may exist stereoisomers, optical isomers due to an asymmetric carbon atom, geometric isomers, tautomers, or optical isomers such as d-forms, I-forms and atropisomers for the antibody-drug conjugate of the present invention, and a free drug or production intermediate of the antibody-drug conjugate, and these isomers, optical isomers, and mixtures of them are all included in the present invention.

I(a) is preferred as the partial structure of the PBD derivative of the present invention. Preferably, the partial structure of the PBD derivative of the present invention is any one selected from the following group:

[Formula 20]

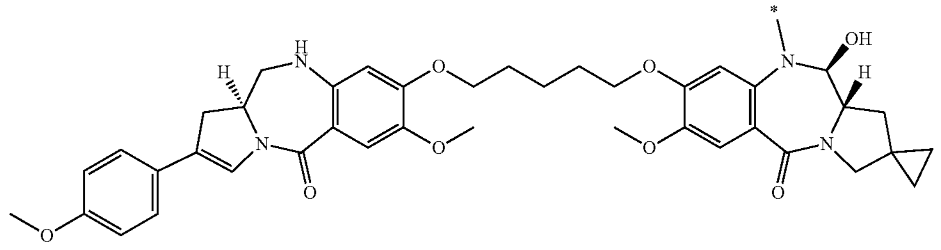

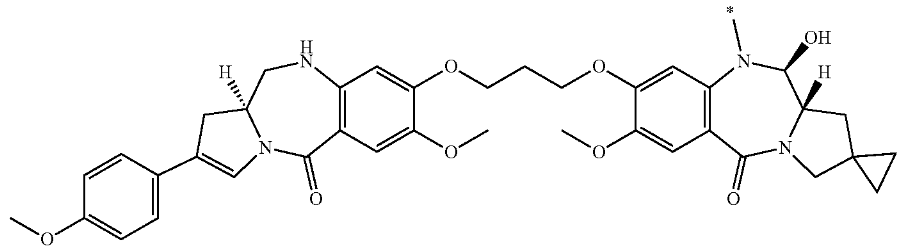

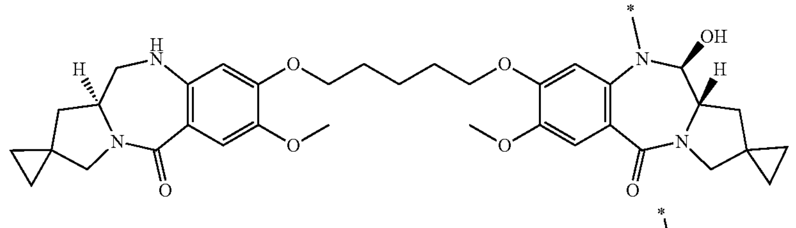

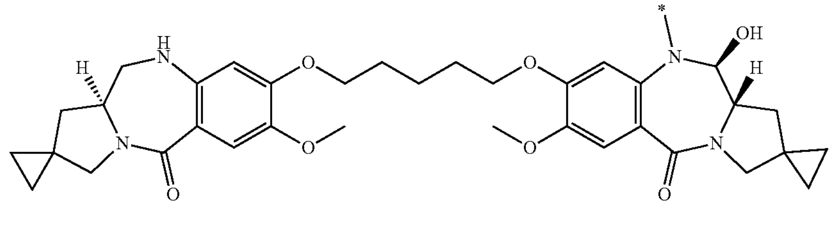

wherein the asterisk represents bonding to L.

<Linker Structure>

Linker L of the present invention is a linker linking the N297 glycan and D.

Linker L is represented by the following formula:

$$\text{-Lb-La-Lp-NH—B—CH}_2\text{—O(C═O)—*}$$

The asterisk * represents bonding to the nitrogen atom at the N10'-position of drug D, Lb represents a spacer which connects La to a N297 glycan or remodeled N297 glycan.

B represents a phenyl group or a heteroaryl group, and is preferably a 1,4-phenyl group, a 2,5-pyridyl group, a 3,6-pyridyl group, a 2,5-pyrimidyl group, or a 2,5-thienyl group, and more preferably a 1,4-phenyl group.

Lp represents a linker consisting of an amino acid sequence cleavable in vivo or in a target cell. Lp is, for example, cleaved by the action of an enzyme such as esterase and peptidase.

Lp is a peptide residue composed of two to seven (preferably, two to four) amino acids. That is, Lp is composed of an oligopeptide residue in which two to seven amino acids are connected via peptide bonding.

Lp is bound at the N terminal to a carbonyl group of La in Lb-La—, and forms at the C terminal an amide bond with the amino group (—NH—) of the part —NH—B—$CH_2$—O(C═O)— of the linker. The bond between the C terminal of Lp and —NH— is cleaved by the enzyme such as esterase.

The amino acids constituting Lp are not limited to particular amino acids, and, for example, are L- or D-amino acids, and preferably L-amino acids. The amino acids may be not only α-amino acids, but may include an amino acid with structure, for example, of β-alanine, ε-aminocaproic acid, or γ-aminobutyric acid, and may further include a non-natural amino acid such as an N-methylated amino acid.

The amino acid sequence of Lp is not limited to a particular amino acid sequence, and examples of amino acids that constitute Lp may include, but are not limited to, glycine (Gly; G), valine (Val; V), alanine (Ala; A), phenylalanine (Phe; F), glutamic acid (Glu; E), isoleucine (Ile; I), proline (Pro; P), citrulline (Cit), leucine (Leu; L), serine (Ser; S), lysine (Lys; K), and aspartic acid (Asp; D). Preferred among them are glycine (Gly; G), valine (Val; V), alanine (Ala; A), and citrulline (Cit).

Any of these amino acids may appear multiple times, and Lp has an amino acid sequence including arbitrarily selected amino acids. Drug release pattern may be controlled via amino acid type.

Specific examples of linker Lp may include, but are not limited to, -GGVA-, -GG-(D-)VA-, -VA-, -GGFG-, -GGPI-, -GGVCit-, -GGVK-, -GG(D-)PI-, -GGPL-, -EGGVA, -PI-, -GGF-, DGGF-, (D-)D-GGF-, -EGGF-, -SGGF-, -KGGF-, -DGGFG-, -GGFGG-, -DDGGFG-, -KDGGFG-, and -GGFGGGF-.

Here, "(D-)V" indicates D-valine, "(D)-P" indicates D-proline, and "(D-)D" indicates D-aspartic acid.

Linker Lp is preferably any of the following:

-GGVA-, -GG-(D-)VA-, -VA-, -GGFG-, -GGPI-, -GGVCit-, -GGVK-, -GG(D-)PI-, and -GGPL-.

Linker Lp is more preferably any of the following:

-GGVA-, -GGVCit-, and -VA-.

La represents any one selected from the following group:

—C(═O)—$(CH_2CH_2)n^2$-C(═O)—, —C(═O)—$(CH_2CH_2)n^2$-C(═O)—NH—$(CH_2CH_2)n^3$-C(═O)—, —C(═O)—$(CH_2CH_2)n^2$-C(═O)—NH—$(CH_2CH_2O)n^3$-$CH_2$—C(═O)—, —C(═O)—$(CH_2CH_2)n^2$-NH—C(═O)—$(CH_2CH_2O)n^3$-$CH_2CH_2$—C(═O)—, —$(CH_2)n^4$-O—C(═O)— wherein, $n^2$ represents an integer of 1 to 3 (preferably, 1 or 2), $n^3$ represents an integer of 1 to 5 (preferably, an integer of 2 to 4, more preferably, 2 or 4), and $n^4$ represents an integer of 0 to 2 (preferably, 0 or 1).

La preferably represents any one selected from the following group:

—C(═O)—$CH_2CH_2$—C(═O)—, —C(═O)—$(CH_2CH_2)_2$—C(═O)—,

—C(═O)—$CH_2CH_2$—C(═O)—NH—$(CH_2CH_2)$ 2-C(═O)—

—C(═O)—$CH_2CH_2$—C(═O)—NH—$(CH_2CH_2O)_2$—$CH_2$—C(═O)—,

—C(═O)—$CH_2CH_2$—NH—C(═O)—$(CH_2CH_2O)_4$—$CH_2CH_2$—C(═O)—,

—$CH_2$—OC(═O)—, and —OC(═O)—, and

La is more preferably-C(═O)—$CH_2CH_2$—C(═O)— or —C(═O)—$(CH_2CH_2)_2$—C(═O)—.

Spacer Lb is not limited to a particular spacer, and examples thereof may include, but are not limited to, a spacer represented by the following formulas.

(Lb-1)

[Formula 21]

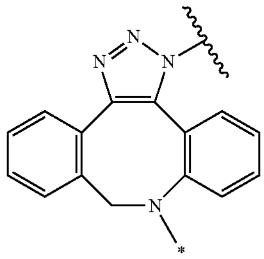

or

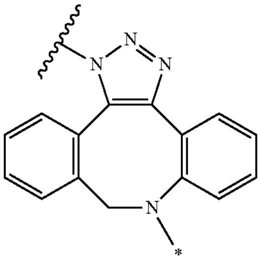

(Lb-2)

[Formula 22]

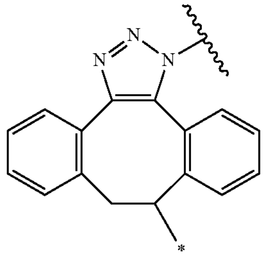

or

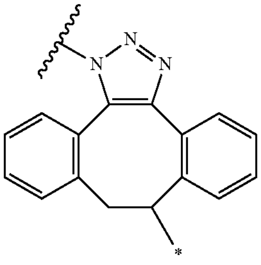

-continued (Lb-3)

[Formula 23]

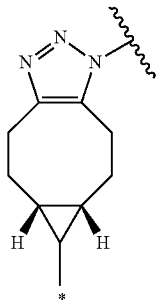

or

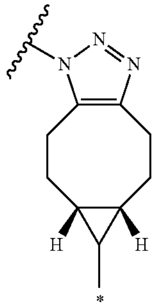

In the structural formulas for Lb shown above, each asterisk * represents bonding to —(C═O) or —$(CH_2)n^4$ at the left end of La, and each wavy line represents bonding to a N297 glycan or remodeled N297 glycan of Ab.

In each structural formula for Lb (Lb-1, Lb-2, or Lb-3) shown above, the triazole ring site formed through click reaction of an azide group and DBCO provides structures of geometric isomers, and one Lb exist as any one of the two structures or as a mixture of both of them. That is, there exist two or four ($m^1$ is 1 or 2) "-L-D" moieties per molecule of the antibody-drug conjugate of the present invention, and either one of the two structures exists or both of them coexist as Lb (Lb-1, Lb-2, or Lb-3) in L of each of the two or four "-L-D" moieties.

L is preferably represented by -Lb-La-Lp-NH—B—$CH_2$—O(C═O)—*, wherein

B is a 1,4-phenyl group,

Lp represents any one selected from the following group: -GGVA-, -GG-(D-)VA-, -VA-, -GGFG-, -GGPI-, -GGVCit-, -GGVK-, and -GGPL-, La represents any one selected from the following group: —C(═O)—$CH_2CH_2$—C(═O)—, —C(═O)—$(CH_2CH_2)_2$—C(═O)—,

—C(═O)—$CH_2CH_2$—C(═O)—NH—$(CH_2CH_2)_2$—C(═O)—,

—C(═O)—$CH_2CH_2$—C(═O)—NH—$(CH_2CH_2O)_2$—$CH_2$—C(═O)—,

—C(═O)—$CH_2CH_2$—NH—C(═O)—$(CH_2CH_2O)_4$—$CH_2CH_2$—C(═O)—, —$CH_2$—OC(═O)—, —OC(═O)—, and Lb represents any of the structural formulas above for Lb.

L is more preferably any one selected from the following group:

—$Z^1$—C(═O)—$CH_2CH_2$—C(═O)-GGVA-NH—B—$CH_2$—OC(═O)—,

—$Z^1$—C(═O)—$CH_2CH_2$—C(═O)-GG-(D-)VA-NH—B—$CH_2$—OC(═O)—,

—$Z^1$—C(═O)—$CH_2CH_2$—C(═O)—VA-NH—B—$CH_2$—OC(═O)—,

—$Z^1$—C(═O)—$(CH_2CH_2)_2$—C(═O)—VA-NH—B—$CH_2$—OC(═O)—,

—$Z^1$—C(═O)—$CH_2CH_2$—C(═O)-GGPI-NH—B—$CH_2$—OC(═O)—,

—$Z^1$—C(═O)—$CH_2CH_2$—C(═O)-GGFG-NH—B—$CH_2$—OC(═O)—,

—$Z^1$—C(═O)—$CH_2CH_2$—C(═O)-GGVCit-NH—B—$CH_2$—OC(═O)—,

—$Z^1$—C(═O)—$CH_2CH_2$—C(═O)-GGVK-NH—B—$CH_2$—OC(—O)—,

—$Z^1$—C(═O)—$CH_2CH_2$—C(═O)-GGPL-NH—B—$CH_2$—OC(═O)—,

—$Z^1$—C(═O)—$CH_2CH_2$—C(═O)—NH—$(CH_2CH_2)_2$—C(═O)—VA-NH—B—$CH_2$—OC(═O)—,

—$Z^1$—C(═O)—$CH_2CH_2$—C(═O)—NH—$(CH_2CH_2O)_2$—$CH_2$—C(═O)-VA-NH—B—$CH_2$—OC(═O)—,

—$Z^1$—C(═O)—$CH_2CH_2$—NH—C(═O)—$(CH_2CH_2O)_4$—$CH_2CH_2$—C(═O)-VA-NH—B—$CH_2$—OC(═O)—,

—$Z^2$—OC(═O)-GGVA-NH—B—$CH_2$—OC(═O)—, and —$Z^3$—$CH_2$—OC(═O)-GGVA-NH—B—$CH_2$—OC(═O)— wherein $Z^1$ represents the following structural formula as described for Lb:

[Formula 24]

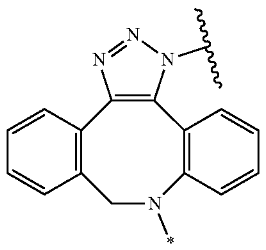

or

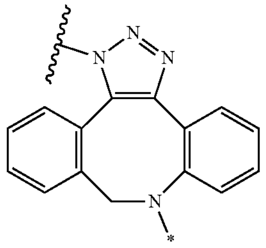

$Z^2$ represents the following structural formula as described for Lb:

[Formula 25]

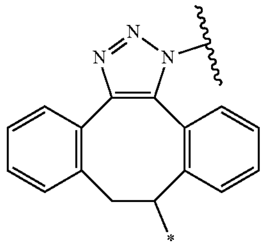

or

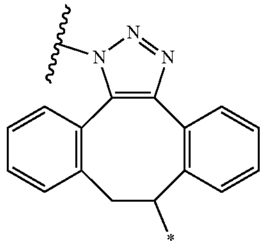

$Z^3$ represents the following structural formula as described for Lb:

[Formula 26]

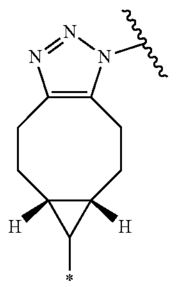
or
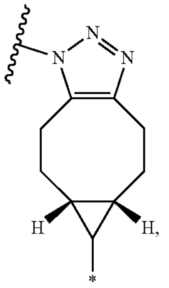

and B is a 1,4-phenyl group.

L is most preferably any of the following:

$—Z^1—C(=O)—CH_2CH_2—C(=O)$-GGVA-NH—B—$CH_2—OC(=O)—$, $—Z^1—C(=O)—CH_2CH_2—C(=O)$—VA-NH—B—$CH_2—OC(=O)—$, $—Z^1—C(=O)—(CH_2CH_2)_2—C(=O)$—VA-NH—B—$CH_2—OC(=O)—$, $—Z^1—C(=O)—CH_2CH_2$-ç (=O)-GGVCit-NH—B—$CH_2—OC(—O)—$, $—Z^1—C(=O)—CH_2CH_2—C(=O)$—NH—$(CH_2CH_2)_2—C(=O)$—VA-NH—B—$CH_2—OC(=O)—$, $—Z^1—C(=O)—CH_2CH_2—C(=O)$—NH—$(CH_2CH_2O)_2—CH_2—C(=O)$—VA-NH—B—$CH_2—OC(=O)—$, and $—Z^1—C(=O)—CH_2CH_2$—NH—$C(=O)—(CH_2CH_2O)_4—CH_2CH_2—C(=O)$—VA-NH—B—$CH_2—OC(=O)—$, wherein B is a 1,4-phenyl group, and $Z^1$ represents the following structural formula as described for Lb:

[Formula 27]

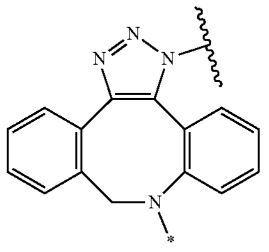
or
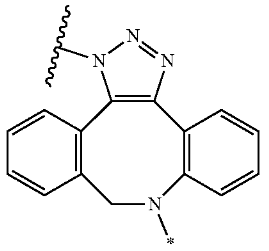

<Free Drug>

The free drug of the antibody-drug conjugate of the present invention is one selected from the following group:

[Formula 28]

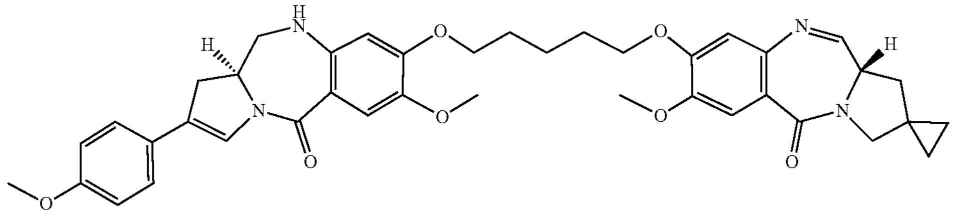

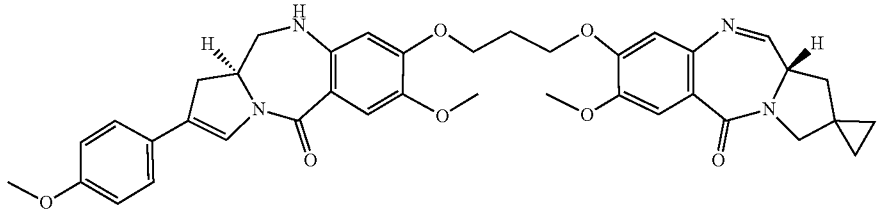

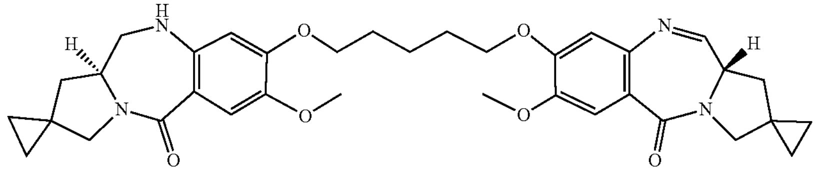

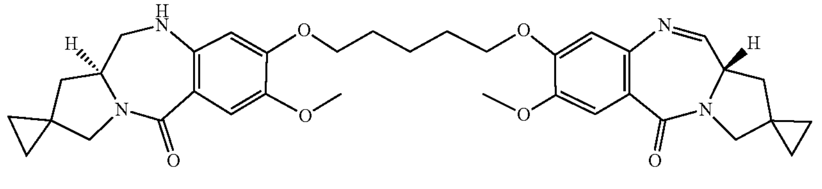

The free drug of the present invention is generated through a process in which the antibody-drug conjugate of the present invention migrates into tumor cells and the portion of linker L in the antibody-drug conjugate is then cleaved. This free drug was found to have anti-tumor cell effect.

<Antibody>

In the present invention, “cancer” and “tumor” are used for the same meaning.

In the present invention, a “gene” refers to nucleotides or a nucleotide sequence including a nucleotide sequence encoding amino acids of protein or a complementary strand thereof. The meaning of a “gene” encompasses, for example, a polynucleotide, an oligonucleotide, DNA, mRNA, cDNA, and RNA as a nucleotide sequence including a nucleotide sequence encoding amino acids of protein or a complementary strand thereof. Examples of the “CLDN6 gene” include DNA, mRNA, cDNA, and cRNA including a nucleotide sequence encoding the amino acid sequence of CLDN6 protein.

In the present invention, “nucleotides”, “polynucleotide”, and “nucleotide sequence” have the same meaning as that of “nucleic acids”, and the meaning of “nucleotides” and “nucleotide sequence” encompasses, for example, DNA, RNA, a probe, an oligonucleotide, a polynucleotide, and a primer.

In the present invention, “polypeptide”, “peptide”, and “protein” are used interchangeably.

In the present invention, “CLDN6” is used for the same meaning as CLDN6 protein.

In the present invention, “cells” include cells in an animal individual and cultured cells.

In the present invention, “cellular cytotoxic activity” refers to causing pathological change to cells in any way, which includes causing, not only direct traumas, but also all types of damage in the structure and function of cells such as cleavage of DNA, formation of a nucleotide dimer, cleavage of a chromosome, damage of the mitotic apparatus, and lowered activity of various enzymes.

In the present invention, a “functional fragment of an antibody” is also referred to as an “antigen-binding fragment of an antibody”, and means a partial fragment of an antibody with binding activity to an antigen, and examples thereof may include, but are not limited to, Fab, F(ab')2, Fv, scFv, diabodies, linear antibodies, and multispecific antibodies formed from antibody fragments. In addition, the meaning of an antigen-binding fragment of an antibody encompasses Fab', a monovalent fragment of a variable region of an antibody obtained by treating F(ab')2 under reducing conditions. However, there is no limitation to those molecules as long as the molecules have binding ability to an antigen. Those antigen-binding fragments include not only those obtained by treating a full-length molecule of an antibody protein with an appropriate enzyme, but also protein produced in an appropriate host cell by using a genetically engineered antibody gene.

The functional fragment of the present invention includes a functional fragment that has well conserved asparagine (Asn297) to be modified with an N-linked glycan in the IgG heavy chain Fc region and amino acids around Asn297, while retains binding activity to an antigen.

In the present invention, an “epitope” refers to a partial peptide or partial three-dimensional structure of an antigen to which a particular antibody (e.g., an anti-CLDN6 antibody) binds (a partial peptide or partial three-dimensional structure of CLDN6). An epitope as such a partial peptide (e.g., a partial peptide of CLDN6) can be determined by using any method well known to those skilled in the art, such as immunoassay.

A “CDR” in the present invention refers to a complementarity determining region. It is known that each of heavy chains and light chains of an antibody molecule have three CDRs. CDRs, which are also called a hypervariable region, are located in variable regions of heavy chains and light chains of an antibody and is a site with particularly high variation of the primary structure. Three CDRs are separately located in the primary structure of the polypeptide chain of each of heavy chains and light chains. Regarding CDRs of antibodies, herein, CDRs of a heavy chain refer to CDRH1, CDRH2, and CDRH3 from the amino terminus of the heavy chain amino acid sequence, and CDRs of a light chain refer to CDRL1, CDRL2, and CDRL3 from the amino terminus of the light chain amino acid sequence. These sites are located in the proximity of each other in the three-dimensional structure, determining specificity to an antibody to bind.

In the present invention, “hybridize under stringent conditions” refers to hybridization in the commercially available hybridization solution ExpressHyb Hybridization Solution (Clontech) at 68° C., or hybridization using a filter with DNA fixed thereto in the presence of 0.7 to 1.0 M NaCl at 68° C. and washing at 68° C. with 0.1 to 2×SSC solution (1×SSC solution contains 150 mM NaCl and 15 mM sodium citrate), or hybridization under conditions equivalent thereto.

In the present invention, “one to several” refers to 1 to 10, one to nine, one to eight, one to seven, one to six, one to five, one to four, one to three, or one or two.

In the present invention, an antibody capable of recognizing or binding to CLDN6 and that capable of recognizing or binding to CLDN6 and CLDN9 are occasionally called as an “anti-CLDN6 antibody” and an “anti-CLDN6/CLDN9 antibody”, respectively. Such antibodies include chimeric antibodies, humanized antibodies, and human antibodies. An antibody capable of recognizing or binding to CLDN6 and CLDN9 is occasionally called as an “anti-CLDN6 antibody”.

The antibody to be used for the antibody-drug conjugate of the present invention refers to immunoglobulin, and is a molecule including an antigen-binding site which immunospecifically binds to an antigen. The antibody of the present invention may be of any class of IgG, IgE, IgM, IgD, IgA, and IgY, and preferred is IgG. The subclass may be any of IgG1, IgG2, IgG3, IgG4, IgAQ1, and IgA2, and preferred are IgG1, IgG2, and IgG4. If IgG1 or IgG4 is used, the effector function may be adjusted by substituting some of amino acid residues in the constant region (see WO 88/07089, WO 94/28027, WO 94/29351).

If IgG1 is used as the isotype of the antibody of the present invention, the effector function may be adjusted by substituting some amino acid residues in the constant region. Examples of variants of IgG1 with the effector function lowered or attenuated may include, but are not limited to, IgG1 LALA (IgG1-L234A, L235A) and IgG1 LAGA (IgG1-L235A, G237A), and a preferred variant of IgG1 is IgG1 LALA. The L234A, L235A indicates substitution of leucine with alanine at the 234- and 235-positions specified by EU-index numbering (Proc. Natl. Acad. Sci. U.S.A., Vol. 63, No. 1 (May 15, 1969), pp. 78-85), and the G237A indicates substitution of glycine with alanine at the 237-position specified by EU-index numbering:

The antibody of the present invention is preferably an antibody capable of targeting a tumor cell.

Since the compound conjugated in the antibody-drug conjugate of the present invention exerts an antitumor effect, it is preferred but not essential that the antibody itself should have an antitumor effect. For the purpose of specifically and selectively exerting the cytotoxicity of the antitumor compound against tumor cells, it is important and preferred that the antibody or antibody-drug conjugate should have the property of internalizing to migrate into tumor cells. To exert antitumor effect, it is important and preferred that the antibody or antibody-drug conjugate should have the property of internalizing to migrate into tumor cells, from the viewpoint that the drug specifically and selectively damages tumor cells. The antitumor activity of the antibody refers to the cellular cytotoxic activity or anticellular effect against tumor cells. The antitumor activity may be confirmed by using any known in vitro or in vivo evaluation system. The internalization ability of the antibody can be measured by using a known evaluation system.

Examples of such an antibody may include, but are not limited to, antibodies to tumor-related antigens, including an anti-CLDN6 antibody, an anti-CLDN9 antibody, an anti-CLDN6/CLDN9 antibody, an anti-HER2 antibody, an anti-HER3 antibody, an anti-DLL3 (Delta like protein 3) antibody, an anti-A33 antibody, an anti-CanAg antibody, an anti-CD19 antibody, an anti-CD20 antibody, an anti-CD22 antibody, an anti-CD25 antibody, an anti-CD30 antibody, an anti-CD33 antibody, an anti-CD37 antibody, an anti-CD56 antibody, an anti-CD70 antibody, an anti-CD98 antibody, an anti-B7-H3 (CD276) antibody, an anti-TROP2 antibody, an anti-CEA antibody, an anti-Cripto antibody, an anti-EphA2 antibody, an anti-FGFR2 antibody (e.g., WO 201315206), an anti-G250 antibody, an anti-MUC1 antibody (e.g., WO 2011012309), an anti-GPNMB antibody, an anti-integrin antibody, an anti-PSMA antibody, an anti-tenascin-C antibody, an anti-SLC44A4 antibody, an anti-mesothelin antibody, an anti-EGFR antibody, an anti-ST4 (oncofetal antigen 5T4; also TPBG and trophoblast glycoprotein) antibody, an anti-LRRC15 (Leucine-rich repeat-containing protein 15) antibody, an anti-DR5 antibody, an anti-CDH3 (cadherin 3) antibody, an anti-PDPN (podoplanin) antibody, or an anti-CD123 antibody.

The antibody of the present invention is preferably an anti-CLDN6 antibody, an anti-CLDN6/CLDN9 antibody, an anti-HER2 antibody, an anti-CD98 antibody, or an anti-TROP2 antibody, and more preferably an anti-CLDN6 antibody or an anti-HER2 antibody (e.g., trastuzumab, a trastuzumab variant, a trastuzumab variant 2).

Now, the anti-CLDN6 antibody used in the present invention will be described.

1. CLDN6 and CLDN9

CLDN6, a four-transmembrane protein belonging to the claudin family and consisting of 220 amino acids, has the N terminus and C terminus in a cell.

The amino acid sequence of and DNA sequence for human CLDN6 are published in public databases, and can be referred to, for example, from accession numbers of NP_067018 (SEQ ID NO: 1) and NM_021195 (SEQ ID NO: 2 (both in NCBI).

In the amino acid sequence of human CLDN6 protein (hereinafter, referred to as "CLDN6 amino acid sequence"), the extracellular region is composed of an extracellular domain (EC1) consisting of amino acid residues 29 to 81 of SEQ ID NO: 1 in Sequence Listing and an extracellular domain (EC2) consisting of amino acid residues 138 to 160 of SEQ ID NO: 1 in Sequence Listing.

CLDN9, a four-transmembrane protein belonging to the claudin family and consisting of 217 amino acids, has the N terminus and C terminus in a cell. CLDN9 is highly homologous to CLDN6.

The amino acid sequence of and DNA sequence for human CLDN9 are published in public databases, and can be referred to, for example, from accession numbers of NP_066192 (SEQ ID NO: 3) and NM_020982 (SEQ ID NO: 4 (both in NCBI).

2. Anti-CLDN6 Antibody

An example of the anti-CLDN6 antibody of the present invention is an anti-CLDN6 antibody that recognizes a higher order structure including two extracellular regions, specifically, an amino acid sequence of the 29- to 81-positions and amino acid sequence of the 138- to 160-positions from the N terminus of CLDN6 as represented by SEQ ID NO: 1 in Sequence Listing, and has internalization activity.

The anti-CLDN6 antibody of the present invention is an antibody capable of targeting tumor cells, and specifically has a property of recognizing a tumor cell, a property of binding to a tumor cell, a property of being incorporated and internalizing in a tumor cell, and so on. Accordingly, the anti-CLDN6 antibody according to the present invention can be used for an antibody-drug conjugate by conjugating via a linker with a compound having antitumor activity.

The anti-CLDN6 antibody of the present invention may have antitumor activity.

(1) The anti-CLDN6 antibody of the present invention has the following properties (a) and (b).

(a) Recognizing or binding to the CLDN family.

The antibody of the present invention recognizes the CLDN family. In other words, the antibody of the present invention binds to the CLDN family. The antibody of the present invention preferably binds to CLDN6, and more preferably specifically binds to CLDN6. Further, the antibody of the present invention may recognize CLDN9 or bind to CLDN9.

In the present invention, "specific recognition", that is, "specific binding" refers to binding being not nonspecific adsorption. Examples of determination criteria on whether binding is specific or not may include, but are not limited to, dissociation constants (hereinafter, referred to as "KD"). A preferred KD value of the antibody of the present invention to CLDN6 and/or CLDN9 is $1\times10^{-5}$ M or less, $5\times10^{-6}$ M or less, $2\times10^{-6}$ M or less, or $1\times10^{-6}$ M or less, and more preferably $5\times10^{-7}$ M or less, $2\times10^{-7}$ M or less, or $1\times10^{-7}$ M or less.

Binding between an antigen and an antibody in the present invention may be measured or determined by an analysis method such as an ELISA method, an RIA method, and surface plasmon resonance (hereinafter, referred to as "SPR"). Binding between an antigen expressed on a cell surface and an antibody may be measured, for example, by a flow cytometry method.

(b) Having activity to internalize in CLDN6- and/or CLDN9-expressing cells through binding to CLDN6 and/or CLDN9.

(2) The antibody according to (1), wherein CLDN6 and/or CLDN9 are/is human CLDN6 and/or human CLDN9.

For example, the anti-CLDN6 monoclonal antibody of the present invention can be obtained with a method using a hybridoma. Examples of a monoclonal anti-CLDN6 antibody may include, but are not limited to, the mouse anti-CLDN6 antibodies B1 and C7. In the present invention, the "B1" and the "C7" are occasionally called as the "B1 antibody" and the "C7 antibody", respectively.

The nucleotide sequence for and the amino acid sequence of the heavy chain variable region of the B1 antibody are respectively represented by SEQ ID NO: 20 and SEQ ID NO: 21 in Sequence Listing. The nucleotide sequence for and the amino acid sequence of the light chain variable region of the B1 antibody are respectively represented by SEQ ID NO: 18 and SEQ ID NO: 19 in Sequence Listing.

The amino acid sequences of CDRH1, CDRH2, CDRH3, CDRL1, CDRL2, and CDRL3 of the B1 antibody are represented by SEQ ID NO: 9, SEQ ID NO: 10, SEQ ID NO: 11, SEQ ID NO: 5, SEQ ID NO: 6, and SEQ ID NO: 7, respectively.

The nucleotide sequence for and the amino acid sequence of the heavy chain variable region of the C7 antibody are respectively represented by SEQ ID NO: 24 and SEQ ID NO: 25 in Sequence Listing. The nucleotide sequence for and the amino acid sequence of the light chain variable region of the C7 antibody are respectively represented by SEQ ID NO: 22 and SEQ ID NO: 23 in Sequence Listing.

The amino acid sequences of CDRH1, CDRH2, CDRH3, CDRL1, CDRL2, and CDRL3 of the C7 antibody are represented by SEQ ID NO: 15, SEQ ID NO: 16, SEQ ID NO: 17, SEQ ID NO: 12, SEQ ID NO: 13, and SEQ ID NO: 14, respectively.

An example of the anti-CLDN6 antibody of the present invention is an antibody that binds to an epitope for the B1 antibody or C7 antibody. If the antibody binds to a partial peptide or partial three-dimensional structure to which the B1 antibody or C7 antibody binds, it can be determined that the antibody binds to an epitope for the B1 antibody or C7 antibody. By confirming that the antibody competes with the B1 antibody or C7 antibody for binding to CLDN6 (i.e., the antibody interferes with binding between the B1 antibody or C7 antibody and CLDN6), it can be determined, even when the specific sequence or structure of an epitope has not been determined, that the antibody binds to an epitope for the anti-CLDN6 antibody. If epitope identity has been confirmed, the antibody is strongly expected to have antigen-binding ability, biological activity, and/or internalization activity equivalent to that of the B1 antibody or C7 antibody.

The antibody of the present invention includes, in addition to the monoclonal antibody against CLDN6, a gene recombinant antibody obtained by artificial modification for the purpose of decreasing heterologous antigenicity to humans such as a chimeric antibody, a humanized antibody, and a human antibody. These antibodies can be produced using a known method.

(1) Chimeric Antibody

Examples of the chimeric antibody may include, but are not limited to, an antibody in which antibody variable and constant regions are derived from different species, for example, a chimeric antibody in which a mouse- or rat-derived antibody variable region is connected to a human-derived antibody constant region.

A chimeric antibody derived from the mouse anti-human CLDN6 antibody B1 antibody, as an example of the chimeric antibody of the present invention, is an antibody comprising a heavy chain comprising a heavy chain variable region consisting of an amino acid sequence represented by SEQ ID NO: 21 and a light chain comprising a light chain variable region represented by SEQ ID NO: 19, which may comprise any human-derived constant region.

Specific examples of the chimeric antibody derived from the mouse anti-human CLDN6 antibody B1 antibody may include, but are not limited to, the chimeric antibody chB1 antibody (hereinafter, also called as "chB1") derived from the mouse anti-human CLDN6 antibody B1 antibody. Examples of the chB1 antibody, in terms of the amino acid sequence, may include, but are not limited to, an antibody comprising a heavy chain having an amino acid sequence consisting of amino acid residues 20 to 471 of SEQ ID NO: 32 in Sequence Listing and a light chain having an amino acid sequence consisting of amino acid residues 21 to 234 of SEQ ID NO: 28 in Sequence Listing.

In the heavy chain sequence represented by SEQ ID NO: 32 in Sequence Listing, the amino acid sequence consisting of amino acid residues 1 to 19 is the signal sequence, the amino acid sequence consisting of amino acid residues 20 to 141 is the heavy chain variable region, and the amino acid sequence consisting of amino acid residues 142 to 471 is the heavy chain constant region. In the light chain sequence represented by SEQ ID NO: 28 in Sequence Listing, the amino acid sequence consisting of amino acid residues 1 to 20 is the signal sequence, the amino acid sequence consisting of amino acid residues 21 to 127 is the light chain variable region, and the amino acid sequence consisting of amino acid residues 128 to 234 is the light chain constant region.

The amino acid sequences of the heavy chain and light chain variable regions of the chB1 antibody are respectively represented by SEQ ID NO: 34 and SEQ ID NO: 30 in Sequence Listing.

The heavy chain amino acid sequence of the chB1 antibody is encoded by a nucleotide sequence represented by SEQ ID NO: 33 in Sequence Listing. A nucleotide sequence consisting of nucleotide residues 1 to 57 of a nucleotide sequence represented by SEQ ID NO: 33 in Sequence Listing is encoding the signal sequence of the chB1 antibody heavy chain, a nucleotide sequence consisting of nucleotide residues 58 to 423 of a nucleotide sequence represented by SEQ ID NO: 33 in Sequence Listing is encoding the heavy chain variable region of the chB1 antibody, and a nucleotide sequence consisting of nucleotide residues 424 to 1413 of a nucleotide sequence represented by SEQ ID NO: 33 in Sequence Listing is encoding the heavy chain constant region of the chB1 antibody.

The nucleotide sequence for the heavy chain variable region of the chB1 antibody is represented by SEQ ID NO: 35 in Sequence Listing.

The light chain amino acid sequence of the chB1 antibody is encoded by a nucleotide sequence represented by SEQ ID NO: 29 in Sequence Listing. A nucleotide sequence consisting of nucleotide residues 26 to 85 of a nucleotide sequence represented by SEQ ID NO: 29 in Sequence Listing is encoding the signal sequence of the chB1 antibody light chain, a nucleotide sequence consisting of nucleotide residues 86 to 406 of a nucleotide sequence represented by SEQ ID NO: 29 in Sequence Listing is encoding the light chain variable region of the chB1 antibody, and a nucleotide sequence consisting of nucleotide residues 407 to 727 of a nucleotide sequence represented by SEQ ID NO: 29 in Sequence Listing is encoding the light chain constant region of the chB1 antibody.

The nucleotide sequence for the light chain variable region of the chB1 antibody is represented by SEQ ID NO: 31 in Sequence Listing.

(2) Humanized Antibody

Examples of the humanized antibody may include, but are not limited to, an antibody obtained by incorporating only the complementarity determining regions (CDRs) into a human-derived antibody (see Nature (1986) 321, p. 522-525), an antibody obtained by grafting a part of the amino acid residues of a framework as well as the CDR sequences to a human antibody by a CDR-grafting method (WO 90/07861), and an antibody in which a part of the CDR amino acid sequences has been modified with the binding ability to an antigen maintained.

The amino acid sequences of CDRs can be determined according to a known method such as the Kabat definition, the Chothia definition, the Abm definition, and IMGT; however, CDRs in the present invention may be those defined according to any method.

If the humanized antibody is derived from the B1 antibody or C1 antibody, however, the humanized antibody may be any humanized antibody, without limited to a particular humanized antibody, that retains all the six CDR sequences of the B1 antibody or C1 antibody and has CLDN6-binding activity, and in addition the humanized antibody may be any humanized antibody, without limited to a particular humanized antibody, such that its humanized antibody variant in which one to several (preferably, one or two, more preferably, one) CDR amino acid sequences have been modified also recognizes CLDN6 protein, or has the CLDN6 protein-binding activity of the original antibody.

Examples of the humanized anti-CLDN6 antibody of the present invention or a functional fragment thereof may include, but are not limited to, an antibody comprising a heavy chain having a variable region comprising:

- CDRH1 consisting of an amino acid sequence represented by SEQ ID NO: 9 in Sequence Listing, or an amino acid sequence obtained by substituting one to several (preferably, one or two) amino acids in the aforementioned amino acid sequence;
- CDRH2 consisting of an amino acid sequence represented by SEQ ID NO: 10 in Sequence Listing, or an amino acid sequence obtained by substituting one to several (preferably, one or two) amino acids in the aforementioned amino acid sequence; and
- CDRH3 consisting of an amino acid sequence represented by SEQ ID NO: 11 in Sequence Listing, or an amino acid sequence obtained by substituting one to several (preferably, one or two) amino acids in the aforementioned amino acid sequence; and a light chain having a variable region comprising:
- CDRL1 consisting of an amino acid sequence represented by SEQ ID NO: 5 in Sequence Listing, or an amino acid sequence obtained by substituting one to several (preferably, one or two) amino acids in the aforementioned amino acid sequence;
- CDRL2 consisting of an amino acid sequence represented by SEQ ID NO: 6 in Sequence Listing, or an amino acid sequence obtained by substituting one to several (preferably, one or two) amino acids in the aforementioned amino acid sequence; and
- CDRL3 consisting of an amino acid sequence represented by SEQ ID NO: 7 in Sequence Listing, or an amino acid sequence obtained by substituting one to several (preferably, one or two) amino acids in the aforementioned amino acid, and
- recognizing the CLDN6 protein of the present invention or retaining the CLDN6 protein-binding activity of the antibody, or a functional fragment of the antibody.

Preferred examples of CDR amino acid substitution in the humanized anti-CLDN6 antibody or functional fragment thereof may include, but are not limited to, substitution of one to several (preferably, one or two) amino acids in CDRL3 as described above, and an example thereof is CDRL3 represented by SEQ ID NO: 8 in Sequence Listing, which is obtained by substituting amino acid residues 4 and 5 of SEQ ID NO: 7 in Sequence Listing.

Examples of the heavy chain variable region of the humanized antibody comprising the above-described CDRHs may include, but are not limited to, an amino acid sequence represented by SEQ ID NO: 54 in Sequence Listing, an amino acid sequence represented by SEQ ID NO: 58 in Sequence Listing, and an amino acid sequence represented by SEQ ID NO: 62 in Sequence Listing, and examples of the light chain variable region of the humanized antibody comprising the above-described CDRLs may include, but are not limited to, an amino acid sequence represented by SEQ ID NO: 38 in Sequence Listing, an amino acid sequence represented by SEQ ID NO: 42 in Sequence Listing, an amino acid sequence represented by SEQ ID NO: 46 in Sequence Listing, and an amino acid sequence represented by SEQ ID NO: 50 in Sequence Listing.

Preferred examples of humanized antibodies including a combination of the above heavy chain variable region and light chain variable region may include, but are not limited to:

- a humanized antibody comprising a heavy chain variable region consisting of an amino acid sequence represented by SEQ ID NO: 54 in Sequence Listing and a light chain variable region consisting of an amino acid sequence represented by SEQ ID NO: 38 in Sequence Listing;
- a humanized antibody comprising a heavy chain variable region consisting of an amino acid sequence represented by SEQ ID NO: 58 in Sequence Listing and a light chain variable region consisting of an amino acid sequence represented by SEQ ID NO: 42 in Sequence Listing;
- a humanized antibody comprising a heavy chain variable region consisting of an amino acid sequence represented by SEQ ID NO: 54 in Sequence Listing and a light chain variable region consisting of an amino acid sequence represented by SEQ ID NO: 46 in Sequence Listing;
- a humanized antibody comprising a heavy chain variable region consisting of an amino acid sequence represented by SEQ ID NO: 58 in Sequence Listing and a light chain variable region consisting of an amino acid sequence represented by SEQ ID NO: 50 in Sequence Listing; and
- a humanized antibody comprising a heavy chain variable region consisting of an amino acid sequence represented by SEQ ID NO: 62 in Sequence Listing and a light chain variable region consisting of an amino acid sequence represented by SEQ ID NO: 46 in Sequence Listing.

Examples of full-length sequences of humanized antibodies including a combination of the above heavy chain variable region and light chain variable region may include, but are not limited to:

- a humanized antibody comprising a heavy chain consisting of an amino acid sequence consisting of amino acid residues 20 to 471 of SEQ ID NO: 52 in Sequence Listing and a light chain consisting of an amino acid sequence consisting of amino acid residues 21 to 234 of SEQ ID NO: 36 in Sequence Listing (H1L1);
- a humanized antibody comprising a heavy chain consisting of an amino acid sequence consisting of amino acid residues 20 to 471 of SEQ ID NO: 56 in Sequence Listing and a light chain consisting of an amino acid sequence consisting of amino acid residues 21 to 234 of SEQ ID NO: 40 in Sequence Listing (H2L2);

a humanized antibody comprising a heavy chain consisting of an amino acid sequence consisting of amino acid residues 20 to 471 of SEQ ID NO: 52 in Sequence Listing and a light chain consisting of an amino acid sequence consisting of amino acid residues 21 to 234 of SEQ ID NO: 44 in Sequence Listing (H1L3);

a humanized antibody comprising a heavy chain consisting of an amino acid sequence consisting of amino acid residues 20 to 471 of SEQ ID NO: 56 in Sequence Listing and a light chain consisting of an amino acid sequence consisting of amino acid residues 21 to 234 of SEQ ID NO: 48 in Sequence Listing (H2L4); and a humanized antibody comprising a heavy chain consisting of an amino acid sequence consisting of amino acid residues 20 to 471 of SEQ ID NO: 60 in Sequence Listing and a light chain consisting of an amino acid sequence consisting of amino acid residues 21 to 234 of SEQ ID NO: 44 in Sequence Listing (H3L3).

In the heavy chain amino acid sequence represented by SEQ ID NO: 52, 56, or 60 in Sequence Listing, an amino acid sequence consisting of amino acid residues 1 to 19 is the signal sequence, an amino acid sequence consisting of amino acid residues 20 to 141 is the heavy chain variable region, and an amino acid sequence consisting of amino acid residues 142 to 471 is the heavy chain constant region.

In the light chain amino acid sequence represented by SEQ ID NO: 36, 40, 44, or 48, an amino acid sequence consisting of amino acid residues 1 to 20 is the signal sequence, an amino acid sequence consisting of amino acid residues 21 to 127 is the light chain variable region, and an amino acid sequence consisting of amino acid residues 128 to 234 is the light chain constant region.

As described later, one or two amino acids may be deleted at the carboxyl terminus of each of the humanized antibodies H1L1, H2L2, H1L3, H2L4, and H3L3, and such deletion variants are also included in the present invention.

Examples of the heavy chain of deletion variants may include, but are not limited to, a heavy chain including an amino acid sequence consisting of amino acid residues 20 to 470 of SEQ ID NO: 52, 56, or 60 in Sequence Listing.

Examples of such deletion variants may include:

a humanized antibody comprising a heavy chain consisting of an amino acid sequence consisting of amino acid residues 20 to 470 of SEQ ID NO: 52 in Sequence Listing and a light chain consisting of an amino acid sequence consisting of amino acid residues 21 to 234 of SEQ ID NO: 36 in Sequence Listing (H1L1);

a humanized antibody comprising a heavy chain consisting of an amino acid sequence consisting of amino acid residues 20 to 470 of SEQ ID NO: 56 in Sequence Listing and a light chain consisting of an amino acid sequence consisting of amino acid residues 21 to 234 of SEQ ID NO: 40 in Sequence Listing (H2L2);

a humanized antibody comprising a heavy chain consisting of an amino acid sequence consisting of amino acid residues 20 to 470 of SEQ ID NO: 52 in Sequence Listing and a light chain consisting of an amino acid sequence consisting of amino acid residues 21 to 234 of SEQ ID NO: 44 in Sequence Listing (H1L3);

a humanized antibody comprising a heavy chain consisting of an amino acid sequence consisting of amino acid residues 20 to 470 of SEQ ID NO: 56 in Sequence Listing and a light chain consisting of an amino acid sequence consisting of amino acid residues 21 to 234 of SEQ ID NO: 48 in Sequence Listing (H2L4); and a humanized antibody comprising a heavy chain consisting of an amino acid sequence consisting of amino acid residues 20 to 470 of SEQ ID NO: 60 in Sequence Listing and a light chain consisting of an amino acid sequence consisting of amino acid residues 21 to 234 of SEQ ID NO: 44 in Sequence Listing (H3L3).

As long as having binding activity to CLDN6, any antibody that has an identity or homology of 80% or higher, preferably of 90% or higher, more preferably of 95% or higher, even more preferably of 97% or higher, most preferably of 99% or higher, to the amino acid sequence of any of the antibodies including the above combinations of a heavy chain variable region and a light chain variable region and the antibodies including the above combinations of a heavy chain and a light chain is also included in the antibody of the present invention.

As long as having binding activity to CLDN6, any antibody that includes CDRs consisting of the amino acid sequences of the CDRs of any of the antibodies including the above combinations of a heavy chain variable region and a light chain variable region and the antibodies including the above combinations of a heavy chain and a light chain, wherein the amino acid sequence of the antibody excluding the amino acid sequences of the CDRs has an amino acid identity or homology of 80% or higher, preferably of 90% or higher, more preferably of 95% or higher, even more preferably of 97% or higher, most preferably of 99% or higher, is also included in the antibody of the present invention.

Further, an antibody having biological activity equivalent to each of the above antibodies may be selected through combining amino acid sequences obtained by substituting, deleting, or adding one or several amino acid residues in the amino acid sequence of the heavy chain or light chain. The substitution of an amino acid herein is preferably conservative amino acid substitution (WO 2013154206).

The conservative amino acid substitution is substitution that occurs in an amino acid group with related amino acid side chains. Such amino acid substitution is preferably carried out to such a degree that the properties of the substance having the original amino acid sequence are not decreased.

Homology between two amino acid sequences may be determined by using default parameters of Blast algorithm version 2.2.2 (Altschul, Stephen F., Thomas L. Madden, Alejandro A. Schaaffer, Jinghui Zhang, Zheng Zhang, Webb Miller, and David J. Lipman (1997), "Gapped BLAST and PSI-BLAST: a new generation of protein database search programs", Nucleic Acids Res. 25:3389-3402)

Blast algorithm may be used by accessing www.ncbi.nlm.nih.gov/blast on the Internet.

(3) Human Antibody

Further examples of the antibody of the present invention may include, but are not limited to, human antibodies capable of binding to CLDN6 and/or CLDN9. The human anti-CLDN6 and/or CLDN9 antibody refers to a human antibody having only an antibody gene sequence derived from a human chromosome. Human anti-CLDN6 antibodies that can be obtained by using known methods (Nature Genetics (1997) 16, p. 133-143, Nucl. Acids Res. (1998) 26, p. 3447-3448, Animal Cell Technology: Basic and Applied Aspects, vol. 10, p. 69-73, Kluwer Academic Publishers, 1999., Proc. Natl. Acad. Sci. USA (2000) 97, p. 722-727, Investigative Ophthalmology & Visual Science. (2002) 43 (7), p. 2301-2308, Briefings in Functional Genomics and Proteomics (2002), 1 (2), p. 189-203, Ophthalmology (2002) 109 (3), p. 427-431, WO92/01047, WO92/20791, WO93/06213, WO93/11236, WO93/19172, WO95/01438, WO95/15388, Annu.Rev.Immunol (1994) 12, p. 433-455, Nature Biotechnology (2005) 23 (9), p. 1105-1116) are also known.

The anti-HER2 antibody to be used in the present invention will be described in the following.

The anti-HER2 antibody of the present invention has the following properties.

(1) An anti-HER2 antibody having the following properties:

(a) specifically binding to HER2; and (b) internalizing into HER2-expressing cells by binding to HER2.

(2) The antibody according to (1), binding to the extracellular domain of HER2.

(3) The antibody according to (1) or (2), being a monoclonal antibody.

(4) The antibody according to any one of (1) to (3), having activities or activity of antibody-dependent cellular cytotoxicity (ADCC) and/or complement-dependent cytotoxicity (CDC).

(5) The antibody according to any one of (1) to (4), being a mouse monoclonal antibody, a chimeric monoclonal antibody, or a humanized monoclonal antibody.

(6) The antibody according to any one of (1) to (3) and (5), wherein the heavy chain constant region is a heavy chain constant region of human IgG1, and comprises a mutation that causes lowering of activities or activity of ADCC and/or CDC.

(7) The antibody according to (6), wherein the heavy chain constant region is a heavy chain constant region of human IgG1, and leucine at the 234- and 235-positions specified by EU Index numbering is substituted with alanine.

(8) The antibody according to any one of (1) to (5), being an antibody comprising a heavy chain consisting of an amino acid sequence represented by SEQ ID NO: 65 and a light chain consisting of an amino acid sequence represented by SEQ ID NO: 64.

(9) The antibody according to any one of (1) to (3) and (5) to (7), being an antibody comprising a heavy chain variable region consisting of an amino acid sequence consisting of amino acid residues 20 to 139 of SEQ ID NO: 75 and a light chain variable region consisting of an amino acid sequence consisting of amino acid residues 21 to 127 of SEQ ID NO: 73.

(10) The antibody according to any one of (1) to (3), (5) to (7), and (9), being an antibody comprising a heavy chain consisting of an amino acid sequence consisting of amino acid residues 20 to 469 of SEQ ID NO: 75 and a light chain consisting of an amino acid sequence consisting of amino acid residues 21 to 234 of SEQ ID NO: 73.

(11) The antibody according to any one of (1) to (3), (5) to (7), and (9), being an antibody comprising a heavy chain consisting of an amino acid sequence consisting of amino acid residues 20 to 469 of SEQ ID NO: 77 and a light chain consisting of an amino acid sequence consisting of amino acid residues 21 to 234 of SEQ ID NO: 76.

(12) The antibody according to any one of (1) to (11), wherein one or two amino acids are deleted at the carboxyl terminus of the heavy chain.

(13) The antibody according to any one of (1) to (5), (8), and (12), comprising a heavy chain consisting of an amino acid sequence consisting of amino acid residues 1 to 449 of SEQ ID NO: 65 and a light chain consisting of an amino acid sequence consisting of amino acid residues 1 to 214 of SEQ ID NO: 64.

(14) The antibody according to any one of (1) to (3), (5) to (7), (9), (10), and (12), comprising a heavy chain consisting of an amino acid sequence consisting of amino acid residues 20 to 468 of SEQ ID NO: 75 and a light chain consisting of an amino acid sequence consisting of amino acid residues 21 to 234 of SEQ ID NO: 73.

(15) The antibody according to any one of (1) to (3), (5) to (7), (9), (11), and (12), comprising a heavy chain consisting of an amino acid sequence consisting of amino acid residues 20 to 468 of SEQ ID NO: 77 and a light chain consisting of an amino acid sequence consisting of amino acid residues 21 to 234 of SEQ ID NO: 76.

(16) An antibody obtained by using a method for producing the antibody according to any one of (1) to (15), the method including the steps of: culturing a host cell transformed with an expression vector containing a polynucleotide encoding the antibody; and collecting the targeted antibody from a culture obtained from the step of culturing.

In the present application, such an antibody that leucine at the 234- and 235-positions specified by EU Index numbering in the heavy chain constant region of trastuzumab (SEQ ID NO: 65) is substituted with alanine is referred to as a trastuzumab variant or trastuzumab variant 2.

The antibody of the present invention includes modified variants of the antibody. The modified variant refers to a variant obtained by subjecting the antibody of the present invention to chemical or biological modification. Examples of the chemically modified variant may include, but are not limited to, variants including a linkage of a chemical moiety to an amino acid skeleton, and variants with chemical modification of an N-linked or O-linked carbohydrate chain. Examples of the biologically modified variant may include, but are not limited to, variants obtained by post-translational modification (e.g., N-linked or O-linked glycosylation, N- or C-terminal processing, deamidation, isomerization of aspartic acid, oxidation of methionine), and variants in which a methionine residue has been added to the N terminus by being expressed in a prokaryotic host cell. Further, an antibody labeled so as to enable the detection or isolation of the antibody of the present invention or an antigen, for example, an enzyme-labeled antibody, a fluorescence-labeled antibody, and an affinity-labeled antibody are also included in the meaning of the modified variant. Such a modified variant of the antibody of the present invention is useful for improving the stability and blood retention of the antibody, reducing the antigenicity thereof, detecting or isolating an antibody or an antigen, and so on.

Further, by regulating the modification of a glycan which is linked to the antibody of the present invention (glycosylation, defucosylation, etc.), the antibody-dependent cellular cytotoxic activity can be enhanced. As the technique for regulating the modification of a glycan of antibodies, WO 1999/54342, WO 2000/61739, WO 2002/31140, WO 2007/133855, WO 2013/120066 etc., are known. However, the technique is not limited thereto. In the antibody of the present invention, antibodies in which the modification of a glycan is regulated are also included.

Such modification may be applied at any position or a desired position in an antibody or a functional fragment of the antibody, and the same type or two or more different types of modification may be applied at one or two or more positions.

In the present invention, the meaning of a "modified variant of an antibody fragment" also includes a "fragment of a modified variant of an antibody".

If an antibody gene is temporarily isolated and then introduced into an appropriate host to produce an antibody, an appropriate combination of a host and an expression vector can be used. Specific examples of the antibody gene may include, but are not limited to, combination of a gene encoding the heavy chain sequence or the like of an antibody described herein and a gene encoding the light chain sequence or the like of an antibody described herein. To transform host cells, a heavy chain sequence gene or the like and a light chain sequence gene or the like may be inserted into the same expression vector, or inserted into separate expression vectors.

If eukaryotic cells are used as a host, animal cells, plant cells, and eukaryotic microorganisms may be used. Particularly, examples of animal cells may include, but are not limited to, mammalian cells, such as COS cells (Cell (1981) 23, p. 175-182, ATCC CRL-1650), as monkey cells, the mouse fibroblast NIH3T3 (ATCC No. CRL-1658), a dihydrofolate reductase-deficient strain (Proc. Natl. Acad. Sci. U.S.A. (1980) 77, p. 4126-4220) of Chinese hamster ovary cells (CHO cells, ATCC CCL-61), and FreeStyle 293F cells (Invitrogen).

If prokaryotic cells are used, for example, *Escherichia coli* or *Bacillus subtilis* may be used.

A targeted antibody gene is introduced into these cells by transformation, and the transformed cells are cultured in vitro to afford an antibody. Sequence difference among antibodies may result in different yields in the culture, and hence antibodies that allow easy production of a medicine may be selected out of antibodies having equivalent binding activity by using yields as an indicator. Accordingly, the antibody of the present invention includes antibodies obtained by using a method for producing the antibody, the method including the steps of: culturing the transformed host cell; and collecting a targeted antibody or a functional fragment of the antibody from a culture obtained in the step of culturing.

The antibody gene is preferably a polynucleotide including a polynucleotide described in any one of (a) to (e):

(a) a combination of a polynucleotide encoding the heavy chain amino acid sequence and a polynucleotide encoding the light chain amino acid sequence of an antibody of any one of the B1 or C7 antibody, the chB1 antibody, the humanized antibodies H1L1, H2L2, H1L3, H2L4, and H3L3, trastuzumab, and a variant thereof;

(b) a combination of a polynucleotide encoding a heavy chain amino acid sequence including the sequences of CDRH1 to CDRH3 and a polynucleotide encoding a light chain amino acid sequence including the sequences of CDRL1 to CDRL3 of an antibody of any one of the B1 or C7 antibody, the chB1 antibody, the humanized antibodies H1L1, H2L2, H1L3, H2L4, and H3L3, trastuzumab, and a variant thereof;

(c) a combination of a polynucleotide encoding a heavy chain amino acid sequence comprising the amino acid sequence of the heavy chain variable region and a polynucleotide encoding a light chain amino acid sequence comprising the amino acid sequence of the light chain variable region of an antibody of any one of the B1 or C7 antibody, the chB1 antibody, the humanized antibodies H1L1, H2L2, H1L3, H2L4, and H3L3, trastuzumab, and a variant thereof;

(d) a polynucleotide that is hybridizable with nucleotides consisting of a polynucleotide complementary to the polynucleotide according to any one of (a) to (c) under stringent conditions and is encoding the amino acid sequence of an antibody capable of binding to CDLN6 or HER2; and (e) a polynucleotide encoding the amino acid sequence of a polypeptide obtained by substituting, deleting, adding, or inserting 1 to 50, 1 to 45, 1 to 40, 1 to 35, 1 to 30, 1 to 25, 1 to 20, 1 to 15, 1 to 10, one to eight, one to six, one to five, one to four, one to three, one or two, or one amino acid(s) in the polynucleotide according to any one of (a) to (c), and is encoding the amino acid sequence of an antibody capable of binding to CLDN6 or HER2.

The present invention includes a nucleotide encoding the antibody of the present invention or a functional fragment of the antibody, or a modified variant of the antibody or functional fragment; a recombinant vector including the gene inserted therein; and a cell including the gene or the vector introduced therein.

The present invention includes a method for producing an antibody or a functional fragment of the antibody, or a modified variant of the antibody or functional fragment, the method including the steps of: culturing the cell; and collecting from the culture an antibody or a functional fragment of the antibody, or a modified variant of the antibody or functional fragment.

It is known that a lysine residue at the carboxyl terminus of the heavy chain of an antibody produced in a cultured mammalian cell is deleted (Journal of Chromatography A, 705:129-134 (1995)), and it is also known that two amino acid residues, glycine and lysine, at the carboxyl terminus of the heavy chain of an antibody produced in a cultured mammalian cell are deleted and that a proline residue newly located at the carboxyl terminus is amidated (Analytical Biochemistry, 360:75-83 (2007)). However, such deletion and modification of the heavy chain sequence do not affect the antigen-binding ability and the effector function (the activation of complement, antibody-dependent cellular cytotoxicity, etc.) of the antibody. Therefore, in the antibody according to the present invention, antibodies subjected to such modification and functional fragments of the antibody are also included, and deletion variants in which one or two amino acids have been deleted at the carboxyl terminus of the heavy chain, variants obtained by amidation of deletion variants (for example, a heavy chain in which the carboxyl terminal proline residue has been amidated), and the like are also included. The type of deletion variants having a deletion at the carboxyl terminus of the heavy chain of the antibody according to the present invention is not limited to the above variants as long as the antigen-binding ability and the effector function are conserved. The two heavy chains constituting the antibody according to the present invention may be of one type selected from the group consisting of a full-length heavy chain and the above-described deletion variant, or may be of two types in combination selected therefrom. The ratio of the amount of each deletion variant can be affected by the type of cultured mammalian cells which produce the antibody according to the present invention and the culture conditions; however, an antibody in which one amino acid residue at the carboxyl terminus has been deleted in both of the two heavy chains in the antibody according to the present invention can be preferably exemplified as a main component of molecules of the antibody.

The antibody obtained may be purified to a homogeneous state. For separation/purification of the antibody, separation/purification methods commonly used for protein can be used. For example, the antibody may be separated/purified by appropriately selecting and combining column chromatography, filter filtration, ultrafiltration, salting-out, dialysis, preparative polyacrylamide gel electrophoresis, isoelectric focusing, and so on (Strategies for Protein Purification and Characterization: A Laboratory Course Manual, Daniel R. Marshak et al. eds., Cold Spring Harbor Laboratory Press (1996); Antibodies: A Laboratory Manual. Ed Harlow and David Lane, Cold Spring Harbor Laboratory (1988)), but separation/purification methods are not limited thereto.

<N297 Glycan>

A method for remodeling heterogeneous glycoprotein of an antibody by enzymatic reaction or the like to homogeneously introduce a glycan having a functional group (ACS Chemical Biology 2012, 7, 110, ACS Medicinal Chemistry Letters 2016, 7, 1005, Bioconjugate Chemistry 2015, 26, 2233, Angew. Chem. Int. Ed. 2016, 55, 2361-2367, US2016361436) has been recently reported.

In the glycan remodeling of the present invention, using hydrolase, heterogeneous glycans added to a protein (e.g., an antibody) are cleaved off to leave only GlcNAc at each terminus, thereby producing a homogenous protein moiety with GlcNAc (hereinafter, referred to as an "acceptor"). Subsequently, an arbitrary glycan separately prepared (hereinafter, referred to as a "donor") is provided, and the acceptor and the donor are linked together by using transglycosidase. Thereby, a homogeneous glycoprotein with arbitrary glycan structure can be synthesized.

In the present invention, a "glycan" refers to a structural unit of two or more monosaccharides bonded together via glycosidic bonds. Specific monosaccharides and glycans are occasionally abbreviated, for example, as "GlcNAc-", "MSG-", and so on. When any of these abbreviations is used in a structural formula, the abbreviation is shown with an intention that an oxygen atom or nitrogen atom involved in a glycosidic bond at the reducing terminal to another structural unit is not included in the abbreviation indicating the glycan, unless specifically defined.

In the present invention, a monosaccharide as a basic unit of a glycan is indicated for convenience so that in the ring structure, the position of a carbon atom bonding to an oxygen atom constituting the ring and directly bonding to a hydroxy group (or an oxygen atom involved in a glycosidic bond) is defined as the 1-position (the 2-position only for sialic acids), unless otherwise specified. The names of compounds in Examples are each provided in view of the chemical structure as a whole, and that rule is not necessarily applied.

When a glycan is indicated as a sign (e.g., GLY, SG, MSG, GlcNAc) in the present invention, the sign is intended, unless otherwise defined, to include carbon atoms ranging to the reducing terminal and not to include N or O involved in an N- or O-glycosidic bond.

In the present invention, unless specifically stated, a partial structure when a glycan is linking to a side chain of an amino acid is indicated in such a manner that the side chain portion is indicated in parentheses, for example, "(SG-) Asn".

The antibody-drug conjugate of the present invention is represented by the following formula:

[Formula 29]

$$\mathrm{Ab}\!-\!\!\left[(\text{N297 glycan})\!-\!\!\left[\mathrm{L}-\mathrm{D}\right]_{m^1}\right]_2$$

wherein an antibody Ab or a functional fragment of the antibody bonds via a N297 glycan or remodeled N297 glycan to L, and preferably bonds via a remodeled glycan of Ab to L.

Glycans in Ab of the present invention are N-linked glycans or O-linked glycans, and preferably N-linked glycans.

N-linked glycans and O-linked glycans bond to an amino acid side chain of an antibody via an N-glycosidic bond and an O-glycosidic bond, respectively.

IgG has a well conserved N-linked glycan on an asparagine residue at the 297-position of the Fc region of the heavy chain (hereinafter, referred to as "Asn297 or N297"), and the N-linked glycan is known to contribute to the activity and kinetics of the antibody molecule (Biotechnol. Prog., 2012, 28, 608-622, Anal. Chem., 2013, 85, 715-736).

The amino acid sequence in the constant region of IgG is well conserved, and each amino acid is specified by Eu index numbering in Edelman et al. (Proc. Natl. Acad. Sci. U.S.A., Vol. 63, No. 1 (May 15, 1969), p. 78-85). For example, Asn297, to which an N-linked glycan is added in the Fc region, corresponds to the 297-position in Eu index numbering, and each amino acid is uniquely specified by Eu index numbering, even if the actual position of the amino acid has varied through fragmentation of the molecule or deletion of a region.

In the antibody-drug conjugate of the present invention, the antibody or functional fragment of the antibody preferably bonds to L via a glycan bonding to a side chain of Asn297 thereof (hereinafter, referred to as "N297 glycan"), and the antibody or functional fragment of the antibody more preferably bonds via the N297 glycan to L, wherein the N297 glycan is a remodeled glycan.

SGP, an abbreviation for sialyl glycopeptide, is a representative N-linked complex glycan. SGP can be isolated/purified from the yolk of a hen egg, for example, by using a method described in WO 2011/0278681. Purified products of SGP are commercially available (Tokyo Chemical Industry Co., Ltd., FUSHIMI Pharmaceutical Co., Ltd.), and may be purchased. For example, disialooctasaccharide (Tokyo Chemical Industry Co., Ltd.), a glycan formed by deleting one GlcNAc at the reducing terminal in the glycan moiety of SG (hereinafter, referred to as "SG (10)", is commercially available.

In the present invention, a glycan structure formed by deleting a sialic acid at a non-reducing terminal only in either one of the branched chains of β-Man in SG (10) refers to MSG (9), and a structure having a sialic acid only in the 1-3 branched chains is called as MSG1, and a structure having a sialic acid only in the 1-6 branched chains is called as MSG2.

The remodeled glycan of the present invention is N297-(Fuc)MSG1, N297-(Fuc)MSG2, or a mixture of N297-(Fuc)MSG1 and N297-(Fuc)MSG2, or N297-(Fuc)SG, and is preferably N297-(Fuc)MSG1, N297-(Fuc)MSG2, or N297-(Fuc)SG, and is more preferably N297-(Fuc)MSG1 or N297-(Fuc)MSG2.

N297-(Fuc)MSG1 is represented by the following structural formula or sequence formula:

[Formula 30]

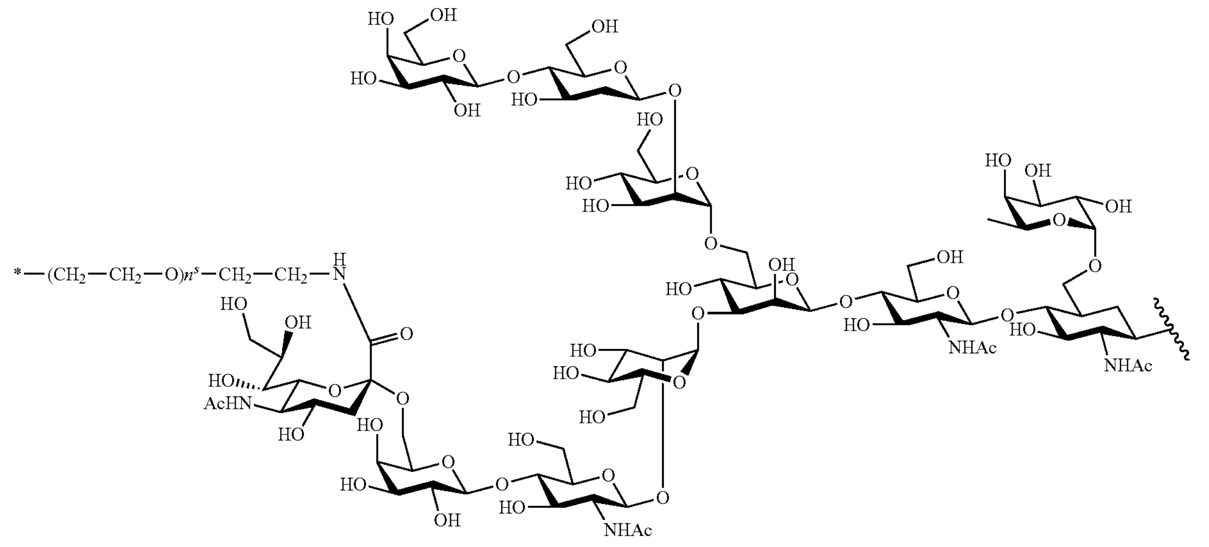

[N297-(Fuc)MSG1]

=

[Formula 31

Fucα1
|
6
Galβ1—4GlcNAcβ1-2Manα1—6
Manβ1—4GlcNAcβ1-4GlcNAcβ1—
*—L(PEG)—NeUAcα2—6Galβ1—4GlcNAcβ1—2Manα3—3

[N297-(Fuc)MSG1]

In the formulas, each wavy line represents bonding to Asn297 of the antibody, L(PEG) represents *—$(CH_2CH_2—O)_3$—$CH_2CH_2$—NH—, wherein the amino group at the right end represents bonding via an amide bond to carboxylic acid at the 2-position of a sialic acid at the non-reducing terminal in the 1-3 branched chains of β-Man in the N297 glycan, the asterisk * at the left end represents bonding to a nitrogen atom at the 1- or 3-position of the 1,2,3-triazole ring of Lb in linker L, and $n^5$ is an integer of 2 to 10, and preferably an integer of 2 to 5.

N297-(Fuc)MSG2 is represented by the following structural formula or sequence formula:

[Formula 32]

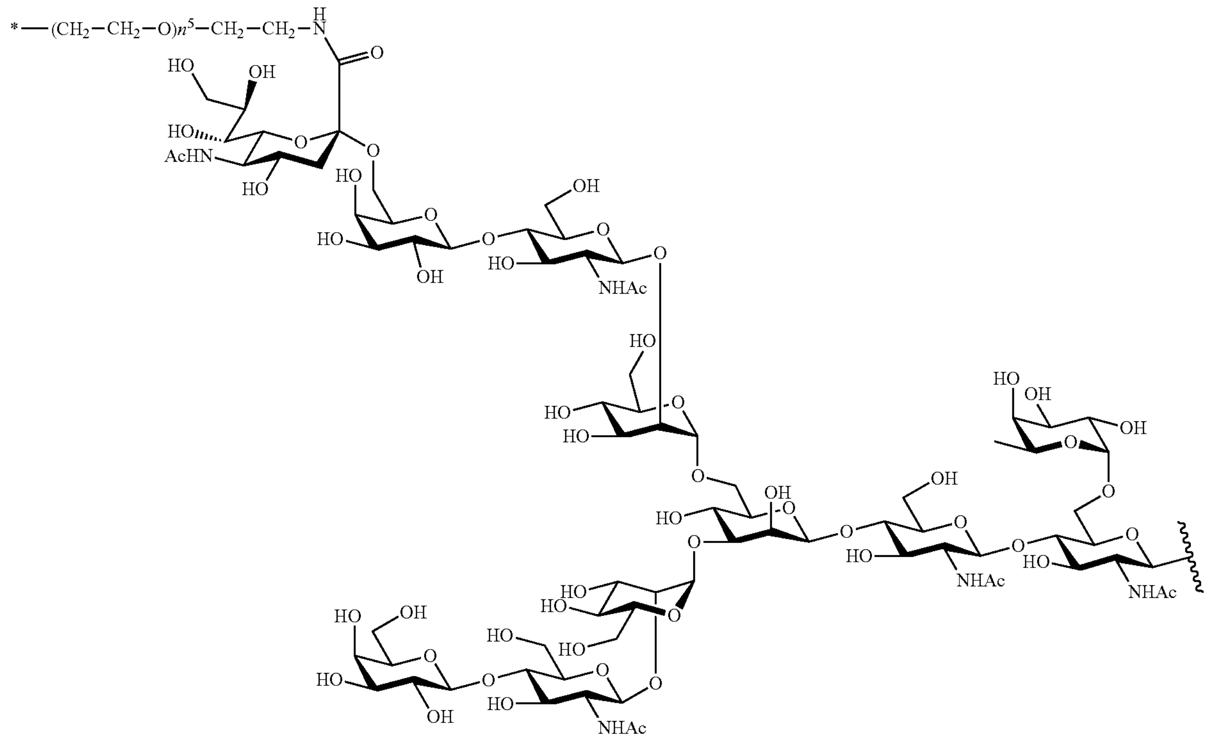

[N297-(Fuc)MSG2]

[Formula 33]

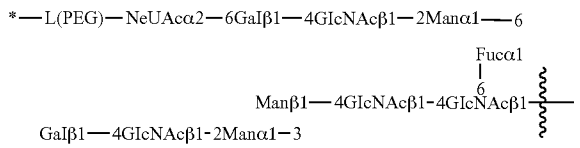

[N297-(Fuc)MSG2]

In the formulas, each wavy line represents bonding to Asn297 of the antibody,

L(PEG) represents *—$(CH_2CH_2—O)_3$—$CH_2CH_2$—NH—, wherein the amino group at the right end represents bonding via an amide bond to carboxylic acid at the 2-position of a sialic acid at the non-reducing terminal in the 1-6 branched chains of β-Man in the N297 glycan, the asterisk * at the left end represents bonding to a nitrogen atom at the 1- or 3-position of the 1,2,3-triazole ring of Lb in linker L, and $n^5$ is an integer of 2 to 10, and preferably an integer of 2 to 5.

N297-(Fuc)SG is represented by the following structural formula or sequence formula:

[Formula 34]

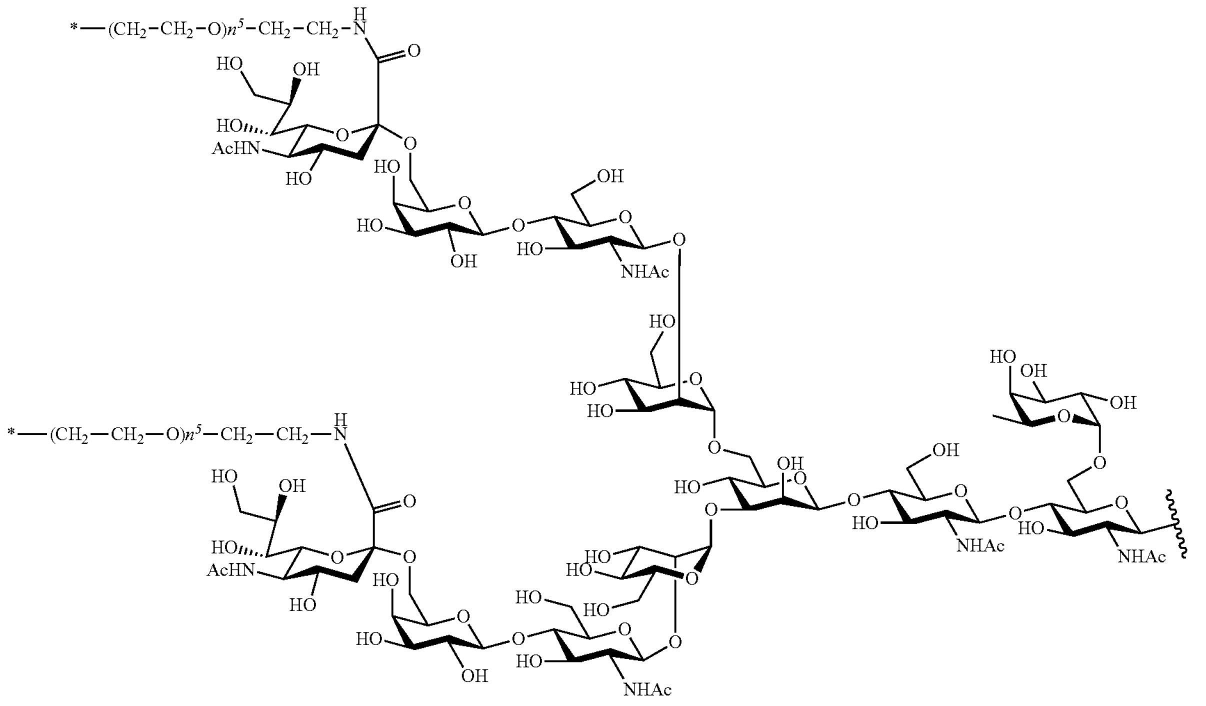

[N297-(Fuc)SG]

[Formula 35]

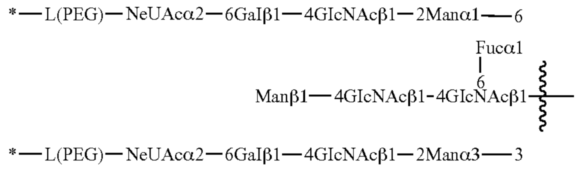

[N297-(Fuc)SG]

In the formulas, each wavy line represents bonding to Asn297 of the antibody,

L(PEG) represents *—$(CH_2CH_2—O)_3$—$CH_2CH_2$—NH—, wherein the amino group at the right end represents amide-bonding to carboxylic acid at the 2-position of a sialic acid at the non-reducing terminal in each of the 1-3 branched chains and 1-6 branched chains of β-Man in the N297 glycan, the asterisk * at the left end represents bonding to a nitrogen atom at the 1- or 3-position of the 1,2,3-triazole ring of Lb in linker L, and $n^5$ is an integer of 2 to 10, and preferably an integer of 2 to 5.

If N297 glycan of the antibody in the antibody-drug conjugate of the present invention is N297-(Fuc)MSG1, N297-(Fuc)MSG2, or a mixture of them, the antibody-drug conjugate is a molecule to which two molecules of drug-linker (-L-D) have been conjugated ($m^1$=1) since the antibody is a dimer (see FIG. 1).

For example, Example 19: ADC1 is in the case that N297 glycan is N297-(Fuc)MSG1.

If N297 glycan of the antibody in the antibody-drug conjugate of the present invention is N297-(Fuc)SG, the antibody-drug conjugate is a molecule to which four molecules of drug linker (-L-D) have been conjugated ($m^1$=2) since the antibody is a dimer.

N297 glycan is preferably N297-(Fuc)MSG1, N297-(Fuc)MSG2, or N297-(Fuc)SG, more preferably N297-(Fuc)MSG1 or N297-(Fuc)MSG2, and most preferably N297-(Fuc)MSG1.

If N297 glycan of the antibody in the antibody-drug conjugate of the present invention is N297-(Fuc)MSG1, N297-(Fuc)MSG2, or N297-(Fuc)SG, an ADC of homogenous quality can be obtained.

The present invention provides a method for producing a glycan-remodeled antibody or a functional fragment of the antibody, the method including the following steps of:

i) culturing the above-described host cell (e.g., an animal cell (such as a CHO cell)) and collecting a targeted antibody from a culture obtained;

ii) treating the antibody obtained in step i) with hydrolase to produce an antibody with N297 glycan being (Fucα1,6) GlcNAc ((Fucα1,6) GlcNAc-antibody) (FIG. 3A);

preferably further purifying the (Fucα1,6) GlcNAc-antibody through a step including purification of the reaction solution with a hydroxyapatite column; and iii) reacting the (Fucα1,6) GlcNAc-antibody with a glycan donner molecule in the presence of transglycosidase to synthesize a glycan-remodeled antibody with an azide group introduced to a sialic acid, the glycan donner molecule obtained by introducing a PEG linker having an azide group (N3-L(PEG)) to the carbonyl group of carboxylic acid at the 2-position of a sialic acid in MSG (9) or SG (10) and oxazolinating the reducing terminal.

The present invention includes glycan-remodeled antibodies and functional fragments of the antibodies, and modified variants of the antibodies and functional fragments obtained by using the production method.

The production intermediate of the present antibody-drug conjugate has an alkyne structure reactive with an azide group, such as DBCO (dibenzocyclooctyne) (see compound 3-14 in Example 2-1). Therefore, the antibody-drug conjugate of the present invention can be produced by reacting the production intermediate with an MSG1-type, MSG2-type, or SG-type glycan-remodeled antibody or a functional fragment of the antibody, where the antibody, in which a PEG linker having an azide group has been introduced to a sialic acid of a glycan, is obtained through steps i) to iii).

With regard to N297 glycan in the present invention, fucosylated GlcNAc-(Fucα1,6) GlcNAc) at the reducing terminal is preferably derived from an antibody produced in an animal cell, and a portion of the glycan located to the non-reducing terminal side of (Fucα1,6) GlcNAc preferably has been remodeled into the above-described glycan structure as MSG (MSG1, MSG2) or SG. In each case, carboxylic acid bonding to the 2-position of a sialic acid at the non-reducing terminal is used for bonding to L(PEG).

Such a glycan-remodeled antibody having MSG-(MSG1-, MSG2-) or SG-type N297 glycan may be produced by using a method as illustrated in FIG. 3, for example, on the basis of a method described in WO 2013/120066. If an antibody is produced as a gene-recombinant protein by using an animal cell as a host on the basis of a known method (step i), the N297 glycan has, as a base structure, a fucosylated N-linked glycan structure, whereas a mixture of antibody molecules having glycans of various structures with various modifications for the structure of the non-reducing terminal or constituent saccharides or fragments of such antibody molecules is provided (IV in FIG. 3A). Treatment of such an antibody produced with an animal cell with hydrolase such as EndoS causes hydrolysis of the glycosidic bond at GlcNAcβ1-4GlcNAc in the chitobiose structure at the reducing terminal, providing antibody molecules of single glycan structure having only (Fucα1,6) GlcNAc as N297 glycan (referred to as "(Fucα1,6) GlcNAc-antibody", see A in FIG. 2) (FIG. 3A) (step ii)).

For the enzyme for the hydrolysis reaction of N297 glycan, for example, Endo S or a variant enzyme retaining the hydrolysis activity may be used.

By reacting the (Fucα1,6) GlcNAc-antibody obtained in the above hydrolysis reaction, as a glycan acceptor molecule, and an MSG-(MSG1-, MSG2-) or SG-type glycan donor molecule with use of transglycosidase (e.g., WO 2017010559) such as EndoS D233Q and EndoS D233Q/Q303L variants, an antibody of the above-described structure including MSG-(MSG1-, MSG2-) or SG type N297 glycan (see B in FIG. 2) can be obtained (FIG. 3B) (step iii)).

If the number of conjugated drug molecules per drug-linker, $m^1$, in the antibody-drug conjugate is 1, a glycan donor molecule having MSG (MSG1, MSG2) as glycan is employed. For such glycan, commercially available monosialo-Asn free (1S2G/1G2S-10NC-Asn, GlyTech, Inc., hereinafter, referred to as "(MSG-)Asn") as a raw material may be separated on the basis of a method described in Example 3 to obtain (MSG-)Asn1 or (MSG2-) Asn, which may be employed, or a mixture of them may be employed without separation.

If the number of conjugated drug molecules per drug-linker, $m^1$, in the antibody-drug conjugate is 2, a glycan donor molecule including SG (10) as glycan is used for the transglycosylation reaction. For such SG (10) glycan, for example, that obtained from SGP through hydrolysis or the like may be used, or SG (10) glycan such as commercially available disialooctasaccharide (Tokyo Chemical Industry Co., Ltd.) may be used.

MSG-(MSG1-, MSG2-) or SG-type glycan included in the donor molecule has a PEG linker having an azide group (N3-L(PEG)) at the 2-position of a sialic acid therein.

It is preferred to use an activated form such as an oxazolinated form formed by treatment with 2-chloro-1,3-dimethyl-1H-benzimidazol-3-ium-chloride for GlcNAc at the reducing terminal of MSG (MSG1, MSG2) or SG-type glycan included in the donor molecule (J.org.Chem., 2009, 74 (5), 2210-2212).

Various enzymes for use in transglycosylation reaction (transglycosidase) may be employed that have activity of transferring complex glycan to N297 glycan; however, EndoS D233Q, a modified product for which hydrolysis reaction is suppressed by substituting Asp at the 233-position of EndoS with Gln, is a preferred transglycosidase. Transglycosylation reaction using EndoS D233Q is described, for example, in WO 2013/120066. Alternatively, a modified enzyme such as EndoS D233Q/Q303L (WO 2017/010559), which is obtained by further adding a mutation to EndoS D233Q, may be used.

The purification operation for the antibody after the glycan remodeling for the antibody (glycohydrolysis and transglycosylation reaction) is intended to separate low-molecular-weight compounds and enzymes used for the reaction, and gel filtration chromatography, ion-exchange chromatography, affinity chromatography, and so on are typically used for such purification, and additional purification with a hydroxyapatite column may be further carried out. That is, the present invention provides a method for producing an antibody-drug conjugate, the method including, in the step of purifying an intermediate from reaction solution after glycohydrolysis of an antibody, the additional step of purifying with a hydroxyapatite column. According to an example of reports on glycan remodeling (JACS. 2012, 134, 12308-12318., Angew. Chem. Int. Ed. 2016, 55, 2361-2367), reaction solution after treatment of an antibody with hydrolase is purified only with a Protein A column (affinity chromatography column); however, this purification method has been proved to be incapable of completely removing hydrolase (e.g., EndoS), and affect the subsequent transglycosylation reaction because of the residual enzyme. In view of such a result, examination was made on purification methods to find that when purification of reaction solution after treatment of an antibody with hydrolase was carried out using a Protein A column and a hydroxyapatite column (CHT column, Bio-Rad Laboratories, Inc.) in the order presented, the reaction efficiency of the subsequent glycosylation reaction was enhanced, without the influence of a residual enzyme.

The antibody-drug conjugate of the present invention is most preferably one antibody-drug conjugate selected from the following group:

[Formula 36]
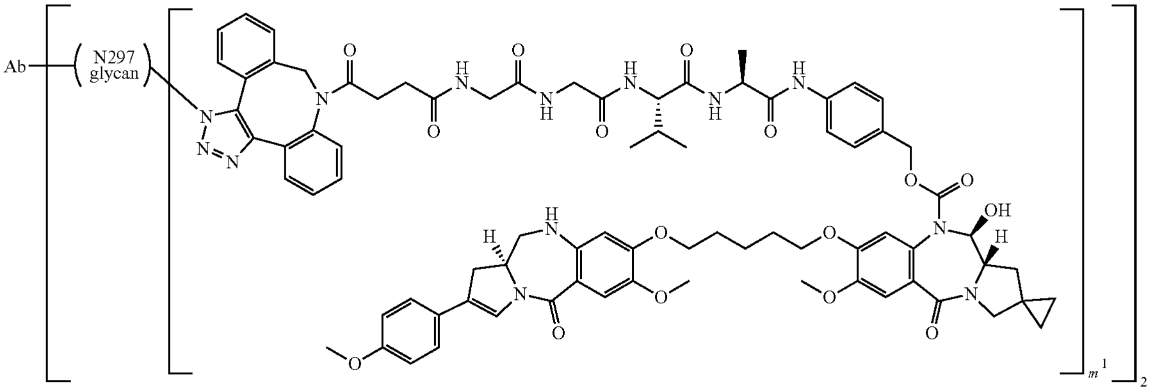
or
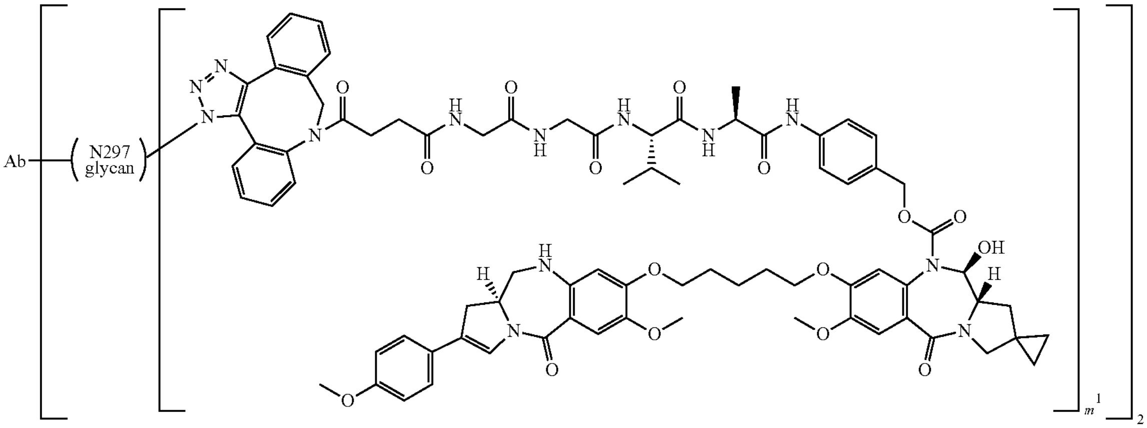
[Formula 37]
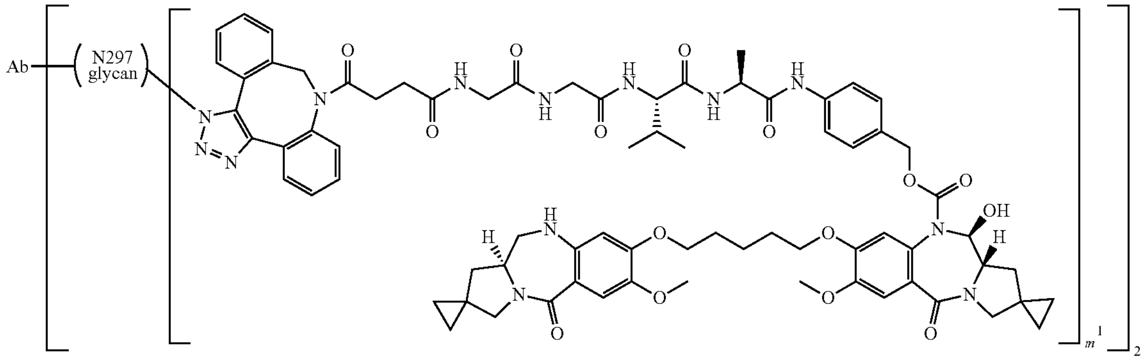
or
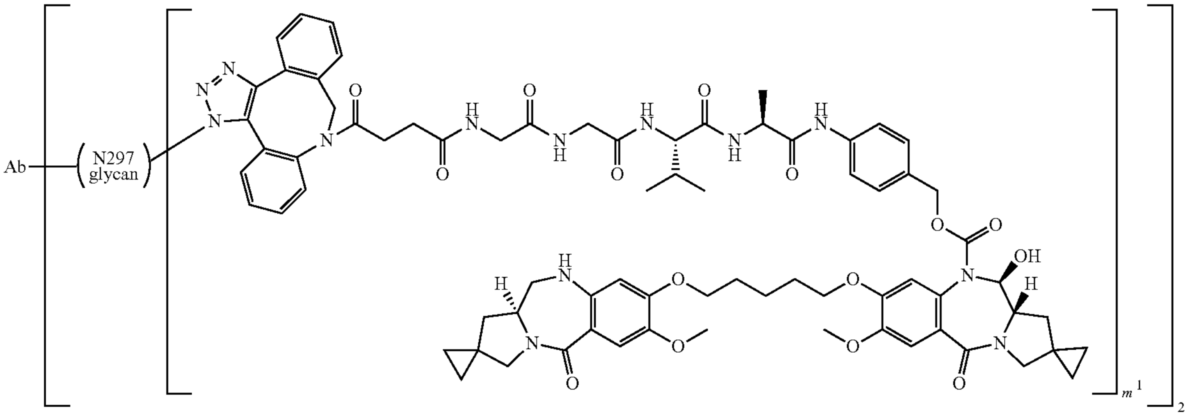

-continued
[Formula 38]
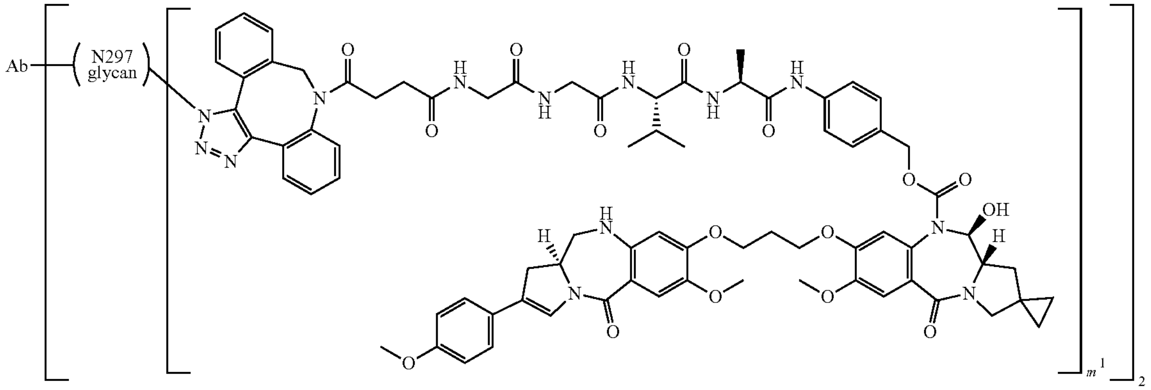
or
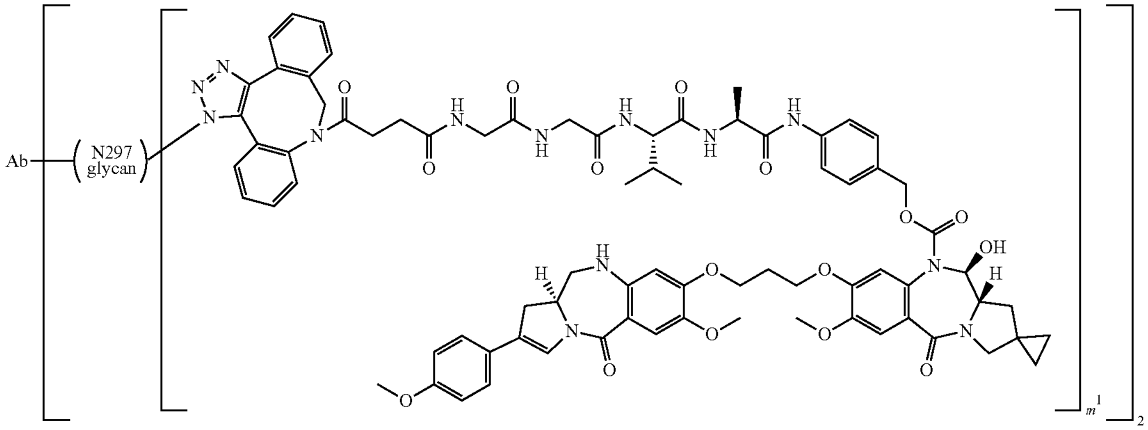
[Formula 39]
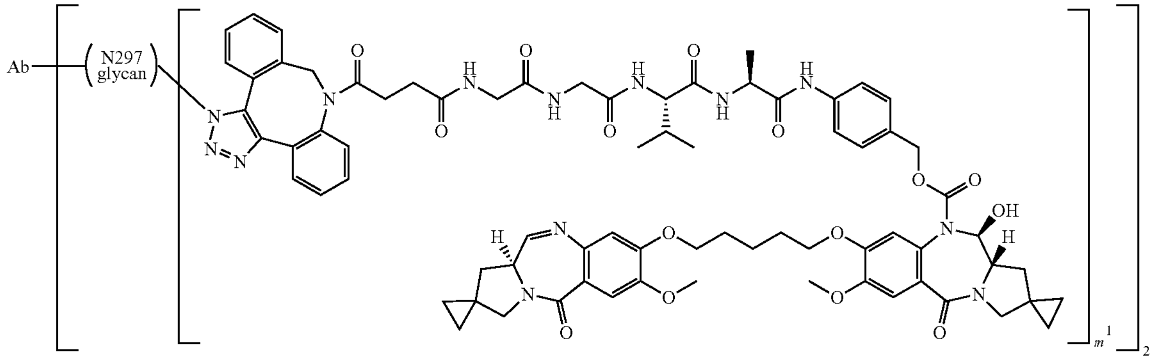
or
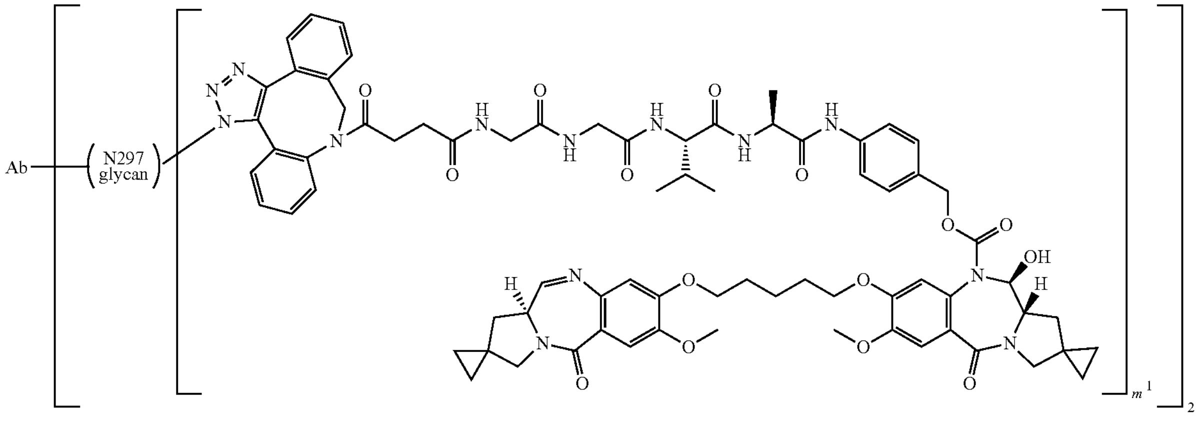

In each of the structural formulas above, $m^1$ represents an integer of 1 or 2 (preferably, $m^1$ is an integer of 1), antibody Ab represents an anti-CLDN6 antibody, an anti-CLDN9 antibody, an anti-CLDN6/CLDN9 antibody, an anti-HER2 antibody, an anti-HER3 antibody, an anti-DLL3 antibody, an anti-FAP antibody, an anti-CDH11 antibody, an anti-A33 antibody, an anti-CanAg antibody, an anti-CD19 antibody, an anti-CD20 antibody, an anti-CD22 antibody, an anti-CD25 antibody, an anti-CD30 antibody, an anti-CD33 antibody, an anti-CD37 antibody, an anti-CD56 antibody, an anti-CD70 antibody, an anti-CD98 antibody, an anti-B7-H3 antibody, an anti-TROP2 antibody, an anti-CEA antibody, an anti-Cripto antibody, an anti-EphA2 antibody, an anti-FGFR2 antibody, an anti-G250 antibody, an anti-MUC1 antibody, an anti-GPNMB antibody, an anti-Integrin antibody, an anti-PSMA antibody, an anti-Tenascin-C antibody, an anti-SLC44A4 antibody, an anti-Mesothelin antibody, an anti-EGFR antibody, an anti-5T4 antibody, an anti-LRRC15 antibody, an anti-DR5 antibody, an anti-CDH3 antibody, an anti-PDPN antibody, or an anti-CD123 antibody (preferably, the anti-CLDN6 antibody or anti-HER2 antibody), N297 glycan represents any one of N297-(Fuc)MSG1, N297-(Fuc)MSG2, and a mixture of them, and N297-(Fuc)SG (preferably, N297-(Fuc)MSG1), L(PEG) represents $*—(CH_2CH_2—O)_3—CH_2CH_2—NH—$, wherein the amino group at the right end represents bonding via an amide bond to carboxylic acid at the 2-position of a sialic acid at the non-reducing terminal of each or either one of the 1-3 and 1-6 branched chains (preferably, the 1-3 branched chains) of β-Man in N297 glycan, and the asterisk at the left end represents bonding to a nitrogen atom at the 1- or 3-position of the triazole ring in the structural formula.

Although structures with two or four units ($m^{2=1}$ or 2) of "-(N297 glycan)-L-D" in each of which N297 glycan bonds to the nitrogen atom at the 1-position of the triazole ring of Lb in L in one conjugate molecule ("(N297 glycan)-(N1Lb) L-D") or structures with two or four units ($m^{2=1}$ or 2) of "-(N297 glycan)-L-D" in each of which N297 glycan bonds to the nitrogen atom at the 3-position of the triazole ring of Lb in L in one conjugate molecule ("(N297 glycan)-(N3Lb) L-D") are illustrated as the most preferred antibody-drug conjugate for convenience, antibody-drug conjugates having both "(N297 glycan)-(N1Lb) L-D" (if $m^{2=1}$, then one unit, if $m^{2=2}$, then one, two, or three units) and "(N297 glycan)-(N3Lb) L-D" (if $m^{2=1}$, then one unit, if $m^{2=2}$, then three, two, or one unit) in one conjugate molecule are also included. In other words, either one of "(N297 glycan)-(N1Lb) L-D" and "(N297 glycan)-(N3Lb) L-D" exists or both of them coexist in one conjugate molecule.

There may exist stereoisomers, optical isomers due to an asymmetric carbon atom, geometric isomers, tautomers, or optical isomers such as d-forms, I-forms and atropisomers for the antibody-drug conjugate of the present invention, and a free drug or production intermediate of the antibody-drug conjugate, and these isomers, optical isomers, and mixtures of them are all included in the present invention.

The antibody-drug conjugate of the present invention exhibits strong tumor activity (in vivo antitumor activity, in vitro anticellular activity) and satisfactory in vivo kinetics and physical properties, and has high safety, and hence is useful as a pharmaceutical.

The number of conjugated drug molecules per antibody molecule is an important factor having influence on efficacy and safety for the antibody-drug conjugate of the present invention. Antibody-drug conjugates are produced with reaction conditions, such as the amounts of raw materials and reagents to be reacted, specified so as to give a constant number of conjugated drug molecules, but, in contrast to chemical reaction of low-molecular-weight compounds, a mixture with different numbers of conjugated drug molecules is typically obtained. Numbers of conjugated drug molecules per antibody molecule are specified as the average value, namely, the average number of conjugated drug molecules (DAR: Drug to Antibody Ratio). The number of pyrrolobenzodiazepine derivative molecules conjugated to an antibody molecule is controllable, and 1 to 10 pyrrolobenzodiazepine derivative molecules can be conjugated as the average number of conjugated drug molecules per antibody molecule (DAR), but preferably the number is one to eight, and more preferably one to five.

If the antibody bonds via a remodeled glycan of the antibody to L in the antibody-drug conjugate of the present invention, the number of conjugated drug molecules per antibody molecule in the antibody-drug conjugate, $m^2$, is an integer of 1 or 2. If the glycan is N297 glycan and the glycan is N297-(Fuc)MSG1, N297-(Fuc)MSG2, or a mixture of N297-(Fuc)MSG1 and N297-(Fuc)MSG2, $m^2$ is 1, and DAR is in the range of 1 to 3 (preferably, in the range of 1.0 to 2.5, more preferably, in the range of 1.2 to 2.2, or 1.6 to 2.2). If the N297 glycan is N297-(Fuc)SG, $m^2$ is 2, and DAR is in the range of 3 to 5 (preferably, in the range of 3.2 to 4.8, more preferably, in the range of 3.5 to 4.2).

Those skilled in the art could engineer the reaction method to conjugate a required number of drug molecules to each antibody molecule on the basis of the description in Examples herein, and obtain an antibody with a controlled number of conjugated pyrrolobenzodiazepine derivative molecules.

The antibody-drug conjugate, free drug, or production intermediate of the present invention may absorb moisture, allow adhesion of adsorbed water, or become a hydrate when being left to stand in the atmosphere or recrystallized, and such compounds and salts containing water are also included in the present invention.

The antibody-drug conjugate, free drug, or production intermediate of the present invention may be converted into a pharmaceutically acceptable salt, as desired, if it has a basic group such as an amino group. Examples of such salts may include, but are not limited to, hydrohalic acid salts such as hydrochlorides and hydroiodides; inorganic acid salts such as nitrates, perchlorates, sulfates, and phosphates; lower alkanesulfonates such as methanesulfonates, trifluoromethanesulfonates, and ethanesulfonates; arylsufonates such as benzenesulfonates and p-toluenesulfonates; organic acid salts such as formates, acetates, malates, fumarates, succinates, citrates, tartrates, oxalates, and maleates; and amino acid salts such as ornithinates, glutamates, and aspartates.

If the antibody-drug conjugate, free drug, or production intermediate of the present invention has an acidic group such as a carboxy group, a base addition salt can be generally formed. Examples of pharmaceutical acceptable salts may include, but are not limited to, alkali metal salts such as sodium salts, potassium salts, and lithium salts; alkali earth metal salts such as calcium salts and magnesium salts; inorganic salts such as ammonium salts; and organic amine salts such as dibenzylamine salts, morpholine salts, phenylglycine alkyl ester salts, ethylenediamine salts, N-methylglucamates, diethylamine salts, triethylamine salts, cyclohexylamine salts, dicyclohexylamine salts, N,N'- dibenzylethylenediamine salts, diethanolamine salts, N-benzyl-N-(2-phenylethoxy) amine salts, piperazine salts, tetramethylammonium salts, and tris(hydroxymethyl)aminomethane salts.

The antibody-drug conjugate, free drug, or production intermediate of the present invention may exist as a hydrate, for example, by absorbing moisture in the air. The solvate of the present invention is not limited to a particular solvate and may be any pharmaceutically acceptable solvate, and specifically hydrates, ethanol solvates, 2-propanol solvates, and so on are preferred. The antibody-drug conjugate, free drug, or production intermediate of the present invention may be its N-oxide form if a nitrogen atom is present therein. These solvates and N-oxide forms are included in the scope of the present invention.

The present invention includes compounds labeled with various radioactive or nonradioactive isotopes. The antibody-drug conjugate, free drug, or production intermediate of the present invention may contain one or more constituent atoms with non-natural ratios of atomic isotopes. Examples of atomic isotopes may include, but are not limited to, deuterium ($^2H$), tritium ($^3H$), iodine-125 ($^{125}I$), and carbon-14 ($^{14}C$).

The compound of the present invention may be radiolabeled with a radioactive isotope such as tritium ($^3H$), iodine-125 ($^{125}I$), and carbon-14 ($^{14}C$). The radiolabeled compound is useful as a therapeutic or prophylactic agent, a reagent for research such as an assay reagent, and a diagnostic agent such as a diagnostic agent for in vivo imaging. Isotopic variants of the antibody-drug conjugate of the present invention are all included in the scope of the present invention, regardless of whether they are radioactive or not.

[Production Methods]

Scheme R: Preparation of Antibody

A glycan-remodeled antibody may be produced by using a method as illustrated in FIG. 3, for example, according to a method described in WO 2013/120066.

In preparing the glycan-remodeled antibody, concentration of an aqueous solution of an antibody, measurement of concentration, and buffer exchange may be carried out according to common operations A to C in the following.

(Common Operation A: Concentration of Aqueous Solution of Antibody)

A solution of an antibody or antibody-drug conjugate was placed in a container of an Amicon Ultra (30,000 to 50,000 MWCO, Millipore Corporation), and the solution of an antibody or antibody-drug conjugate, which is described later, was concentrated through a centrifugation operation (centrifugation at 2000 G to 4000 G for 5 to 20 minutes) using a centrifuge (Allegra X-15R, Beckman Coulter, Inc.).

(Common Operation B: Measurement of Antibody Concentration)

Measurement of antibody concentration was carried out by using a UV measurement apparatus (Nanodrop 1000, Thermo Fisher Scientific Inc.) according to a method specified by the manufacturer. Then, 280 nm absorption coefficients, being different among antibodies (1.3 mL mg-1 cm-1 to 1.8 mL mg-1 cm-1), were used.

(Common Operation C: Buffer Exchange for Antibody)

A buffer solution (e.g., phosphate buffered saline (pH 6.0), phosphate buffer (pH 6.0)) was added to an aqueous solution of an antibody, which was concentrated according to common operation A. This operation was carried out several times, and the antibody concentration was then measured by using common operation B, and adjusted to 10 mg/mL with a buffer solution (e.g., phosphate buffered saline (pH 6.0), phosphate buffer (pH 6.0)).

Scheme S: Conjugation

The production method is a method for producing an antibody-drug conjugate by conjugating the above-described glycan-remodeled antibody to production intermediate (2) through SPAAC reaction (strain-promoted alkyne azide cycloaddition: JACS. 2004, 126, 15046-15047).

[Formula 40]

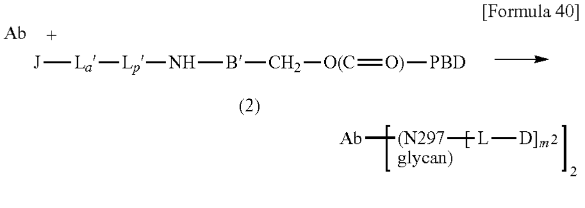

In the formula, Ab represents the glycan-remodeled antibody,

La', Lp', B', and $m^2$ are synonymous with La, Lp, B, and $m^1$, respectively,

J represents any one of the following structures, wherein each asterisk * represents bonding to La'.

[Formula 41]

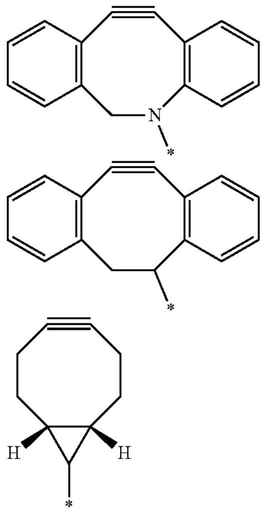

J-La'-Lp'—NH—B'—$CH_2$—O(C═O)-PBD can be synthesized, for example, by using any of methods described in Examples 2-1 to 2-6.

SPAAC reaction proceeds by mixing a buffer solution (sodium acetate solution, sodium phosphate, sodium borate solution, or the like, or a mixture thereof) of antibody Ab and a solution dissolving compound (2) in an appropriate solvent (dimethyl sulfoxide (DMSO), dimethylformamide (DMF), dimethylacetamide (DMA), N-methyl-2-pyridone (NMP), propylene glycol (PG), or the like, or a mixture thereof).

The amount of moles of compound (2) to be used is 2 mol to an excessive amount of moles, preferably 1 mol to 30 mol, per mole of the antibody, and the ratio of the organic solvent is preferably 1 to 200% v/v to the buffer of the antibody. The reaction temperature is 0° C. to 37° C., and preferably 10° C. to 25° C., and the reaction time is 1 to 150 hours, and preferably 6 hours to 100 hours. The pH in the reaction is preferably 5 to 9.

Antibody-drug conjugate compounds (ADCs) can be identified from each other through buffer exchange, purification, and measurement of antibody concentration and average number of conjugated drug molecules per antibody molecule according to common operations A to C described above and common operations D to F described later.

Common Operation D: Purification of Antibody-Drug Conjugate

An NAP-25 column was equilibrated with acetic acid buffer solution (10 mM, pH 5.5; herein, referred to as ABS) containing commercially available sorbitol (5%). To this NAP-25 column, an aqueous reaction solution of an antibody-drug conjugate (about 1.5 to 2.5 mL) was applied, and eluted with a buffer in an amount specified by the manufacturer to separate and collect an antibody fraction. The fraction separated and collected was again applied to the NAP-25 column, and a gel filtration purification operation to elute with a buffer was repeated twice or three times in total to afford the antibody-drug conjugate with an unbound drug-linker, dimethyl sulfoxide, and propylene glycol removed. As necessary, the concentration of the solution of the antibody-drug conjugate was adjusted through common operations A to C.

Common Operation E: Measurement of Antibody Concentration of Antibody-Drug Conjugate The concentration of the conjugated drug in an antibody-drug conjugate can be calculated by using the Lambert-Beer's law shown below. Expression (I) using the Lambert-Beer's law is as follows.

[Expression 1]

$$\underset{\text{Absorbance}}{A_{280}} = \underset{\text{Molar absorption coefficient} \times \text{Molarity} \times \text{Optical path length}}{\varepsilon_{280}(L\cdot\text{mol}^{-1}\cdot\text{cm}^{-1})\cdot C(\text{mol}\cdot L^{-1})\cdot l(\text{cm})} \quad \text{Expression(I)}$$

Here, A280 denotes absorbance of an aqueous solution of an antibody-drug conjugate at 280 nm, ¿280 denotes the molar absorption coefficient of an antibody-drug conjugate at 280 nm, and C (mol·L-1) denotes the molarity of an antibody-drug conjugate. From expression (I), the molarity of an antibody-drug conjugate, C (mol·L'1), can be determined by using expression (II) below.

[Expression 2]

$$C(\text{mol}\cdot L^{-1}) = \frac{A_{280}}{\varepsilon_{280}(L\cdot\text{mol}^{-1}\cdot\text{cm}^{-1})\cdot \text{l}(\text{cm})} \quad \text{Expression (II)}$$

Further, the both sides are multiplied by the molar mass of the antibody-drug conjugate, MW (g·mol-1), to determine the weight concentration of the antibody-drug conjugate, C' (mg·mL-1) (expression (III)).

[Expression 3]

$$C'(\text{mg}\cdot\text{mL}^{-1}) = MW(g\cdot\text{mol}^{-1})\cdot C(\text{mol}\cdot L^{-1}) = \frac{A_{280}\cdot MW(g\cdot\text{mol}^{-1})}{\varepsilon_{280}(L\cdot\text{mol}^{-1}\cdot\text{cm}^{-1})\cdot l(\text{cm})} \quad \text{Expression(III)}$$

Values used for the expression and applied to Examples will be described.

The absorbance A280 used was a measured value of UV absorbance of an aqueous solution of an antibody-drug conjugate at 280 nm. For molar mass, MW (g·mol-1), an estimated value of the molecular weight of an antibody was calculated from the amino acid sequence of the antibody, and used as an approximate value of the molar mass of an antibody-drug conjugate. The optical path length, 1 (cm), used in measurement was 1 cm.

The molar absorption coefficient, ¿280, of the antibody-drug conjugate can be determined by using expression (IV) below.

[Expression 4]

$$\varepsilon_{280} = \underset{\text{Coefficient of antibody}}{\text{Molar absorption}}\ \varepsilon_{Ab,280} + \underset{\text{Coefficient of drug}}{\text{Molar absorption}}\ \varepsilon_{DL,280} \times \underset{\text{drug molecules}}{\text{Number of conjugated}} \quad \text{Expression (IV)}$$

Here, $\varepsilon_{Ab}$, 280 denotes the molar absorption coefficient of an antibody at 280 nm, and $\varepsilon_{DL,\ 280}$ denotes the molar absorption coefficient of a drug at 280 nm.

By using a known calculation method (Protein Science, 1995, vol. 4, 2411-2423), $\varepsilon_{Ab}$, 280 can be estimated from the amino acid sequence of an antibody. In Examples, the molar absorption coefficient of trastuzumab used was $\varepsilon_{Ab,\ 280}$=215400 (calculated estimated value). The molar absorption coefficient of the CLDN6 antibody used was $\varepsilon_{Ab,\ 280}$=221340 (calculated estimated value), the molar absorption coefficient of the TROP2 antibody used was $\varepsilon_{Ab,\ 280}$=226400 (calculated estimated value), the molar absorption coefficient of the CD98 antibody used was $\varepsilon_{Ab}$, 280-240400 (calculated estimated value), the molar absorption coefficient of the LPS antibody used was $\varepsilon_{Ab,\ 280}$=230300 (calculated estimated value), and the molar absorption coefficient of the trastuzumab variant used was $\varepsilon_{Ab,\ 280}$=215057 (calculated estimated value).

$\varepsilon_{DL,\ 280}$ was calculated for use from a measured value obtained in each UV measurement. Specifically, the absorbance of a solution dissolving a conjugate precursor (drug) with a certain molarity was measured, and expression (I), the Lambert-Beer's law, was applied thereto, and the resulting value was used.

Common Operation F: Measurement of Average Number of Conjugated Drug Molecules Per Antibody Molecule in Antibody-Drug Conjugate The average number of conjugated drug molecules per antibody molecule in an antibody-drug conjugate can be determined through high-performance liquid chromatography (HPLC) with the following method.

[F-1. Preparation of Sample for HPLC Analysis (Reduction of Antibody-Drug Conjugate)]

A solution of an antibody-drug conjugate (about 1 mg/mL, 60 μL) is mixed with an aqueous solution of dithiothreitol (DTT) (100 mM, 15 μL). The mixture is incubated at 37° C. for 30 minutes to prepare a sample in which the disulfide bond between the L chain and H chain of the antibody-drug conjugate cleaved, and this sample is used for HPLC analysis.

[F-2. HLPC Analysis]

HPLC analysis is carried out under the following conditions.

HPLC system: Agilent 1290 HPLC system (Agilent Technologies) Detector: Ultraviolet absorption spectrometer (measurement wavelength: 280 nm, 329 nm)

Column: BEH Phenyl (2.1×50 mm, 1.7 μm, Waters Acquity) Column temperature: 75° C.

Mobile phase A: 0.1% trifluoroacetic acid (TFA)-15% isopropyl alcohol aqueous solution
Mobile phase B: 0.075% TFA-15% isopropyl alcohol acetonitrile solution
Gradient program: 14%-36% (0 min to 15 min), 36%-80% (15 min to 17 min), 80%-14% (17 min to 17.1 min), 14%-14% (17.1 min to 23 min)
Sample injection volume: 5 μL

[F-3. Data Analysis]

[F-3-1] An H chain with a conjugated drug molecule(s) (H chain with one conjugated drug molecule: $H_1$, H chain with two conjugated drug molecules: $H_2$) have hydrophobicity increased in proportion to the number of conjugated drug molecules and have longer retention time as compared to the L chain ($L_0$) and H chain ($H_0$) of an antibody without any conjugated drug molecule, and hence $L_0$, $H_0$, $H_1$, and $H_2$, are eluted in the presented order. Through comparison of retention time, each peak detected can be assigned to $L_0$, $H_0$, $H_1$, or $H_2$. In addition, conjugation of the drug can be confirmed via absorption at a wavelength of 329 nm, which is characteristic to the drug.

[F-3-2] Since each drug-linker absorbs UV, peak area values are corrected by using the following expression with the molar absorption coefficients of an L chain, H chain, and drug-linker according to the number of conjugated drug-linker molecules.

[Expression 5]

$$\text{Corrected } H \text{ chain peak area } (Hi) = \text{Peak area} \times \frac{\text{Molar absorption coefficient of } H \text{ chain}}{\text{Molar absorption coefficient of } H \text{ chain} + \text{Number of conjugated drug molecules} \times \text{Molar absorption coefficient of drug-linker}}$$

Here, for the molar absorption coefficients (280 nm) of the L chain and H chain of each antibody, values estimated from the amino acid sequences of the L chain and H chain of the antibody by using a known calculation method (Protein Science, 1995, vol. 4, 2411-2423) may be used. In the case of trastuzumab, 81290 was used as the molar absorption coefficient of the H chain estimated from the amino acid sequence. In the case of the CLDN6 antibody, similarly, 77280 was used as the molar absorption coefficient of the H chain; in the case of the TROP2 antibody, 68990 was used as the molar absorption coefficient of the H chain; in the case of the CD98 antibody, 78500 was used as the molar absorption coefficient of the H chain; in the case of the LPS antibody, 77470 was used as the molar absorption coefficient of the H chain; in the case of the trastuzumab variant, 81488 was used as the molar absorption coefficient of the H chain; and the molar absorption coefficient (280 nm) measured for compound (1), as a conjugate precursor, was used as the molar absorption coefficient (280 nm) of each drug-linker.

[F-3-3] The peak area ratio (%) of each chain to the total of corrected peak areas is calculated by using the following expression.

[Expression 6]

$$H \text{ chain peak area ratio} = \frac{A_{Hi}}{A_{H0} + A_{H1} + A_{H2}} \times 100$$

$A_{Hi}$ : $Hi$ corrected peak area

[F-3-4] The average number of conjugated drug molecules per antibody molecule in an antibody-drug conjugate is calculated by using the following expression.

[Expression 7]

$$\text{Average number of conjugated drug molecules} = (H_0 \text{ peak area ratio} \times 0 + H_1 \text{ peak area ratio} \times 1 + H_2 \text{ peak area ratio} \times 2) / 100 \times 2$$

2. PARP Inhibitor

In the present invention, a "PARP inhibitor" refers to an agent having a function to interfere with repair of single-strand breaks by inhibiting PARP (poly adenosine 5' diphosphate (ADP) ribose polymerase) (Benafif S, et al., Onco. Targets Ther. (2015) 8, 519-528.) (Fong P C, et al., N. Engl. J. Med. (2009) 361, 123-134.) (Gelmon K A, et al., Lancet Oncol. (2011) 12, 852-861.). There are multiple subtypes of PARP, and the PARP inhibitor in the present invention preferably inhibits PARP-1 and PARP-2. There is no limitation to the PARP inhibitor in the present invention as long as the PARP inhibitor is an agent having a function to interfere with repair of single-strand breaks by inhibiting PARP, but preferred examples of the PARP inhibitor may include, but not limited to, olaparib (Menear K A, et al., J. Med. Chem. (2008) 51, 6581-6591.), rucaparib (Gillmore A T, et al., Org. Process Res. Dev. (2012) 16, 1897-1904.), niraparib (Jones P, et al., J. Med. Chem. (2009) 52, 7170-7185.), talazoparib (Shen Y, et al., Clin. Cancer Res. (2013) 19 (18), 5003-15.), veliparib, pamiparib, and fluzoparib, and pharmacologically acceptable salts of them, and olaparib, rucaparib, niraparib, and talazoparib, and pharmacologically acceptable salts of them can be more preferably exemplified.

The "pharmacologically acceptable salt" of the PARP inhibitor in the present invention may be any of an acid addition salt and a base addition salt, but is preferably an acid addition salt, and examples thereof may include, lower alkanesulfonates such as camsilates (camphorsulfonates), methanesulfonates, trifluoromethanesulfonates, and ethanesulfonates; arylsulfonates such as tosilates (p-toluenesulfonates) and benzenesulfonates; inorganic acid salts such as phosphates, nitrates, perchlorates, and sulfates; hydrogen halide salts such as hydrochlorides, hydrobromides, hydroiodides, and hydrofluorides; organic acid salts such as acetates, malates, fumarates, succinates, citrates, tartrates, oxalates, and maleates; and amino acid salts such as ornithinates, glutamates, and aspartates.

The PARP inhibitor and pharmacologically acceptable salt thereof may exist as a solvate, and such a solvate is included in the scope of the PARP inhibitor and pharmacologically acceptable salt thereof in the present invention.

3. Medicine

Hereinafter, the pharmaceutical composition and method of treatment (including prevention), wherein the antibody-drug conjugate and PARP inhibitor according to the present invention are administered in combination, will be described.

The pharmaceutical composition and method of treatment of the present invention may be characterized in that the antibody-drug conjugate and PARP inhibitor are individually contained as an active ingredient in separate formulations and administered simultaneously or at different times, or in that the antibody-drug conjugate and PARP inhibitor are contained as active ingredients in a single formulation and administered.

The pharmaceutical composition and method of treatment of the present invention can be used for treatment of cancer, and preferably for treatment of at least one selected from the group consisting of breast cancer, gastric cancer (also referred to as gastric adenocarcinoma), colorectal cancer (also referred to as colon and rectal cancer and including colon cancer and rectal cancer), lung cancer (including small cell lung cancer and non-small cell lung cancer), esophageal cancer, head-and-neck cancer (including salivary gland cancer and pharyngeal cancer), gastroesophageal junction adenocarcinoma, bile duct cancer (including biliary tract cancer), Paget's disease, pancreatic cancer, ovarian cancer, uterine carcinosarcoma, urothelial cancer, prostate cancer, bladder cancer, gastric and intestinal stromal tumor, gastrointestinal stromal tumor, uterine cervix cancer, squamous cell carcinoma, peritoneal cancer, liver cancer, hepatocellular cancer, endometrial cancer, kidney cancer, vulvar cancer, thyroid cancer, penis cancer, leukemia, malignant lymphoma, plasmacytoma, myeloma, glioblastoma multiforme, osteosarcoma, and melanoma, and more preferably used for treatment of at least one cancer selected from the group consisting of breast cancer, gastric cancer, colorectal cancer, lung cancer, esophageal cancer, salivary gland cancer, gastroesophageal junction adenocarcinoma, bile duct cancer, Paget's disease, pancreatic cancer, ovarian cancer, bladder cancer, prostate cancer, and uterine carcinosarcoma.

An antibody-drug conjugate having a particularly preferred antibody among antibody-drug conjugates used in the present invention can be determined by testing the type of cancer or tumor markers. Examples of the type of cancer to which the anti-CLDN6 antibody-drug conjugate of the present invention is applied may include lung cancer (e.g., non-small cell lung cancer, small cell lung cancer), kidney cancer, urothelial cancer, colorectal cancer, prostate cancer, glioblastoma multiforme, ovarian cancer (e.g., surface epithelial tumor, stromal tumor, germ cell tumor), pancreatic cancer, breast cancer, melanoma, liver cancer, bladder cancer, gastric cancer, esophageal cancer or the like, endometrial cancer, testicular cancer (seminoma, non-seminoma), uterine cervix cancer, placental choriocarcinoma, brain tumor, and head- and -neck cancer, and metastatic forms of them; examples of the type of cancer to which the anti-HER2 antibody-drug conjugate is applied may include lung cancer, urothelial cancer, colorectal cancer, prostate cancer, ovarian cancer, pancreatic cancer, breast cancer, bladder cancer, gastric cancer, gastric and intestinal stromal tumor, uterine cervix cancer, esophageal cancer, squamous cell carcinoma, peritoneal cancer, liver cancer, hepatocellular cancer, colon cancer, rectal cancer, colon and rectal cancer, endometrial cancer, uterine cancer, salivary gland cancer, kidney cancer, vulvar cancer, thyroid cancer, and penis cancer, and metastatic forms of them; however, there is no limitation thereto as long as cancer cells to be treated are expressing a protein recognizable to the antibody in the antibody-drug conjugate.

In some embodiments, the cancer is independent of a homologous recombination (HR)-dependent DNA double-strand break (DSB) repair pathway. Being independent of a DSB repair pathway means that the DSB repair pathway may be of wild type or mutated type (the function of HR is deleted or decreased). Examples of genes that can function in HR may include, BRCA1, BRCA2, BLM, RBBP8, DNA polymerase δ (POLD1 to 4), POLH, DNA2, EME1, ERCC1, EXO1, FANCM, GENI, MRE11, MUS81, NBS1, PALB2, PCNA, RAD50, RAD51, RAD51AP1, RAD51B, RAD51C, RAD51D, RAD54, RAD54B, RM11, RM12, RPA, RTEL1, SLX1, SLX2, SLX4, TOP2A, XPF, XRCC2, and XRCC3. The cancer is preferably independent of BRCA1 or BRCA2.

The antibody-drug conjugate and PARP inhibitor of the present invention exhibit cell growth-suppressing effect through being administered in combination, regardless of the presence or absence of mutation of the DSB repair pathway.

In certain embodiments, the cancer is insensitive to the PARP inhibitor, or the cancer is insensitive to the PARP inhibitor and independent of a homologous recombination (HR)-dependent DNA double-strand break (DSB) repair pathway.

Another embodiment is a pharmaceutical composition for treatment of cancer or a method for treating cancer, wherein an antibody-drug conjugate containing a PBD derivative that does not form any crosslink in minor grooves of DNA and a PARP inhibitor are administered in combination, and the cancer is insensitive to the PARP inhibitor, or independent of a homologous recombination (HR)-dependent DNA double-strand break (DSB) repair pathway, or insensitive to the PARP inhibitor and independent of a homologous recombination (HR)-dependent DNA double-strand break (DSB) repair pathway.

The pharmaceutical composition and method of treatment of the present invention can be preferably used for a mammal, and can be more preferably used for a human.

The antitumor effect of the pharmaceutical composition and method of treatment of the present invention can be confirmed by, for example, generating a model in which cancer cells are transplanted to a test animal, and measuring reduction in tumor volume or life-prolonging effects due to applying the pharmaceutical composition and method of treatment of the present invention. Furthermore, comparison with the antitumor effect of single administration of each of the antibody-drug conjugate and the PARP inhibitor used in the present invention can provide confirmation of the combined effect of the antibody-drug conjugate and the PARP inhibitor used in the present invention.

In addition, the antitumor effect of the pharmaceutical composition and method of treatment of the present invention can be confirmed, in a clinical study, with the Response Evaluation Criteria in Solid Tumors (RECIST) evaluation method, WHO's evaluation method, Macdonald's evaluation method, measurement of body weight, and other methods; and can be determined by indicators such as Complete response (CR), Partial response (PR), Progressive disease (PD), Objective response rate (ORR), Duration of response (DoR), Progression-free survival (PFS), and Overall survival (OS).

The foregoing methods can provide confirmation of superiority in terms of the antitumor effect of the pharmaceutical composition and method of treatment of the present invention compared to existing pharmaceutical compositions and methods of treatment for cancer therapy.

The pharmaceutical composition and method of treatment of the present invention can retard growth of cancer cells, suppress their proliferation, and further can kill cancer cells. These effects can allow cancer patients to be free from symptoms caused by cancer or can achieve an improvement in the QOL of cancer patients and attain a therapeutic effect by sustaining the lives of the cancer patients. Even if the pharmaceutical composition and method of treatment of the present invention do not accomplish the killing of cancer cells, they can achieve higher QOL of cancer patients while achieving longer-term survival, by suppressing or controlling the growth of cancer cells.

The pharmaceutical composition of the present invention can be expected to exert a therapeutic effect by application as systemic therapy to patients, and additionally, by local application to cancer tissues.

The pharmaceutical composition of the present invention may be administered as a pharmaceutical composition containing one or more pharmaceutically suitable ingredients. Such pharmaceutically suitable ingredients can be suitably selected and applied from formulation additives or the like that are generally used in the art, in view of the dosage, administration concentration, or the like of the antibody-drug conjugate and the PARP inhibitor used in the present invention. For example, the antibody-drug conjugate used in the present invention may be administered as a pharmaceutical composition containing a buffer such as histidine buffer, a vehicle such as sucrose and trehalose, and a surfactant such as Polysorbates 80 and 20. The pharmaceutical composition containing the antibody-drug conjugate used in the present invention can be preferably used as an injection, can be more preferably used as an aqueous injection or a lyophilized injection, and can be even more preferably used as a lyophilized injection.

In the case that the pharmaceutical composition containing the antibody-drug conjugate used in the present invention is an aqueous injection, the aqueous injection can be preferably diluted with a suitable diluent and then administered as an intravenous infusion. For the diluent, a dextrose solution, physiological saline, and the like, can be exemplified, and a dextrose solution can be preferably exemplified, and a 5% dextrose solution can be more preferably exemplified.

In the case that the pharmaceutical composition containing the antibody-drug conjugate used in the present invention is a lyophilized injection, it can be preferably dissolved in water for injection, subsequently a required amount can be diluted with a suitable diluent and then administered as an intravenous infusion. For the diluent, a dextrose solution, physiological saline, and the like, can be exemplified, and a dextrose solution can be preferably exemplified, and a 5% dextrose solution can be more preferably exemplified.

Examples of the administration route which may be used to administer the pharmaceutical composition of the present invention may include, intravenous, intradermal, subcutaneous, intramuscular, and intraperitoneal routes; and preferably may include an intravenous route.

The composition and concentration of the pharmaceutical composition may vary depending on the administration method. However, the antibody-drug conjugate contained in the pharmaceutical composition of the present invention can exhibit a pharmaceutical effect even at a small dosage when the antibody-drug conjugate has a higher affinity for an antigen, that is, a higher affinity (lower Kd value) in terms of the dissociation constant (Kd value) for the antigen. Thus, for determining the dosage of the antibody-drug conjugate, the dosage may be set in view of the situation relating to the affinity of the antibody-drug conjugate with the antigen. When the antibody-drug conjugate of the present invention is administered to a human, for example, about 0.001 to 100 mg/kg can be administered once or administered in several portions with intervals of 1 to 180 days.

The PARP inhibitor according to the present invention can be administered to a human once or twice at intervals of 1 to 7 days, and can be preferably administered once a day or twice per day. Also, the PARP inhibitor used in the present invention can be administered at a dose of 0.1 mg to 3000 mg, and can be preferably administered at a dose of 0.25 mg to 600 mg.

In the case that the PARP inhibitor used in the present invention is olaparib or a pharmacologically acceptable salt thereof, the PARP inhibitor can be preferably orally administered twice per day at a dose of 100 mg, 150 mg, 200 mg, or 300 mg.

In the case that the PARP inhibitor used in the present invention is rucaparib or a pharmacologically acceptable salt thereof, the PARP inhibitor can be preferably orally administered twice per day at a dose of 200 mg, 250 mg, 300 mg, 400 mg, 500 mg, or 600 mg.

In the case that the PARP inhibitor used in the present invention is niraparib or a pharmacologically acceptable salt thereof, the PARP inhibitor can be preferably orally administered once a day at a dose of 100 mg, 200 mg, or 300 mg.

In the case that the PARP inhibitor used in the present invention is talazoparib or a pharmacologically acceptable salt thereof, the PARP inhibitor can be preferably orally administered once a day at a dose of 0.25 mg, 0.5 mg, or 1 mg.

The pharmaceutical composition and method of treatment of the present invention may further include a cancer therapeutic agent other than the antibody-drug conjugate and PARP inhibitor according to the present invention. The pharmaceutical composition and method of treatment of the present invention can also be applied in combination with another cancer therapeutic agent, thereby enhancing the antitumor effect. Other cancer therapeutic agents to be used for such purpose may be administered to an individual simultaneously with, separately from, or subsequently to the pharmaceutical composition of the present invention, or may be administered with varying the dosage interval for each. Such cancer therapeutic agents are not limited as long as they are agents having antitumor activity, and can be exemplified by at least one selected from the group consisting of irinotecan (CPT-11), cisplatin, carboplatin, oxaliplatin, fluorouracil (5-FU), gemcitabine, capecitabine, doxorubicin, epirubicin, cyclophosphamide, mitomycin C, a tegafur-gimeracil-oteracil combination drug, cetuximab, panitumumab, bevacizumab, ramucirumab, regorafenib, a trifluridine-tipiracil combination drug, gefitinib, erlotinib, afatinib, methotrexate, pemetrexed, trastuzumab, pertuzumab, and lapatinib.

The pharmaceutical composition and method of treatment of the present invention can also be used in combination with radiotherapy. For example, a cancer patient receives radiotherapy before and/or after or simultaneously with receiving treatment with the pharmaceutical composition of the present invention.

The pharmaceutical composition and method of treatment of the present invention can also be used as adjuvant chemotherapy in combination with a surgical procedure. The pharmaceutical composition of the present invention may be administered for the purpose of diminishing the size of a tumor before a surgical procedure (referred to as pre-operative adjuvant chemotherapy or neoadjuvant therapy), or may be administered after a surgical procedure for the purpose of preventing the recurrence of a tumor (referred to as post-operative adjuvant chemotherapy or adjuvant therapy).

EXAMPLES

The present invention will be specifically described with reference to Examples shown below; however, the present invention is not limited to Examples. Examples should not be interpreted as limitation in any sense.

Reference Example 1: Anti-HER2 Antibody Trastuzumab

The anti-HER2 antibody was produced with reference to US $821337. The amino acid sequences of the light chain and heavy chain of trastuzumab are represented by SEQ ID NO: 64 and SEQ ID NO: 65, respectively.

Reference Example 2: Anti-TROP2 Antibody hRS7

The anti-TROP2 antibody was produced with reference to WO 2003/074566 and WO 2015/098099 (Reference Example 1). The amino acid sequences of the light chain and heavy chain of hRS7 are represented by SEQ ID NO: 68 and SEQ ID NO: 69, respectively.

[Synthesis of Production Intermediate (Drug-Linker)]

Example 1

Example 1-1: Intermediate 1

[Formula 42]

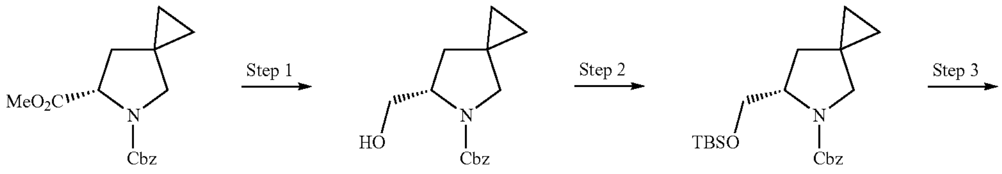

1-1 1-2 1-3

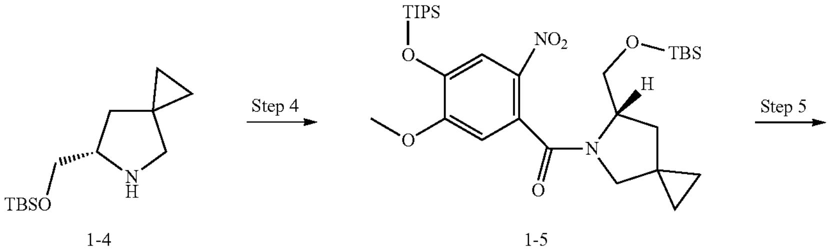

1-4 1-5

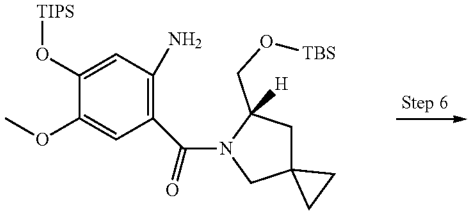

1-6

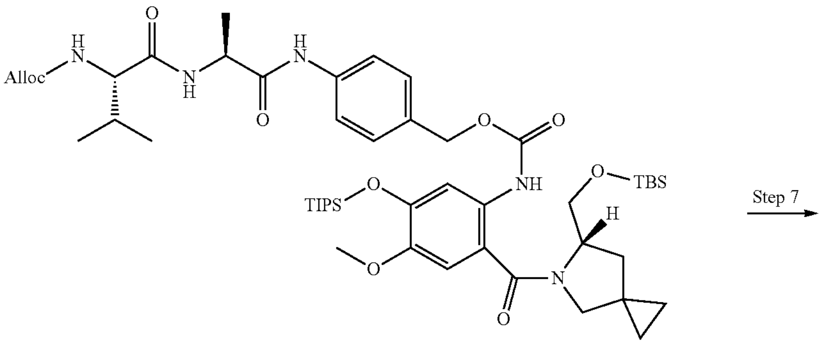

1-7

-continued

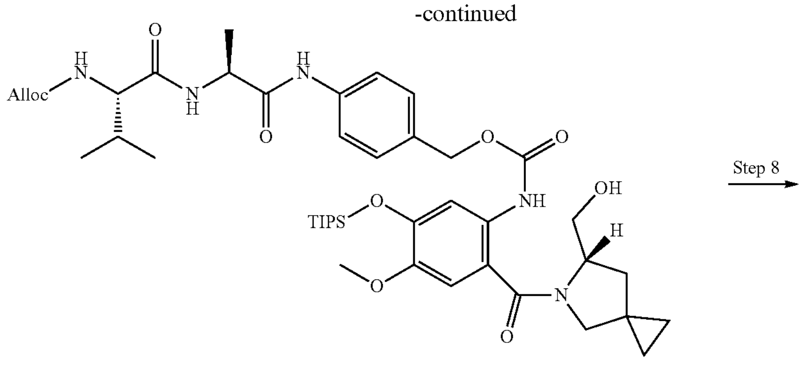

1-8

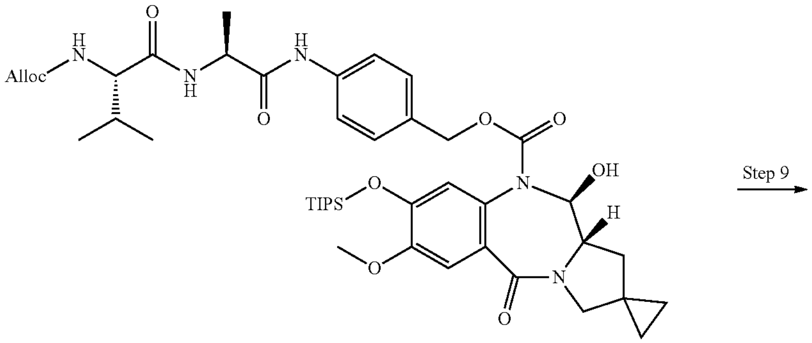

1-9

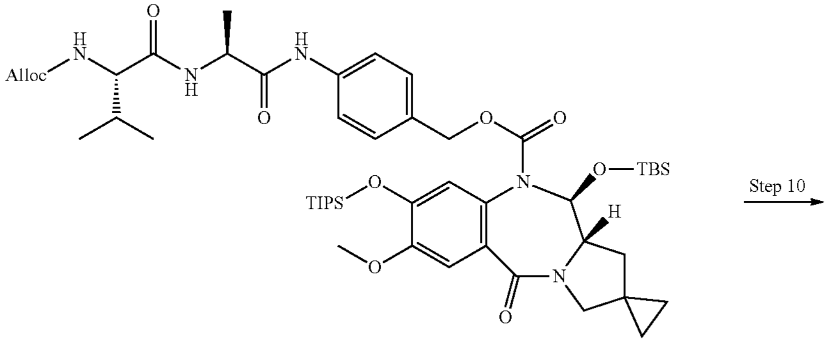

1-10

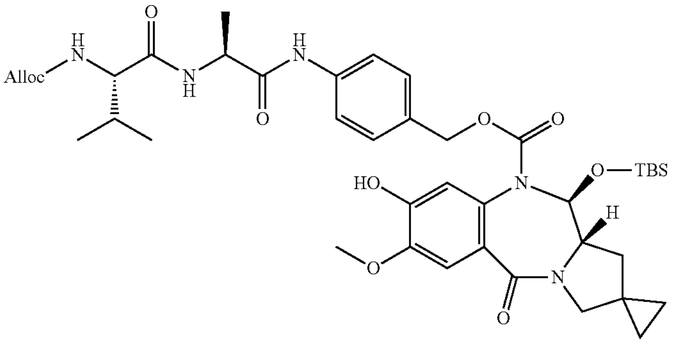

1-11

Step 1: Benzyl(6S)-6-(hydroxymethyl)-5-azaspiro[2.4]heptane-5-carboxylate (1-2)

To a solution of 5-benzyl 6-methyl(6S)-5-azaspiro[2.4]heptane-5,6-dicarboxylate (1-1) (104 mmol, WO 2012087596) in tetrahydrofuran (500 mL), lithium borohydride (4.30 g, 178 mmol) was added in small portions at 0° C. The resultant was stirred at 0° C. for 30 minutes, and then stirred at room temperature for 2 hours. Water (180 mL) and 2N hydrochloric acid (186 mL) were added at 0° C., and the resultant was distilled under reduced pressure. The resulting residue was extracted with ethyl acetate four times, and the organic layer was washed with brine and then dried over anhydrous sodium sulfate. The resultant was distillated under reduced pressure, and the resulting residue (1-2) (27.9 g, 90%) was directly used for the subsequent reaction.

Step 2: Benzyl(6S)-6-({[tert-butyl(dimethyl)silyl]oxy}methyl)-5-azaspiro[2.4]heptane-5-carboxylate (1-3)

To a solution of the compound (1-2) obtained in Step 1 (27.9 g, 107 mmol) and imidazole (14.5 g, 214 mmol) in dichloromethane (300 mL), tert-butyldimethylsilyl chloride (24.2 g, 160 mmol) was added at room temperature, and the resultant was stirred at room temperature for 18 hours. The reaction solution was washed with a saturated aqueous citric acid, a saturated aqueous sodium hydrogen carbonate, and brine, dried over anhydrous sodium sulfate, and then distillated under reduced pressure. The resulting residue was purified by silica gel column chromatography [hexane:ethyl acetate=100:0 (v/v) to 50:50 (v/v)] to afford the desired compound (1-3) (32.5 g, 81%).

$^1$H-NMR ($CDCl_3$) δ: 7.39-7.34 (5H, m), 5.23-5.11 (2H, m), 4.10-3.48 (4H, m), 3.16-3.14 (1H, m), 2.15-2.04 (1H, m), 1.81-1.77 (1H, m), 0.91-0.88 (9H, m), 0.65-0.55 (4H, m), 0.08-0.01 (6H, m).

MS (APCI) m/z: 376 $(M+H)^+$

Step 3: (6S)-6-({[tert-Butyl(dimethyl)silyl]oxy}methyl)-5-azaspiro[2.4]heptane (1-4)

To a solution of compound (1-3) obtained in Step 2 (32.5 g, 86.5 mmol) in ethanol (400 mL), 7.5% palladium carbon catalyst (moisture content: 54%, 5.00 g) was added at room temperature, and the resultant was stirred under the hydrogen atmosphere at room temperature for 6 hours. The reaction solution was filtered through a Celite, and the filtrate was distillated under reduced pressure to afford the desired compound (1-4) (21.3 g, quantitative).

$^1$H-NMR ($CDCl_3$) δ: 3.79-3.77 (1H, m), 3.71-3.69 (1H, m), 3.65-3.60 (1H, m), 3.01-2.98 (2H, m), 1.81-1.71 (2H, m), 0.90 (9H, s), 0.65-0.57 (4H, m), 0.08 (3H, s), 0.07 (3H, s). MS (APCI, ESI) m/z: 242 $(M+H)^+$

Step 4: [(6S)-6-({[tert-Butyl(dimethyl)silyl]oxy}methyl)-5-azaspiro[2.4]hept-5-yl] (5-methoxy-2-nitro-4-{[tri(propan-2-yl)silyl]oxy}phenyl)methanone (1-5)

To a solution of 5-methoxy-2-nitro-4-{tri(propan-2-yl)silyl]oxy}benzoic acid (52.2 g, 141 mmol, US20150283262) and 1-hydroxybenzotriazole monohydrate (23.8 g, 155 mmol) in dichloromethane (500 mL), N,N'-dicyclohexylcarbodiimide (35.0 g, 170 mmol) was added under ice-cooling. The reaction mixture was stirred at room temperature. After the carboxylic acid disappeared, a solution of compound (1-4) obtained in Step 3 (34.1 g, 141 mmol) and triethylamine (29.4 mL, 212 mmol) in dichloromethane (100 mL) was slowly added dropwise thereto. After the reaction solution was stirred at room temperature overnight, saturated aqueous sodium hydrogen carbonate was added to the reaction mixture, and the reaction mixture was extracted with chloroform. The organic layer was washed with water and brine, and dried over anhydrous magnesium sulfate. The resultant was distillated under reduced pressure, and to the resulting residue ethyl acetate and diethyl ether were added, and the solid contents were removed through filtration, and the filtrate was distillated under reduced pressure, and the resulting residue was purified by silica gel column chromatography [hexane:ethyl acetate=100:0 (v/v) to 25:75 (v/v)] to afford the desired compound (1-5) (55.0 g, 66%).

$^1$H-NMR ($CDCl_3$) δ: 7.72-7.66 (1H, m), 6.80-6.73 (1H, m), 4.53-4.49 (1H, m), 4.04-3.95 (1H, m), 3.91-3.88 (3H, m), 3.59-3.54 (1H, m), 3.36-3.25 (0.5H,m), 3.01-2.96 (1.5H, m), 2.24-2.20 (0.3H,m), 2.09-2.05 (0.7H,m), 2.00-1.97 (0.7H,m), 1.69-1.67 (0.3H,m), 1.32-1.24 (3H, m), 1.12-1.05 (18H, m), 0.93-0.91 (6H, m), 0.79-0.77 (3H, m), 0.71-0.62 (2H, m), 0.57-0.40 (2H, m), 0.12-0.10 (4H, m), 0.11-0.15 (2H, m). MS (APCI, ESI) m/z: 593 $(M+H)^+$

Step 5: (2-Amino-5-methoxy-4-{[tri(propan-2-yl)silyl]oxy}phenyl)[(6S)-6-({[tert-butyl(dimethyl)silyl]oxy}methyl)-5-azaspiro[2.4]hept-5-yl]methanone (1-6)

To a solution of compound (1-5) obtained in Step 4 (55.0 g, 92.8 mmol) in ethanol (300 mL), 7.5% palladium carbon (10.0 g) was added under the nitrogen atmosphere. The nitrogen balloon was immediately replaced with a hydrogen balloon, and the reaction mixture was vigorously stirred under the hydrogen atmosphere at room temperature. After the raw materials disappeared, the reaction mixture was filtered, and the filtrate was distillated under reduced pressure to afford the desired compound (1-6) (52.2 g, 100%), which was directly used for the subsequent reaction.

$^1$H-NMR ($CDCl_3$) δ: 6.71 (1H, s), 6.25 (1H, s), 4.55-4.28 (2H, m), 3.97 (1H, m), 3.75-3.62 (3H, m), 3.70 (3H, s), 3.09-3.07 (1H, m), 2.24-2.19 (1H, m), 1.81-1.68 (1H, m), 1.27-1.22 (3H, m), 1.09-1.05 (18H, m), 0.90 (9H, s), 0.65-0.46 (4H, m), 0.07-0.03 (6H, m). MS (APCI, ESI) m/z: 563 $(M+H)^+$

Step 6: N-[(Prop-2-en-1-yloxy)carbonyl]-L-valyl-N-[4-({[(2-{[(6S)-6-({[tert-butyl(dimethyl)silyl]oxy}methyl)-5-azaspiro[2.4]hept-5-yl]carbonyl}-4-methoxy-5-{[tri(propan-2-yl)silyl]oxy}phenyl)carbamoyl]oxy}methyl)phenyl]-L-alaninamide (1-7)

To a solution of compound (1-6) obtained in Step 5 (18.6 g, 33.0 mmol) and triethylamine (6.26 mL, 45.2 mmol) in THF (300 mL), triphosgene (4.22 g, 14.2 mmol) was slowly added on an ethanol-ice bath. After the addition, a mixed solution of N-[(prop-2-en-1-yloxy)carbonyl]-L-valyl-N-[4-(hydroxymethyl)phenyl]-L-alaninamide (11.4 g, 30.2 mmol, WO 2011130598) and triethylamine (6.26 mL, 45.2 mmol) in tetrahydrofuran (100 mL) and N,N-dimethylformamide (30 mL) was slowly added dropwise to the ice-cooled reaction mixture. After the dropwise addition, the ice bath was removed, and the reaction mixture was stirred under the nitrogen atmosphere at 40° C. After the raw materials disappeared, water was added to the reaction mixture, and the reaction mixture was extracted with ethyl acetate. The organic layer was washed with brine, and dried over anhydrous sodium sulfate. After filtration followed by distillation under reduced pressure, the resulting residue was purified by silica gel column chromatography [hexane:ethyl acetate=100:0 (v/v) to 40:60 (v/v)] to afford the desired compound (1-7) (23.5 g, 74%).

$^1$H-NMR ($CDCl_3$) δ: 8.99 (1H, m), 8.58 (1H, s), 7.80 (1H, s), 7.55-7.53 (2H, m), 7.34-7.32 (2H, m), 6.77-6.75 (2H, m), 5.94-5.87 (1H, m), 5.40-5.38 (1H, m), 5.33-5.29 (1H, m), 5.23-5.21 (1H, m), 5.13 (1H, m), 5.10 (2H, m), 4.69-4.64 (1H, m), 4.62-4.52 (2H, m), 4.06-4.03 (1H, m), 3.98 (1H, m), 3.76-3.65 (6H, m), 3.04 (1H, m), 2.28-2.26 (1H, m), 2.18-2.13 (1H, m), 1.46 (3H, m), 1.32-1.25 (3H, m), 1.11-1.09 (18H, m), 0.99-0.84 (15H, m), 0.65-0.40 (4H, m), 0.08-0.00 (6H, m).

MS (APCI, ESI) m/z: 966 $(M+H)^+$

Step 7: N-[(Prop-2-en-1-yloxy)carbonyl]-L-valyl-N-[4-({[(2-{[(6S)-6-(hydroxymethyl)-5-azaspiro[2.4]hept-5-yl]carbonyl}-4-methoxy-5-{[tri(propan-2-yl)silyl]oxy}phenyl)carbamoyl]oxy}methyl)phenyl]-L-alaninamide (1-8)

To a solution of compound (1-7) obtained in Step 6 (23.5 g, 24.3 mmol) in tetrahydrofuran (50 mL), methanol (50 mL) and water (44 mL), acetic acid (200 mL) was added at room temperature. The reaction mixture was stirred at room temperature. After the raw materials disappeared, the reaction mixture was extracted with ethyl acetate. The organic layer was washed with water and brine, and dried over anhydrous sodium sulfate. After filtration followed by distillation under reduced pressure, the resulting residue was purified by silica gel column chromatography [hexane:ethyl acetate=100:0 (v/v) to 0:100 (v/v)] to afford the desired compound (1-8) (18.0 g, 87%).

$^1$H-NMR ($CDCl_3$) δ: 8.64-8.62 (1H, m), 8.50 (1H, m), 7.69 (1H, m), 7.55-7.53 (2H, m), 7.34-7.32 (2H, m), 6.79-6.75 (3H, m), 5.91-5.89 (1H, m), 5.39 (1H, m), 5.32-5.29 (1H, m), 5.23-5.21 (1H, m), 4.68-4.54 (4H, m), 4.31 (1H, m), 4.06-4.04 (1H, m), 3.81-3.79 (3H, m), 3.76 (3H, s), 3.63-3.61 (1H, m), 3.13-3.11 (1H, m), 2.16-2.13 (1H, m), 1.87-1.81 (2H, m), 1.46-1.43 (3H, m), 1.30-1.24 (3H, m), 1.12-1.08 (18H, m), 0.98-0.91 (6H, m), 0.63-0.45 (4H, m).

MS (APCI, ESI) m/z: 852 $(M+H)^+$

Step 8: N-[(Prop-2-en-1-yloxy)carbonyl]-L-valyl-N-{4-[({[(11'S,11a'S)-11'-hydroxy-7'-methoxy-5'-oxo-8'-{[tri(propan-2-yl)silyl]oxy}-11',11a'-dihydro-1'H-spiro[cyclopropane-1,2'-pyrrolo[2,1-c][1,4]benzodiazepine]-10' (5'H)-yl]carbonyl}oxy)methyl]phenyl}-L-alaninamide (1-9)

To a solution of dimethyl sulfoxide (3.75 mL, 52.8 mmol) in dichloromethane (300 mL), oxalyl chloride (2.17 mL, 25.3 mmol) was slowly added dropwise under the nitrogen atmosphere at −78° C. After the dropwise addition, the reaction mixture was stirred at −78° C. A solution of compound (1-8) obtained in Step 7 (18.0 g, 21.1 mmol) in dichloromethane (50.0 mL) was slowly added to the reaction mixture.

Triethylamine (14.6 mL, 105 mmol) was added to the reaction solution at −78° C. After the addition, the refrigerant bath was removed, and the temperature was slowly raised to room temperature. After the raw materials disappeared, water was added to the reaction mixture, and the reaction mixture was extracted with chloroform (200 mL). The organic layer was washed with water and brine, and dried over anhydrous magnesium sulfate. After filtration followed by distillation under reduced pressure, the resulting residue was purified by silica gel column chromatography [hexane:ethyl acetate=100:0 (v/v) to 0:60 (v/v)] to afford the desired compound (1-9) (16.5 g, 92%).

$^1$H-NMR ($CDCl_3$) δ: 8.51-8.36 (1H, m), 7.54-7.38 (2H, m), 7.22-7.07 (3H, m), 6.73-6.64 (1H, m), 5.94-5.87 (2H, m), 5.33-5.22 (3H, m), 5.09 (1H, m), 4.97 (1H, m), 4.64-4.58 (4H, m), 4.02-4.00 (1H, m), 3.86-3.83 (3H, m), 3.75-3.70 (1H, m), 3.61-3.54 (2H, m), 3.38-3.29 (1H, m), 2.40 (1H, m), 2.16-2.14 (1H, m), 1.74-1.71 (1H, m), 1.44 (3H, m), 1.18-1.16 (3H, m), 1.05-1.00 (18H, m), 0.97-0.92 (6H, m), 0.72-0.60 (4H, m).

MS (APCI, ESI) m/z: 850 $(M+H)^+$

Step 9: N-[(Prop-2-en-1-yloxy)carbonyl]-L-valyl-N-{4-[({[(11'S,11a'S)-11'-{[tert-butyl(dimethyl)silyl]oxy}-7'-methoxy-5'-oxo-8'-{[tri(propan-2-yl)silyl]oxy}-11',11a'-dihydro-1'H-spiro[cyclopropane-1,2'-pyrrolo[2,1-c][1,4]benzodiazepine]-10' (5'H)-yl]carbonyl}oxy)methyl]phenyl}-L-alaninamide (1-10)

To a solution of compound (1-9) obtained in Step 8 (12.0 g, 14.1 mmol) and 2,6-lutidine (6.58 mL, 56.5 mmol) in dichloromethane (200 mL), tert-butyldimethylsilyl trifluoromethylsulfonate (9.73 mL, 42.3 mmol) was slowly added dropwise under the nitrogen atmosphere at 0° C. After stirring under ice-cooling for 10 minutes, the ice bath was removed, and stirring was performed at room temperature. After the raw materials disappeared, water was added to the reaction mixture, and the reaction mixture was extracted with chloroform, washed with water and brine, and dried over anhydrous sodium sulfate. After filtration followed by distillation under reduced pressure, the resulting residue was purified by silica gel column chromatography [hexane: ethyl acetate=100:0 (v/v) to 25:75 (v/v)] to afford the desired compound (1-10) (8.12 g, 60%).

$^1$H-NMR ($CDCl_3$) δ: 8.67-8.45 (1H, m), 7.50-7.44 (2H, m), 7.19 (1H, s), 7.13 (2H, m), 6.95 (2H, m), 6.62-6.57 (2H, m), 6.01 (1H, m), 5.95-5.86 (1H, m), 5.33-5.13 (3H, m), 4.82 (1H, m), 4.65-4.54 (3H, m), 4.03-4.01 (1H, m), 3.84-3.82 (3H, m), 3.73-3.66 (1H, m), 3.50-3.48 (1H, m), 3.27 (1H, m), 2.37-2.33 (1H, m), 2.19-2.13 (1H, m), 1.54-1.43 (3H, m), 1.22-1.13 (3H, m), 1.10-1.00 (18H, m), 0.97-. 0.91 (6H, m), 0.81 (9H, s), 0.76-0.59 (4H, m), 0.19--0.09 (6H, m).

MS (APCI, ESI) m/z: 964 $(M+H)^+$

Step 10: N-[(Prop-2-en-1-yloxy)carbonyl]-L-valyl-N-{4-[({[(11'S,11a'S)-11'-{[tert-butyl(dimethyl)silyl]oxy}-8'-hydroxy-7'-methoxy-5'-oxo-11',11a'-dihydro-1'H-spiro[cyclopropane-1,2'-pyrrolo[2,1-c][1,4]benzodiazepine]-10' (5'H)-yl]carbonyl}oxy)methyl]phenyl}-L-alaninamide (1-11)

To a solution of compound (1-10) obtained in Step 9 (8.12 g, 8.42 mmol) in N,N-dimethylformamide (90 mL) and water (2 mL), lithium acetate (0.611 g, 9.26 mmol) was added, and the resultant was stirred at room temperature. After the raw materials disappeared, water was added to the reaction mixture, and the reaction mixture was extracted with ethyl acetate. The organic layer was washed with water and brine, and dried over anhydrous sodium sulfate. After filtration followed by distillation under reduced pressure, the resulting residue was purified by silica gel column chromatography [hexane:ethyl acetate=100:0 (v/v) to 0:100 (v/v)] to afford the desired compound (1-11) (5.48 g, 81%).

$^1$H-NMR (400 MHz, $CDCl_3$, 20.9° C.) δ:8.76-8.60 (1H, m), 7.45-7.44 (2H, m), 7.21 (1H, s), 7.10-7.09 (2H, m), 6.81-6.74 (1H, m), 6.65 (1H, s), 6.23 (1H, s), 6.01-5.99 (1H, m), 5.95-5.84 (1H, m), 5.41-5.20 (2H, m), 5.16 (1H, m), 4.84 (1H, m), 4.67-4.54 (4H, m), 4.05-4.03 (1H, m), 3.87 (3H, s), 3.71 (1H, m), 3.55-3.51 (1H, m), 3.26 (1H, m), 2.35 (1H, m), 2.18-2.12 (1H, m), 1.55-1.42 (4H, m), 0.97-0.92 (6H, m), 0.81 (9H, s), 0.76-0.61 (4H, m), 0.20--0.06 (6H, m).

MS (APCI, ESI) m/z: 808 $(M+H)^+$ $^{1}$H-NMR (500 MHz, $CDCl_3$, 27° C.) δ: 8.76 (1H, s), 7.43 (2H, brd), 7.20 (1H, s), 7.08 (2H, d, J=8.3 Hz), 7.00 (1H, br), 6.66 (1H, s), 6.44 (1H, s), 6.00 (1H, H-11', d, J11', 11'a=9.2 Hz), 5.89 (1H, m), 5.53 (1H, brd), 5.30 (1H, d, J=17.2 Hz), 5.20 (1H, d, J=10.3 Hz), 5.15 (1H, d, JABq=12.5 Hz), 4.85 (1H, d, JABq=12.5 Hz), 4.66 (1H, m), 4.60-4.52 (2H, m), 4.07 (1H, m), 3.84 (3H, s), 3.71 (1H, H-3'B, d, Jgem=11.7 Hz), 3.53 (1H, H-11'a, m), 3.26 (1H, H-3'a, d, Jgem=11.7 Hz), 2.35 (1H, H-1'B, dd, J1| B, 11'a=8.30 Hz, Jgem=13.1 Hz), 2.14 (1H, m), 1.54 (1H, H-1' α, d, Jgem=13.1 Hz), 1.41 (3H, d, J=6.90 Hz), 0.95 (3H, d, J=6.80 Hz), 0.92 (3H, d, J=6.80 Hz), 0.81 (9H, s), 0.80-0.70 (1H, m), 0.70-0.59 (3H, m), 0.2-0.06 (6H, m)

The absolute steric configuration at the 11'-position of compound (1-11) was analyzed by correlation obtained from its selective 1D ROESY spectrum (a figure below). Correlation was found between 1'α-H and 11'-H, between 3'α-H and 11'-H, and between 1'β-H and 3'β-H, and thus the absolute steric configuration at the 11'-position was revealed to be S-configuration.

[Formula 43]

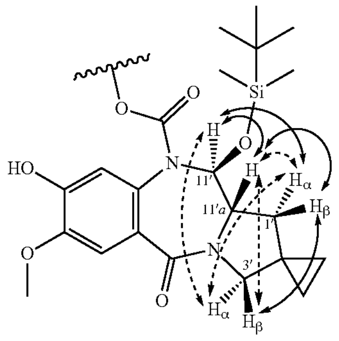

Key ROESY Correlation
(dashed: weak correlation)

Significant Correlation Obtained from Selective 1D ROESY Spectrum

Accordingly, the absolute steric configuration at the 11'-position of each of compound (1-11), compound (1-9) and compound (1-10), each of which had the same absolute steric configuration as compound (1-11), compound (3-11), which was synthesized with compound (1-11), compound (3-12), compound (3-13), and drug-linker 1 (compound (3-14)), compound (4-9), compound (4-10), compound (4-11), and drug-linker 2 (compound (4-12)), and compound (6-10), compound (6-11), compound (6-12), and drug-linker 4 (compound (6-13)) was revealed to be S-configuration. Further, the absolute steric configuration at the 11'-position of each of compound (5-9), compound (5-10), and drug-linker 3 (compound (5-11)), which were obtained by the same synthesis procedure, was determined to be S-configuration.

Example 1-2: Intermediate 2

[Formula 44]

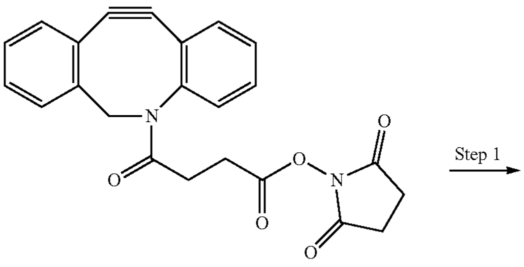

2-1

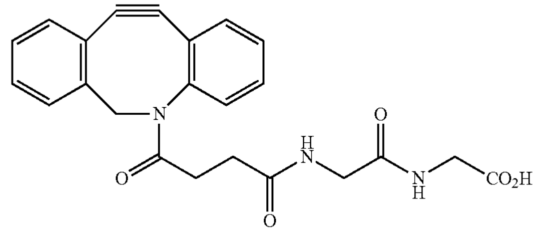

2-2

Step 1: N-[4-(11,12-Didehydrodibenzo[b,f]azocin-5 (6H)-yl))-4-oxobutanoyl]glycylglycine (2-2)

To a solution of glycylglycine (0.328 g, 2.49 mmol) and N,N-diisopropylethylamine (0.433 mL, 2.49 mmol) in N,N-dimethylformamide (20 mL), 1-{[4-(11,12-didehydrodibenzo[b,f]azocin-5 (6H)-yl))-4-oxobutanoyl]oxy}pyrrolidine-2,5-dione (2-1) (1.00 g, 2.49 mmol, Click Chemistry Tools) and water (10 mL) were added at room temperature, and the resultant was stirred at the same temperature overnight. The resultant was distilled under reduced pressure, and the resulting residue was purified by silica gel column chromatography [an organic layer for distribution with chloroform to chloroform:methanol:water=7:3:1 (v/v/v)] to afford the desired compound (0.930 g, 89%).

$^{1}$H-NMR (DMSO-$D_6$) δ: 12.58 (1H, s), 8.14-8.12 (1H, m), 8.08-8.07 (1H, m), 7.69-7.68 (1H, m), 7.62-7.61 (1H, m), 7.53-7.45 (3H, m), 7.40-7.29 (3H, m), 5.05-5.01 (1H, m), 3.73-3.72 (2H, m), 3.66-3.60 (3H, m), 2.66-2.60 (1H, m), 2.33-2.24 (1H, m), 2.08-2.04 (1H, m), 1.81-1.77 (1H, m).

MS (APCI, ESI) m/z: 420 [$(M+H)^+$].

Example 2

Example 2-1: Drug-Linker 1

[Formula 45]

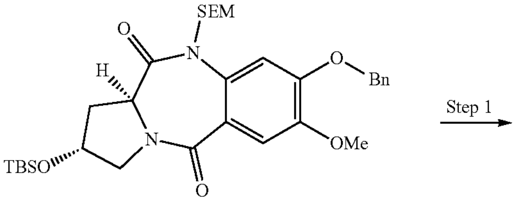

3-1

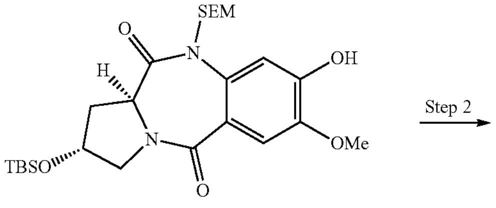

3-2

-continued
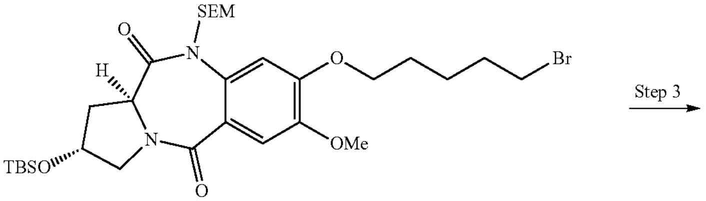
3-3
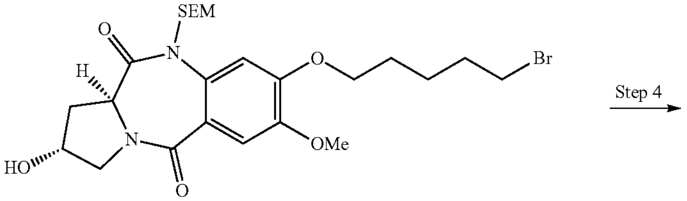
3-4
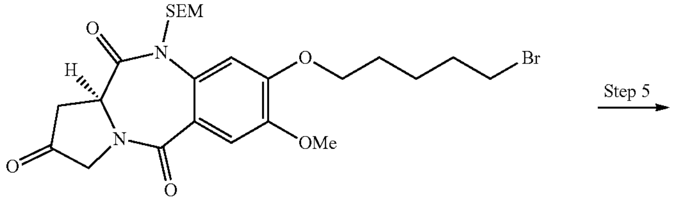
3-5
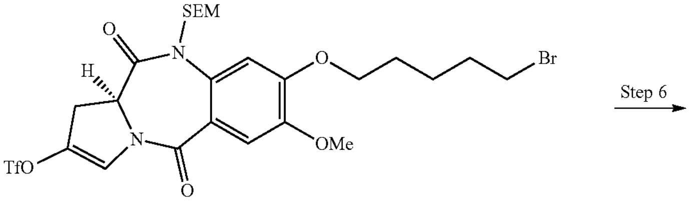
3-6
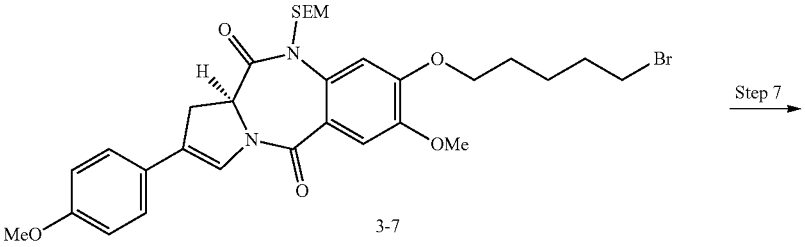
3-7
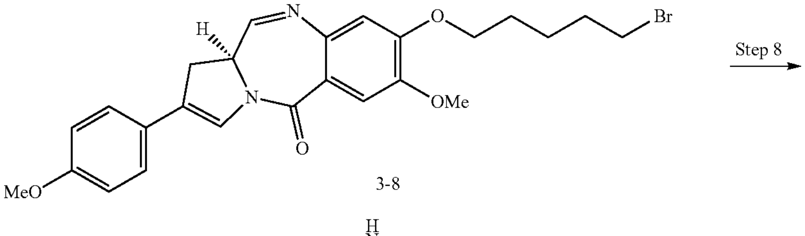
3-8
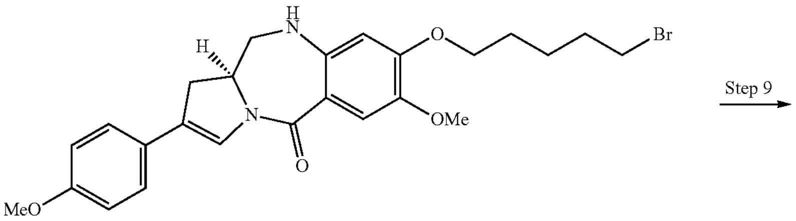
3-9

-continued
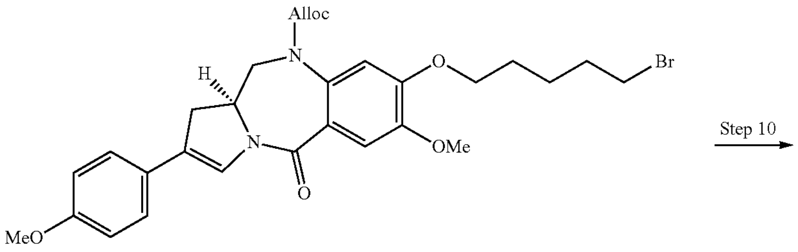
3-10
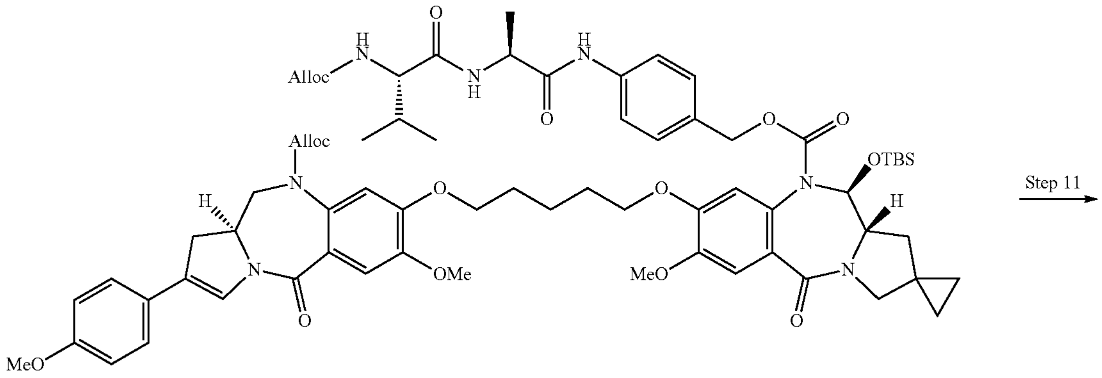
3-11
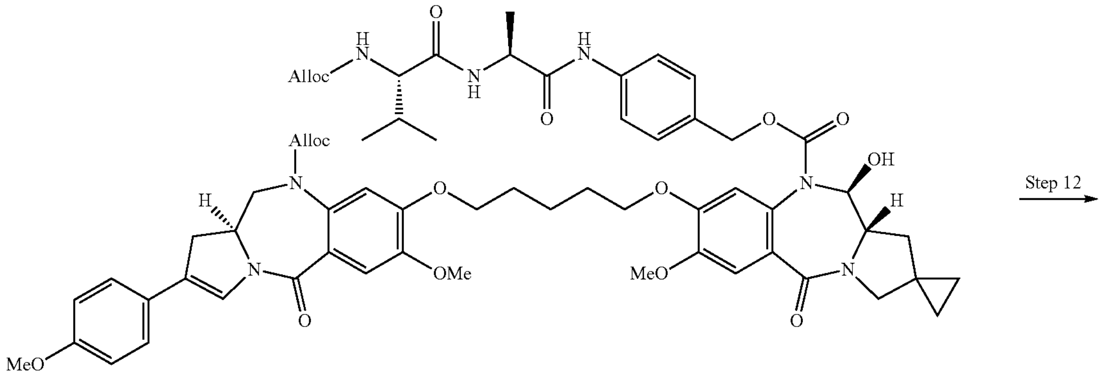
3-12
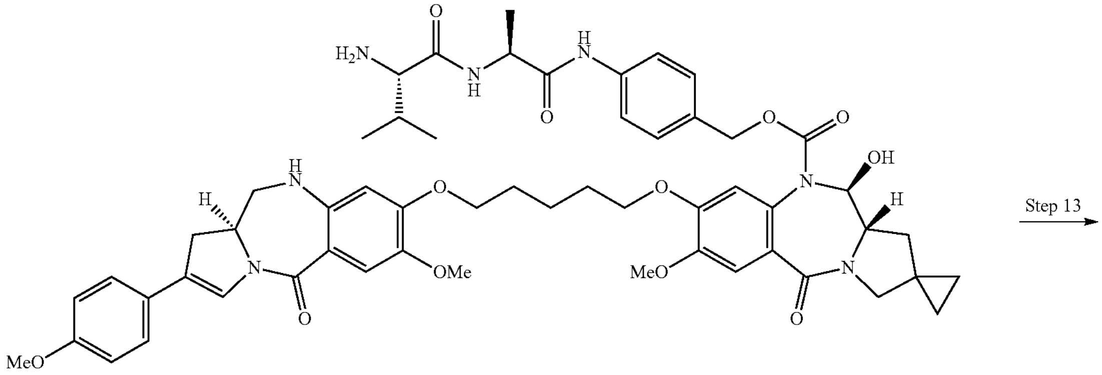
3-13

-continued

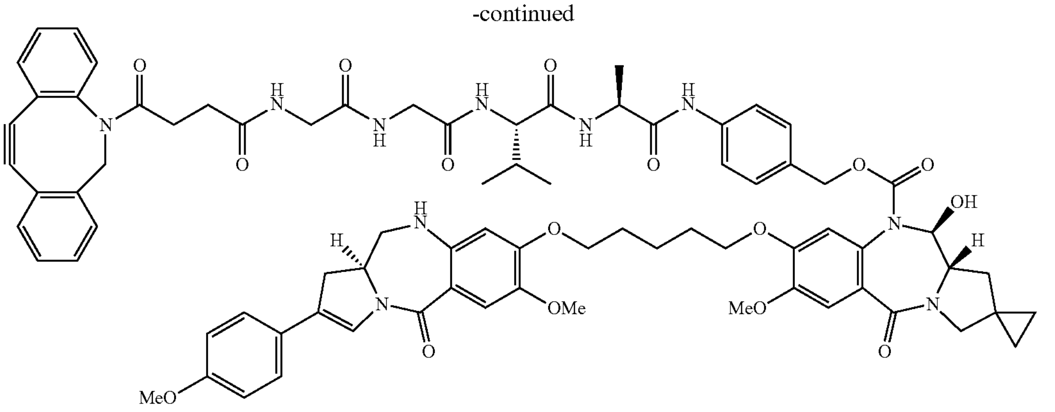

3-14

Step 1: (2R,11aS)-2-{[tert-Butyl(dimethyl)silyl]oxy}-8-hydroxy-7-methoxy-10-{[2-(trimethylsilyl)ethoxy]methyl}-2,3-dihydro-1H-pyrrolo[2,1-c][1,4]benzodiazepin-5,11 (10H,11aH)-dione (3-2)

To a solution of (2R,11aS)-8-(benzyloxy)-2-{[tert-butyl(dimethyl)silyl]oxy}-7-methoxy-10-{[2-(trimethylsilyl)ethoxy]methyl}-2,3-dihydro-1H-pyrrolo[2,1-c][1,4]benzodiazepin-5,11 (10H,11aH)-dione (3-1) (25.5 g, 41.6 mmol, WO 2016149546) in tetrahydrofuran (150 mL) and ethanol (150 mL), 5% palladium carbon (moisture content: 54%, 10.0 g) was added under the nitrogen atmosphere, and the reaction solution was then stirred under the hydrogen atmosphere at room temperature for 3 days. Chloroform was added to the reaction solution, which was filtered through a Celite, and the filtrate was then distillated under reduced pressure. The resulting residue was purified by silica gel column chromatography [hexane:ethyl acetate=100:0 (v/v) to 50:50 (v/v)] to afford the desired compound (3-2) (19.4 g, 89%).

$^1$H-NMR ($CDCl_3$) δ: 7.36 (1H, s), 7.25 (1H, s), 6.01 (1H, s), 5.45-5.43 (1H, m), 4.69-4.67 (1H, m), 4.60-4.55 (1H, m), 4.23-4.21 (1H, m), 3.96 (3H, s), 3.76-3.68 (2H, m), 3.63-3.61 (1H, m), 3.56-3.53 (1H, m), 2.88-2.83 (1H, m), 2.03-2.00 (1H, m), 1.00-0.98 (2H, m), 0.87 (9H, s), 0.10 (6H, s), 0.02 (9H, s).

MS (APCI, ESI) m/z: 523 $(M+H)^+$

Step 2: (2R,11aS)-8-[(5-Bromopentyl)oxy]-2-{[tert-butyl(dimethyl)silyl]oxy}-7-methoxy-10-{[2-(trimethylsilyl)ethoxy]methyl}-2,3-dihydro-1H-pyrrolo[2,1-c][1,4]benzodiazepin-5,11 (10H,11aH)-dione (3-3)

To a solution of compound (3-2) obtained in Step 1 (10.8 g, 20.7 mmol) in N,N-dimethylformamide (30 mL), 1,5-dibromopentane (23.8 g, 103 mmol) and potassium carbonate (3.43 g, 24.8 mmol) were added at room temperature. After stirring at room temperature for 3 hours, water was added to the reaction solution, which was extracted with ethyl acetate. The organic layer obtained was washed with brine and dried over sodium sulfate, and distillated under reduced pressure. The resulting residue was purified by silica gel column chromatography [hexane:ethyl acetate-90:10 (v/v) to 50:50 (v/v)] to afford the desired compound (3-3) (14.5 g, quantitative).

$^1$H-NMR ($CDCl_3$) δ: 7.34 (1H, s), 7.21 (1H, s), 5.52-5.49 (1H, m), 4.63-4.62 (1H, m), 4.58-4.55 (1H, m), 4.24-4.22 (1H, m), 4.07-4.04 (2H, m), 3.92 (3H, s), 3.82-3.64 (3H, m), 3.56-3.53 (1H, m), 3.45-3.43 (2H, m), 2.86-2.84 (1H, m), 2.04-2.00 (1H, m), 1.97-1.87 (4H, m), 1.66-1.62 (2H, m), 1.01-0.98 (2H, m), 0.87 (9H, s), 0.10 (6H, s), 0.04 (9H, s).

MS (APCI, ESI) m/z: 673 [81Br, $(M+H)^+$],671 [79Br, $(M+H)^+$].

Step 3: (2R,11aS)-8-[(5-Bromopentyl)oxy]-2-hydroxy-7-methoxy-10-{[2-(trimethylsilyl)ethoxy]methyl}-2,3-dihydro-1H-pyrrolo[2,1-c][1,4]benzodiazepin-5,11 (10H,11aH)-dione (3-4)

To a solution of compound (3-3) obtained in Step 2 (21.5 mmol) in tetrahydrofuran (40 mL), a 1 mol/L tetrahydrofuran solution of tetrabutylammonium fluoride (28.0 mL, 28.0 mmol) was added at 0° C. After stirring at room temperature for 30 minutes, water was added to the reaction solution, which was extracted with ethyl acetate, and the organic layer obtained was washed with brine. The resultant was dried over sodium sulfate, and then distillated under reduced pressure. The resulting residue was purified by silica gel column chromatography [chloroform:methanol=97.5:2.5 (v/v) to 92.5:7.5 (v/v)] to afford the desired compound (3-4) (11.3 g, 94%).

$^1$H-NMR ($CDCl_3$) δ: 7.34 (1H, s), 7.21 (1H, s), 5.53-5.50 (1H, m), 4.69-4.64 (2H, m), 4.32-4.30 (1H, m), 4.10-4.00 (2H, m), 3.91 (3H, s), 3.88-3.75 (2H, m), 3.73-3.64 (2H, m), 3.45-3.44 (2H, m), 2.99-2.96 (1H, m), 2.15-2.09 (1H, m), 1.99-1.85 (5H, m), 1.68-1.62 (2H, m), 1.01-0.95 (2H, m), 0.04 (9H, s).

MS (APCI, ESI) m/z: 559 [81Br, $(M+H)^+$], 557 [79Br, $(M+H)^+$].

Step 4: (11aS)-8-[(5-Bromopentyl)oxy]-7-methoxy-10-{[2-(trimethylsilyl)ethoxy]methyl}-1H-pyrrolo[2,1-c][1,4]benzodiazepin-2,5,11 (3H,10H,11aH)-trione (3-5)

Compound (3-4) obtained in step 3 (11.3 g, 20.2 mmol), tetrabutylammonium bromide (0.325 g, 1.01 mmol), and potassium bromide (0.240 g, 2.02 mmol) were dissolved in a saturated aqueous sodium hydrogen carbonate (60 mL)/dichloromethane (60 mL), to which nor-AZADO (0.0279 g, 0.202 mmol) and sodium hypochlorite pentahydrate (2.03 g, 27.2 mmol) were added at 0° C., and the resultant was stirred at 0° C. for 30 minutes. Because the raw materials remained, sodium hypochlorite pentahydrate (1.00 g, 13.4 mmol) was added thereto at 0° C., and the resultant was stirred at 0° C. for 15 minutes. Sodium hypochlorite pentahydrate (0.300 g, 4.03 mmol) was further added thereto at 0° C., and the resultant was stirred at 0° C. for 15 minutes, and the disappearance of the raw materials was confirmed by TLC. An aqueous solution of sodium thiosulfate was added to the reaction solution, which was extracted with chloroform, and the organic layer obtained was dried over sodium sulfate. The resultant was distillated under reduced pressure, and the resulting residue was purified by silica gel column chromatography [hexane:ethyl acetate=75:25 (v/v) to 40:60 (v/v)] to afford the desired compound (3-5) (9.74 g, 87%).

$^1$H-NMR ($CDCl_3$) δ: 7.33 (1H, s), 7.24 (1H, s), 5.56-5.53 (1H, m), 4.71-4.69 (1H, m), 4.66-4.63 (1H, m), 4.27-4.22 (1H, m), 4.12-4.02 (2H, m), 3.93-3.88 (4H, m), 3.82-3.75 (1H, m), 3.69-3.67 (1H, m), 3.61-3.56 (1H, m), 3.46-3.44 (2H, m), 2.82-2.77 (1H, m), 1.97-1.89 (4H, m), 1.68-1.64 (2H, m), 1.05-0.93 (2H, m), 0.04 (9H, s).

MS (APCI, ESI) m/z: 557 [81Br, $(M+H)^+$], 555 [79Br, $(M+H)^+$].

Step 5: (11aS)-8-[(5-Bromopentyl)oxy]-7-methoxy-5,11-dioxo-10-{[2-(trimethylsilyl)ethoxy]methyl}-5,10,11,11a-tetrahydro-1H-pyrrolo[2,1-c][1,4]benzodiazepin-2-yl trifluoromethanesulfonate (3-6)

To a solution of compound (3-5) obtained in Step 4 (9.74 g, 17.5 mmol) in dichloromethane (160 mL), 2,6-lutidine (8.17 mL, 70.1 mmol) was added at −40° C., and the resultant was stirred at −40° C. for 10 minutes. Anhydrous trifluoromethanesulfonic acid (8.85 mL, 52.6 mmol) was added to the reaction solution at −40° C., and the resultant was stirred at −40° C. for 30 minutes. To the reaction solution, a 10% aqueous solution of citric acid was added, which was extracted with chloroform, and the organic layer obtained was dried over sodium sulfate. The resultant was distillated under reduced pressure, and the resulting residue was purified by silica gel column chromatography [hexane: ethyl acetate=95:5 (v/v) to 70:35 (v/v)] and then purified by NH2 silica gel chromatography [hexane:ethyl acetate=95:5 (v/v) to 65:35 (v/v)] to afford the desired compound (3-6) (7.10 g, 59%).

$^1$H-NMR ($CDCl_3$) δ: 7.32 (1H, s), 7.24 (1H, s), 7.15-7.14 (1H, m), 5.56-5.53 (1H, m), 4.70-4.68 (1H, m), 4.66-4.63 (1H, m), 4.11-4.01 (2H, m), 3.94-3.90 (4H, m), 3.84-3.75 (1H, m), 3.73-3.68 (1H, m), 3.46-3.44 (2H, m), 3.18-3.14 (1H, m), 1.96-1.88 (4H, m), 1.69-1.61 (2H, m), 1.02-0.92 (2H, m), 0.04 (9H, s).

MS (APCI, ESI) m/z: 689 [81Br, $(M+H)^+$],687 [79Br, $(M+H)^+$].

Step 6: (11aS)-8-[(5-Bromopentyl)oxy]-7-methoxy-2-(4-methoxyphenyl)-10-{[2-(trimethylsilyl)ethoxy]methyl}-1H-pyrrolo[2,1-c][1,4]benzodiazepin-5,11(10H,11aH)-dione (3-7)

To a mixture of compound (3-6) obtained in Step 5 (2.00 g, 2.91 mmol), 4-methoxyphenylboronic acid (0.884 g, 5.82 mmol), tetrakis(triphenylphosphine) palladium (0) (0.336 g, 0.291 mmol) and sodium carbonate (1.23 g, 11.6 mmol), toluene (20 mL), ethanol (10 mL) and water (10 mL) were added at room temperature. The reaction solution was stirred at room temperature for 30 minutes, and the reaction solution was then extracted with ethyl acetate, and the extract was washed with water and brine. The organic layer was dried over sodium sulfate, and then distillated under reduced pressure. The resulting residue was purified by silica gel column chromatography [hexane:ethyl acetate=90:10 (v/v) to 50:50 (v/v)] to afford the desired compound (3-7) (1.71 g, 91%).

$^1$H-NMR ($CDCl_3$) δ: 7.38-7.37 (3H, m), 7.33 (1H, s), 7.25 (1H, s), 6.89-6.88 (2H, m), 5.56-5.54 (1H, m), 4.71-4.68 (1H, m), 4.65-4.62 (1H, m), 4.09-4.04 (2H, m), 3.96-3.91 (4H, m), 3.85-3.66 (5H, m), 3.46-3.45 (2H, m), 3.16-3.12 (1H, m), 1.99-1.94 (4H, m), 1.69-1.64 (2H, m), 1.00-0.98 (2H, m), 0.04 (9H, s).

MS (APCI, ESI) m/z: 647 [81Br, $(M+H)^+$],645 [79Br, $(M+H)^+$].

Step 7: (11aS)-8-[(5-Bromopentyl)oxy]-7-methoxy-2-(4-methoxyphenyl)-1,11a-dihydro-5H-pyrrolo[2,1-c][1,4]benzodiazepin-5-one (3-8)

Compound (3-7) obtained in Step 6 (0.789 g, 1.22 mmol) was dissolved in ethanol (10 mL) and tetrahydrofuran (10 mL), and 2.0 M tetrahydrofuran solution of lithium borohydride (6.11 mL, 12.2 mmol) was added thereto at 0° C., and the resultant was stirred at 0° C. for 3 hours. Water was added to the reaction solution, which was extracted with chloroform, and the organic layer obtained was dried over sodium sulfate. The resultant was distillated under reduced pressure, and the resulting residue was dissolved in dichloromethane (10 mL), ethanol (20 mL) and water (10 mL), to which silica gel (4 g) was added at room temperature, and the resultant was stirred at room temperature for 4 days. The silica gel was removed through filtration, and water was added thereto, and the resultant was extracted with chloroform. The organic layer obtained was dried over sodium sulfate. The resultant was distillated under reduced pressure, and the resulting residue was purified by silica gel column chromatography [hexane:ethyl acetate=60:40 (v/v) to 25:75 (v/v)] to afford the desired compound (3-8) (0.496 g, 81%).

$^1$H-NMR ($CDCl_3$) δ: 7.90-7.89 (1H, m), 7.53 (1H, s), 7.40-7.40 (1H, m), 7.35-7.34 (2H, m), 6.92-6.90 (2H, m), 6.83-6.81 (1H, m), 4.43-4.40 (1H, m), 4.13-4.06 (2H, m), 3.96 (3H, s), 3.84 (3H, s), 3.61-3.57 (1H, m), 3.47-3.36 (3H, m), 2.00-1.92 (4H, m), 1.67-1.63 (2H, m).

MS (APCI, ESI) m/z: 501 [81Br, $(M+H)^+$], 499 [79Br, $(M+H)^+$].

Step 8: (11aS)-8-[(5-Bromopentyl)oxy]-7-methoxy-2-(4-methoxyphenyl)-1,10,11,11a-tetrahydro-5H-pyrrolo[2,1-c][1,4]benzodiazepin-5-one (3-9)

To a solution of compound (3-8) obtained in Step 7 (0.496 g, 0.992 mmol) in dichloromethane (20 mL), sodium triacetoxyborohydride (0.421 g, 1.99 mmol) was added at 0° C. After stirring at room temperature for 2 hours, a saturated aqueous sodium hydrogen carbonate was added thereto, and the resultant was extracted with chloroform. The organic layer was dried over sodium sulfate, and distillated under reduced pressure, and the resulting residue was then purified by silica gel column chromatography [hexane:ethyl acetate=60:40 (v/v) to 25:75 (v/v)] to afford the desired compound (3-9) (0.426 g, 86%).

$^1$H-NMR ($CDCl_3$) δ: 7.53-7.53 (2H, m), 7.32-7.30 (2H, m), 6.89-6.87 (2H, m), 6.05 (1H, s), 4.33-4.27 (2H, m), 4.00-3.98 (2H, m), 3.86 (3H, s), 3.82 (3H, s), 3.57-3.55 (2H, m), 3.42-3.38 (3H, m), 2.76-2.72 (1H, m), 1.96-1.88 (4H, m), 1.65-1.62 (2H, m).

MS (APCI, ESI) m/z: 503 [81Br, $(M+H)^+$], 501 [79Br, $(M+H)^+$].

Step 9: Prop-2-en-1-yl(11aS)-8-[(5-bromopentyl)oxy]-7-methoxy-2-(4-methoxyphenyl)-5-oxo-11,11a-dihydro-1H-pyrrolo[2,1-c][1,4]benzodiazepin-10(5H)-carboxylate (3-10)

To a solution of compound (3-9) obtained in Step 8 (0.426 g, 0.849 mmol) in dichloromethane (30 mL), pyridine (0.102 mL 1.27 mmol) and allyl chloroformate (0.374 mL, 3.54 mmol) were added at 0° C., and the resultant was stirred at 0° C. for 15 minutes. To the reaction solution, a 10% aqueous solution of citric acid was added, which was extracted with chloroform, and the organic layer obtained was washed with a saturated aqueous sodium hydrogen carbonate, and then dried over sodium sulfate. The resultant was distilled under reduced pressure, and the resulting residue was purified by silica gel column chromatography [hexane:ethyl acetate-90:10 (v/v) to 50:50 (v/v)] to afford the desired compound (3-10) (0.465 g, 94%).

$^1$H-NMR ($CDCl_3$) δ: 7.38 (1H, s), 7.31-7.29 (2H, m), 7.26-7.25 (1H, m), 6.89-6.87 (2H, m), 6.71 (1H, s), 5.80-5.78 (1H, m), 5.14-5.11 (2H, m), 4.65-4.62 (1H, m), 4.39-4.26 (3H, m), 4.03-4.01 (2H, m), 3.92 (3H, s), 3.82 (3H, s), 3.66-3.64 (1H, m), 3.46-3.44 (2H, m), 3.30-3.27 (1H, m), 2.72-2.68 (1H, m), 1.96-1.88 (4H, m), 1.68-1.60 (2H, m).

MS (APCI, ESI) m/z: 587 [81Br, $(M+H)^+$], 585 [79Br, $(M+H)^+$].

Step 10: N-[(Prop-2-en-1-yloxy)carbonyl]-L-valyl-N-{4-[({[(11'S,11a'S)-11'-{[tert-butyl(dimethyl)silyl]oxy}-7'-methoxy-8'-{[5-({(11aS)-7-methoxy-2-(4-methoxyphenyl)-5-oxo-10-[(prop-2-en-1-yloxy)carbonyl]-5,10,11,11a-tetrahydro-1H-pyrrolo[2,1-c][1,4]benzodiazepin-8-yl}oxy) pentyl]oxy}-5'-oxo-11',11a'-dihydro-1'H-spiro[cyclopropane-1,2'-pyrrolo[2,1-c][1,4]benzodiazepine]-10' (5'H)-yl]carbonyl}oxy)methyl]phenyl}-L-alaninamide (3-11)

To a solution of compound (1-11) obtained in Step 10 of Example 1-1 (0.130 g, 0.161 mmol) and compound (3-10) obtained in Step 9 (0.104 g, 0.177 mmol) in N,N-dimethylformamide (3 mL), potassium carbonate (0.0266 g, 0.193 mmol) was added at room temperature, and the resultant was stirred at room temperature overnight. The reaction solution was diluted with ethyl acetate, and washed with water and brine, and then dried over sodium sulfate. The resultant was distilled under reduced pressure, and the resulting residue was then purified by NH2-silica gel column chromatography [hexane:ethyl acetate=70:30 (v/v) to 0:100 (v/v)] to afford the desired compound (3-11) (0.184 g, 87%).

$^1$H-NMR ($CDCl_3$) δ: 8.76 (1H, s), 7.58-7.56 (2H, m), 7.39 (1H, s), 7.32-7.30 (2H, m), 7.26-7.24 (2H, m), 7.19-7.17 (3H, m), 6.90-6.88 (2H, m), 6.78 (1H, s), 6.68-6.66 (1H, m), 6.37 (1H, s), 5.99-5.93 (3H, m), 5.34-5.20 (6H, m), 4.66-4.01 (11H, m), 3.90 (3H, s), 3.89 (3H, s), 3.78-3.54 (9H, m), 3.31-3.28 (2H, m), 2.73-2.69 (1H, m), 2.38-2.35 (1H, m), 2.19-2.13 (1H, m), 1.82-1.80 (2H, m), 1.46-1.29 (6H, m), 0.98-0.90 (6H, m), 0.83 (9H, s), 0.69-0.63 (4H, m), 0.19-0.16 (6H, m).

MS (APCI, ESI) m/z: 1312 $(M+H)^+$

Step 11: N-[(Prop-2-en-1-yloxy)carbonyl]-L-valyl-N-{4-[({[(11'S, 11a'S)-11'-hydroxy-7'-methoxy-8'-{[5-({(11aS)-7-methoxy-2-(4-methoxyphenyl)-5-oxo-10-[(prop-2-en-1-yloxy)carbonyl]-5,10,11,11a-tetrahydro-1H-pyrrolo[2,1-c][1,4]benzodiazepin-8-yl}oxy) pentyl]oxy}-5'-oxo-11',11a'-dihydro-1'H-spiro[cyclopropane-1,2'-pyrrolo[2,1-c][1,4]benzodiazepine]-10' (5'H)-yl]carbonyl}oxy)methyl]phenyl}-L-alaninamide (3-12)

To a solution of compound (3-11) obtained in Step 10 (0.1837 g, 0.140 mmol) and acetic acid (0.048 mL, 0.840 mmol) in tetrahydrofuran (5.00 mL), a 1 mol/L tetrahydrofuran solution of tetrabutylammonium fluoride (0.700 mL, 0.700 mmol) was added at room temperature, and the resultant was stirred at room temperature for 3 hours. The reaction solution was diluted with ethyl acetate, and the organic layer was washed with a saturated aqueous sodium hydrogen carbonate and brine, and then dried over sodium sulfate. The resultant was distilled under reduced pressure, and the resulting residue was purified by silica gel chromatography [chloroform:methanol=99.5:0.5 (v/v) to 95:5 (v/v)] to afford the desired compound (3-12) (0.178 g, quantitative).

$^1$H-NMR ($CDCl_3$) δ: 8.86 (1H, s), 7.60-7.59 (2H, m), 7.39 (1H, s), 7.32-7.20 (7H, m), 6.90-6.88 (2H, m), 6.78 (1H, s), 6.68 (1H, s), 6.38 (1H, s), 5.90-5.87 (3H, m), 5.39-5.22 (6H, m), 4.72-4.02 (11H, m), 3.90 (3H, s), 3.88 (3H, s), 3.83 (3H, s), 3.70-3.63 (6H, m), 3.32-3.29 (3H, m), 2.73-2.69 (1H, m), 2.43-2.40 (1H, m), 2.12-2.06 (1H, m), 1.77-1.74 (2H, m), 1.39-1.25 (6H, m), 0.96-0.89 (6H, m), 0.73-0.66 (4H, m).

MS (APCI, ESI) m/z: 1198 $(M+H)^+$

Step 12: L-Valyl-N-{4-[({[(11'S,11a'S)-11'-hydroxy-7'-methoxy-8'-[(5-{[(11aS)-7-methoxy-2-(4-methoxyphenyl)-5-oxo-5,10,11,11a-tetrahydro-1H-pyrrolo[2,1-c][1,4]benzodiazepin-8-yl]oxy}pentyl)oxy]-5'-oxo-11',11a'-dihydro-1'H-spiro[cyclopropane-1,2'-pyrrolo[2,1-c][1,4]benzodiazepine]-10' (5'H)-yl]carbonyl}oxy)methyl]phenyl}-L-alaninamide (3-13)

To a solution of compound (3-12) obtained in Step 11 (0.140 mmol) in dichloromethane (2 mL), pyrrolidine (0.0579 mL, 0.700 mmol) and tetrakis(triphenylphosphine) palladium (0) (0.0162 g, 0.0140 mmol) were added at room temperature, and the resultant was stirred at room temperature for 15 minutes. After distillation under reduced pressure, the resulting residue was purified by silica gel chromatography [chloroform:methanol=99.5:0.5 (v/v) to 92.5:7.5 (v/v)] to afford the desired compound (3-13) (0.143 g, 99%).

$^1$H-NMR ($CDCl_3$) δ: 9.12 (1H, s), 7.94-7.92 (1H, m), 7.57-7.53 (4H, m), 7.33-7.31 (2H, m), 7.20-7.18 (3H, m), 6.90-6.88 (2H, m), 6.36 (1H, s), 6.07 (1H, s), 5.91-5.88 (1H, m), 5.47-5.44 (1H, m), 5.21-5.13 (1H, m), 4.66-4.58 (3H, m), 4.32 (1H, s), 4.03-3.49 (17H, m), 3.38-3.29 (4H, m), 3.15-3.14 (1H, m), 2.77-2.73 (1H, m), 2.57 (2H, s), 2.43-2.40 (1H, m), 2.32-2.27 (1H, m), 1.81-1.39 (8H, m), 0.98-0.96 (3H, m), 0.85-0.83 (3H, m), 0.75-0.62 (4H, m).

MS (APCI, ESI) m/z: 1030 $(M+H)^+$

Step 13: N-[4-(11,12-Didehydrodibenzo[b,f]azocin-5 (6H)-yl)-4-oxobutanoyl]glycylglycyl-L-valyl-N-{4-[({[(11'S,11a'S)-11'-hydroxy-7'-methoxy-8'-[(5-{[(11aS)-7-methoxy-2-(4-methoxyphenyl)-5-oxo-5,10,11,11a-tetrahydro-1H-pyrrolo[2,1-c][1,4]benzodiazepin-8-yl]oxy}pentyl)oxy]-5'-oxo-11',11a'-dihydro-1'H-spiro[cyclopropane-1,2'-pyrrolo[2,1-c][1,4]benzodiazepine]-10' (5'H)-yl]carbonyl}oxy)methyl]phenyl}-L-alaninamide (3-14)

To a mixture of compound (2-2) obtained in Step 1 of Example 1-2 (0.0640 g, 0.153 mmol) and N-ethoxycarbonyl-2-ethoxy-1,2-dihydroquinoline (0.0446 g, 0.180 mmol), dichloromethane (2 mL) was added at room temperature, and the resultant was stirred at room temperature for 15 minutes. To the reaction solution, a solution of compound (3-13) obtained in Step 12 (0.143 g, 0.139 mmol) in dichloromethane (2 mL) was added, and the resultant was stirred at room temperature for 5 hours, and then distillated under reduced pressure. The resulting residue was purified by silica gel column chromatography [chloroform:methanol=99.5:0.5 (v/v) to 92.5:7.5 (v/v)] to afford the desired compound (3-14) (0.103 g, 52%).

$^1$H-NMR (DMSO-$D_6$) δ: 9.93 (1H, s), 8.21-8.16 (2H, m), 8.07-8.04 (1H, m), 7.83-7.64 (2H, m), 7.60-7.55 (3H, m), 7.51-7.28 (10H, m), 7.19-7.16 (2H, m), 7.10-7.04 (1H, m), 6.92-6.90 (2H, m), 6.76-6.70 (1H, m), 6.39 (1H, s), 5.77-5.75 (1H, m), 5.21-5.18 (1H, m), 5.03-4.99 (1H, m), 4.82-4.79 (1H, m), 4.37-4.35 (1H, m), 4.21-4, 20 (2H, m), 4.02-3.24 (26H, m), 3.16-3.13 (1H, m), 2.79-2.59 (2H, m), 2.39-2.28 (2H, m), 2.05-1.97 (2H, m), 1.91-1.77 (4H, m), 1.57-1.54 (3H, m), 1.28-1.23 (3H, m), 0.85-0, 80 (6H, m), 0.67-0.61 (4H, m).

MS (APCI, ESI) m/z: 1431 $(M+H)^+$

Example 2-2: Drug-Linker 2

[Formula 46]

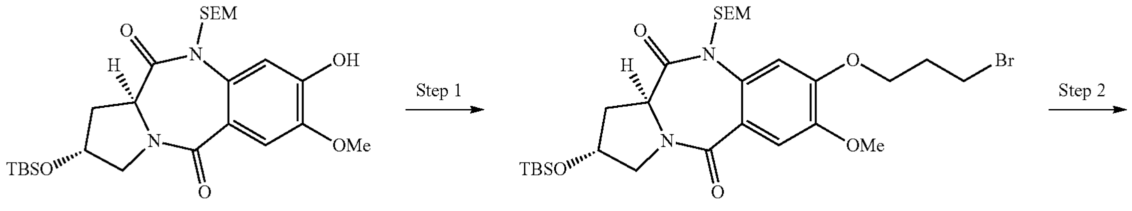

3-2

4-1

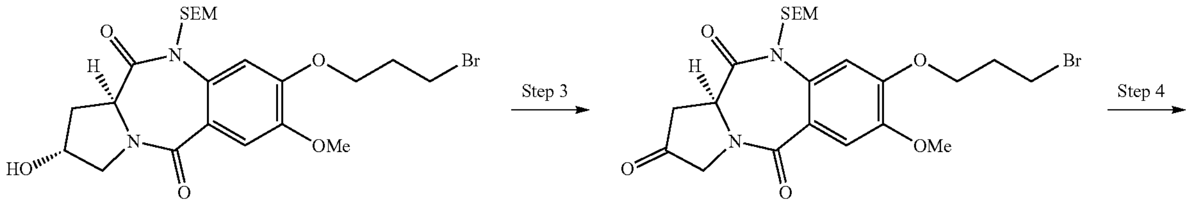

4-2

4-3

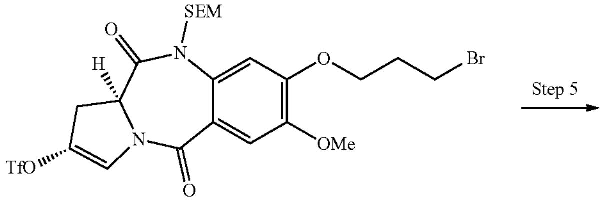

4-4

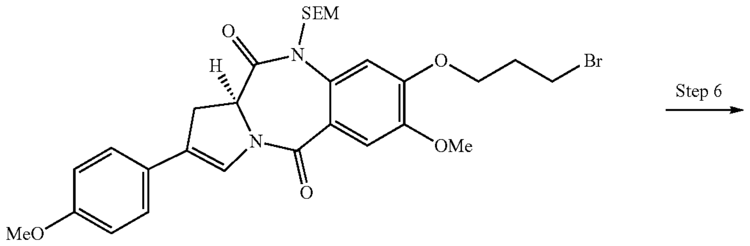

4-5

-continued
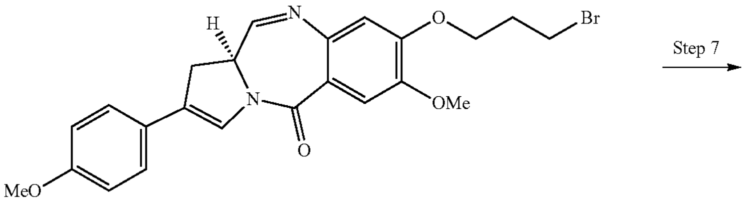
4-6
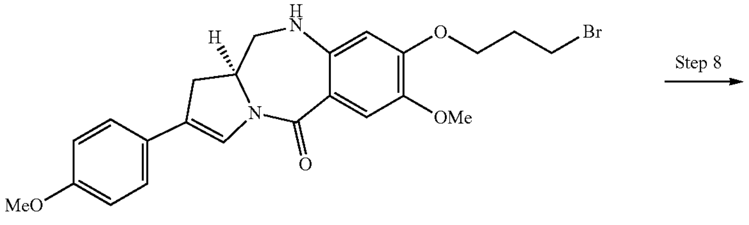
4-7
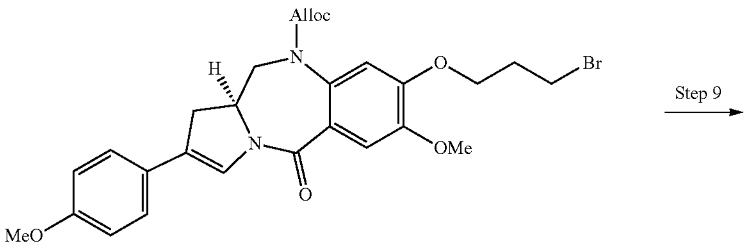
4-8
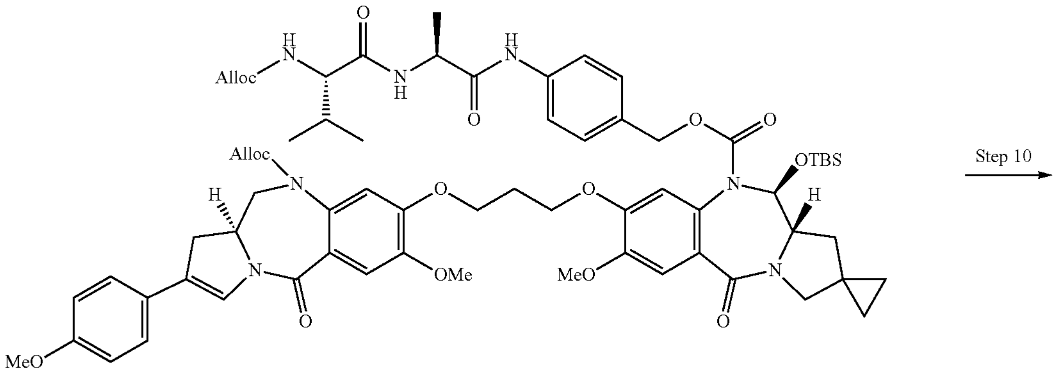
4-9
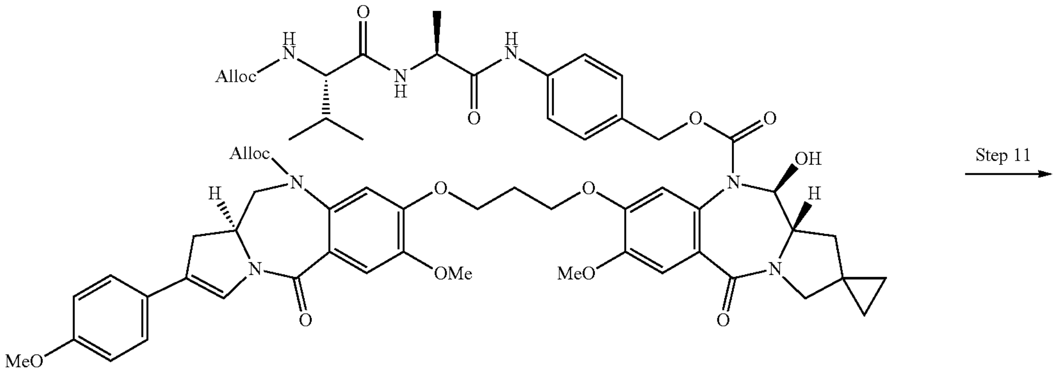
4-10

-continued

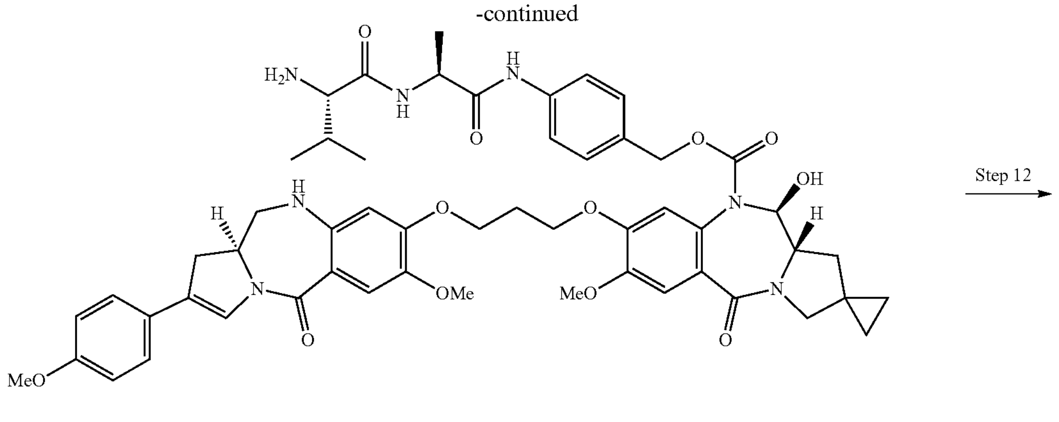

4-11

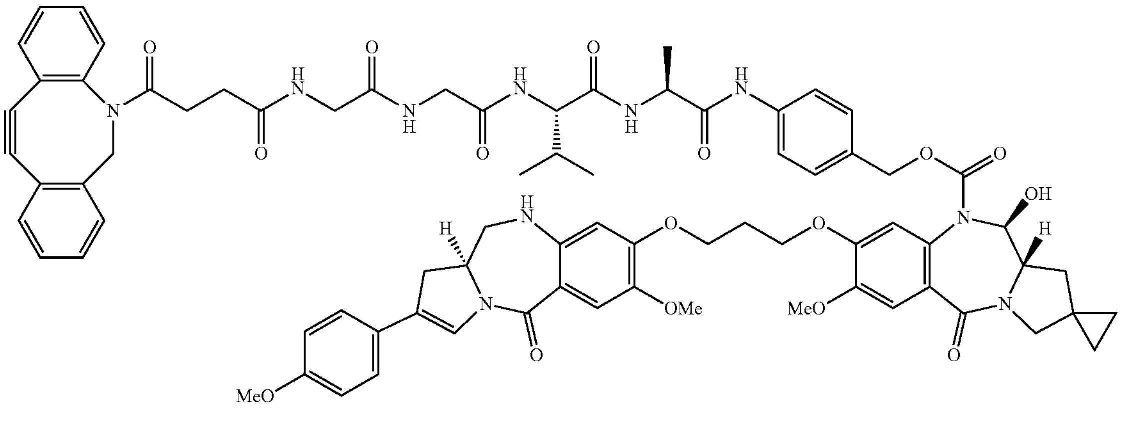

4-12

Step 1: (2R,11aS)-8-(3-Bromopropoxy)-2-{[tert-butyl(dimethyl)silyl]oxy}-7-methoxy-10-{[2-(trimethylsilyl)ethoxy]methyl}-2,3-dihydro-1H-pyrrolo[2,1-c][1,4]benzodiazepin-5,11 (10H,11aH)-dione (4-1)

Compound (3-2) obtained in Step 1 of Example 2-1 (5.06 g, 9.67 mmol) and 1,3-dibromopropane (4.93 mL, 48.4 mmol) were reacted in the same manner as in Step 2 of Example 2-1 to afford the desired compound (4-1) (4.85 g, 78%).

MS (APCI, ESI) m/z: 645 [81Br, $(M+H)^+$],643 [79Br, $(M+H)^+$].

Step 2: (2R,11aS)-8-(3-Bromopropoxy)-2-hydroxy-7-methoxy-10-{[2-(trimethylsilyl)ethoxy]methyl}-2,3-dihydro-1H-pyrrolo[2,1-c][1,4]benzodiazepin-5,11 (10H,11aH)-dione (4-2)

Compound (4-1) obtained in Step 1 (4.85 g, 7.54 mmol) was reacted in the same manner as in Step 3 of Example 2-1 to afford the desired compound (4-2) (4.05 g, quantitative).

MS (APCI, ESI) m/z: 531 [81Br, $(M+H)^+$], 529 [79Br, $(M+H)^+$].

Step 3: (11aS)-8-(3-Bromopropoxy)-7-methoxy-10-{[2-(trimethylsilyl)ethoxy]methyl}-1H-pyrrolo[2,1-c][1,4]benzodiazepin-2,5,11 (3H,10H,11aH)-trione (4-3)

Compound (4-2) obtained in Step 2 (7.54 mmol) was reacted in the same manner as in Step 4 of Example 2-1 to afford the desired compound (4-3) (3.73 g, 93%).

$^1$H-NMR ($CDCl_3$) δ: 7.34 (1H, s), 7.29 (1H, s), 5.56-5.53 (1H, m), 4.72-4.69 (1H, m), 4.67-4.61 (1H, m), 4.23-4.17 (3H, m), 3.97-3.88 (4H, m), 3.82-3.75 (1H, m), 3.74-3.56 (4H, m), 2.82-2.77 (1H, m), 2.43-2.38 (2H, m), 1.06-0.94 (2H, m), 0.08-0.00 (9H, m).

Step 4: (11aS)-8-(3-Bromopropoxy)-7-methoxy-5,11-dioxo-10-{[2-(trimethylsilyl)ethoxy]methyl}-5,10,11,11a-tetrahydro-1H-pyrrolo[2,1-c][1,4]benzodiazepin-2-yl trifluoromethanesulfonate (4-4)

Compound (4-3) obtained in Step 3 (3.73 g, 7.08 mmol) was reacted in the same manner as in Step 5 of Example 2-1 to afford the desired compound (4-4) (3.27 g, 70%).

MS (APCI, ESI) m/z: 661 [81Br, $(M+H)^+$],659 [79Br, $(M+H)^+$].

Step 5: (11aS)-8-(3-Bromopropoxy)-7-methoxy-2-(4-methoxyphenyl-10-{[2-(trimethylsilyl)ethoxy]methyl}-1H-pyrrolo[2,1-c][1,4]benzodiazepin-5,11 (10H,11aH)-dione (4-5)

Compound (4-4) obtained in Step 4 (3.27 g, 4.96 mmol) was reacted in the same manner as in Step 6 of Example 2-1 to afford the desired compound (4-5) (2.49 g, 81%).

MS (APCI, ESI) m/z: 619 [81Br, $(M+H)^+$],617 [79Br, $(M+H)^+$].

Step 6: (11aS)-8-(3-Bromopropoxy)-7-methoxy-2-(4-methoxyphenyl)-1,11a-dihydro-5H-pyrrolo[2,1-c][1,4]benzodiazepin-5-one (4-6)

Compound (4-5) obtained in Step 5 (2.49 g, 4.04 mmol) was reacted in the same manner as in Step 7 of Example 2-1 to afford the desired compound (4-6) (1.59 g, 84%).

MS (APCI, ESI) m/z: 473 [81Br, $(M+H)^+$], 471 [79Br, $(M+H)^+$].

Step 7: (11aS)-8-(3-Bromopropoxy)-7-methoxy-2-(4-methoxyphenyl)-1,10,11,11a-tetrahydro-5H-pyrrolo[2,1-c][1,4]benzodiazepin-5-one (4-7)

Compound (4-6) obtained in Step 6 (1.59 g, 3.38 mmol) was reacted in the same manner as in Step 8 of Example 2-1 to afford the desired compound (4-7) (1.39 g, 87%).

MS (APCI, ESI) m/z: 475 [81Br, $(M+H)^+$], 473 [79Br, $(M+H)^+$].

Step 8: Prop-2-en-1-yl(11aS)-8-(3-bromopropoxy)-7-methoxy-2-(4-methoxyphenyl)-5-oxo-11,11a-dihydro-1H-pyrrolo[2,1-c][1,4]benzodiazepin-10(5H)-carboxylate (4-8)

Compound (4-7) obtained in Step 7 (1.40 g, 2.95 mmol) was reacted in the same manner as in step 9 of Example 2-1 to afford the desired compound (4-8) (0.885 g, 54%).

MS (APCI, ESI) m/z: 559 [81Br, $(M+H)^+$], 557 [79Br, $(M+H)^+$].

Step 9: N-{[(Prop-2-en-1-yl)oxy]carbonyl}-L-valyl-N-[4-({[(11'S,11'aS)-11'-{[tert-butyl(dimethyl)silyl]oxy}-7'-methoxy-8'-(3-{[(11aS)-7-methoxy-2-(4-methoxyphenyl)-5-oxo-10-{[(prop-2-en-1-yl)oxy]carbonyl}-5,10,11,11a-tetrahydro-1H-pyrrolo[2,1-c][1,4]benzodiazepin-8-yl]oxy}propoxy)-5'-oxo-11',11'a-dihydro-1'H,3'H-spiro[cyclopropane-1,2'-pyrrolo[2,1-c][1,4]benzodiazepine]-10'(5'H)-carbonyl]oxy}methyl)phenyl]-L-alaninamide (4-9)

Compound (4-8) obtained in Step 8 (0.0381 g, 0.0683 mmol) and compound (1-11) obtained in Step 10 of Example 1-1 (0.0552 g, 0.0683 mmol) were reacted in the same manner as in Step 10 of Example 2-1 to afford the desired compound (4-9) (0.0712 g, 81%).

MS (APCI, ESI) m/z: 1284 $(M+H)^+$.

Step 10: N-{[(Prop-2-en-1-yl)oxy]carbonyl}-L-valyl-N-[4-({[(11'S, [1'aS)-11'-hydroxy-7'-methoxy-8'-(3-{[(11aS)-7-methoxy-2-(4-methoxyphenyl)-5-oxo-10-{[(prop-2-en-1-yl)oxy]carbonyl}-5,10,11,11a-tetrahydro-1H-pyrrolo[2,1-c][1,4]benzodiazepin-8-yl]oxy}propoxy)-5'-oxo-11',11'a-dihydro-1'H,3'H-spiro[cyclopropane-1,2'-pyrrolo[2,1-c][1,4]benzodiazepine]-10'(5'H)-carbonyl]oxy}methyl)phenyl]-L-alaninamide (4-10)

Compound (4-9) obtained in Step 9 (0.0712 g, 0.0554 mmol) was reacted in the same manner as in Step 11 of Example 2-1 to afford the desired compound (4-10) (0.0671 g, quantitative).

MS (APCI, ESI) m/z: 1170 $(M+H)^+$.

Step 11: L-Valyl-N-[4-({[(11'S,11'aS)-11'-hydroxy-7'-methoxy-8'-(3-{[(11aS)-7-methoxy-2-(4-methoxyphenyl)-5-oxo-5,10,11,11a-tetrahydro-1H-pyrrolo[2,1-c][1,4]benzodiazepin-8-yl]oxy}propoxy)-5'-oxo-11',11'a-dihydro-1'H,3'H-spiro[cyclopropane-1,2'-pyrrolo[2,1-c][1,4]benzodiazepine]-10'(5'H)-carbonyl]oxy}methyl)phenyl]-L-alaninamide (4-11)

Compound (4-10) obtained in Step 10 (0.0571 mmol) was reacted in the same manner as in Step 12 of Example 2-1 to afford the desired compound (4-11) (0.0574 g, 99%).

$^1$H-NMR ($CDCl_3$) δ: 9.16 (1H, s), 7.93-7.91 (1H, m), 7.55-7.52 (1H, m), 7.50-7.47 (3H, m), 7.35-7.32 (2H, m), 7.21 (1H, s), 7.13-7.11 (2H, m), 6.90-6.87 (2H, m), 6.40 (1H, s), 6.08 (1H, s), 5.90-5.87 (1H, m), 5.37-5.34 (1H, m), 4.73-4.53 (3H, m), 4.23-4.08 (5H, m), 3.89 (3H, s), 3.82 (3H, s), 3.78-3.72 (5H, m), 3.57-3.51 (3H, m), 3.38-3.30 (3H, m), 2.76-2.71 (1H, m), 2.36-2.24 (4H, m), 1.78-1.42 (6H, m), 1.00-0.98 (3H, m), 0.87-0.84 (3H, m), 0.74-0.62 (4H, m).

MS (APCI, ESI) m/z: 1002 $(M+H)^+$.

Step 12: N-[4-(11,12-Didehydrodibenzo[b,f]azocin-5 (6H)-yl)-4-oxobutanoyl]glycylglycyl-L-valyl-N-[4-({[(11'aS)-11'-hydroxy-7'-methoxy-8'-(3-{[(11aS)-7-methoxy-2-(4-methoxyphenyl)-5-oxo-5,10,11,11a-tetrahydro-1H-pyrrolo[2,1-c][1,4]benzodiazepin-8-yl]oxy}propoxy)-5'-oxo-11',11'a-dihydro-1'H,3'H-spiro[cyclopropane-1,2'-pyrrolo[2,1-c][1,4]benzodiazepine]-10'(5'H); carbonyl]oxy}methyl)phenyl]-L-alaninamide (4-12)

Compound (4-11) obtained in Step 11 (0.189 g, 0.189 mmol) and compound (2-2) obtained in Step 1 of Example 1-2 (0.087 g, 0.207 mmol) were reacted in the same manner as in Step 13 of Example 2-1 to afford the desired compound (4-12) (0.169 g, 64%).

MS (APCI, ESI) m/z: 1402 $(M+H)^+$.

Example 2-3: Drug-Linker 3

[Formula 47]

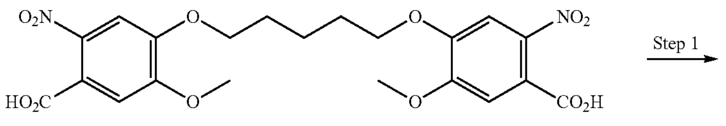

5-1

-continued
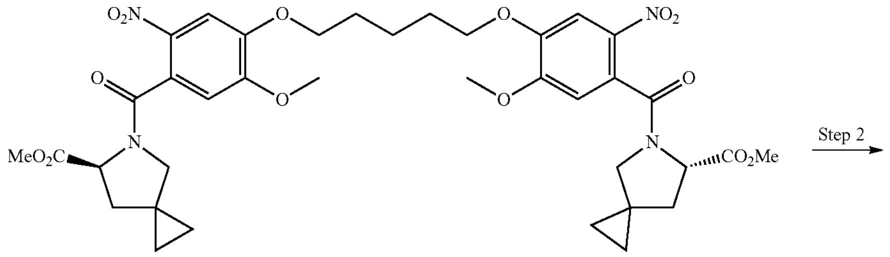
5-2
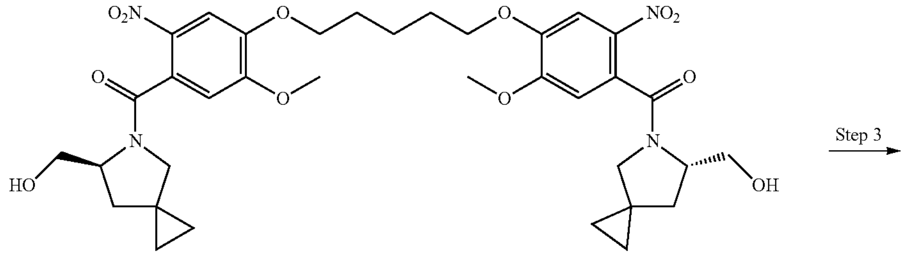
5-3
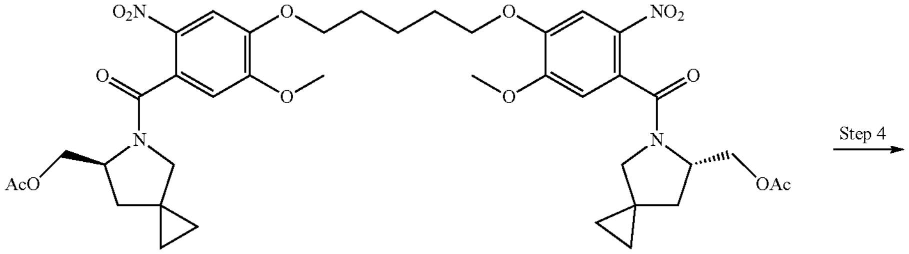
5-4
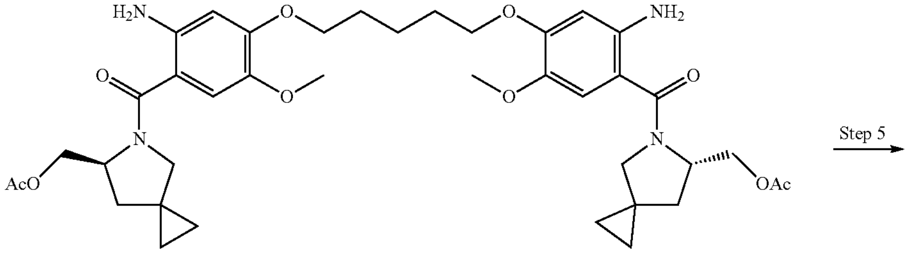
5-5
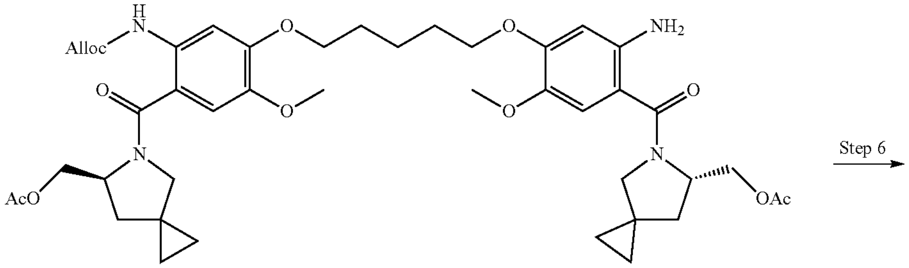
5-6

-continued
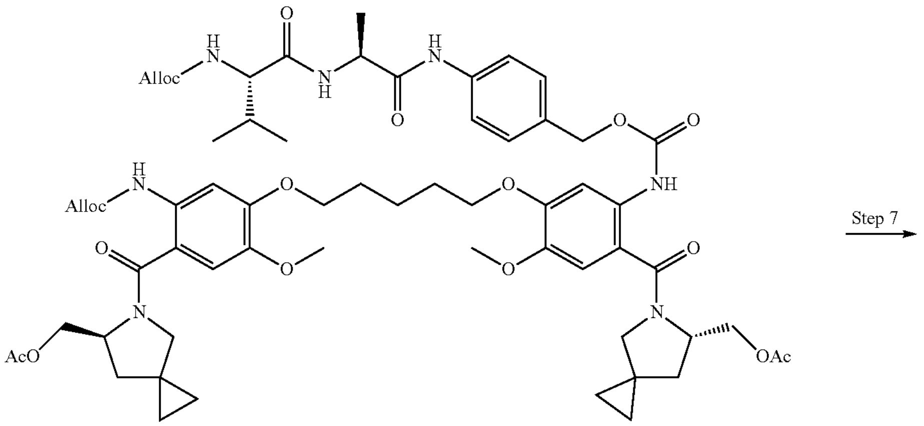
5-7
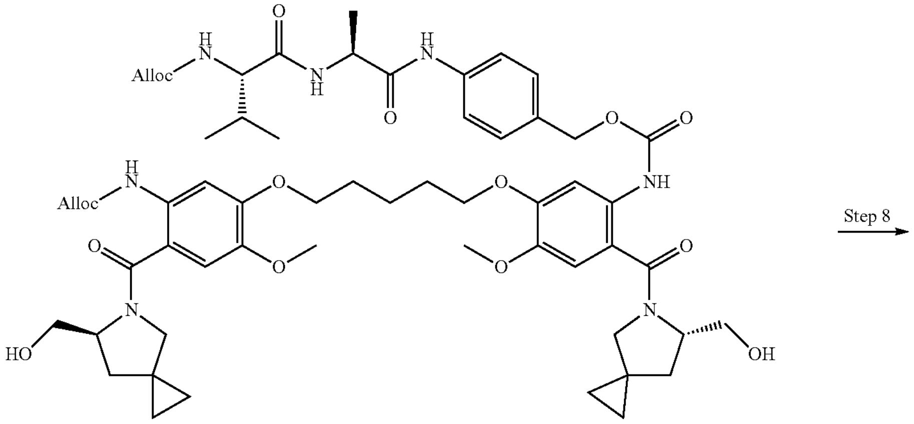
5-8
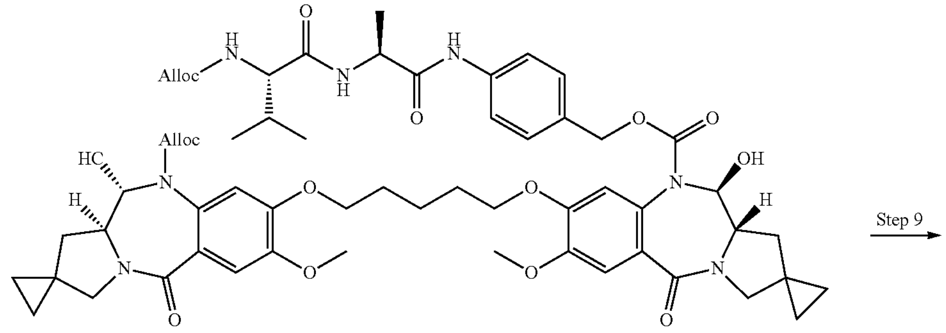
5-9
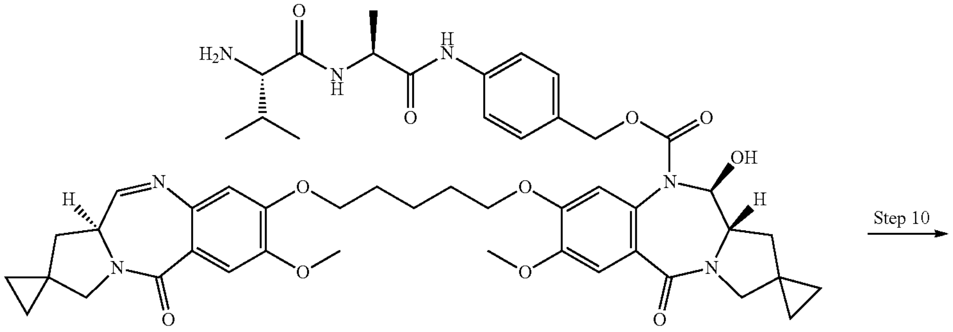
5-10

-continued

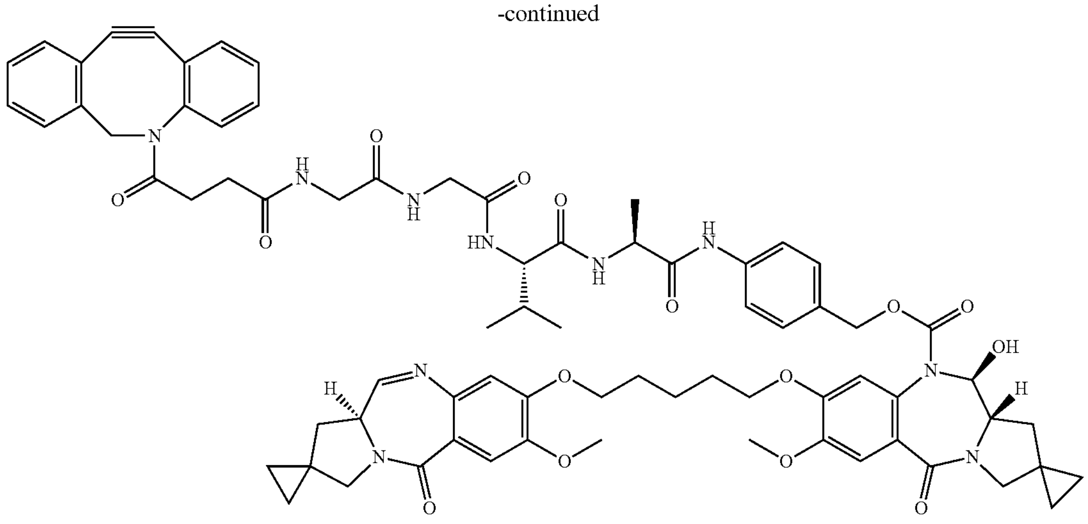

5-11

Step 1: Dimethyl(6S,6'S)-5,5'-{1,5-pentanediylbis[oxy (5-methoxy-2-nitrobenzene-4,1-diyl)carbonyl]}bis(5-azaspiro[2.4]heptane-6-carboxylate) (5-2)

To a solution of 4,4'-[1,5-pentanediylbis(oxy)]bis(5-methoxy-2-nitrobenzoic acid) (5-1) (5.41 g, 10.9 mmol, Journal of Medicinal Chemistry 2004, 47, 1161) in dichloromethane (50 mL), oxalyl chloride (5.63 mL, 65.7 mmol) was added at 0° C., and N,N-dimethylformamide (0.0844 mL, 1.09 mmol) was added dropwise. The temperature of the reaction solution was raised to room temperature, and the reaction solution was stirred for 2 hours. The resultant was distillated under reduced pressure, and the resulting residue was dissolved in dichloromethane (100 mL), which was added dropwise to dichloromethane solution (100 mL) of methyl(6S)-5-azaspiro[2.4]heptane-6-carboxylate hydrochloride (4.28 g, 24.1 mmol, Tetrahedron Letters 2012. 53. 3847) and triethylamine (6.07 mL, 43.8 mmol) under the nitrogen atmosphere at −40° C. The temperature of the reaction solution was raised to 0° C., and the reaction solution was stirred for 2 hours. To the reaction mixture, 1N hydrochloric acid (100 mL) was added, and the organic layer was washed with water and brine, and dried over anhydrous sodium sulfate. The resultant was distillated under reduced pressure to afford the desired compound (5-2) (8.40 g, quantitative).

MS (APCI, ESI) m/z: 769 $(M+H)^+$.

Step 2: {1,5-Pentanediylbis[oxy (5-methoxy-2-nitrobenzen-4,1-diyl)]}bis {[(6S)-6-(hydroxymethyl)-5-azaspiro[2.4]hept-5-yl]methanone} (5-3)

To a solution of compound (5-2) obtained in Step 1 (8.40 g, 10.9 mmol) in tetrahydrofuran (100 mL), lithium borohydride (714 mg, 32.8 mmol) was added, and the resultant was stirred at 0° C. for 30 minutes, and the temperature was raised to room temperature, and stirring was performed for 1 hour. After 1 N hydrochloric acid was added at 0° C., the resultant was extracted with ethyl acetate, and washed with brine, and then dried over anhydrous sodium sulfate. The solvent was distilled off under reduced pressure to afford the desired compound (5-3) (7.70 g, 99%).

MS (APCI, ESI) m/z: 713 $(M+H)^+$.

Step 3: Pentan-1,5-diylbis[oxy (5-methoxy-2-nitrobenzen-4,1-diyl)carbonyl(6S)-5-azaspiro[2.4]heptan-5,6-diylmethanediyl]diazetate (5-4)

Compound (5-3) obtained in Step 2 (7.70 g, 10.8 mmol) was dissolved in pyridine (20 mL) and acetic anhydride (10 mL, 105.9 mmol), which was stirred at room temperature. The resultant was distillated under reduced pressure to afford the desired compound (5-4) (8.38 g, 97%).

MS (APCI, ESI) m/z: 797 $(M+H)^+$.

Step 4:1,5-Pentanediylbis[oxy (2-amino-5-methoxybenzen-4,1-diyl)carbonyl(6S)-5-azaspiro[2.4]heptan-5,6-diylmethanediyl]diacetate (5-5)

To a solution of compound (5-4) obtained in Step 3 (8.28 g, 10.4 mmol) in N,N-dimethylformamide (100 mL), 5% palladium carbon (moisture content: 54%, 1.00 g) was added, and the reaction solution was then vigorously stirred under the hydrogen atmosphere at room temperature for 6 hours. The resultant was filtered through a Celite, and the filtrate was then distillated under reduced pressure, and the resulting residue was purified by silica gel column chromatography [chloroform:methanol=100:0 (v/v) to 90:10 (v/v)] to afford the desired compound (5-5) (5.05 g, 66%).

MS (APCI, ESI) m/z: 737 $(M+H)^+$.

Step 5: {(6S)-5-[4-({5-[4-({(6S)-6-[(Acetyloxy)methyl]-5-azaspiro[2.4]hept-5-yl}carbonyl)-5-amino-2-methoxyphenoxy]pentyl}oxy)-5-methoxy-2-{[(prop-2-en-1-yloxy)carbonyl]amino}benzoyl]-5-azaspiro[2.4]hept-6-yl}methylacetate (monoallyloxycarbonyl form) (5-6)

To a solution of compound (5-5) obtained in Step 4 (5.05 g, 6.85 mmol) in dichloromethane (100 mL), pyridine (1.10 mL, 13.7 mmol) was added, and allyl chloroformate (0.725 mL, 6.85 mmol) was added thereto under the nitrogen atmosphere at −78° C., and the resultant was stirred for 2 hours. The resultant was distillated under reduced pressure, and the resulting residue was purified by silica gel column chromatography [hexane:ethyl acetate=70:30 (v/v) to 100:0 (v/v), chloroform:methanol=100:0 (v/v) to 90:10 (v/v)] to afford the monoallyloxycarbonyl form (5-6) (2.63 g, 47%) as the desired compound.

MS (APCI, ESI) m/z: 821 $(M+H)^+$.

Step 6: N-[(2-Propen-1-yloxy)carbonyl]-L-valyl-N-{4-[({[2-({(6S)-6-[(acetyloxy)methyl]-5-azaspiro[2.4]hept-5-yl}carbonyl)-5-({5-[4-({(6S)-6-[(acetyloxy)methyl]-5-azaspiro[2.4]hept-5-yl}carbonyl)-2-methoxy-5-{[(2-propen-1-yloxy)carbonyl]amino}phenoxy]pentyl}oxy)-4-methoxyphenyl]carbamoyl}oxy)methyl]phenyl}-L-alaninamide (5-7)

Monoallyloxycarbonyl form (5-6) obtained in Step 5 (2.00 g, 2.44 mmol) and N-[(prop-2-en-1-yloxy)carbonyl]-L-valyl-N-[4-(hydroxymethyl)phenyl]-L-alaninamide (1.10 g, 2.92 mmol, WO2011130598) were reacted in the same manner as in Step 6 of Example 1-1 to afford the desired compound (5-7) (2.64 g, 89%).

MS (APCI, ESI) m/z: 1224 $(M+H)^+$.

Step 7: N-[(2-Propen-1-yloxy)carbonyl]-L-valyl-N-[4-({[(2-{[(6S)-6-(hydroxymethyl)-5-azaspiro[2.4]hept-5-yl]carbonyl}-5-{[5-(4-{[(6S)-6-(hydroxymethyl)-5-azaspiro[2.4]hept-5-yl]carbonyl}-2-methoxy-5-{[(2-propen-1-yloxy)carbonyl]amino}phenoxy) pentyl]oxy}-4-methoxyphenyl)carbamoyl]oxy}methyl)phenyl]-L-alaninamide (5-8)

To a solution of compound (5-7) obtained in Step 6 (2.64 g, 2.16 mmol) in methanol (10 mL), potassium carbonate (1.49 g, 10.8 mmol) was added, and the resultant was stirred at room temperature for 3 hours. A saturated aqueous ammonium chloride (100 mL) was added to the reaction mixture, which was extracted with ethyl acetate. The organic layer was dried over anhydrous sodium sulfate. The resultant was distillated under reduced pressure to afford the desired compound (5-8) (2.21 g, 90%).

MS (APCI, ESI) m/z: 1140 $(M+H)^+$.

Step 8: N-[(2-Propen-1-yloxy)carbonyl]-L-valyl-N-{4-[({[(11'S,11a'S)-11'-hydroxy-8'-{[5-({(11'S,11a'S)-11'-hydroxy-7'-methoxy-5'-oxo-10'-[(2-propen-1-yloxy)carbonyl]-5',10',11',11a'-tetrahydro-1'H-spiro[cyclopropane-1,2'-pyrrolo[2,1-c][1,4]benzodiazepine]-8'-yl}oxy) pentyl]oxy}-7'-methoxy-5'-oxo-11',11a'-dihydro-1'H-spiro[cyclopropane-1,2'-pyrrolo[2,1-c][1,4]benzodiazepine]-10' (5'H)-yl]carbonyl}oxy)methyl]phenyl}-L-alaninamide (5-9)

To a solution of compound (5-8) obtained in Step 7 (2.03 g, 1.78 mmol) in dichloromethane (50 mL), Dess-Martin periodinane (1.59 g, 3.74 mmol) was added, and the resultant was stirred at room temperature overnight. A saturated aqueous sodium hydrogen carbonate (100 mL) was added to the reaction mixture, which was extracted with chloroform. The organic layer was dried over anhydrous sodium sulfate. The resultant was distillated under reduced pressure, and the resulting residue was purified by silica gel column chromatography [chloroform:methanol=100:0 (v/v) to 90:10 (v/v)] to afford the desired compound (5-9) (2.05 g, quantitative).

MS (APCI, ESI) m/z: 1136 $(M+H)^+$.

Step 9: L-Valyl-N-{4-[({[(11'S,11a'S)-11'-hydroxy-7'-methoxy-8'-[(5-{[(11a'S)-7'-methoxy-5'-oxo-5',11a'-dihydro-1'H-spiro[cyclopropane-1,2'-pyrrolo[2,1-c][1,4]benzodiazepine]-8'-yl]oxy}pentyl)oxy]-5'-oxo-11',11a'-dihydro-1'H-spiro[cyclopropane-1,2'-pyrrolo[2,1-c][1,4]benzodiazepine]-10' (5'H)-yl]carbonyl}oxy)methyl]phenyl}-L-alaninamide (5-10)

Compound (5-9) obtained in Step 8 (2.05 g, 1.80 mmol) was reacted in the same manner as in Step 12 of Example 2-1 to afford the desired compound (5-10) (1.02 g, 60%).

MS (APCI, ESI) m/z: 950 $(M+H)^+$.

Step 10: N-[4-(11,12-Didehydrodibenzo[b,f]azocin-5 (6H)-yl)-4-oxobutanoyl]glycylglycyl-L-valyl-N-{4-[({[(11'S,11a'S)-11'-hydroxy-7'-methoxy-8'-[(5-{[(11a'S)-7'-methoxy-5'-oxo-5',11a'-dihydro-1'H-spiro[cyclopropane-1,2'-pyrrolo[2,1-c][1,4]benzodiazepine]-8'-yl]oxy}pentyl)oxy]-5'-oxo-11',11a'-dihydro-1'H-spiro[cyclopropane-1,2'-pyrrolo[2,1-c][1,4]benzodiazepine]-10' (5'H)-yl]carbonyl}oxy)methyl]phenyl}-L-alaninamide (5-11)

Compound (5-10) obtained in Step 9 (0.710 g, 0.747 mmol) and compound (2-2) obtained in Step 1 of Example 1-2 (0.313 g, 0.747 mmol) were dissolved in mixed solvent of dichloromethane (1.5 mL) and methanol (0.1 mL). Thereto, 4-(4,6-dimethoxy-1,3,5-triazin-2-yl)-4-methylmorpholinium chloride (0.264 g, 0.897 mmol) was added, and the resultant was stirred at room temperature for 1 hour. The resultant was distillated under reduced pressure, and the resulting residue was purified by silica gel column chromatography [chloroform:methanol=100:0 (v/v) to 80:20 (v/v)] to afford the desired compound (5-11) (0.671 g, 66%).

$^1$H-NMR (DMSO-$D_6$) δ: 9.91 (1H, s), 8.32 (1H, s), 8.23-7.91 (3H, m), 7.81-7.19 (14H, m), 7.04 (1H, m), 6.80-6.62 (3H, m), 5.77-5.75 (1H, m), 5.20 (1H, m), 5.01 (1H, m), 4.79 (1H, m), 4.46-4.35 (1H, m), 4.04 (4H, m), 3.86-3.38 (18H, m), 3.22-3.15 (2H, m), 2.67-2.63 (1H, m), 2.46-2.23 (3H, m), 2.09-1.91 (2H, m), 1.80-1.78 (5H, m), 1.57 (3H, m), 1.27 (3H, s), 1.11-1.04 (1H, m), 0.87-0.79 (6H, m), 0.63-0.55 (6H, m).

MS (APCI, ESI) m/z: 1351 $(M+H)^+$.

Example 2-4: Drug-Linker 4

[Formula 48]

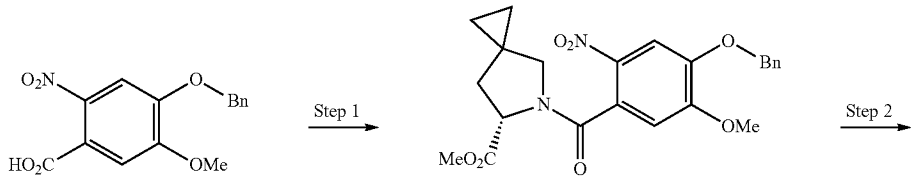

6-1 6-2

-continued
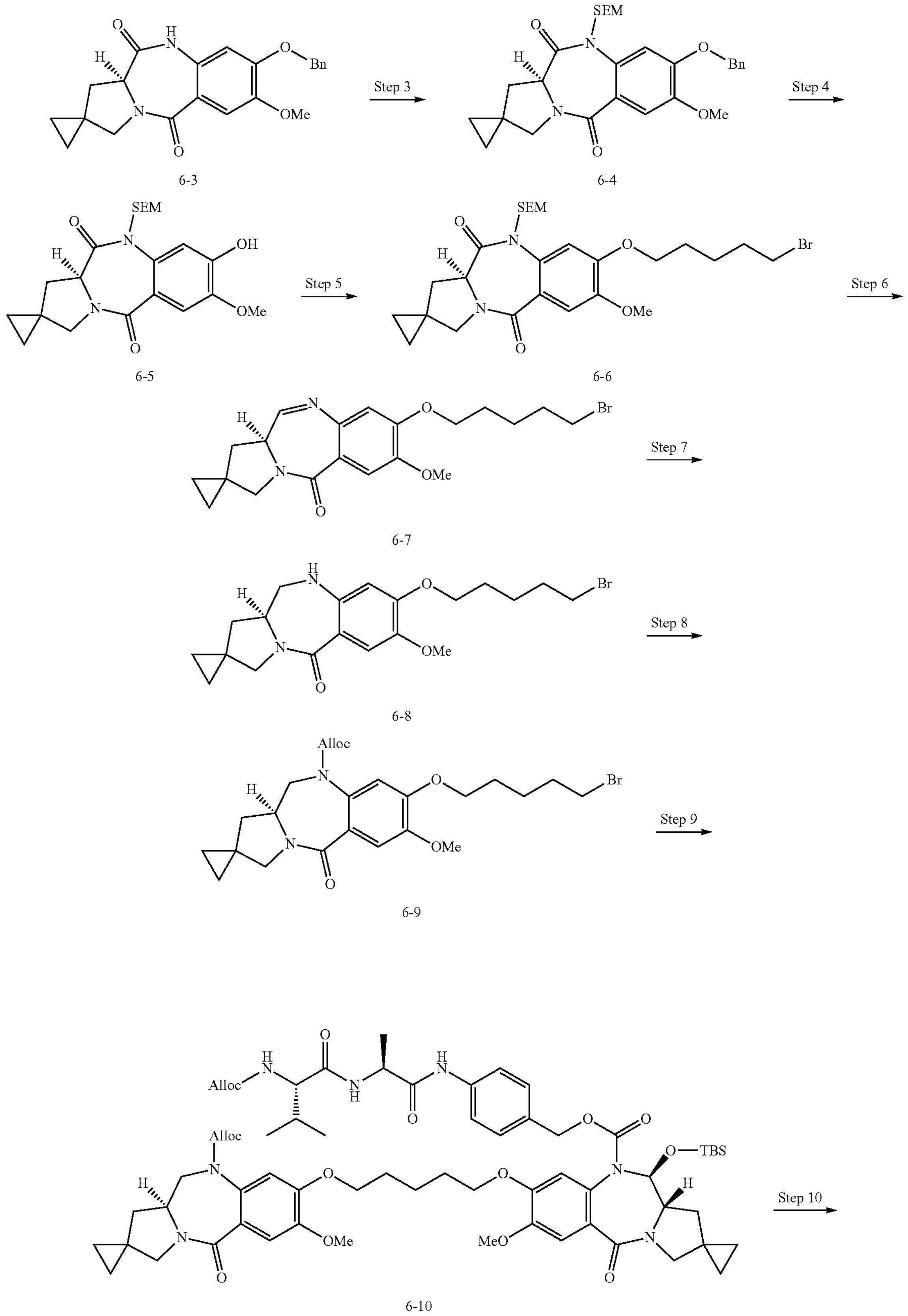

-continued

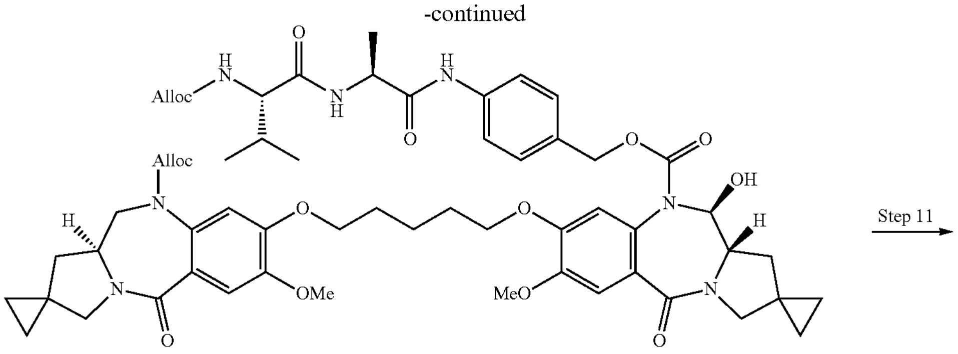

6-11

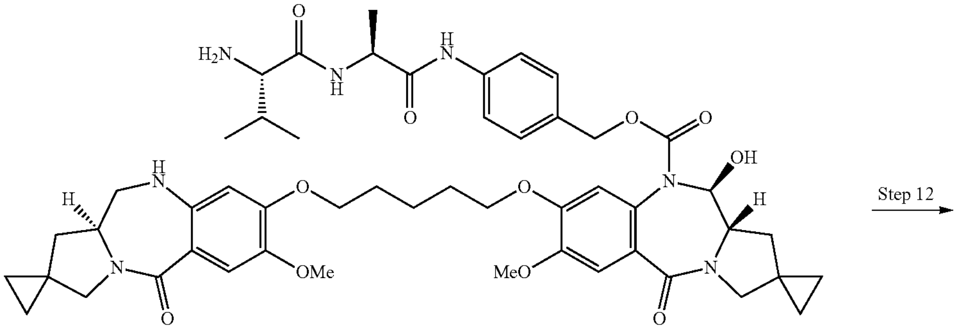

6-12

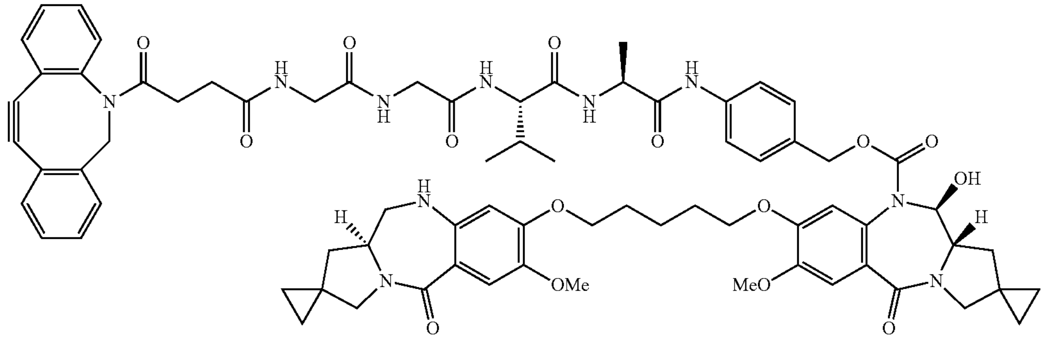

6-13

Step 1: Methyl(6S)-5-[4-(benzyloxy)-5-methoxy-2-nitrobenzoyl]-5-azaspiro[2.4]heptane-6-carboxylate (6-2)

To a solution of 4-(benzyloxy)-5-methoxy-2-nitrobenzoic acid (6-1) (6.07 g, 20.0 mmol, Tetrahedron 1995, 51, 5617) and N,N-dimethylformamide (1.08 mL, 13.9 mmol) in dichloromethane (100 mL), oxalyl chloride (3.43 mL, 40.0 mmol) was added dropwise under ice-cooling over 5 minutes. The reaction solution was stirred at room temperature for 5 hours, and then distillated under reduced pressure, and the resulting residue was dissolved in dichloromethane (20 mL), which was distillated under reduced pressure. After this operation was repeated three times, the residue was suspended in dichloromethane (5 mL), to which excessive amounts of diethyl ether and hexane were added, and the following filtration and drying under reduced pressure afforded the crude acyl chloride. The acyl chloride obtained was dissolved in dichloromethane and cooled to −40° C. (dry ice-acetonitrile bath), to which methyl(6S)-5-azaspiro[2.4]heptane-6-carboxylate hydrochloride (4.22 g, 22.0 mmol, Tetrahedron Letters 2012. 53. 3847) and triethylamine (3.36 mL, 24.2 mmol) were gradually added. The temperature of the reaction mixture was raised to room temperature overnight. To the reaction mixture, 1 N hydrochloric acid was added, and the reaction mixture was extracted with dichloromethane. The organic layer was washed with water, a saturated aqueous sodium hydrogen carbonate, and brine, and dried over anhydrous sodium sulfate. The resultant was distillated under reduced pressure, and the resulting residue was purified by silica gel column chromatography [hexane:ethyl acetate=100:0 to 50:50] to afford the desired compound (6-2) (6.55 g, 80%).

MS (APCI, ESI) m/z: 441 $(M+H)^+$

Step 2: (11a'S)-8'-(Benzyloxy)-7'-methoxy-1'H-spiro[cyclopropane-1,2'-pyrrolo[2,1-c][1,4]benzodiazepine]-5',11' (10'H,11a'H)-dione (6-3)

To a solution of compound (6-2) obtained in Step 1 (6.55 g, 16.0 mmol) in ethanol (150 mL) and tetrahydrofuran (150 mL), Raney-nickel (7.00 g) was added under the nitrogen atmosphere. Hydrazine monohydrate (7 mL) was added to the reaction mixture, and the temperature was gradually raised to 50° C. After stirring at 50° C. for 2 hours, Raney-nickel (3.00 g) and hydrazine monohydrate (3 mL) were added thereto, and the resultant was stirred for 1 hour. THF (100 mL) was added to the reaction mixture, which was filtered through a Celite. The resultant was distillated under reduced pressure, and the resulting residue was purified by silica gel column chromatography [hexane:ethyl acetate=100:0 to 25:75] to afford the desired compound (6-3) (4.42 g, 73%).

MS (APCI, ESI) m/z: 379 $(M+H)^+$

Step 3: (11a'S)-8'-(Benzyloxy)-7'-methoxy-10'-{[2-(trimethylsilyl)ethoxy]methyl}-1'H-spiro[cyclopropane-1,2'-pyrrolo[2,1-c][1,4]benzodiazepine]-5',11' (10'H,11a'H)-dione (6-4)

To a solution of compound (6-3) obtained in Step 2 (10.0 g, 26.4 mmol) in tetrahydrofuran (150 mL), a 2.6 mol/L normal-hexane solution of normal-butyllithium (12.0 mL, 31.8 mmol) was added slowly dropwise at −40° C. The reaction solution was stirred at −40° C. for 15 minutes, and 2-(chloromethoxy)ethyltrimethylsilane (5.57 mL, 31.7 mmol) was then added slowly dropwise thereto. After the reaction solution was stirred at room temperature for 3 hours, water was added thereto, and the resultant was extracted with ethyl acetate. The organic layer was washed with water and brine, and dried over anhydrous sodium sulfate. After distillation under reduced pressure, the resulting residue was purified by silica gel column chromatography [hexane:ethyl acetate=100:0 to 30:70] to afford the desired compound (6-4) (11.8 g, 88%).

MS (APCI, ESI) m/z: 509 $(M+H)^+$

Step 4: (11a'S)-8'-Hydroxy-7'-methoxy-10'-{[2-(trimethylsilyl)ethoxy]methyl}-1'H-spiro[cyclopropane-1,2'-pyrrolo[2,1-c][1,4]benzodiazepine]-5',11' (10'H,11a'H)-dione (6-5)

To a solution of compound (6-4) obtained in Step 3 (18.7 g, 36.8 mmol) in tetrahydrofuran (50 mL) and ethanol (100 mL), a 5% palladium carbon catalyst (5.00 g) was added under the nitrogen atmosphere. The nitrogen balloon was immediately replaced with a hydrogen balloon, and the reaction mixture was stirred under the hydrogen atmosphere for 6 hours. The reaction mixture was diluted by addition of chloroform and filtered through a Celite, and the filtrate was then distillated under reduced pressure, and the resulting residue was purified by silica gel column chromatography [hexane:ethyl acetate=100:0 to 25:75] to afford the desired compound (6-5) (15.1 g, 98%).

MS (APCI, ESI) m/z: 419 $(M+H)^+$

Step 5: (11a'S)-8'-[(5-Bromopentyl)oxy]-7'-methoxy-10'-{[2-(trimethylsilyl)ethoxy]methyl}-1'H-spiro[cyclopropane-1,2'-pyrrolo[2,1-c][1,4]benzodiazepine]-5',11' (10'H,11a'H)-dione (6-6)

Compound (6-5) obtained in Step 4 (2.77 g, 6.62 mmol) was reacted in the same manner as in Step 2 of Example 2-1 to afford the desired compound (6-6) (3.31 g, 88%).

$^1$H-NMR ($CDCl_3$) δ: 7.36 (1H, s), 7.25 (1H, s), 5.55 (1H, m), 4.65 (1H, m), 4.24-4.23 (1H, m), 4.11-4.03 (2H, m), 3.93 (3H, s), 3.85-3.78 (1H, m), 3.72-3.69 (2H, m), 3.46-3.39 (3H, m), 2.47-2.44 (1H, m), 2.25-2.22 (1H, m), 1.95-1.91 (4H, m), 1.67-1.59 (1H, m), 1.03-0.95 (2H, m), 0.90-0.85 (1H, m), 0.70-0.66 (4H, m), 0.05 (9H, s).

Step 6: (11a'S)-8'-[(5-Bromopentyl)oxy]-7'-methoxy-1',11a'-dihydro-5'H-spiro[cyclopropane-1,2'-pyrrolo[2,1-c][1,4]benzodiazepine]-5'-one (6-7)

Compound (6-6) obtained in Step 5 (3.31 g, 5.83 mmol) was reacted in the same manner as in Step 7 of Example 2-1 to afford the desired compound (6-7) (1.11 g, 45%).

$^1$H-NMR ($CDCl_3$) δ: 7.81 (1H, m), 7.53 (1H, s), 6.82 (1H, s), 4.13-4.06 (2H, m), 3.97 (3H, s), 3.88-3.83 (1H, m), 3.69 (1H, m), 3.52-3.39 (3H, m), 2.55-2.52 (1H, m), 2.06-1.89 (5H, m), 1.67-1.63 (2H, m), 0.76-0.72 (4H, m).

Step 7: (11a'S)-8'-[(5-Bromopentyl)oxy]-7'-methoxy-1',10',11',11a'-tetrahydro-5'H-spiro[cyclopropane-1,2'-pyrrolo[2,1-c][1,4]benzodiazepine]-5'-one (6-8)

Compound (6-7) obtained in Step 6 (2.56 g, 6.08 mmol) was reacted in the same manner as in Step 8 of Example 2-1 to afford the desired compound (6-8) (1.15 g, 45%).

$^1$H-NMR ($CDCl_3$) δ: 7.60 (1H, s), 6.07 (1H, s), 4.11-4.04 (1H, m), 3.99 (2H, m), 3.87-3.84 (1H, m), 3.85 (3H, s), 3.73 (1H, m), 3.58-3.53 (2H, m), 3.47-3.42 (3H, m), 2.03-1.78 (6H, m), 1.65-1.63 (2H, m), 0.77-0.56 (4H, m).

Step 8: Prop-2-en-1-yl(11a'S)-8'-[(5-bromopentyl)oxy]-7'-methoxy-5'-oxo-11',11a'-dihydro-1'H-spiro[cyclopropane-1,2'-pyrrolo[2,1-c][1,4]benzodiazepine]-10' (5'H)-carboxylate (6-9)

Compound (6-8) obtained in Step 7 (1.15 g, 2.72 mmol) was reacted in the same manner as in Step 9 of Example 2-1 to afford the desired compound (6-9) (1.14 g, 82%).

$^1$H-NMR ($CDCl_3$) δ: 7.23 (1H, s), 6.69 (1H, s), 5.79 (1H, s), 5.13-5.10 (2H, m), 4.68-4.66 (1H, m), 4.48-4.45 (2H, m), 4.01 (2H, m), 3.92 (3H, s), 3.76 (1H, m), 3.54-3.37 (3H, m), 2.39 (1H, m), 1.95-1.90 (4H, m), 1.68-1.61 (3H, m), 1.44 (1H, m), 0.75-0.66 (4H, m).

Step 9: N-[(Prop-2-en-1-yloxy)carbonyl]-L-valyl-N-{4-[({[(11'S, 11a'S)-11'-{[tert-butyl(dimethyl)silyl]oxy}-7'-methoxy-8'-{[5-({(11a'S)-7'-methoxy-5'-oxo-10'-[(prop-2-en-1-yloxy)carbonyl]-5',10',11',11a'-tetrahydro-1'H-spiro[cyclopropane-1,2'-pyrrolo[2,1-c][1,4]benzodiazepine]-8'-yl}oxy) pentyl]oxy}-5'-oxo-11', 11a'-dihydro-1'H-spiro[cyclopropane-1,2'-pyrrolo[2,1-c][1,4]benzodiazepine]-10' (5'H)-yl]carbonyl}oxy)methyl]phenyl}-L-alaninamide (6-10)

Compound (6-9) obtained in Step 8 (0.374 g, 0.737 mmol) and compound (1-11) obtained in Step 10 of Example 1-1 (0.452 g, 0.56 mmol) were reacted in the same manner as in Step 10 of Example 2-1 to afford the desired compound (6-10) (0.589 g, 65%).

MS (APCI, ESI) m/z: 1234 $(M+H)^+$

Step 10: N-[(Prop-2-en-1-yloxy)carbonyl]-L-valyl-N-{4-[({[(11'S,11a'S)-11'-hydroxy-7'-methoxy-8'-{[5-({(11a'S)-7'-methoxy-5'-oxo-10'-[(prop-2-en-1-yloxy)carbonyl]-5',10',11',11a'-tetrahydro-1'H-spiro[cyclopropane-1,2'-pyrrolo[2,1-c][1,4]benzodiazepine]-8'-yl}oxy) pentyl]oxy}-5'-oxo-11', 11a'-dihydro-1'H-spiro[cyclopropane-1,2'-pyrrolo[2,1-c][1,4]benzodiazepine]-10' (5'H)-yl]carbonyl}oxy) methyl]phenyl}-L-alaninamide (6-11)

Compound (6-10) obtained in Step 9 (0.589 g, 0.477 mmol) was reacted in the same manner as in Step 11 of Example 2-1 to afford the desired compound (6-11) (0.382 g, 71%).

$^1$H-NMR ($CDCl_3$) δ: 8.90 (1H, s), 7.55 (2H, m), 7.25-7.21 (2H, m), 6.74 (2H, m), 6.38 (1H, s), 5.90-5.87 (5H, m), 5.33-5.09 (8H, m), 4.66-4.60 (8H, m), 3.98-3.91 (10H, m), 3.77-3.30 (12H, m), 2.42-2.36 (2H, m), 1.77-1.39 (6H, m), 0.91-0.70 (14H, m).

Step 11: L-Valyl-N-{4-[({[(11'S,11a'S)-11'-hydroxy-7'-methoxy-8'-[(5-{[(11a'S)-7'-methoxy-5'-oxo-5',10',11',11a'-tetrahydro-1'H-spiro[cyclopropane-1,2'-pyrrolo[2,1-c][1,4]benzodiazepine]-8'-yl]oxy}pentyl)oxy]-5'-oxo-11',11a'-dihydro-1'H-spiro[cyclopropane-1,2'-pyrrolo[2,1-c][1,4]benzodiazepine]-10' (5'H)-yl]carbonyl}oxy)methyl]phenyl}-L-alaninamide (6-12)

Compound (6-11) obtained in Step 10 (0.382 g, 0.341 mmol) was reacted in the same manner as in Step 12 of Example 2-1 to afford the desired compound (6-12) (0.200 g, 62%).

MS (APCI, ESI) m/z: 952 $(M+H)^+$

Step 12: N-[4-(11,12-Didehydrodibenzo[b,f]azocin-5 (6H)-yl)-4-oxobutanoyl]glycylglycyl-L-valyl-N-{4-[({[(11'S, 11a'S)-11'-hydroxy-7'-methoxy-8'-[(5-{[(11a'S)-7'-methoxy-5'-oxo-5',10',11',11a'-tetrahydro-1'H-spiro[cyclopropane-1,2'-pyrrolo[2,1-c][1,4]benzodiazepine]-8'-yl]oxy}pentyl)oxy]-5'-oxo-11',11a'-dihydro-1'H-spiro[cyclopropane-1,2'-pyrrolo[2,1-c][1,4]benzodiazepine]-10' (5'H)-yl]carbonyl}oxy)methyl]phenyl}-L-alaninamide (6-13)

Compound (6-12) obtained in Step 11 (0.0560 g, 0.0588 mmol) and compound (2-2) obtained in Step 1 of Example 1-2 (0.022 g, 0.053 mmol) were reacted in the same manner as in step 13 of Example 2-1 to afford the desired compound) (6-13) (0.0500 g, 63%).

MS (APCI, ESI) m/z: 1354 $(M+H)^+$

[Synthesis of Glycan Donor]

Example 3: $[N_3\text{-PEG(3)}]$-MSG1-Ox

[Formula 49]

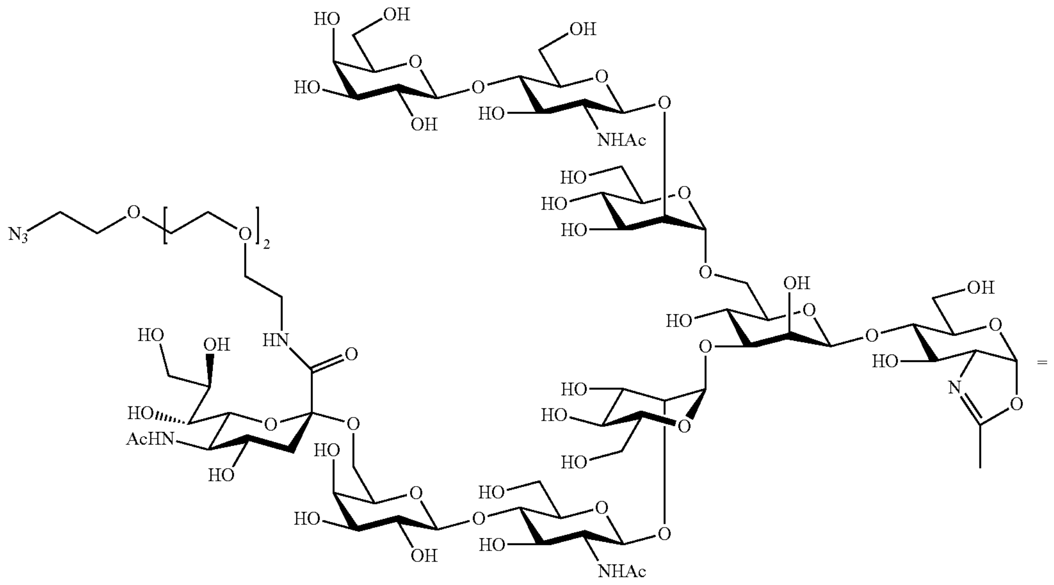

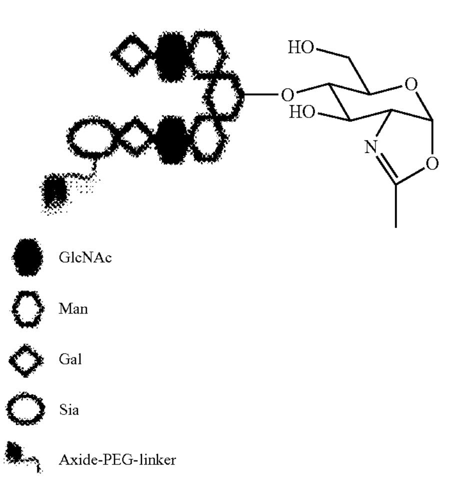

Step 1: (MSG1-) Asn

The commercially available product monosialo-Asn free (1S2G/1G2S-10NC-Asn, produced by GlyTech, Inc.) (referred to as "(MSG-)Asn") (500 mg) was subjected to separation/purification by reversed-phase HPLC under conditions below to separate into (MSG1-) Asn eluted as the 1st main peak (retention time: around 15 to 19 min) and (MSG2-) Asn eluted as the 2nd main peak (retention time: around 21 to 26 min). The eluent used was a 0.1% formic acid aqueous solution, the apparatus used was an ELS-PDA trigger preparative system (produced by JASCO Corporation), the column used was an Inertsil ODS-3 (10 μm, 300×250 mm, produced by GL Sciences, Inc.), and the flow rate was 30 mL/min. Fractions of the first peak UV-detected (210 nm) during the elution were separated, and freeze-dried to afford the desired compound (238 mg).

Step 2: MSG1

The compound obtained in Step 1 (229 mg) was dissolved in 200 mM phosphate buffer solution (pH 6.25) (1145 μL), to which an aqueous solution (100 μL) of EndoM (produced by Tokyo Chemical Industry Co., Ltd., 1 U/mL)) was added, and the resultant was incubated at 35° C. for 6 days. After the completion of the reaction, the reaction solution was subjected to ultrafiltration with a VIVASPIN 15R (Hydrosart membrane, 30K, 6,000×G), and the filtered solution obtained was subjected to separation/purification by reversed-phase HPLC. The eluent used was a 0.1% trifluoroacetic acid aqueous solution, the apparatus used was an ELS-PDA trigger preparative system (produced by JASCO Corporation), and the column used was an Inertsil ODS-3 (produced by GL Sciences, Inc.). Fractions corresponding to the peak of the desired compound UV-detected (210 nm) during the elution were separated, and freeze-dried to afford the desired compound (117 mg).

Step 3: [$N_3$-PEG(3)]-MSG1

Into a 5 mL sampling tube (Ina-Optica Co., Ltd.), 11-azide-3,6,9-trioxaundecane-1-amine (0.108 mL, 0.541 mmol) and an aqueous solution (1.2 mL) of MSG1 obtained in Step 2 (117 mg, 0.068 mmol) were added, and the resultant was stirred for 1 hour and then freeze-dried. Into the 5 mL sampling tube after freeze-drying, an N,N-dimethylformamide solution (1.2 mL) of O-(7-azabenzotriazol-1-yl)-N,N,N',N'-tetramethyluronium hexafluorophosphate (103 mg, 0.27 mmol) and diisopropylethylamine (0.046 mL, 0.27 mmol) were added, followed by stirring at 37° C. for 3 hours. After the completion of the reaction, the reaction solution was transferred into a centrifuge tube (50 mL) into which diethyl ether (20 mL) had been added in advance. The solid matter was precipitated by using a small centrifuge (Hitachi Koki Co., Ltd., CF16RX) and the supernatant was removed. Diethyl ether (10 mL) was further added, and the resultant was centrifuged and then decanted. Subsequently, acetonitrile (10 mL) was added and the resultant was subjected twice to an operation of centrifugation followed by decantation, and dried under reduced pressure to afford a crude product. The resulting solid matter was subjected to separation/purification by reversed-phase HPLC under the same conditions as in Step 2 to afford the desired compound (94.2 mg).

Step 4: [$N_3$-PEG(3)]-MSG1-Ox

Into a 5 mL sampling tube (produced by Ina-Optica Co., Ltd.), the compound synthesized in Step 3 (100 mg) and an aqueous solution (520 μL) of 2-chloro-1,3-dimethyl-1H-benzimidazol-3-ium-chloride (produced by FUSHIMI Pharmaceutical Co., Ltd., 56 mg, 0.257 mmol) was added. To the reaction solution after being ice-cooled, an aqueous solution (520 μL) of tripotassium phosphate (165 mg, 0.78 mmol) was added, followed by stirring under ice-cooling for 3 hours. The resulting reaction solution was subjected to ultrafiltration with an Amicon Ultra (Ultracel 30K, produced by Merck Millipore) to remove the solid matter. The filtered solution was purified by gel filtration chromatography. The apparatus used was a Purif-Rp2 (produced by Shoko Scientific Co., Ltd.), the column used was a HiPrep 26/10 Desalting (produced by GE Healthcare), the mobile phase used was 0.03% NH3 aqueous solution, and the flow rate was 10 mL/min and the fraction volume was 10 mL. Fractions containing the desired compound UV-detected (220 nm) during the elution were collected together, to which a 1 N aqueous solution of sodium hydroxide (104 μL, 0.104 mmol) was added, and the resultant was freeze-dried to afford the desired compound (84 mg).

Example 4: [$N_3$-PEG(3)]-MSG-Ox

[Formula 50]

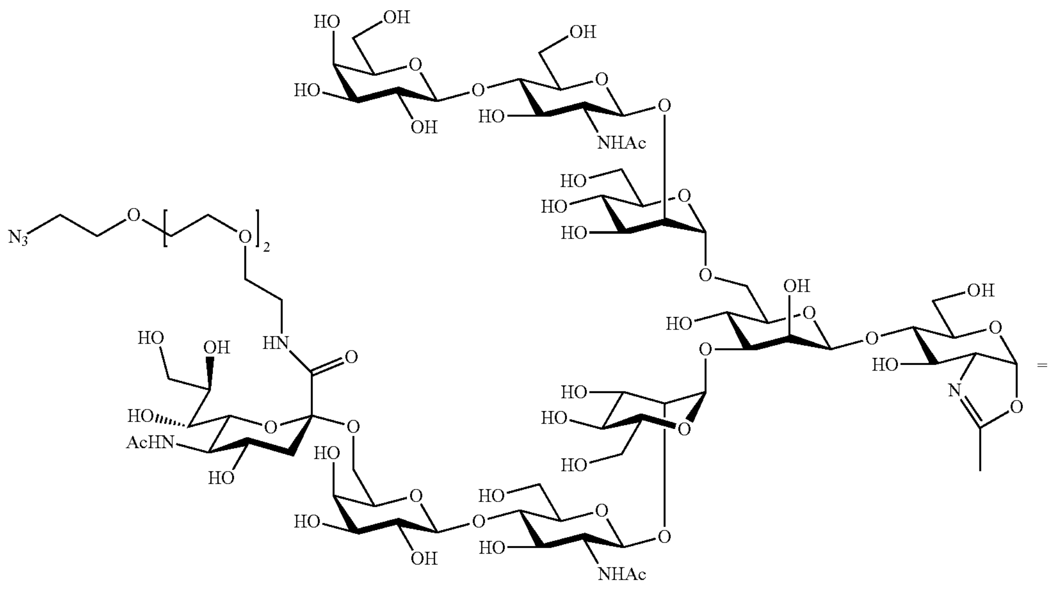

-continued

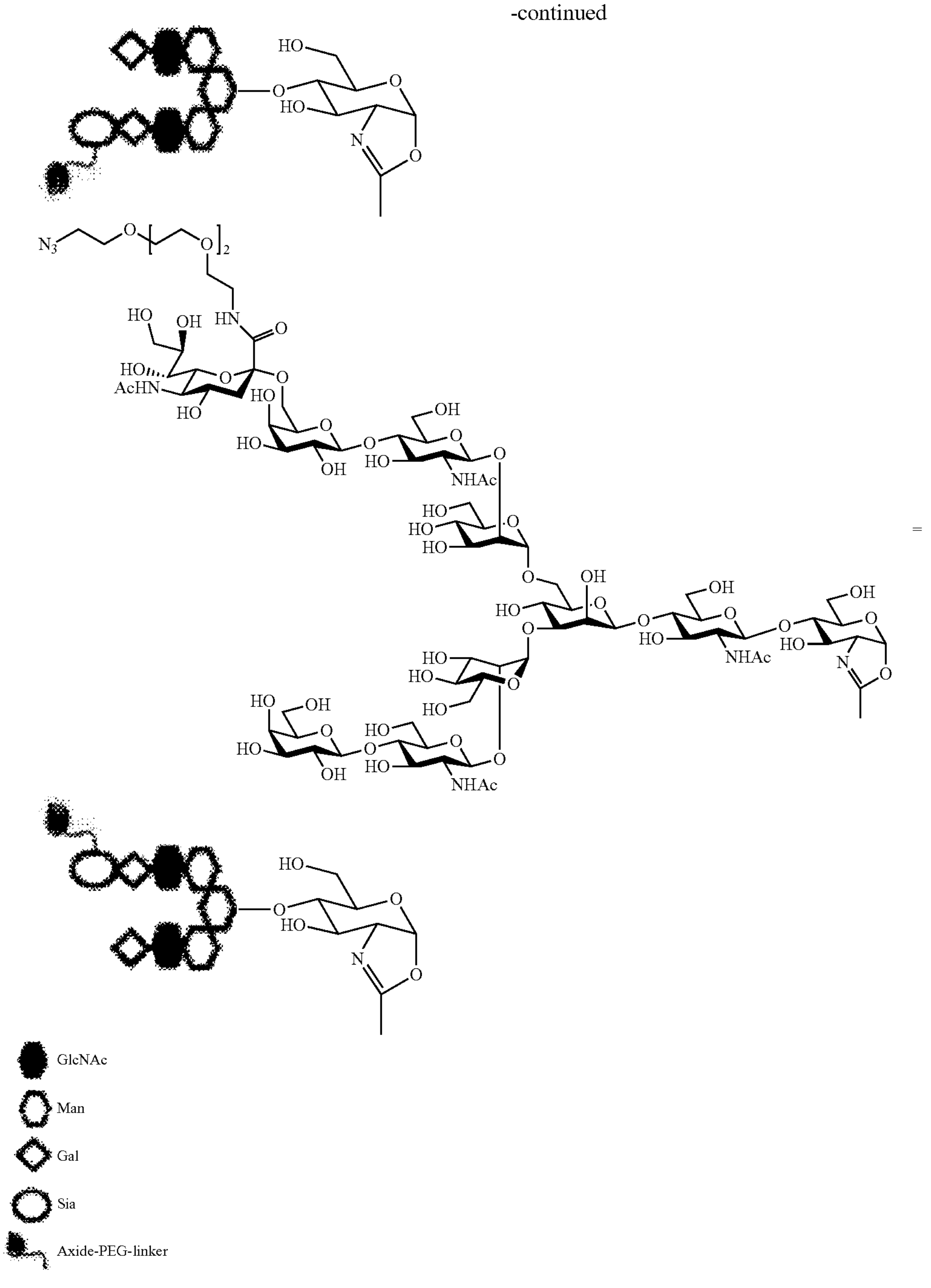

Step 1: Preparation of (MSG-)Asn

The commercially available product 1S2G/1G2S-10NC-Asn-Fmoc (produced by GlyTech, Inc.) (referred to as "Fmoc-(MSG-)Asn") (1000 mg) was dissolved in ethanol/water (1/1) (10 mL), to which a 1 N aqueous solution of sodium hydroxide (1.75 mL, 4 equivalents) was added, followed by stirring at room temperature for 3 hours. After the completion of the reaction, the reaction solution was subjected to ultrafiltration with an Amicon Ultra (30K, produced by Millipore Corporation) to remove the solid matter, and 1 N hydrochloric acid (832 μL, 1.9 equivalents) was added to the filtered solution obtained. The solvent was removed with the high-speed evaporator V-10 (produced by Biotage). Acetonitrile was added thereto, and the solvent was removed with the high-speed evaporator V-10 (produced by Biotage), and the resultant was then subjected to separation/purification by reversed-phase HPLC. The eluent was a 0.1% trifluoroacetic acid aqueous solution and a 0.1% trifluoroacetic acid acetonitrile solution, the apparatus used was a Purif-Rp2 (produced by Shoko Scientific Co., Ltd.), and the column used was an Inertsil ODS-3 (produced by GL Sciences, Inc.). Fractions containing the desired compound UV-detected (220 nm) during the elution were collected together, and freeze-dried. This was dissolved again in pure water, and a pH test paper strip indicated that the solution was acidic. Hence, 18% aqueous ammonia (150 μL) was added thereto and it was confirmed with a pH test paper strip that the solution had become basic, and the solution was freeze-dried again. The desired compound obtained (840 mg) was directly used for the subsequent reaction.

Step 2: Synthesis of MSG

The compound obtained in Step 1 (840 mg) was dissolved in 200 mM phosphate buffer solution (pH 6.25) (6000 μL), to which an aqueous solution (200 μL) of EndoM (produced by Tokyo Chemical Industry Co., Ltd., 1 U/mL)) was added, and the resultant was incubated at 28° C. for 26 hours. Because the reaction had not completed, an aqueous solution (50 μL) of EndoM (produced by Tokyo Chemical Industry Co., Ltd., 1 U/mL)) was added, and the resultant was incubated at 28° C. for 2 hours, and then left to stand at room temperature until the completion of the reaction. After the completion of the reaction, the reaction solution was subjected to ultrafiltration with an Amicon Ultra (30K, produced by Millipore Corporation). Trifluoroacetic acid (80 μL) was added to the filtered solution obtained, which was subjected to separation/purification by reversed-phase HPLC. The eluent was a 0.1% trifluoroacetic acid aqueous solution and a 0.1% trifluoroacetic acid acetonitrile solution, the apparatus used was a Purif-Rp2 (produced by Shoko Scientific Co., Ltd.), and the column used was an Inertsil ODS-3 (produced by GL Sciences, Inc.). Fractions containing the desired compound UV-detected (220 nm) during the elution were collected together, and freeze-dried. This was dissolved again in pure water in order to remove the residual trifluoroacetic acid, and thus the desired compound (618 mg) was obtained as a colorless solid.

ESI-MS: Calcd for $C_{66}H_{110}N_4O_{49}$: $[M+H]^+$ 1743.62, Found 1743.63

Step 3: Synthesis of $[N_3$-PEG(3)]-MSG

In accordance with the procedure of Step 3 of Example 3 using the compound obtained in Step 2 (120 mg), the desired compound (88.6 mg) was obtained. ESI-MS: Calcd for $C_{73}H_{124}N_8O_{51}$: $[M+2H]^{2+}$ 965.37, Found 965.37

Step 4 Synthesis of $[N_3$-PEG(3)]-MSG-Ox

In accordance with the procedure of Step 4 of Example 3 using the compound obtained in Step 3 (100 mg), the desired compound (88 mg) was obtained.

Example 5: $[N_3$-PEG(3)$]_2$-SG (10)-Ox

[Formula 51]

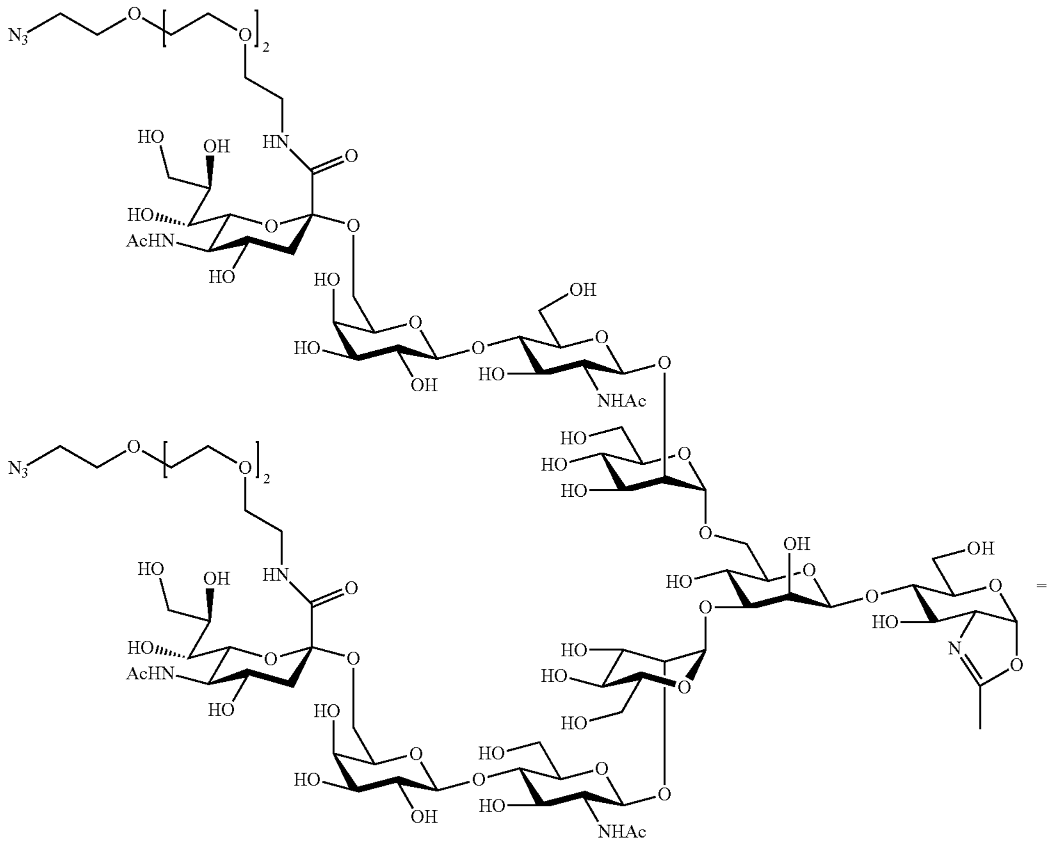

-continued

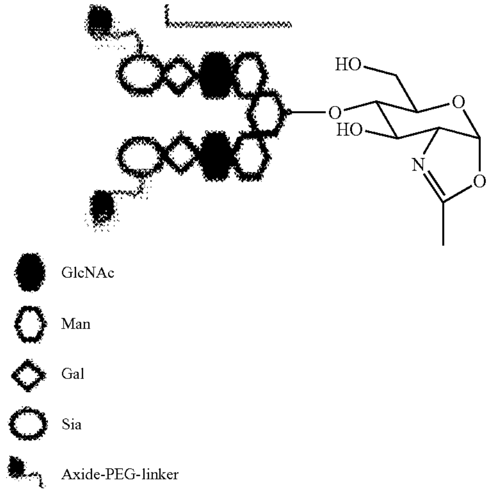

Step 1: $[N_3\text{-PEG(3)}]_2$-SG (10)

Into a 5 mL sampling tube (Ina-Optica Co., Ltd), an aqueous solution (0.5 mL) of 11-azide-3,6,9-trioxaundecane-1-amine (0.096 mL, 0.485 mmol) and disialooctasaccharide (50 mg, 0.24 mmol) were added, and the resultant was stirred for 1 hour and then freeze-dried. Into the 5 mL sampling tube after freeze-drying, an N,N-dimethylformamide solution (0.6 mL) of O-(7-azabenzotriazol-1-yl)-N,N,N',N'-tetramethyluronium hexafluorophosphate (92 mg, 0.24 mmol) and diisopropylethylamine (0.042 mL, 0.24 mmol) were added, followed by stirring at 37° C. for 4 hours. After the completion of the reaction, the reaction solution was transferred into a centrifuge tube (50 mL) into which diethyl ether (20 mL) had been added in advance. The solid matter was precipitated by using a small centrifuge (Hitachi Koki Co., Ltd., CF16RX) and the supernatant was removed. Diethyl ether (20 mL) was added and the resultant was decanted. Subsequently, acetonitrile (20 mL) was added and the resultant was decanted, and then dried under reduced pressure to afford a crude product. The resulting solid matter was dissolved in an appropriate amount of a 0.2% trifluoroacetic acid aqueous solution, and subjected to separation/purification by reversed-phase HPLC. The eluent was a 0.1% trifluoroacetic acid aqueous solution and a 0.1% trifluoroacetic acid acetonitrile solution, the apparatus used was a Purif-Rp2 (produced by Shoko Scientific Co., Ltd.), and the column used was an Inertsil ODS-3 (produced by GL Sciences, Inc.). Fractions containing the desired compound UV-detected (220 nm) during the elution were collected together, and freeze-dried to afford the desired compound (42 mg).

Step 2: $[N_3\text{-PEG(3)}]_2$-SG (10)-Ox

Into a 5 mL sampling tube (produced by Ina-Optica Co., Ltd), the compound synthesized in Step 1 (40 mg) and an aqueous solution (200 μL) of 2-chloro-1,3-dimethyl-1H-benzimidazol-3-ium-chloride (produced by FUSHIMI Pharmaceutical Co., Ltd. 17.9 mg, 0.083 mmol) was added. To the reaction solution after being ice-cooled, an aqueous solution (200 μL) of tripotassium phosphate (52.6 mg, 0.25 mmol) was added, followed by stirring under ice-cooling for 2 hours. The resulting reaction solution was subjected to ultrafiltration with an Amicon Ultra (Ultracel 30K, produced by Merck Millipore) to remove the solid matter. The filtered solution was purified by gel filtration chromatography. The apparatus used was a Purif-Rp2 (produced by Shoko Scientific Co., Ltd.), the column used was a HiPrep 26/10 Desalting (produced by GE Healthcare), the mobile phase used was 0.03%-NH3 aqueous solution, and the flow rate was 10 mL/min and the fraction volume was 10 mL. Fractions containing the desired compound UV-detected (220 nm) during the elution were collected together, to which a 1 N aqueous solution of sodium hydroxide (33 μL, 0.033 mmol) was added, and the resultant was freeze-dried to afford the desired compound (34 mg).

Example 6: Mouse Anti-CLDN6 Antibody B1-Producing Hybridoma (218B1) and Mouse Anti-CLDN6 Antibody C7-Producing Hybridoma (218C7)

6-1. Immunization of Mice and Acquisition of Hybridomas 1-1) Preparation of Cells for Immunization of Mice In RPMI-1640 (Roswell Park Memorial Institute-1640) 10% FBS (fetal bovine serum) (+) medium (10 mL or 20 mL), $2\times10^6$ or $5\times10^6$ NOR-P1 cells (human pancreatic cancer cell line, RIKEN RCB-2139) were cultured for 5 days and then collected, and washed twice with PBS (phosphate buffered saline) and resuspended in PBS (300 μL).

1-2) Immunization of Mice

Each BALB/c mouse (12-week-old) was intraperitoneally immunized with NOR-P1 cells ($2\times10^6$ cells) at intervals of about 1 week for the first to fifth immunization. About 2 weeks after the fifth immunization, each BALB/c mouse was intraperitoneally immunized with NOR-P1 cells ($5\times10^6$ cells). About 3 weeks after the sixth immunization, each BALB/c mouse was intraperitoneally immunized with NOR-P1 cells ($2\times10^6$ cells). Each BALB/c mouse was intraperitoneally immunized with $2\times10^6$ NOR-P1 cells at intervals of about 2 weeks for the 8th to 10th immunization. About 3 weeks after the 10th immunization (11th immunization) and 3 days thereafter (12th immunization, final immunization), each BALB/c mouse was intraperitoneally immunized with $5\times10^6$ NOR-P1 cells. Splenocytes were isolated 3 days after the final immunization.

1-3) Preparation of Splenocytes from Immunized Mice

The spleen was isolated from each immunized mouse, triturated, and suspended in RPMI1640 10% FBS (+)

medium. The cell suspension was passed through a Cell Strainer (70 μm, BD Falcon), and then centrifuged at 1500 rpm at room temperature for 5 minutes to discard the supernatant. Tris-NH4C1 solution (20 mM Tris-HCl pH 7.2, 77.6 mM $NH_4Cl$; 20 mL) was added thereto, and the resultant was treated at room temperature for 5 minutes. PBS (20 mL) was added thereto, and the resultant was centrifuged at 1500 rpm at room temperature for 5 minutes. After the supernatant was discard, RPMI1640 FBS (+) medium (10 mL) was added to the residue.

1-4) Preparation of Myeloma Cells

P3U1 cells (mouse myeloma cell line) was cultured in RPMI1640 FBS (+) medium for 5 days, and then collected and resuspended in RPMI1640 FBS (+) medium (20 mL).

1-5) Cell Fusion

Splenocytes and myeloma cells were mixed together at 5:1, and centrifuged at 1500 rpm at room temperature for 5 minutes. The cells were washed twice with RPMI1640 FBS (−) medium (10 mL), and then centrifuged (1500 rpm, 5 minutes). The group of cells in the precipitated fraction obtained was sufficiently loosened, and polyethylene glycol-1500 (PEG-1500; 1 mL) was then gradually added thereto with stirring over about 1 minute. After stirring for 3 minutes 30 seconds, the resultant was left to stand at room temperature for 30 seconds. Thereafter, RPMI medium 10% Low IgG FBS (+) (10 mL) was added to the cell solution over 1 minute. The cell suspension was centrifuged (1500 rpm, 5 minutes), and the cells in the precipitated fraction obtained were gently loosened, and then gently suspended in HAT medium (RPMI1640 medium containing 10% Low IgG FBS, HAT Media Supplement, and 5% BriClone; 200 mL). The suspension was aliquoted into a 96-well culture plate at 200 μL/well, and cultured in an incubator at 37° C. and 5% $CO_2$ for 6 days.

1-6) Screening of Hybridomas/Preparation of Probe

DT3C, a recombinant complex protein, was produced for the purpose of assaying internalization of antibodies and immunotoxin activity. This DT30 is a protein formed by fusing the catalytic domain of diphtheria toxin (DT) and the antibody-binding domain of streptococcal protein G through genetic engineering. DT3C specifically binds to the Fc region of antibodies, and induce cell death through protein synthesis inhibition when being incorporated in a cell. Use of this system allows simultaneous observation of the internalization of an antibody and the cytocidal effect of immunotoxin (Yamaguchi, M. et al., Biochemical and Biophysical Research Communications 454 (2014) 600-603).

1-7) Screening of Hybridomas with DT3C

To a 96-well plate, 4 μg/mL DT3C (25 μL) was added, and the culture supernatant of the hybridoma obtained in Step 1-5 (25 μL) was further added, and the resultant was incubated at room temperature for 30 minutes. NOR-P1 cells (50 μL) were seeded at $2\times10^5$ cells/mL (RPMI medium 10% Low IgG FBS (+)), and cultured in a $CO_2$ incubator at 37° C. for 3 days. Through microscopic observation after culturing, wells with the number of adhering cells being about 25% or less of that in using a negative control antibody were determined to be positive. Selected clones were subjected to one or two subcloning steps to establish eight monoclonal hybridoma cell lines.

6-2: Identification of Antigen to which Antibody Produced by Hybridoma Binds

Antigens were identified for two clones, 218B1 and 218C7, of antibodies produced by the hybridomas prepared in Example 6-1.

2-1) Immunoprecipitation of Biotin-Labeled Cell Surface Protein with 218B1 Antibody and 218C7 Antibody Culture supernatant of $2\times10^6$ NTERA-2 cells (human testicular cancer cell line, ATCC CRL-1973) was removed, and the residue was washed twice with PBS. EZ-Link Sulfo-NHS-Biotin (Thermo Fisher Scientific) was suspended in PBS to a concentration of 0.1 mg/mL. After PBS was removed, Biotin/PBS solution was added, and the resultant was incubated on a shaker for 30 minutes, and then washed twice with 100 mM glycine/PBS solution (25 mL) and then washed once with PBS (10 mL). The washed cells were resuspended in 200 μL of lysis buffer (150 mM NaCl, 50 mM Tris-HCl pH 7.4, 1% DDM, Protease inhibitor, Complete EDTA free (F. Hoffmann-La Roche, Ltd.) 1 particle/50 mL), and treated at 4° C. for 30 minutes. The resultant was centrifuged (13000 rpm, 20 minutes, 4° C.) to prepare a cell lysate. To the cell lysate, Protein G Sepharose/lysis buffer (50% slurry; 30 μL) obtained by substituting the buffer of Protein G Sepharose (Protein G Sepharose 4 Fast Flow (GE Healthcare)) with the lysis buffer was added, and the resultant was rotated at 4° C. for 30 minutes and then centrifuged at 4° C. for 1 minute, and the supernatant was collected. To this supernatant the 218B1 antibody or 218C7 antibody (about 3 μg) was added, and the resultant was rotated at 4° C. for 30 minutes, to which Protein G Sepharose/lysis buffer (50% slurry; 60 μL) was then added, and the resultant was rotated at 4° C. for 1 hour. The Protein G Sepharose was washed six times with the lysis buffer (1 mL), and then resuspended in 1×SDS sample buffer (Bio-Rad Laboratories, Inc.). After the suspension was treated at 100° C. for 5 minutes, the solution was collected as a sample for SDS-PAGE (polyacrylamide gel electrophoresis).

2-2) SDS-PAGE and Western Blotting

The SDS-PAGE sample prepared in 2-1) was stacked with SuperSep Ace 5-20% (Wako Pure Chemical Industries, Ltd.) at 50 mV for 30 minutes, and then subjected to electrophoresis at 200 mV for 1 hour, and blotted from the gel onto a membrane at 12 mV for 47 minutes. The membrane was washed with PBS-T (PBS (−)-0.02% Tween 20), and then blocked for 1 hour. The membrane was washed three times with PBS-T for 5 minutes, and then reacted with a Streptavidin-horseradish peroxidase conjugate (GE Healthcare; 2000-fold diluted with PBS-T in use) for 1 hour. The membrane was washed twice with PBS-T for 5 minutes, and a targeted band was then detected by using an enhanced chemiluminescence (ECL)method. A band indicating a molecular weight of 18 kDa was detected for any of the case with the 218B1 antibody and the case with the 218C7 antibody, regardless of the presence or absence of DTT added.

2-3) Mass Spectrometry of Immunoprecipitated Product of Cell Protein with 218B1 Antibody and 218C7 Antibody $2\times10^7$ NTERA-2 cells were collected and washed twice with PBS. The cells were collected by using a cell scraper, and centrifuged at 1500 rpm for 5 minutes. After the supernatant was removed, the cells were resuspended in 2 mL of the lysis buffer, and treated at 4° C. for 30 minutes. The resultant was centrifuged (13000 rpm, 20 minutes, 4° C.) to prepare a cell lysate. Protein G Sepharose/lysis buffer (50% slurry; 180 μL) was added to the cell lysate, and the resultant was rotated at 4° C. for 30 minutes and then centrifuged at 4° C. for 1 hour, and the supernatant was collected. The 218B1 antibody (about 9 μg) was added to the supernatant, and the resultant was rotated at 4° C. for 30 minutes, to which Protein G Sepharose/lysis buffer (50% slurry; 180 μL) was then added, and the resultant was rotated at 4° C. for 1 hour. The Protein G Sepharose was washed six times with the lysis buffer (1 mL), and then resuspended in 1×SDS sample buffer. After the suspension was treated at 100° C. for 5 minutes, the solution was collected as a sample for SDS-PAGE. SDS-PAGE was carried out in the same manner as in 2-2), and the electrophoresis gel was stained with CBB. The part corresponding to 18 kDa was cut out of the electrophoresis gel, and subjected to mass spectrometry. The mass spectrometry found that the gel piece contained claudin-6.

2-4) FACS Analysis

Since the antigen for the 218B1 antibody and 218C7 antibody was estimated to be claudin-6 from the mass spectrometry, forced expression analysis by cDNA transfection was carried out. FACS analysis results showed that the 218B1 antibody and 218C7 antibody exhibited strong positive reaction for human claudin-6-expressing CHO-K1 cells, demonstrating that the antigen for the 218B1 antibody and 218C7 antibody is claudin-6.

2-5) Purification of Antibody from Hybridoma Culture Supernatant

The mouse anti-CLDN6 antibody B1-producing hybridoma (218B1) and mouse anti-CLDN6 antibody C7-producing hybridoma (218C7) were cultured in Hybridoma-SFM (Thermo Fisher Scientific) containing 10% Fetal Bovine Serum, Ultra-Low IgG (Thermo Fisher Scientific). The culture supernatant was collected by centrifugation, and filtered through a filter of 0.45 μm (produced by Corning Incorporated). The antibody was purified from the culture supernatant through rProtein A affinity chromatography (at 4 to 6° C.) in one step. The step of buffer displacement after rProtein A affinity chromatography was carried out at 4 to 6° C. First, the culture supernatant was applied to a column packed with MabSelectSuRe (produced by GE Healthcare Bioscience) equilibrated with PBS. After the culture solution completely entered the column, the column was washed with PBS in an amount twice or more the column volume. Subsequently, elution was carried out with a 2 M solution of arginine hydrochloride (pH 4.0), and a fraction containing the antibody was collected. The fraction was subjected to liquid displacement to PBS (−) by dialysis (Thermo Scientific, Slide-A-Lyzer Dialysis Cassette). Finally, the fraction was concentrated with a Centrifugal UF Filter Device VIVASPIN20 (molecular weight cutoff: UF10K, Sartorius AG, at 4° C.) to adjust the IgG concentration to 1 mg/mL or more. The fraction was filtered through a Minisart-Plus filter (Sartorius AG), and the resultant was used as a purified sample.

Example 7: In Vitro Evaluation of Mouse Anti-CLDN6 Antibodies B1 and C7

7-1: Evaluation of Binding Ability of Mouse Anti-CLDN6 Antibodies by Flow Cytometry Binding activity of the mouse anti-CLDN6 antibodies produced in Example 6 to human CLDN6 and its family molecules, CLDN3, CLDN4, and CLDN9, was evaluated by using a flow cytometry method. Human CLDN3/pCMV6-Entry, human CLDN4/pCMV6-Entry, human CLDN6/pCMV-Entry, human CLDN9/pCMV6-Entry, or pCMV6-Entry purchased from OriGene Technologies, Inc. was transiently transferred into 293T cells (Thermo Fisher Scientific, HCL4517) by using Lipofectamine 2000 (Thermo Fisher Scientific), and the cells were cultured under conditions of 37° C. and 5% $CO_2$ overnight, and then a cell suspension was prepared. The transfected 293T cell suspension was centrifuged to remove the supernatant, and a mouse anti-CLDN6 antibody (clone number: B1 or C7) or a mouse IgG1 control antibody (R&D Systems, Inc.) was then added and suspended to a final concentration of 30 μg/mL, 10 μg/mL, 3.3 μg/mL, or 1.1 μg/mL, and the resultant was left to stand at 4° C. for 1 hour. The cells were washed twice with Dulbecco's phosphate buffered saline (Sigma-Aldrich Co. LLC) containing 5% fetal bovine serum (Hyclone) (hereinafter, referred to as 5% FBS-containing PBS), and FLUORESCEIN-CONJUGATED GOAT IGG FRACTION TO MOUSE IGG (WHOLE MOLECULE) (MP Biomedicals, Inc.) 500-fold diluted with 5% FBS-containing PBS was then added thereto, and the cells were suspended and left to stand at 4° C. for 1 hour. After washing twice with 5% FBS-containing PBS, detection was carried out by using a flow cytometer (FC500; Beckman Coulter, Inc.). Data analysis was carried out by using FlowJo (Tree Star, Inc.). To confirm each transfection, the cells were permeabilized with 0.25% Tween 20-containing PBS, and then a mouse anti-FLAG antibody (Sigma-Aldrich Co. LLC) was used. FIG. 11 shows the results. In each graph in FIG. 11, the ordinate represents FITC fluorescence intensity indicating the amount of the binding antibody and the abscissa represents antibody concentrations. The mouse anti-CLDN6 antibodies produced bound to human CLDN6 and human CLDN9 to a similar degree, and did not bind to human CLDN3 or human CLDN4. The mouse control IgG1 did not bind to any of the cells.

7-2: Internalization Activity of Antibodies

Internalization activity of the mouse anti-CLDN6 antibodies B1 and C7 was evaluated by using the anti-mouse IgG reagent, to which a toxin that inhibits protein synthesis (saporin) had been conjugated, Mab-ZAP (Advanced Targeting Systems). In this evaluation, Mab-ZAP is incorporated into cells in a manner depending on the internalization activity of a mouse anti-CLDN6 antibody, and saporin, which inhibits protein synthesis, is released in the cells to suppress cell growth.

JEG-3 (ATCC HTB-36), a human choriocarcinoma cell line of human CLDN6-positive cells, NIH: OVCAR-3 (ATCC HTB-161), a human ovarian cancer cell line of human CLDN6-positive cells, or BxPC-3 (ATCC CRL-1687), a human pancreatic cancer cell line of human CLDN6-negative cells, was seeded in a 96-well cell culture microplate at $2\times10^3$ cells/well, and cultured under conditions of 37° C. and 5% $CO_2$ overnight. On the next day, a mixed solution obtained by mixing each mouse anti-CLDN6 antibody or mouse IgG1 antibody (R&D Systems, Inc.) to a final concentration of 1 nM, with Mab-ZAP (final concentration: 0.5 nM) or AffiniPure Goat Anti-Mouse IgG, Fcγ Fragment Specific (Jackson ImmunoResearch Laboratories Inc.) (final concentration: 0.5 nM), without conjugated toxin, was added, and the cells were cultured under conditions of 37° C. and 5% $CO_2$ for 5 days. The number of surviving cells was determined through quantification of ATP activity by using CellTiter-Glo Luminescent Cell Viability Assay (Promega Corporation). The cell growth-suppressing effect by addition of each anti-CLDN6 antibody was determined as a relative survival rate to the value for the well without the mixed solution as 100%. FIG. 12 shows the results. The mouse anti-CLDN6 antibodies (B1, C7) were found to have cell growth-suppressing effect on the human CLDN6-positive cell lines JEG-3 and NIH: OVCAR-3. On the other hand, they were found to have no cell growth-suppressing effect on the human CLDN6-negative cell line BxPC-3. The mouse IgG1 antibody was found to have no cell growth-suppressing effect on any of the cell lines. These results suggest that the anti-CLDN6 antibodies (B1, C7)

produced have internalization activity and are each suitable as an antibody for antibody-drug conjugates.

Example 8: Nucleotide Sequencing of cDNA Encoding Variable Region of Each of Mouse Anti-CLDN6 Antibodies B1 and C7

8-1: Nucleotide Sequencing of cDNA Encoding Variable Region of B1 Antibody 8-1-1: Preparation of Total RNA of B1 Antibody-Producing Hybridoma To amplify cDNA encoding the variable region of the B1 antibody, total RNA was prepared from the B1 antibody-producing hybridoma by using TRIzol Reagent (Ambion).

8-1-2: Amplification and Sequencing of cDNA Encoding Light Chain Variable Region of B1 Antibody Through 5'-RACE PCR Amplification of cDNA encoding the light chain variable region was carried out by using about 1 μg of the total RNA prepared in Example 8-1-1 and a SMARTer RACE 5'/3' Kit (Clontech). As a primer to amplify cDNA encoding the variable region of the light chain gene of the B1 antibody through PCR, UPM (Universal Primer A Mix: attached to the SMARTer RACE 5'/3' Kit) and a primer designed on the basis of the sequence of a known mouse light chain constant region were used.

The cDNA encoding the variable region of the light chain amplified through 5'-RACE PCR was cloned into a plasmid, and subsequently sequence analysis was carried out for the nucleotide sequence of the cDNA encoding the variable region of the light chain.

The determined nucleotide sequence of the cDNA encoding the variable region of the light chain of the B1 antibody is represented by SEQ ID NO: 18, and the corresponding amino acid sequence is represented by SEQ ID NO: 19.

8-1-3: Amplification and Sequencing of cDNA Encoding Heavy Chain Variable Region of B1 Antibody Through 5'-RACE PCR Amplification of cDNA encoding the heavy chain variable region was carried out by using about 1 μg of the total RNA prepared in Example 8-1-1 and a SMARTer RACE 5'/3' Kit (Clontech). As a primer to amplify cDNA encoding the variable region of the heavy chain gene of the LB1 antibody through PCR, UPM (Universal Primer A Mix: attached to the SMARTer RACE 5'/3' Kit) and a primer designed on the basis of the sequence of a known mouse heavy chain constant region were used.

The cDNA encoding the variable region of the heavy chain amplified through 5'-RACE PCR was cloned into a plasmid, and subsequently sequence analysis was carried out for the nucleotide sequence of the cDNA encoding the variable region of the heavy chain. The determined nucleotide sequence of the cDNA encoding the variable region of the heavy chain of the B1 antibody is represented by SEQ ID NO: 20, and the corresponding amino acid sequence is represented by SEQ ID NO: 21.

8-2: Nucleotide Sequencing of cDNA Encoding Variable Region of C7 Antibody

Nucleotide sequencing was carried out in the same manner in Example 8-1. The determined nucleotide sequence of the cDNA encoding the variable region of the light chain of the C7 antibody is represented by SEQ ID NO: 22, and the corresponding amino acid sequence is represented by SEQ ID NO: 23. The nucleotide sequence of the cDNA encoding the variable region of the heavy chain of the C7 antibody is represented by SEQ ID NO: 24, and the corresponding amino acid sequence is represented by SEQ ID NO: 25.

Example 9: Production of Chimeric Anti-CLDN6 Antibody chB1

9-1: Construction of Expression Vector for Chimeric Anti-CLDN6 Antibody chB1

9-1-1: Construction of Expression Vector pCMA-LK for Chimeric and Humanized Light Chains About 5.4 kb of a fragment obtained by digesting the plasmid pcDNA3.3-TOPO/LacZ (Invitrogen) with the restriction enzymes XbaI and PmeI was linked to a DNA fragment including a DNA sequence encoding the human light chain signal sequence and human K chain constant region, as represented by SEQ ID NO: 26, by using an In-Fusion HD PCR Cloning Kit (Clontech) to prepare pcDNA3.3/LK. A neomycin expression unit was removed from the pcDNA3.3/LK to construct pCMA-LK.

9-1-2: Construction of Expression Vector pCMA-G1LALA for Chimeric and Humanized IgG1LALA-Type Heavy Chains A DNA fragment obtained by digesting the pCMA-LK with XbaI and PmeI to remove the light chain signal sequence and human K chain constant region was linked to a DNA fragment including a DNA sequence encoding the human heavy chain signal sequence and human IgG1LALA constant region, as represented by SEQ ID NO: 27, by using an In-Fusion HD PCR Cloning Kit (Clontech) to construct pCMA-G1LALA.

9-1-3: Construction of Chimeric chB1 Heavy Chain Expression Vector

The DNA fragment consisting of nucleotide residues 36 to 440 of the nucleotide sequence for the chB1 heavy chain, as represented by SEQ ID NO: 33, was synthesized (GeneArt). The pCMA-G1LALA was cleaved with the restriction enzyme BlpI, and the synthesized DNA fragment was inserted into the cleaved portion by using an In-Fusion HD PCR Cloning Kit (Clontech) to construct a chB1 heavy chain expression vector. The amino acid sequence of the chB1 heavy chain is represented by SEQ ID NO: 32.

9-1-4: Construction of Chimeric chB1 Light Chain Expression Vector

A DNA fragment including a DNA sequence encoding the chB1 light chain, as represented by SEQ ID NO: 29, was synthesized (GeneArt). By using an In-Fusion HD PCR Cloning Kit (Clontech), the synthesized DNA fragment was linked to a DNA fragment obtained by digesting the pCMA-LK with XbaI and PmeI for removal of the light chain signal sequence and human K chain constant region to construct a chB1 light chain expression vector. The amino acid sequence of the chB1 light chain is represented by SEQ ID NO: 28.

9-2: Production and Purification of Chimeric Anti-CLDN6 Antibody chB1

9-2-1: Production of Chimeric Antibody chB1

FreeStyle 293F cells (Invitrogen) were passaged and cultured in accordance with the instruction manual. Into a 3 L Fernbach Erlenmeyer Flask (Corning Incorporated), $1.2\times10^9$ FreeStyle 293F cells (Invitrogen) in the logarithmic growth phase were seeded, and diluted with FreeStyle293 expression medium (Invitrogen) to adjust to $2.0\times10^6$ cells/mL. To 40 mL of Opti-Pro SFM medium (Invitrogen), 0.24 mg of the heavy chain expression vector, 0.36 mg of the light chain expression vector, and 1.8 mg of polyethyleneimine (Polyscience, Inc., #24765) were added and gently stirred, and further left to stand for 5 minutes, and then added to the FreeStyle 293F cells. After shaking culture at 90 rpm in an incubator at 37° C. and 8% $CO_2$ for 4 hours, 600 mL of EX-CELL VPRO medium (SAFC Biosciences, Inc.), 18 mL of GlutaMAX I (Gibco), and 30 mL of Yeastolate Ultrafiltrate (Gibco) were added, and the resultant was subjected to shaking culture at 90 rpm in an incubator at 37° C. and 8% $CO_2$ for 7 days, and the resulting culture supernatant was filtered through a Disposable Capsule Filter (ADVANTEC, #CCS-045-E1H). The chimeric anti-CLDN6 antibody obtained was designated as "chB1".

9-2-2: Purification of Chimeric Antibody chB1

The antibody was purified from the culture supernatant obtained in Example 9-2-1 through rProtein A affinity chromatography in one step. The culture supernatant was applied to a column packed with MabSelectSuRe (produced by GE Healthcare Bioscience) equilibrated with PBS, and the column was then washed with PBS in an amount twice or more the column volume. Subsequently, elution was carried out with a 2 M solution of arginine hydrochloride (pH 4.0), and a fraction containing the antibody was collected. The fraction was subjected to buffer displacement to PBS (-) by dialysis (Thermo Scientific, Slide-A-Lyzer Dialysis Cassette). The antibody was concentrated with a Centrifugal UF Filter Device VIVASPIN20 (molecular weight cutoff: UF10K, Sartorius AG) to adjust the IgG concentration to 1 mg/mL or more. Finally, the fraction was filtered through a Minisart-Plus filter (Sartorius AG), and the resultant was used as a purified sample.

Example 10: Production of Humanized Anti-CLDN6 Antibody 10-1: Design of Humanized Form of Anti-CLDN6 Antibody 10-1-1: Molecular Modeling of Variable Region of Chimeric Antibody chB1

A method known as homology modeling (Methods in Enzymology, 203, 121-153 (1991)) was used for molecular modeling of the variable region of chB1. Molecular modeling was carried out by using the commercially available protein conformational analysis program BioLuminate (Schrodinger, Inc.) with a structure (PDB ID: 1XIW), as a template, registered in Protein Data Bank (Nuc. Acid Res. 35, D301-D303 (2007)) with high sequence identity to the variable regions of the heavy chain and light chain of chB1.

10-1-2: Design of Humanized Amino Acid Sequence chB1 was humanized by CDR grafting (Proc. Natl. Acad. Sci. USA 86, 10029-10033 (1989)). The consensus sequence of human gamma chain subgroup 1 and that of human kappa chain subgroup 1 specified in Kabat et al. (Sequences of Proteins of Immunological Interest, 5th Ed. Public Health Service National Institutes of Health, Bethesda, MD. (1991)) had high identity to the framework regions of the chB1, and hence were respectively selected as acceptors for the heavy chain and the light chain. Donor residues to be transferred on the acceptors were selected through analysis of the three-dimensional model, for example, with reference to criteria provided by Queen et al. (Proc. Natl. Acad. Sci. USA 86, 10029-10033 (1989)). Because the CDRL3 was rich in hydrophobic amino acids, a humanized light chain with mutation in the CDRL3 was additionally designed.

10-2: Humanization of chB1 Heavy Chain

The three heavy chains designed were designated as hH1, hH2, and hH3. The heavy chain full-length amino acid sequence of hH1 is represented by SEQ ID NO: 52. The nucleotide sequence encoding the amino acid sequence of SEQ ID NO: 52 is represented by SEQ ID NO: 53. The heavy chain full-length amino acid sequence of hH2 is represented by SEQ ID NO: 56. The nucleotide sequence encoding the amino acid sequence of SEQ ID NO: 56 is represented by SEQ ID NO: 57. The heavy chain full-length amino acid sequence of hH3 is represented by SEQ ID NO: 60. The nucleotide sequence encoding the amino acid sequence of SEQ ID NO: 60 is represented by SEQ ID NO: 61.

10-3: Humanization of chB1 Light Chain

The four light chains designed were designated as hL1, hL2, hL3, and hL4. The light chain full-length amino acid sequence of hL1 is represented by SEQ ID NO: 36. The nucleotide sequence encoding the amino acid sequence of SEQ ID NO: 36 is represented by SEQ ID NO: 37. The light chain full-length amino acid sequence of hL2 is represented by SEQ ID NO: 40. The nucleotide sequence encoding the amino acid sequence of SEQ ID NO: 40 is represented by SEQ ID NO: 41. The light chain full-length amino acid sequence of hL3 is represented by SEQ ID NO: 44. The nucleotide sequence encoding the amino acid sequence of SEQ ID NO: 44 is represented by SEQ ID NO: 45. The light chain full-length amino acid sequence of hL4 is represented by SEQ ID NO: 48. The nucleotide sequence encoding the amino acid sequence of SEQ ID NO: 48 is represented by SEQ ID NO: 49.

10-4: Design of Humanized Antibody with Combination of Heavy Chain and Light Chain An antibody consisting of hH1 and hL1 is referred to as "H1L1 antibody" or "H1L1". An antibody consisting of hH2 and hL2 is referred to as "H2L2 antibody" or "H2L2". An antibody consisting of hH1 and hL3 is referred to as "H1L3 antibody" or "H1L3". An antibody consisting of hH2 and hL4 is referred to as "H2L4 antibody" or "H2LA". An antibody consisting of hH3 and hL3 is referred to as "H3L3 antibody" or "H3L3".

10-5: Production of Humanized Anti-CLDN6 Antibody 10-5-1: Construction of Humanized Heavy Chain Expression Vector 10-5-1-1: Construction of hH1 Expression Vector The DNA fragment consisting of nucleotide residues 36 to 440 of the nucleotide sequence of SEQ ID NO: 53 for hH1 was synthesized (GeneArt). An hH1 expression vector was constructed in the same manner as in Example 9-1-3.

10-5-1-2: Construction of hH2 Expression Vector

The DNA fragment consisting of nucleotide residues 36 to 440 of the nucleotide sequence of SEQ ID NO: 57 for hH2 was synthesized (GeneArt). An hH2 expression vector was constructed in the same manner as in Example 9-1-3.

10-5-1-3: Construction of hH3 Expression Vector

The DNA fragment consisting of nucleotide residues 36 to 440 of the nucleotide sequence of SEQ ID NO: 61 for hH2 was synthesized (GeneArt). An hH3 expression vector was constructed in the same manner as in Example 9-1-3.

10-5-2: Construction of Humanized Light Chain Expression Vector 10-5-2-1: Construction of hL1 Expression Vector The DNA fragment consisting of nucleotide residues 37 to 402 of the nucleotide sequence of SEQ ID NO: 37 for hL1 was synthesized (GeneArt). The pCMA-LK was cleaved with the restriction enzyme BsiWI, and the synthesized DNA fragment was inserted into the cleaved portion by using an In-Fusion HD PCR Cloning Kit (Clontech) to construct an hL1 expression vector.

10-5-2-2: Construction of hL2 Expression Vector

The DNA fragment consisting of nucleotide residues 37 to 402 of the nucleotide sequence of SEQ ID NO: 41 for hL2 was synthesized (GeneArt). An hL2 expression vector was constructed in the same manner as in Example 10-5-2-1.

10-5-2-3: Construction of hL3 Expression Vector

The DNA fragment consisting of nucleotide residues 37 to 402 of the nucleotide sequence of SEQ ID NO: 45 for hL3 was synthesized (GeneArt). An hL3 expression vector was constructed in the same manner as in Example 10-5-2-1.

10-5-2-4: Construction of hL4 Expression Vector

The DNA fragment consisting of nucleotide residues 37 to 402 of the nucleotide sequence of SEQ ID NO: 49 for hL4 was synthesized (GeneArt). An hL4 expression vector was constructed in the same manner as in Example 10-5-2-1.

10-5-3: Preparation of Humanized Antibodies 10-5-3-1: Production of Humanized Antibodies H1L1, H2L2, H1L3, H2L4, and H3L3

They were produced in the same manner as in Example 9-2-1. H1L1, H2L2, H1L3, H2L4, and H3L3 were produced by using the combinations of a heavy chain expression vector and a light chain expression vector corresponding to the combinations of a heavy chain and a light chain shown in Example 10-4. 10-5-3-2: Two-step purification of humanized antibodies H1L1, H2L2, H1L3, H2L4, and H3L3

The culture supernatant obtained in Example 10-5-3-1 was purified in two steps through rProtein A affinity chromatography and ceramic hydroxyapatite. The culture supernatant was applied to a column packed with MabSelectSuRe (produced by GE Healthcare Bioscience) equilibrated with PBS, and the column was then washed with PBS in an amount twice or more the column volume. Subsequently, the antibody was eluted with a 2 M solution of arginine hydrochloride (pH 4.0). A fraction containing the antibody was subjected to buffer displacement to PBS by dialysis (Thermo Scientific, Slide-A-Lyzer Dialysis Cassette), 5-fold diluted with a buffer of 5 mM sodium phosphate/50 mM MES/pH 7.0, and then applied to a ceramic hydroxyapatite column (Bio-Rad Laboratories Japan, Inc., Bio-Scale CHT Type-1 Hydroxyapatite Column) equilibrated with a buffer of 5 mM NaPi/50 mM MES/30 mM NaCl/pH 7.0. Linear concentration gradient elution was carried out with sodium chloride, and a fraction containing the antibody was collected. The fraction was subjected to buffer displacement to HBS or (25 mM histidine/5% sorbitol, pH 6.0) by dialysis (Thermo Scientific, Slide-A-Lyzer Dialysis Cassette). The antibody was concentrated with a Centrifugal UF Filter Device VIVASPIN20 (molecular weight cutoff: UF10K, Sartorius AG) to adjust the IgG concentration to 50 mg/mL. Finally, the fraction was filtered through a Minisart-Plus filter (Sartorius AG), and the resultant was used as a purified sample.

Example 11: Evaluation of Binding Ability of Humanized Anti-CLDN6 Antibody by Flow Cytometry The binding activity of the humanized anti-CLDN6 antibody produced in Example 10 to human CLDN6 and its family molecules, CLDN3, CLDN4, and CLDN9, was evaluated by using a flow cytometry method. Used were 293T cells transiently transfected in the same manner as in Example 7-1. To cells into which a human CLDN6 or human CLDN9 gene had been transferred, the humanized anti-CLDN6 antibody H1L1, H2L2, H1L3, H2L4, or H3L3, or a human IgG1 control antibody (Calbiochem) was added and suspended to a final concentration of 100 nM, 20 nM, 4 nM, or 0.8 nM, and the resultant was left to stand at 4° C. for 30 minutes. To cells into which a human CLDN3 or human CLDN4 gene, or an empty vector had been transferred, the humanized anti-CLDN6 antibody H1L1, H2L2, H1L3, H2L4, or H3L3 was added and suspended to a final concentration of 100 nM, and the resultant was left to stand at 4° C. for 30 minutes. The cells were washed with Dulbecco's phosphate buffered saline (Sigma-Aldrich Co. LLC) containing 5% fetal bovine serum (Hyclone) (hereinafter, referred to as 5% FBS-containing PBS), and FITC AffiniPureF (ab')2 Fragment Goat Anti-Human IgG (H+L) (Jackson ImmunoResearch Laboratories Inc.) 150-fold diluted with 5% FBS-containing PBS was then added thereto, and the cells were suspended and left to stand at 4° C. for 30 minutes. After washing with 5% FBS-containing PBS, detection was carried out by using a flow cytometer (FC500; Beckman Coulter, Inc.). Data analysis was carried out by using FlowJo (Tree Star, Inc.), and mean fluorescence intensity (MFI) of FITC, which indicates the amount of the binding antibody, was calculated. FIG. 13 shows the results. In each graph in FIG. 13, the abscissa represents antibody concentrations and the ordinate represents MFI. The humanized anti-CLDN6 antibody produced bound to human CLDN6 and human CLDN9 to a similar degree, and did not bind to human CLDN3 or human CLDN4. The human control IgG1 did not bind to any of the cells.

[Preparation of Glycan Remodelling Antibodies]

Example 12: Sugar Chain Remodeling 1 (T-SG) (See FIG. 43)

Step 1: Preparation of (Fucα1,6) GlcNAc-Trastuzumab

The 22 mg/mL trastuzumab solution (25 mM histidine solution (pH 6.0), 5% sorbitol solution) (45.5 mL) prepared in Reference Example 3 was halved and according to common operation C, buffer exchange to 50 mM phosphate buffer (pH 6.0) was conducted twice separately. To the resulting 28.1 mg/mL (18 mL) and 28.0 mg/mL (18 mL) trastuzumab solutions (50 mM phosphate buffer (pH 6.0)), 1.26 mL and 1.27 mL of wild-type EndoS solution (2.0 mg/mL, PBS) were respectively added, and the solutions were incubated at 37° C. for 4 hours. The progress of the reaction was checked by Experion electrophoresis station (produced by Bio-Rad Laboratories, Inc.). After the completion of the reaction, purification by affinity chromatography and purification with a hydroxyapatite column were performed in accordance with the following methods.

(1) Purification by Affinity Chromatography

Purification apparatus: AKTA pure150 (produced by GE Healthcare)

Column: HiTrap rProtein A FF (5 mL) (produced by GE Healthcare)

Flow rate: 5 mL/min (1.25 mL/min in charging)

Each reaction solution obtained above was purified in multiple separate operations. Two columns were linked together into one column, and in connecting to the column the reaction solution was added to the upper part of the column, and 2 CV of binding buffer (20 mM phosphate buffer (pH 6.0)) was flowed at 1.25 mL/min and 5 CV thereof was further flowed at 5 mL/min. In intermediate washing, 15 CV of washing solution (20 mM phosphate buffer (pH 7.0), 0.5 M sodium chloride solution) was flowed. In elution, 6 CV of elution buffer (ImmunoPure IgG Eution buffer, produced by Pierce) was flowed. The eluate was immediately neutralized with 1 M Tris buffer (pH 9.0). Fractions UV-detected (280 nm) during the elution were checked by using the micro-volume spectrophotometer Xpose (produced by Trinean NV) and an Experion electrophoresis station (produced by Bio-Rad Laboratories, Inc.). Fractions containing the desired compound were subjected to buffer exchange to 5 mM phosphate buffer/50 mM 2-morpholinoethanesulfonic acid (MES) solution (pH 6.8) by using common operation C.

(2) Purification by Hydroxyapatite Chromatography

Purification apparatus: AKTA avant25 (produced by GE Healthcare)

Column: Bio-Scale Mini CHT Type I cartridge (5 mL) (produced by Bio-Rad Laboratories, Inc.)

Flow rate: 5 mL/min (1.25 mL/min in charging)

Two columns were linked together into one column, and the solution obtained in (1) was purified in multiple separate operations. The solution was added to the upper part of the column, and 2 CV of solution A (5 mM phosphate buffer/50 mM morpholinoethanesulfonic acid (MES) solution (pH 6.8)) was flowed at 1.25 mL/min and 3 CV thereof was further flowed at 5 mL/min. Thereafter, elution was performed with solution A and solution B (5 mM phosphate buffer/50 mM morpholinoethanesulfonic acid (MES) solution (pH 6.8), 2 M sodium chloride solution). The elution conditions were solution A: solution B=100:0 to 0:100 (15 CV). Further, 5 CV of washing solution (500 mM phosphate buffer (pH 6.5)) was flowed.

Fractions containing the desired compound were subjected to buffer exchange by using common operation C to afford a 25.5 mg/ADmL (Fucax1,6) GloNAc-Trastuzumab solution (50 mM phosphate buffer (pH 6.0)) (35 mL).

Step 2: Preparation of Trastuzumab [SG-$(N_3)_2$]$_2$

To the 23.9 mg/mL (Fucα1,6) GlcNAc-Trastuzumab solution (50 mM phosphate buffer (pH 6.0)) obtained in Step 1 (3.37 mL), a solution (0.258 mL) of the compound synthesized in Step 2 of Example 5 (12.9 mg) in 50 mM phosphate buffer (pH 6.0) and 4.90 mg/mL EndoS D233Q/Q303L solution (PBS) (0.328 mL) were added, and the resultant was incubated at 30° C. for 4.5 hours. These operations were performed in two lots. The progress of the reaction was checked by using an Experion electrophoresis station (produced by Bio-Rad Laboratories, Inc.). After the completion of the reaction, purification by affinity chromatography and purification by hydroxyapatite chromatography were performed as in Step 1, and fractions containing the desired compound were then subjected to buffer exchange to phosphate buffered saline (pH 6.0) by using common operation C to afford a 10.0 mg/mL Trastuzumab [SG-$(N_3)_2$]$_2$ solution (phosphate buffered saline (pH 6.0)) (15.5 mL).

Example 13: Sugar Chain Remodeling 2 (T-MSG) (See FIG. 44)

Step 1: Trastuzumab [MSG-N3] 2

The following operations were performed in five lots. The compound obtained in Step 1 of Example 12 (20 mg/mL, 15.0 mL) was used together with the compound obtained in Step 4 of Example 4 (25.5 mg) as a glycan donor, and incubated at 30° C. for 3 hours, and the operations same as in Step 2 of Example 12 were performed. With the five lots combined, a 14.4 mg/mL Trastuzumab [MSG-N3] 2 solution (phosphate buffered saline (pH 6.0)) (93.5 mL) was obtained.

Example 14: Sugar Chain Remodeling 3 (T-MSG1) (See FIG. 45)

Step 1: Trastuzumab [MSG1-$N_3$]$_2$

The following operations were performed in two lots. The compound obtained in Step 1 of Example 12 (25.5 mL, 7.8 mL) was used together with the compound obtained in Step 4 of Example 3 (25.5 mg) as a glycan donor, and incubated at 30° C. for 3 hours, and the operations same as in Step 2 of Example 12 were performed. With the two lots combined, a 10.6 mg/mL Trastuzumab [MSG1-$N_3$]$_2$ solution (phosphate buffered saline (pH 6.0)) (31 mL) was obtained.

Example 15: Sugar Chain Remodeling 4 (CLDN6-MSG1 (H1L1)) (See FIG. 46)

Step 1: (Fucα1,6) GlcNAc-Anti-CLDN6 Antibody (H1L1)

The operations same as in Step 1 of Example 12 were performed using a ca. 37.7 mg/mL anti-CLDN6 antibody (H1L1) solution (25 mM histidine solution (pH 6.0), 5% sorbitol solution) prepared in Example 10 (2.5 mL) to afford a 19.2 mg/ml (Fucα1,6) GlcNAc-anti-CLDN6 antibody (H1L1) solution (50 mM phosphate buffer (pH 6.0)) (4.8 mL).

Step 2: Anti-CLDN6 Antibody (H1L1)-[MSG1-$N_3$]$_2$

The operations same as in Step 2 of Example 12 were performed using the 19.2 mg/mL (Fucα1,6) GlcNAc-anti-CLDN6 (H1L1) antibody solution (50 mM phosphate buffer (pH 6.0)) obtained in Step 1 (4.8 mL) together with the compound obtained in Step 4 of Example 3 (25.5 mg) as a glycan donor to afford a 10.2 mg/mL anti-CLDN6 antibody (H1L1)-[MSG1-$N_3$]$_2$ solution (phosphate buffered saline (pH 6.0)) (7.2 mL).

Example 16: Sugar Chain Remodeling 5 (CLDN6-MSG1 (H2L2))

Step 1: (Fucα1,6) GlcNAc-Anti-CLDN6 Antibody (H2L2)

The operations same as in Step 1 of Example 12 were performed using a ca. 20 mg/mL anti-CLDN6 antibody (H2L2) solution (25 mM histidine solution (pH 6.0), 5% sorbitol solution) prepared in Example 10 (6 mL) to afford a 21.84 mg/ml (Fucα1,6) GlcNAc-anti-CLDN6 antibody (H2L2) solution (50 mM phosphate buffer (pH 6.0)) (5.7 mL).

Step 2: Anti-CLDN6 Antibody (H2L2)-[MSG1-$N_3$]$_2$

The operations same as in Step 2 of Example 12 were performed using the 21.8 mg/mL (Fucα1,6) GlcNAc-anti-CLDN6 (H2L2) antibody solution (50 mM phosphate buffer (pH 6.0)) obtained in Step 1 (5.7 mL) together with the compound obtained in Step 4 of Example 3 (25.5 mg) as a glycan donor to afford a 10.2 mg/mL anti-CLDN6 antibody (H2L2)-[MSG1-$N_3$]$_2$ solution (phosphate buffered saline (pH 6.0)) (11.1 mL).

Example 17: Sugar Chain Remodeling 6 (CLDN6-MSG1 (H1L3))

Step 1: (Fucα1,6) GlcNAc-Anti-CLDN6 Antibody (H1L3)

The operations same as in Step 1 of Example 12 were performed using a ca. 39.4 mg/mL anti-CLDN6 antibody (H1L3) solution (25 mM histidine solution (pH 6.0), 5% sorbitol solution) prepared in Example 10 (3 mL) to afford a 39.2 mg/ml (Fucα1,6) GlcNAc-anti-CLDN6 antibody (H1L3) solution (50 mM phosphate buffer (pH 6.0)) (4.5 mL).

Step 2: Anti-CLDN6 Antibody (H1L3)-[MSG1-$N_3$]$_2$

The operations same as in Step 2 of Example 12 were performed using the 39.2 mg/mL (Fucα1,6) GlcNAc-anti-CLDN6 (H1L3) antibody solution (50 mM phosphate buffer (pH 6.0)) obtained in Step 1 (4.5 mL) together with the compound obtained in Step 4 of Example 3 (25.5 mg) as a glycan donor to afford a 9.83 mg/mL anti-CLDN6 antibody (H1L3)-[MSG1-$N_3$]$_2$ solution (phosphate buffered saline (pH 6.0)) (7.2 mL).

Example 18: Sugar Chain Remodeling 7 (TROP2-MSG1)

Step 1: (Fucα1,6) GlcNAc-Anti-Trop2 Antibody

The operations same as in Step 1 of Example 12 were performed using a ca. 20 mg/mL anti-Trop2 antibody solution (25 mM histidine solution (pH 6.0), 5% sorbitol solution) prepared in Reference Example 2 (6 mL) to afford a 21.69 mg/mL (Fucα1,6) GlcNAc-anti-Trop2 antibody solution (50 mM phosphate buffer (pH 6.0)) (3.3 mL).

Step 2: Anti-Trop2 Antibody-[MSG1-$N_3$]$_2$

The operations same as in Step 2 of Example 12 were performed using the 21.69 mg/mL (Fucα1,6) GlcNAc-anti-Trop2 antibody solution (50 mM phosphate buffer (pH 6.0)) obtained in Step 1 (3.35 mL) together with the compound obtained in Step 4 of Example 3 (25.5 mg) as a glycan donor to afford a 10.3 mg/mL anti-Trop2 antibody-[MSG1-$N_3$]$_2$ solution (phosphate buffered saline (pH 6.0)) (6.4 mL).

[Synthesis of ADC]

Examples 19 to 23 show preparation methods for ADC1 to ADC6. Each of the R groups in the reaction formulas in Examples 19 to 23 is represented by the following formula:

See FIG. 47.

In the compound obtained in Step 1 of each of Examples 19 to 23, the triazole ring has geometric isomers as illustrated in the formula, and the compound has a drug-linker as a mixture of the two structures shown above as R.

Example 19: ADC1 (see FIG. 48)

Step 1: Conjugation of Antibody and Drug-Linker

To a phosphate buffered saline (pH 6.0) solution of the antibody (10.2 mg/mL, 2.50 mL) obtained in Step 2 of Example 15, 1,2-propanediol (2.29 mL) and a 10 mM dimethyl sulfoxide solution of compound (3-14) obtained in Step 13 of Example 2-1 (0.206 mL; 12 equivalents per antibody molecule) were added at room temperature, and the resultant was reacted using a tube rotator (MTR-103, AS ONE Corporation) at room temperature for 48 hours.

Purification operation: The solution was purified by using common operation D to afford 14.5 mL of a solution of the desired compound.

Characterization: The following characteristic values were obtained by using common operations E and F.

Antibody concentration: 1.54 mg/mL, antibody yield: 22.3 mg (89%), average number of conjugated drug molecules per antibody molecule (n): 1.9

Example 20: ADC2 (see FIG. 49)

Step 1: Conjugation of Antibody and Drug-Linker

To a phosphate buffered saline (pH 6.0) solution of the antibody (10.2 mg/mL, 1.00 mL) obtained in Step 1 of Example 14, 1,2-propanediol (0.917 mL) and a 10 mM dimethyl sulfoxide solution of compound (3-14) obtained in Step 13 of Example 2-1 (0.0825 mL; 12 equivalents per antibody molecule) were added at room temperature, and the resultant was reacted using a tube rotator (MTR-103, AS ONE Corporation) at room temperature for 2 days.

Purification operation: The solution was purified by using common operation D to afford 6.00 mL of a solution of the desired compound.

Characterization: The following characteristic values were obtained by using common operations E and F.

Antibody concentration: 1.41 mg/mL, antibody yield: 8.45 mg (85%), average number of conjugated drug molecules per antibody molecule (n): 1.9

Example 21: ADC3 (see FIG. 50)

Step 1: Conjugation of Antibody and Drug-Linker

To a phosphate buffered saline (pH 6.0) solution of the antibody (10 mg/mL, 1.00 mL) obtained in Step 2 of Example 18, 1,2-propanediol (0.917 mL) and a 10 mM dimethyl sulfoxide solution of compound (3-14) obtained in Step 13 of Example 2-1 (0.0825 mL; 12 equivalents per antibody molecule) were added at room temperature, and the resultant was reacted using a tube rotator (MTR-103, AS ONE Corporation) at room temperature for 2 days.

Purification operation: The solution was purified by using common operation D to afford 6.00 mL of a solution of the desired compound. r Characterization: The following characteristic values were obtained by using common operations E and F.

Antibody concentration: 1.47 mg/mL, antibody yield: 8.8 mg (88%), average number of conjugated drug molecules per antibody molecule (n): 1.9

Example 22: ADC4 (see FIG. 51)

Step 1: Conjugation of Antibody and Drug-Linker

To a phosphate buffered saline (pH 6.0) solution of the antibody (9.96 mg/mL, 2.50 mL) obtained in Step 2 of Example 16, 1,2-propanediol (2.29 mL) and a 10 mM dimethyl sulfoxide solution of compound (3-14) obtained in Step 13 of Example 2-1 (0.206 mL; 12 equivalents per antibody molecule) were added at room temperature, and the resultant was reacted using a tube rotator (MTR-103, AS ONE Corporation) at room temperature for 48 hours.

Purification operation: The solution was purified by using common operation D to afford 14.5 mL of a solution of the desired compound.

Characterization: The following characteristic values were obtained by using common operations E and F.

Antibody concentration: 1.52 mg/mL, antibody yield: 22.0 mg (88%), average number of conjugated drug molecules per antibody molecule (n): 1.9

Example 23: ADC5 (see FIG. 52)

Step 1: Conjugation of Antibody and Drug-Linker

To a phosphate buffered saline (pH 6.0) solution of the antibody (9.83 mg/mL, 2.50 mL) obtained in Step 2 of Example 17, 1,2-propanediol (2.29 mL) and a 10 mM dimethyl sulfoxide solution of compound (3-14) obtained in Step 13 of Example 2-1 (0.206 mL; 12 equivalents per antibody molecule) were added at room temperature, and the resultant was reacted using a tube rotator (MTR-103, AS ONE Corporation) at room temperature for 48 hours.

Purification operation: The solution was purified by using common operation D to afford 14.5 mL of a solution of the desired compound.

Characterization: The following characteristic values were obtained by using common operations E and F.

Antibody concentration: 1.45 mg/mL, antibody yield: 21.0 mg (84%), average number of conjugated drug molecules per antibody molecule (n): 1.9

[Synthesis of Pyrrolobenzodiazepine Derivative]

EXAMPLE 24: PYRROLOBENZODIAZEPINE DERIVATIVE A

Drug 1 was synthesized in accordance with the following scheme.

[Formula 62]

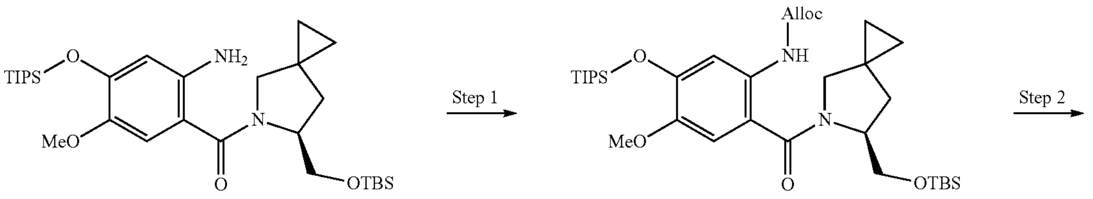

1-6 7-1

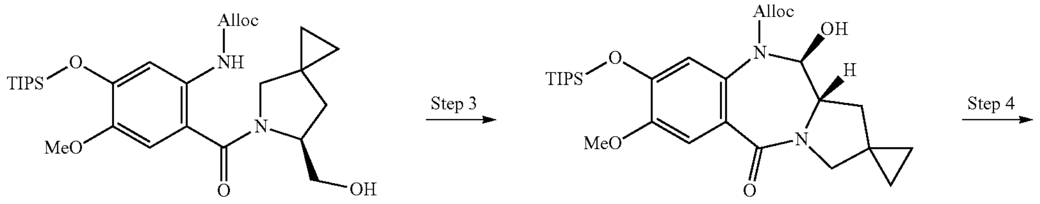

7-2 7-3

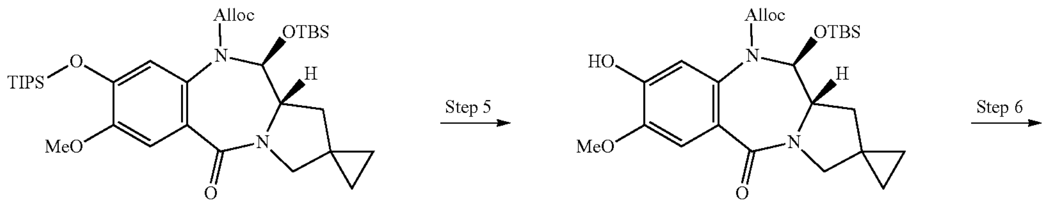

7-4 7-5

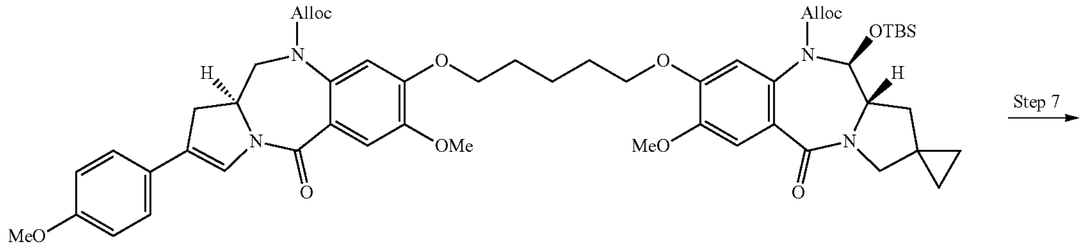

7-6

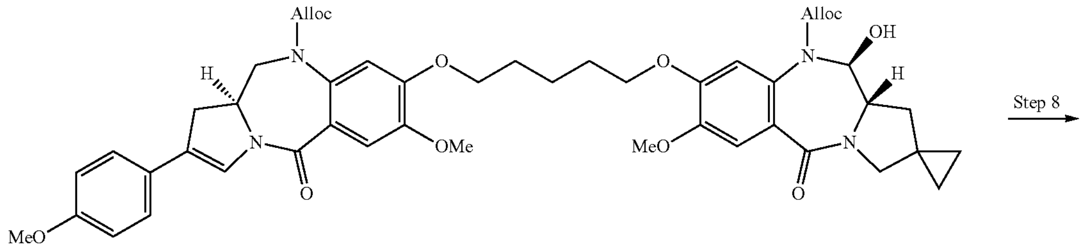

7-7

-continued

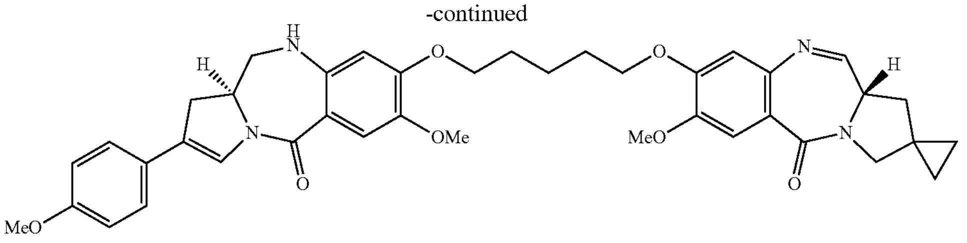

7-8

Step 1: Compound 7-1

Compound (1-6) obtained in Step 5 of Example 1-1 (4.59 g, 8.15 mmol) was reacted in the same manner as in Step 9 of Example 2-1 to afford the desired compound (7-1) (4.86 g, 92%).

MS (APCI, ESI) m/z: 647 $(M+H)^+$

Step 2: Compound 7-2

Compound (7-1) obtained in Step 1 (4.86 g, 7.51 mmol) was reacted in the same manner as in Step 7 of Example 1-1 to afford the desired compound (7-2) (3.42 g, 86%).

MS (APCI, ESI) m/z: 533 $(M+H)^+$

Step 3: Compound 7-3

Compound (7-2) obtained in Step 2 (6.68 g, 12.5 mmol) was reacted in the same manner as in Step 8 of Example 1-1 to afford the desired compound (7-3) (6.44 g, 97%).

MS (APCI, ESI) m/z: 531 $(M+H)^+$

Step 4: Compound 7-4

Compound (7-3) obtained in Step 3 (3.24 g, 6.10 mmol) was reacted in the same manner as in Step 9 of Example 1-1 to afford the desired compound (7-4) (3.86 g, 98%).

MS (APCI, ESI) m/z: 645 $(M+H)^+$

Step 5: Compound 7-5

Compound (7-4) obtained in Step 4 (4.49 g, 6.96 mmol) was reacted in the same manner as in Step 10 of Example 1-1 to afford the desired compound (7-5) (3.24 g, 95%).

MS (APCI, ESI) m/z: 489 $(M+H)^+$

Step 6: Compound 7-6

Compound (7-5) obtained in Step 5 (0.080 g, 0.164 mmol) was reacted in the same manner as in Step 10 of Example 2-1 to afford the desired compound (7-6) (0.160 g, 98%).

MS (APCI, ESI) m/z: 993 $(M+H)^+$

Step 7: Compound 7-7

Compound (7-6) obtained in Step 6 (160 mg, 0.161 mmol) was reacted in the same manner as in Step 11 of Example 2-1 to afford the desired compound (7-7) (141 mg, quantitative).

MS (APCI, ESI) m/z: 879 $(M+H)^+$

Step 8: (11a'S)-7'-Methoxy-8'-[(5-{[(11aS)-7-methoxy-2-(4-methoxyphenyl)-5-oxo-5,10,11,11a-tetrahydro-1H-pyrrolo[2,1-c][1,4]benzodiazepin-8-yl]oxy}pentyl)oxy]-1',11a'-dihydro-5'H-spiro[cyclopropane-1,2'-pyrrolo[2,1-c][1,4]benzodiazepine]-5'-one (7-8)

Compound (7-7) obtained in Step 7 (141 mg, 0.161 mmol) was reacted in the same manner as in Step 12 of Example 2-1 to afford the desired compound (7-8) (109.8 mg, 99%).

$^1$H-NMR (DMSO-$D_6$) δ: 7.92-7.91 (1H, m), 7.45 (1H, s), 7.39-7.37 (2H, m), 7.33 (1H, s), 7.29 (1H, s), 6.92-6.89 (2H, m), 6.85 (1H, s), 6.56-6.54 (1H, m), 6.31 (1H, s), 4.19-4.12 (2H, m), 4.05-3.99 (1H, m), 3.95-3.93 (2H, m), 3.82-3.79 (4H, m), 3.76 (3H, s), 3.66 (3H, s), 3.52-3.46 (3H, m), 3.30-3.21 (2H, m), 2.78-2.74 (1H, m), 2.45-2.42 (1H, m), 2.06-2.05 (1H, m), 1.89-1.82 (4H, m), 1.60-1.58 (2H, m), 0.80-0.63 (4H, m).

MS (APCI, ESI) m/z: 693 $(M+H)^+$

Example 27: Pyrrolobenzodiazepine Derivative B

[Formula 63]

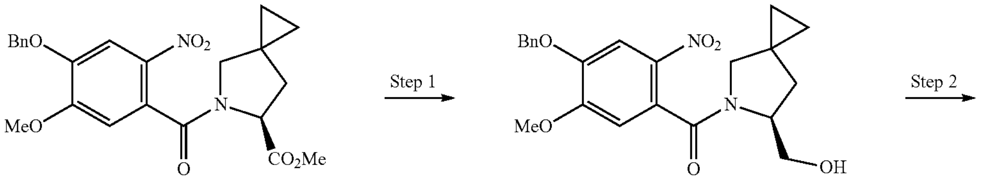

6-2 8-1

-continued

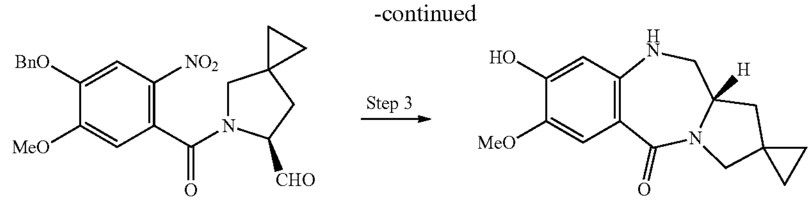

8-2 8-3

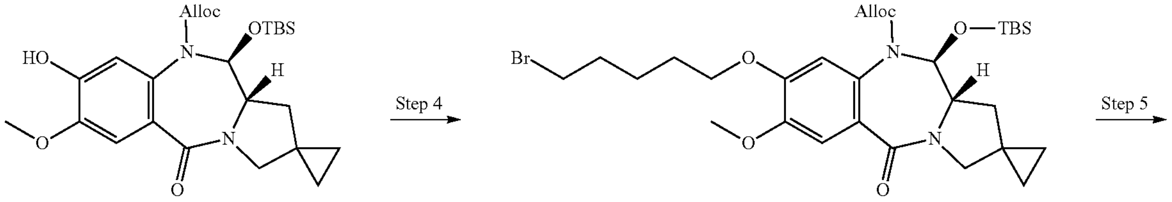

7-5 8-4

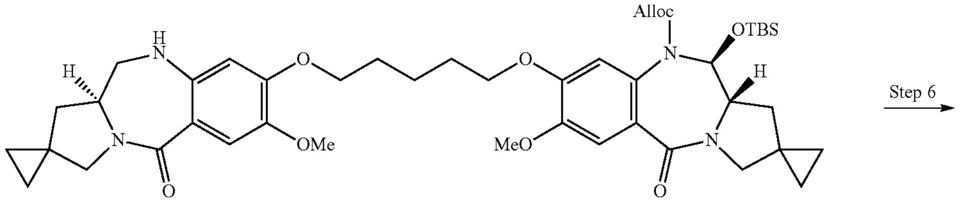

8-5

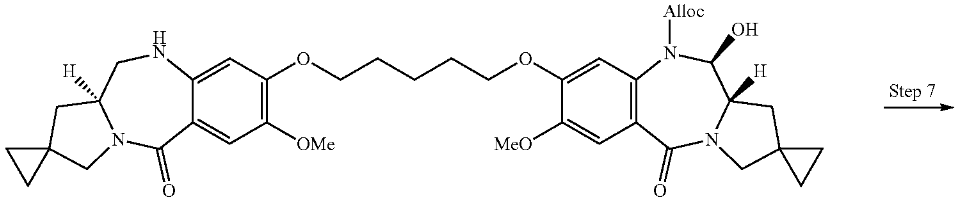

8-6

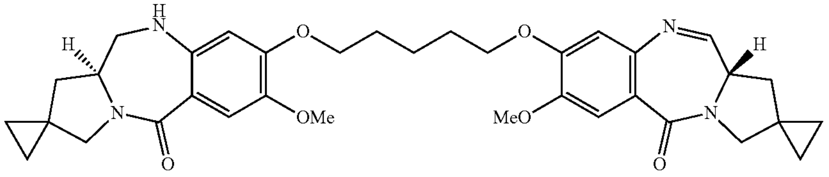

8-7

Step 1: Compound 8-1

To a solution of compound (6-2) obtained in Step 1 of Example 2-4 (6.49 g, 14.7 mmol) in tetrahydrofuran (147 mL), lithium borohydride (0.642 g, 29.5 mmol) was added at 0° C., and the resultant was stirred at room temperature for 2 hours. To the reaction solution, 1 N hydrochloric acid was added, and the resultant was extracted with ethyl acetate. The organic layer obtained was washed with brine, dried over magnesium sulfate, and then distilled under reduced pressure. The resulting residue (6.94 g, quantitative) was used for the subsequent step without purification.

MS (APCI, ESI) m/z: 413 $(M+H)^+$

Step 2: Compound 8-2

Compound (8-1) obtained in Step 1 (4.50 g, 11.0 mmol) was reacted in the same manner as in Step 8 of Example 1 to afford the desired compound (8-2) (1.94 g, 43%).

MS (APCI, ESI) m/z: 411 $(M+H)^+$

Step 3: Compound 8-3

To a mixed solution of compound (8-2) obtained in Step 2 (1.94 g, 4.73 mmol) in tetrahydrofuran (25 mL), ethyl acetate (25 mL), and methanol (25 mL), 5% palladium carbon (moisture content: 54%, 1.0 g) was added under the nitrogen atmosphere, and the reaction solution was then stirred under the hydrogen atmosphere at room temperature for 22 hours. After the reaction solution was filtered through a Celite, the filtrate was distillated under reduced pressure. The resulting residue was purified by silica gel column chromatography [hexane:ethyl acetate=80:20 (v/v) to 0:100 (v/v)] to afford the desired compound (8-3) (1.20 g, 93%).

MS (APCI, ESI) m/z: 275 $(M+H)^+$

Step 4: Compound 8-4

Compound (7-5) obtained in Step 5 of Example 24 (0.300 g, 0,614 mmol) was reacted in the same manner as in Step 2 of Example 2-1 to afford the desired compound (8-4) (0.388 g, 99%).

MS (APCI, ESI) m/z: 639 [8] Br, (M+H)$^+$],637 [79Br, (M+H)$^+$].

Step 5: Compound 8-5

Compound (8-4) obtained in Step 4 (0.203 g, 0.318 mmol) was reacted with compound obtained in Step 3 (0.131 g, 0.478 mmol) in the same manner as in Step 10 of Example 2-1 to afford the desired compound (8-5) (0.0880 g, 33%). MS (APCI, ESI) m/z: 831 (M+H)$^+$ Step 6: Compound 8-6

Compound (8-5) obtained in Step 5 (0.0880 g, 0.106 mmol) was reacted in the same manner as in Step 11 of Example 2-1 to afford the desired compound (8-6) (0.0500 g, 66%).

MS (APCI, ESI) m/z: 717 (M+H)$^+$

Step 7: (11a'S)-7'-Methoxy-8'-[(5-{[(11a'S)-7'-methoxy-5'-oxo-5',11a'-dihydro-1'H-spiro[cyclopropane-1,2'-pyrrolo[2,1-c][1,4]benzodiazepine]-8'-yl]oxy}pentyl)oxy]-1',10',11',11a'-tetrahydro-5'H-spiro[cyclopropane-1,2'-pyrrolo[2,1-c][1,4]benzodiazepine]-5'-one (8-7)

Compound (8-6) obtained in Step 6 (0.0500 g, 0.0698 mmol) was reacted in the same manner as in Step 12 of Example 2-1 to afford the desired compound (8-7) (0.0330 g, 77%).

$^1$H-NMR ($CDCl_3$) δ: 7.80 (1H, m), 7.58 (1H, s), 7.52 (1H, s), 6.81 (1H, s), 6.05 (1H, s), 4.17-3.97 (5H, m), 3.94 (3H, s), 3.87 (1H, m), 3.84 (3H, s), 3.72-3.68 (3H, m), 3.51-3.45 (5H, m), 2.54-2.51 (1H, m), 2.03-1.90 (6H, m), 1.75-1.68 (2H, m), 0.66 (8H, m).

MS (APCI, ESI) m/z: 615 (M+H)$^+$

Example 28: Pyrrolobenzodiazepine Derivative C

[Formula 64]

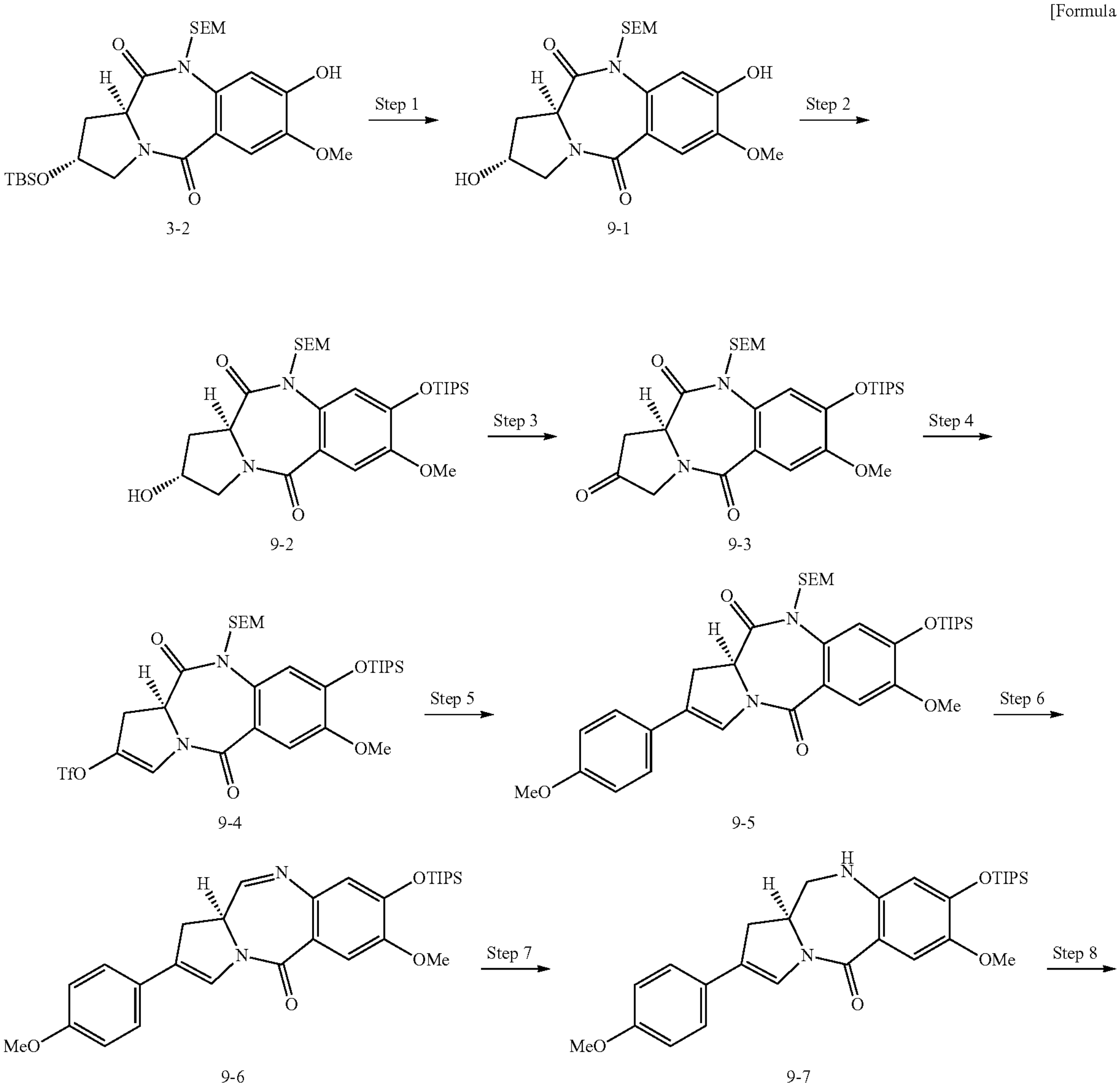

3-2, 9-1, 9-2, 9-3, 9-4, 9-5, 9-6, 9-7

-continued

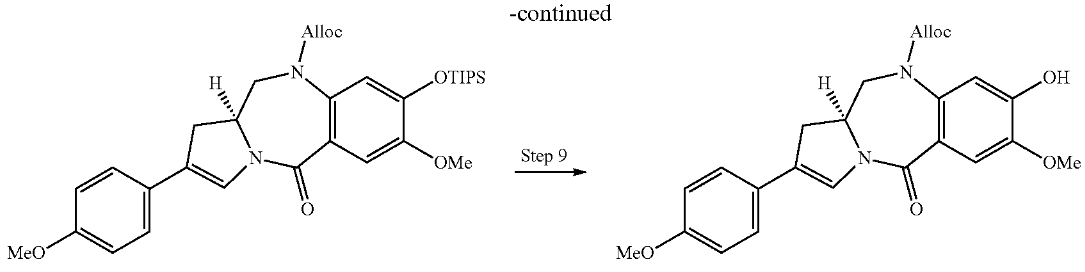

9-8 9-9

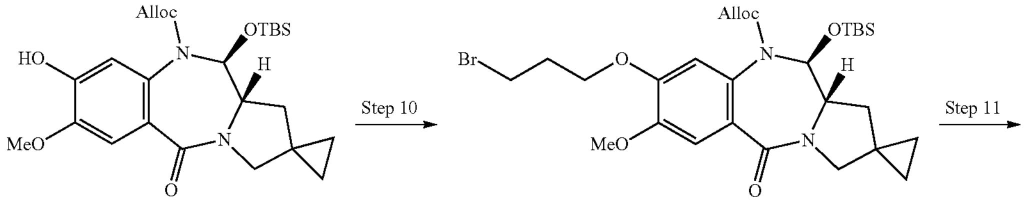

7-5 9-10

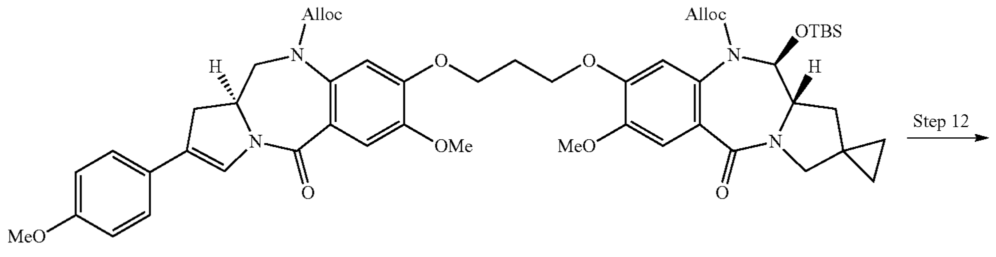

9-11

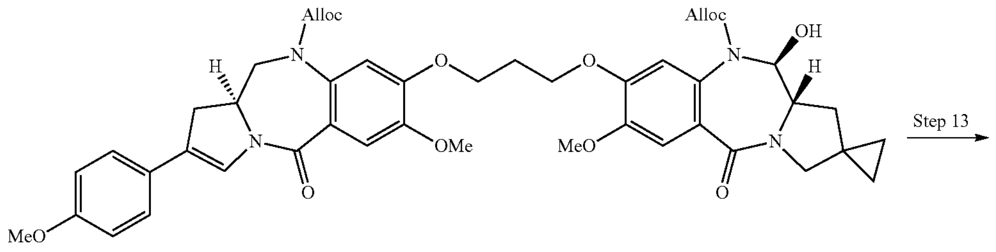

9-12

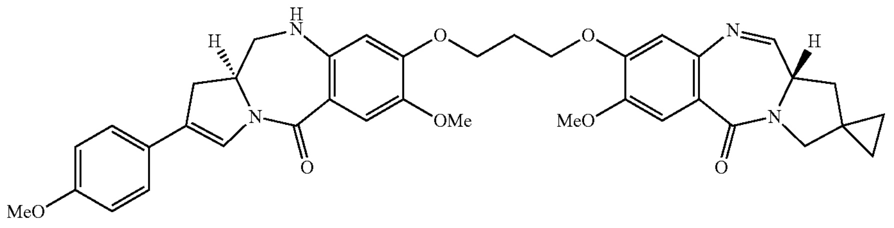

9-13

Step 1: Compound (9-1)

Compound (3-2) obtained in Step 1 of Example 2-1 (5.00 g, 9.66 mmol) was reacted in the same manner as in Step 3 of Example 2-1 to afford the desired compound (9-1) (3.95 g, 100%).

MS (APCI, ESI) m/z: 409 $(M+H)^+$

Step 2: Compound (9-2)

To a solution of compound (9-1) obtained in Step 1 (3.95 g, 9.67 mmol) in dichloromethane (97 mL), imidazole (1.65 g, 24.2 mmol), triisopropylsilyl chloride (2.46 mL, 11.6 mmol), and dimethylformamide (5 mL) were added, and the resultant was stirred at room temperature for 21 hours. Water was added to the reaction solution, which was extracted with chloroform, and the organic layer obtained was washed with water and distilled under reduced pressure. The resulting residue was purified by silica gel chromatography [hexane: ethyl acetate=100:0 (v/v) to 20:80 (v/v)] to afford the desired compound (9-2) (4.78 g, 87%).

MS (APCI, ESI) m/z: 565 $(M+H)^+$

Step 3: Compound (9-3)

Compound (9-2) obtained in Step 2 (4.78 g, 8.43 mmol) was reacted in the same manner as in Step 4 of Example 2-1 to afford the desired compound (9-3) (2.36 g, 50%).

MS (APCI, ESI) m/z: 563 $(M+H)^+$

Step 4: Compound (9-4)

Compound (9-3) obtained in Step 3 (1.53 g, 2.72 mmol) was reacted in the same manner as in Step 5 of Example 2-1 to afford the desired compound (9-4) (1.27 g, 69%).

$^1$H-NMR ($CDCl_3$) δ: 7.31 (2H, s), 7.15 (1H, m), 5.52 (1H, m), 4.65 (1H, m), 4.57 (1H, m), 3.95-3.89 (1H, m), 3.87 (3H, s), 3.75-3.58 (2H, m), 3.18-3.14 (1H, m), 1.33-1.25 (3H, m), 1.10 (18H, m), 1.00-0.96 (2H, m), 0.03 (9H, s).

Step 5: Compound (9-5)

Compound (9-4) obtained in Step 4 (0.519 g, 0.747 mmol) was reacted in the same manner as in Step 6 of Example 2-1 to afford the desired compound (9-5) (0.511 g, quantitative).

MS (APCI, ESI) m/z: 653 [$(M+H)^+$]

Step 6: Compound (9-6)

Compound (9-5) obtained in Step 5 (0.178 g, 0.272 mmol) was reacted in the same manner as in Step 7 of Example 2-1 to afford the desired compound (9-6) (0.094 g, 68%).

MS (APCI, ESI) m/z: 507 [$(M+H)^+$]

Step 7: Compound (9-7)

Compound (9-6) obtained in Step 6 (0.063 g, 0.124 mmol) was reacted in the same manner as in Step 8 of Example 2-1 to afford the desired compound (9-7) (0.046 g, 72%).

MS (APCI, ESI) m/z: 509 [$(M+H)^+$]

Step 8: Compound (9-8)

Compound (9-7) obtained in Step 7 (0.046 g, 0.090 mmol) was reacted in the same manner as in Step 9 of Example 2-1 to afford the desired compound (9-8) (0.03 g, 56%).

MS (APCI, ESI) m/z: 593 [$(M+H)^+$]

Step 9: Compound (9-9)

Compound (9-8) obtained in Step 8 (0.030 g, 0.050 mmol) was reacted in the same manner as in Step 10 of Example 2-1 to afford the desired compound (9-9) (0.015 g, 0.034 mmol).

$^1$H-NMR ($CDCl_3$) δ: 7.39-7.25 (4H, m), 6.92-6.78 (3H, m), 6.03-5.92 (1H, m), 5.86-5.68 (1H, m), 5.20-5.07 (2H, m), 4.66-4.57 (1H, m), 4.52-4.40 (1H, m), 4.40-4.27 (1H, m), 4.27-4.16 (1H, m), 3.95 (3H, s), 3.82 (3H, s), 3.66-3.59 (1H, m), 3.32-3.21 (1H, m), 2.74-2.64 (1H, m).

MS (APCI, ESI) m/z: 437 [$(M+H)^+$]

Step 10: Compound (9-10)

Compound (7-5) obtained in Step 5 of Example 7 (0.131 g, 0.268 mmol) was reacted in the same manner as in Step 1 of Example 2-2 to afford the desired compound (9-10) (0.086 g, 52%).

MS (APCI, ESI) m/z: 611 [81Br, $(M+H)^+$],609 [79Br, $(M+H)^+$]

Step 11: Compound (9-11)

Compound (9-10) obtained in Step 10 (0.015 g, 0.034 mmol) and compound (9-9) obtained in Step 9 (0.030 g, 0.048 mmol) were used and reacted in the same manner as in Step 10 of Example 2-1 to afford the desired compound (9-11) (0.032 g, 96%).

MS (APCI, ESI) m/z: 965 [$(M+H)^+$]

Step 12: Compound (9-12)

Compound (9-11) obtained in Step 11 (0.031 g, 0.032 mmol) was reacted in the same manner as in Step 11 of Example 2-1 to afford the desired compound (9-12) (0.026 g, 95%).

MS (APCI, ESI) m/z: 851 [$(M+H)^+$]

Step 13: (11a'S)-7'-Methoxy-8'-(3-{[(11aS)-7-methoxy-2-(4-methoxyphenyl)-5-oxo-5,10,11,11a-tetrahydro-1H-pyrrolo[2,1-c][1,4]benzodiazepin-8-yl]oxy}propoxy)-1',11a'-dihydro-5'H-spiro[cyclopropane-1,2'-pyrrolo[2,1-c][1,4]benzodiazepine]-5'-one (9-13)

Compound (9-12) obtained in Step 12 (0.026 g, 0.030 mmol) was reacted in the same manner as in Step 12 of Example 2-1 to afford the desired compound (9-13) (0.018 g, 88%).

$^1$H-NMR ($CDCl_3$) δ: 7.80 (1H, m), 7.54-7.51 (3H, m), 7.33-7.29 (2H, m), 6.91-6.85 (3H, m), 6.14 (1H, s), 4.35-4.17 (6H, m), 3.95 (3H, s), 3.85 (3H, s), 3.82 (3H, s), 3.76-3.25 (5H, m), 2.79-2.69 (1H, m), 2.52 (1H, m), 2.45-2.35 (1H, m), 2.03-1.96 (1H, m), 1.28-1.23 (2H, m), 0.78-0.69 (4H, m).

MS (APCI, ESI) m/z: 665 [$(M+H)^+$]

Example 29: Cell Growth Inhibition Test (1)

The human lung cancer cell line Calu-6 obtained from ATCC (American Type Culture Collection) was used for evaluation. Cells were prepared with MEM containing 10% fetal bovine serum (GE Healthcare), MEM Non-Essential Amino Acids Solution (Thermo Fisher Scientific), and Sodium Pyruvate (Thermo Fisher Scientific) (Thermo Fisher Scientific; hereinafter, referred to as EMEM medium) to reach $1.25\times10^4$ cells/mL, and 80 μL portions of them were added into a 96-well cell culture microplate. After addition of the cells, the cells were cultured at 37° C. and 5% $CO_2$ overnight.

On the next day, 10 μL portions of pyrrolobenzodiazepine derivative A, B, or C diluted with EMEM medium to 100 pM, 50 pM, 25 pM, 12.5 pM, 6.25 pM, 3.13 pM, 1.56 pM, or 0.78 pM were added to the microplate. To each well without any pyrrolobenzodiazepine derivative, 10 μL of EMEM medium was added. Further, 10 μL portions of olaparib prepared with EMEM medium to reach 2 μM were added to the microplate. To each well without olaparib, 10 μL of EMEM medium was added. Thereafter, the microplate was cultured at 37° C. and 5% $CO_2$ for 6 days. After culturing, the microplate was taken out of the incubator, and left to stand at room temperature for 30 minutes. CellTiter-Glo Luminescent Cell Viability Assay (Promega Corporation) in an amount equivalent to that of the culture solution was added, and stirred using a plate mixer. The microplate was left to stand at room temperature for 10 minutes, and thereafter the amount of emission was measured by using a plate reader (PerkinElmer).

Cell survival rates in wells with derivative A, B, or C were calculated by using the following formula.

$$\text{Cell survival rate }(\%) = a \div b \times 100$$

a: Mean value of amounts of emission from wells with derivative A, B, or C b: Mean value of amounts of emission from wells with medium $IC_{50}$ values were calculated by using the following formula.

$$IC_{50}(nM) = \text{antilog}((50-d)\times(\text{LOG}_{10}(b)-\text{LOG}_{10}(a))\div(d-c)+\text{LOG}_{10}(b))$$

a: Concentration of derivative A, B, or C, a b: Concentration of derivative A, B, or C, b c: Cell survival rate when derivative A, B, or C of concentration a was added d: Cell survival rate when derivative A, B, or C of concentration b was added a and b satisfy a>b at points sandwiching a cell survival rate of 50%.

Cell survival rates in wells with derivative A, B, or C added together with 2 μM olaparib were calculated by using the following formula.

$$\text{Cell survival rate }(\%) = a \div b \times 100$$

a: Mean value of amounts of emission from wells with derivative A, B, or C added together with 2 μM olaparib b: Mean value of amounts of emission from wells with 2 μM olaparib $IC_{50}$ values were calculated by using the following formula.

$$IC_{50}(nM) = \text{antilog}((50-d)\times(\text{LOG}_{10}(b)-\text{LOG}_{10}(a))\div(d-c)+\text{LOG}_{10}(b))$$

a: Concentration of derivative A, B, or C, a b: Concentration of derivative A, B, or C, b c: Cell survival rate when derivative A, B, or C of concentration a and 2 μM olaparib were added d: Cell survival rate when derivative A, B, or C of concentration b and 2 μM olaparib were added a and b satisfy a>b at points sandwiching a cell survival rate of 50%.

To the Calu-6 cells, 2 μM olaparib did not exhibit growth-suppressing effect (growth inhibition: less than 10%). By contrast, derivative A, B, and C when being added singly provided growth-suppressing effect as $IC_{50}$ values of 6.8 pM, 119.8 pM, and 113.0 pM, respectively, and when being added together with 2 μM olaparib, provided growth-suppressing effect as $IC_{50}$ values of 4.3 pM, 79.4 pM, and 89.4 pM, respectively. Combined use provided superior growth-suppressing effect to those for single use of individual agents.

Example 30: Cell Growth Inhibition Test (2)

The human pharyngeal cancer cell line FaDu obtained from ATCC (American Type Culture Collection) was used for evaluation. Cells were prepared with MEM containing 10% fetal bovine serum (GE Healthcare), MEM Non-Essential Amino Acids Solution (Thermo Fisher Scientific), and Sodium Pyruvate (Thermo Fisher Scientific) (Thermo Fisher Scientific; hereinafter, referred to as EMEM medium) to reach $6.25\times10^3$ cells/mL, and 80 μL portions of them were added into a 96-well cell culture microplate. After addition of the cells, the cells were cultured at 37° C. and 5% $CO_2$ overnight.

On the next day, 10 μL portions of pyrrolobenzodiazepine derivative A, B, or C diluted with EMEM medium to 100 pM, 50 pM, 25 pM, 12.5 pM, 6.25 pM, 3.13 pM, 1.56 pM, or 0.78 pM were added to the microplate. To each well without any pyrrolobenzodiazepine derivative, 10 μL of EMEM medium was added. Further, 10 μL portions of olaparib prepared with EMEM medium to reach 1 μM were added to the microplate. To each well without olaparib, 10 μL of EMEM medium was added. Thereafter, the microplate was cultured at 37° C. and 5% $CO_2$ for 6 days. After culturing, the microplate was taken out of the incubator, and left to stand at room temperature for 30 minutes. CellTiter-Glo Luminescent Cell Viability Assay (Promega Corporation) in an amount equivalent to that of the culture solution was added, and stirred using a plate mixer. The microplate was left to stand at room temperature for 10 minutes, and thereafter the amount of emission was measured by using a plate reader (PerkinElmer).

Cell survival rates in wells with derivative A, B, or CD were calculated by using the following formula.

$$\text{Cell survival rate }(\%) = a \div b \times 100$$

a: Mean value of amounts of emission from wells with derivative A, B, or C b: Mean value of amounts of emission from wells with medium $IC_{50}$ values were calculated by using the following formula.

$$IC_{50}(nM) = \text{antilog}((50-d)\times(\text{LOG}_{10}(b)-\text{LOG}_{10}(a))\div(d-c)+\text{LOG}_{10}(b))$$

a: Concentration of derivative A, B, or C, a b: Concentration of derivative A, B, or C, b c: Cell survival rate when derivative A, B, or C of concentration a was added d: Cell survival rate when derivative A, B, or C of concentration b was added a and b satisfy a>b at points sandwiching a cell survival rate of 50%.

Cell survival rates in wells with derivative A, B, or C added together with 1 μM olaparib were calculated by using the following formula.

$$\text{Cell survival rate }(\%) = a \div b \times 100$$

a: Mean value of amounts of emission from wells with derivative A, B, or C added together with 1 μM olaparib b: Mean value of amounts of emission from wells with 1 μM olaparib $IC_{50}$ values were calculated by using the following formula.

$$IC_{50}(nM) = \text{antilog}((50-d)\times(\text{LOG}_{10}(b)-\text{LOG}_{10}(a))\div(d-c)+\text{LOG}_{10}(b))$$

a: Concentration of derivative A, B, or C, a b: Concentration of derivative A, B, or C, b c: Cell survival rate when derivative A, B, or C of concentration a and 1 μM olaparib were added d: Cell survival rate when derivative A, B, or C of concentration b and 1 μM olaparib were added a and b satisfy a>b at points sandwiching a cell survival rate of 50%.

To the FaDu cells, 1 μM olaparib did not exhibit growth-suppressing effect (growth inhibition: less than 10%). By contrast, derivative A, B, and C when being added singly provided growth-suppressing effect as $IC_{50}$ values of 8.6 pM, 123.2 pM, and 73.2 pM, respectively, and when being added together with 1 μM olaparib, provided growth-suppressing effect as $IC_{50}$ values of 4.4 pM, 71.9 pM, and 44.5 pM, respectively. Combined use provided superior growth-suppressing effect to those for single use of individual agents.

Example 31: Cell Growth Inhibition Test (3)

The human pharyngeal cancer cell line FaDu obtained from ATCC (American Type Culture Collection) was used for evaluation. Cells were prepared with MEM containing 10% fetal bovine serum (GE Healthcare), MEM Non-Essential Amino Acids Solution (Thermo Fisher Scientific), and Sodium Pyruvate (Thermo Fisher Scientific) (Thermo Fisher Scientific; hereinafter, referred to as EMEM medium) to reach $6.25\times10^3$ cells/mL, and 80 μL portions of them were added into a 96-well cell culture microplate. After addition of the cells, the cells were cultured at 37° C. and 5% $CO_2$ overnight.

On the next day, 10 μL portions of pyrrolobenzodiazepine derivative A, B, or C diluted with EMEM medium to 100 pM, 50 pM, 25 pM, 12.5 pM, 6.25 pM, 3.13 pM, 1.56 pM, or 0.78 pM were added to the microplate. To each well without any pyrrolobenzodiazepine derivative, 10 μL of EMEM medium was added. Further, 10 μL portions of talazoparib prepared with EMEM medium to reach 2 nM were added to the microplate. To each well without talazoparib, 10 μL of EMEM medium was added. Thereafter, the microplate was cultured at 37° C. and 5% $CO_2$ for 6 days. After culturing, the microplate was taken out of the incubator, and left to stand at room temperature for 30 minutes. CellTiter-Glo Luminescent Cell Viability Assay (Promega Corporation) in an amount equivalent to that of the culture solution was added, and stirred using a plate mixer. The microplate was left to stand at room temperature for 10 minutes, and thereafter the amount of emission was measured by using a plate reader (PerkinElmer).

Cell survival rates in wells with derivative A, B, or C were calculated by using the following formula.

$$\text{Cell survival rate (\%)} = a \div b \times 100$$

a: Mean value of amounts of emission from wells with derivative A, B, or C b: Mean value of amounts of emission from wells with medium $IC_{50}$ values were calculated by using the following formula.

$$IC_{50}(nM) = \text{antilog}((50-d)\times(\text{LOG}_{10}(b)-\text{LOG}_{10}(a))\div(d-c)+\text{LOG}_{10}(b))$$

a: Concentration of derivative A, B, or C, a b: Concentration of derivative A, B, or C, b c: Cell survival rate when derivative A, B, or C of concentration a was added d: Cell survival rate when derivative A, B, or C of concentration b was added a and b satisfy a>b at points sandwiching a cell survival rate of 50%.

Cell survival rates in wells with derivative A, B, or C added together with 2 nM talazoparib were calculated by using the following formula.

$$\text{Cell survival rate (\%)} = a \div b \times 100$$

a: Mean value of amounts of emission from wells with derivative A, B, or C added together with 2 nM talazoparib b: Mean value of amounts of emission from wells with 2 nM talazoparib $IC_{50}$ values were calculated by using the following formula.

$$IC_{50}(nM) = \text{antilog}((50-d)\times(\text{LOG}_{10}(b)-\text{LOG}_{10}(a))\div(d-c)+\text{LOG}_{10}(b))$$

a: Concentration of derivative A, B, or C, a b: Concentration of derivative A, B, or C, b c: Cell survival rate when derivative A, B, or C of concentration a and 2 nM talazoparib were added d: Cell survival rate when derivative A, B, or C of concentration b and 2 nM talazoparib were added a and b satisfy a>b at points sandwiching a cell survival rate of 50%.

To the FaDu cells, 2 nM talazoparib did not exhibit growth-suppressing effect (growth inhibition: less than 10%). By contrast, derivative A, B, and C when being added singly provided growth-suppressing effect as $IC_{50}$ values of 7.7 pM, 121.2 pM, and 83.1 pM, respectively, and when being added together with 2 nM talazoparib, provided growth-suppressing effect as $IC_{50}$ values of 4.7 pM, 82.1 pM, and 51.2 pM, respectively. Combined use provided superior growth-suppressing effect to those for single use of individual agents.

Example 32: Cell growth inhibition test (4)

Cells of the human ovarian cancer cell line SK-OV-3 purchased from ATCC (American Type Culture Collection) were used for evaluation. Cells were prepared with McCoy's 5A (Modified) Medium containing 10% fetal bovine serum (GE Healthcare) (Thermo Fisher Scientific; hereinafter, referred to as McCoy's SA medium) to reach $1.25\times10^4$ cells/mL, and 80 μL portions of them were added into a 96-well cell culture microplate. After addition of the cells, the cells were cultured at 37° C. and 5% $CO_2$ overnight.

On the next day, 10 μL portions of pyrrolobenzodiazepine derivative A diluted with McCoy's 5A medium to 100 pM, 50 pM, 25 pM, 12.5 pM, 6.25 pM, 3.13 pM, 1.56 pM, or 0.78 pM were added to the microplate. To each well without pyrrolobenzodiazepine derivative A, 10 μL of McCoy's 5A medium was added. Further, 10 μL portions of talazoparib prepared with McCoy's 5A medium to reach 5 nM were added to the microplate. To each well without talazoparib, 10 μL of McCoy's 5A medium was added. Thereafter, the microplate was cultured at 37° C. and 5% $CO_2$ for 6 days. After culturing, the microplate was taken out of the incubator, and left to stand at room temperature for 30 minutes. CellTiter-Glo Luminescent Cell Viability Assay (Promega Corporation) in an amount equivalent to that of the culture solution was added, and stirred using a plate mixer. The microplate was left to stand at room temperature for 10 minutes, and thereafter the amount of emission was measured by using a plate reader (PerkinElmer).

Cell survival rates in wells with derivative A were calculated by using the following formula.

$$\text{Cell survival rate (\%)} = a \div b \times 100$$

a: Mean value of amounts of emission from wells with derivative A b: Mean value of amounts of emission from wells with medium $IC_{50}$ values were calculated by using the following formula.

$$IC_{50}(nM) = \text{antilog}((50-d)\times(LOG_{10}(b)-LOG_{10}(a))\div(d-c)+\text{LOG}_{10}(b))$$

a: Concentration of derivative A, a b: Concentration of derivative A, b c: Cell survival rate when derivative A of concentration a was added d: Cell survival rate when derivative A of concentration b was added a and b satisfy a>b at points sandwiching a cell survival rate of 50%.

Cell survival rates in wells with derivative A added together with 5 nM talazoparib were calculated by using the following formula.

$$\text{Cell survival rate (\%)} = a \div b \times 100$$

a: Mean value of amounts of emission from wells with derivative A added together with 5 nM talazoparib b: Mean value of amounts of emission from wells with 5 nM talazoparib $IC_{50}$ values were calculated by using the following formula.

$$IC_{50}(nM) = \text{antilog}((50-d)\times(\text{LOG}_{10}(b)-\text{LOG}_{10}(a))\div(d-c)+\text{LOG}_{10}(b))$$

a: Concentration of derivative A, a b: Concentration of derivative A, b c: Cell survival rate when derivative A of concentration a and 5 nM talazoparib were added d: Cell survival rate when derivative A of concentration b and 5 nM talazoparib were added a and b satisfy a>b at points sandwiching a cell survival rate of 50%.

To the SK-OV-3 cells, 5 nM talazoparib did not exhibit growth-suppressing effect (growth inhibition: less than 10%). By contrast, derivative A when being added singly provided growth-suppressing effect as an $IC_{50}$ value of 8.1 pM, when being added together with 5 nM talazoparib, provided growth-suppressing effect as an $IC_{50}$ value of 4.6 pM. Combined use provided superior growth-suppressing effect to those for single use of individual agents.

Example 33: Antitumor Test (1)

Mouse: Five- to six-week-old female BALB/c nude mice (Charles River Laboratories Japan, Inc.) were subjected to experiment.

Assay and calculation formula: In all of the studies, the major axis and minor axis of a tumor were measured twice a week by using an electronic digital caliper (CD-15CX, Mitutoyo Corp.), and the tumor volume ($mm^3$) was calculated. The calculation formula is as shown below.

$$\text{Tumor volume (mm}^3) = 1/2 \times \text{Major axis (mm)} \times [\text{Minor axis (mm)}]^2$$

Each of the anti-CLDN6 antibody-drug conjugate ADC1, the anti-HER2 antibody-drug conjugate ADC2, and the anti-TROP2 antibody-drug conjugate ADC3 was diluted with ABS buffer (10 mM acetate buffer (pH 5.5), 5% sorbitol), and a liquid volume of 10 mL/kg was intravenously administered into the tail vein. Olaparib was dissolved in Dimethyl sulfoxide (DMSO), diluted with 10% 2-hydroxy-propyl-β-cyclodextrin (Sigma-Aldrich Co. LLC)/Dulbecco's Phosphate-Buffered Saline, and then a liquid volume of 10 mL/kg was intraperitoneally administered. Talazoparib was dissolved in DMSO, diluted with 10% N,N-dimethylacetamide/5% Kolliphor HS15 (Sigma-Aldrich Co. LLC)/Dulbecco's Phosphate-Buffered Saline, and then a liquid volume of 10 mL/kg was orally administered. Niraparib was dissolved in DMSO, diluted with 0.5% methylcellulose, and then a liquid volume of 10 mL/kg was orally administered. The described method is common to Examples 34 to 37.

The human pancreatic cancer cell line CFPAC-1 purchased from ATCC (American Type Culture Collection) was suspended in physiological saline, and $5.0\times10^6$ cells were subcutaneously transplanted to the right flank of each female nude mouse, and the mice were randomly grouped 10 days after the transplantation (Day 0). ADC2 was administered at a dose of 0.2 mg/kg on Day 0. Talazoparib was administered at a dose of 0.8 mg/kg for 5 days from Day 0. Thus, each single administration group and combined administration group, and a group without drug treatment (No treatment), as a control group, were established.

FIG. 1 shows the combined effect of ADC2 and talazoparib. In the figure, the abscissa represents days after cell transplantation and the ordinate represents tumor volume. The tumor growth inhibition (TGI) on the last day of the test (Day 35) for single administration with talazoparib was 17%. The TGI for single administration with ADC2 was 94%. By contrast, a tumor growth-suppressing effect significantly superior to that for single administration with talazoparib was found for combined administration with ADC2 and talazoparib (P<0.005. Calculated by the Dunnett's test. The same is applied hereinafter.). In addition, the tumor growth-suppressing effect was found to be significantly superior to that for single administration with ADC2 (P<0.05), and the tumor growth inhibition was (TGI, 99%). No particularly significant finding such as weight loss was found any of the single and combined administration groups.

Example 34: Antitumor Test (2)

Cells of the human breast cancer cell line JIMT-1 purchased from DSMZ (Deutsche Sammlung von Mikroorganismen und Zellkulturen GmbH) were suspended in physiological saline, and $5.0\times10^6$ cells were subcutaneously transplanted to the right flank of each female nude mouse, and the mice were randomly grouped 10 days after the transplantation (Day 0). The anti-HER2 antibody-drug conjugate ADC2 was administered at a dose of 0.2 mg/kg on Day 0. For PARP inhibitors, olaparib was administered at a dose of 50 mg/kg or talazoparib was administered at a dose of 0.8 mg/kg for 5 days from Day 0. Thus, each single administration group and each combined administration group with ADC2 and a PARP inhibitor, and a group with administration of ABS buffer, as a control group, were established.

FIG. 2 shows the combined effect of ADC2 and olaparib. In the figure, the abscissa represents days after cell transplantation and the ordinate represents tumor volume. No tumor growth-suppressing effect was found for single administration with olaparib. The tumor growth inhibition (TGI) on the last day of the test (Day 43) for single administration with ADC2 was 75%. By contrast, a tumor growth-suppressing effect significantly superior to that for single administration with olaparib was found for combined administration with ADC2 and olaparib (P<0.005). In addition, the tumor growth inhibition (TGI, 82%) was higher than that for single administration with ADC2, indicating a strong combined effect. No particularly significant finding such as weight loss was found any of the single and combined administration groups.

FIG. 3 shows the combined effect of ADC2 and talazoparib, In the figure, the abscissa represents days after cell transplantation and the ordinate represents tumor volume. No tumor growth-suppressing effect was found for single administration with talazoparib. The tumor growth inhibition (TGI) on the last day of the test (Day 43) for single administration with ADC2 was 75%. By contrast, a tumor growth-suppressing effect significantly superior to that for single administration with talazoparib was found for combined administration with ADC2 and talazoparib (P<0.005). In addition, the tumor growth-suppressing effect was found to be significantly superior to that for single administration with ADC2 (P<0.05), and the tumor growth inhibition was (TGI, 91%). No particularly significant finding such as weight loss was found any of the single and combined administration groups.

Example 35: Antitumor Test (3)

The human pharyngeal cancer cell line FaDu obtained from ATCC (American Type Culture Collection) were suspended in physiological saline, and $3.0\times10^6$ cells were subcutaneously transplanted to the right flank of each female nude mouse, and the mice were randomly grouped 10 days after the transplantation (Day 0). The anti-TROP2 antibody-drug conjugate ADC3 was administered at a dose of 0.2 mg/kg on Day 0. For PARP inhibitors, olaparib was administered at a dose of 50 mg/kg or talazoparib was administered at a dose of 0.8 mg/kg for 5 days from Day 0. Thus, each single administration group and each combined administration group with ADC3 and a PARP inhibitor, and a group with administration of ABS buffer, as a control group, were established.

FIG. 4 shows the combined effect of ADC3 and olaparib. In the figure, the abscissa represents days after cell transplantation and the ordinate represents tumor volume. The tumor growth inhibition (TGI) on the last day of the test (Day 25) for single administration with olaparib was 7%. The tumor growth inhibition (TGI) on the last day of the test for single administration with ADC3 was 67%. By contrast, a tumor growth-suppressing effect significantly superior to that for single administration with olaparib was found for combined administration with ADC3 and olaparib (P<0.005). In addition, the tumor growth-suppressing effect was found to be significantly superior to that for single administration with ADC3 (P<0.05), and the tumor growth inhibition was (TGI, 76%). No particularly significant finding such as weight loss was found any of the single and combined administration groups.

FIG. 5 shows the combined effect of ADC3 and talazoparib. In the figure, the abscissa represents days after cell transplantation and the ordinate represents tumor volume. The tumor growth inhibition (TGI) on the last day of the test (Day 25) for single administration with talazoparib was 33%. The tumor growth inhibition (TGI) on the last day of the test for single administration with ADC3 was 67%. By contrast, a tumor growth-suppressing effect significantly superior to that for single administration with talazoparib was found for combined administration with ADC3 and talazoparib (P<0.005). In addition, the tumor growth-suppressing effect was found to be significantly superior to that for single administration with ADC3 (P<0.005), and the tumor growth inhibition was (TGI, 83%). No particularly significant finding such as weight loss was found any of the single and combined administration groups.

Example 36: Antitumor Test (4)

The human ovarian cancer cell line OV-90 purchased from ATCC (American Type Culture Collection) were suspended in Matrigel (Corning Incorporated), and $2.5\times10^6$ cells were subcutaneously transplanted to the right flank of each female nude mouse, and the mice were randomly grouped 18 days after the transplantation (Day 0). The anti-CLDN6 antibody-drug conjugate ADC1 was administered at a dose of 0.3 mg/kg on Day 0. Niraparib was administered at a dose of 75 mg/kg for 5 days from Day 0. Thus, each single administration group and combined administration group, and a group without drug treatment (No treatment), as a control group, were established.

FIG. 42 shows the combined effect of ADC1 and niraparib. In the figure, the abscissa represents days after cell transplantation and the ordinate represents tumor volume. The tumor growth inhibition (TGI) on Day 21 for single administration with niraparib was 1%, and no particularly significant finding such as weight loss was found on Day 21. TGI on day 21 was 96% for both the single administration group with ADC1 and the combined administration group with ADC1 and niraparib, and no particularly significant finding such as weight loss was found on Day 21. On Day 53, a tumor growth-suppressing effect was found for combined administration with ADC1 and niraparib, in contrast to single administration with ADC1. No significant finding such as weight loss caused by single administration with ADC1 or combined administration with ADC1 and niraparib was found on Day 53.

ADC1 used in this Example was produced in accordance with the same method as in Example 15 and Example 19 with use of the anti-CLDN6 (H1L1) antibody.

Example 37: Antitumor Test (5)

The human ovarian cancer cell line OV-90 purchased from ATCC (American Type Culture Collection) are suspended in Matrigel (Corning Incorporated), and $2.5\times10^6$ cells are subcutaneously transplanted to the right flank of each female nude mouse, and the mice are randomly grouped 13 to 18 days after the transplantation (Day 0). The anti-CLDN6 antibody-drug conjugate ADC1 is administered at a dose of 0.2 mg/kg on Day 0. For a PARP inhibitory drug, olaparib is administered at a dose of 50 mg/kg or talazoparib is administered at a dose of 0.8 mg/kg for 5 days from Day 0. Thus, each single administration group and combined administration group, and a group without drug treatment (No treatment), as a control group, are established.

Example 38: Trastuzumab Variant-[MSG1-$N_3$]$_2$ or Trastuzumab Variant 2-[MSG1-$N_3$]$_2$ Step 1: Preparation of (Fucα1,6) GlcNAc-Trastuzumab Variant To a ca. 22.3 mg/mL Trastuzumab variant (light chain: SEQ ID NO: 73, heavy chain: SEQ ID NO: 75) solution (50 mM phosphate buffer (pH 6.0)) (2.69 mL), 0.156 mL of 7.7 mg/mL wild-type EndoS solution (PBS) was added, and the resultant was incubated at 37° C. for 4 hours. The progress of the reaction was checked by an Experion electrophoresis station (produced by Bio-Rad Laboratories, Inc.). After the completion of the reaction, purification by affinity chromatography and purification with a hydroxyapatite column were performed in accordance with the following methods.

(1) Purification by Affinity Chromatography

Purification apparatus: AKTA avant (produced by GE Healthcare)

Column: HiTrap rProtein A FF (5 mL) (produced by GE Healthcare)

Flow rate: 5 mL/min (1.25 mL/min in charging)

Each reaction solution obtained above was purified in multiple separate operations. In connecting to the column, the reaction solution was added to the upper part of the column, and 4 CV (Column Volume) of binding buffer (20 mM phosphate buffer (pH 6.0)) was flowed at 1.25 mL/min and 5 CV thereof was further flowed at 5 mL/min. In intermediate washing, 15 CV of washing solution (20 mM phosphate buffer (pH 7.0), 0.5 M sodium chloride solution) was flowed. In elution, 6 CV of elution buffer (ImmunoPure IgG Eution buffer, produced by Pierce) was flowed. The eluate was immediately neutralized with 1 M Tris buffer (pH 9.0). Fractions containing the desired compound were subjected to buffer exchange to 5 mM phosphate buffer/50 mM morpholinoethanesulfonic acid (MES) solution (pH 6.8) by using common operation C.

(2) Purification by Hydroxyapatite Chromatography

Purification apparatus: AKTA avant (produced by GE Healthcare)

Column: Bio-Scale Mini CHT Type I cartridge (5 mL) (produced by Bio-Rad Laboratories, Inc.)

Flow rate: 5 mL/min (1.25 mL/min in charging)

The solution obtained in (1) was added to the upper part of the column, and 4 CV of solution A (5 mM phosphate buffer/50 mM morpholinoethanesulfonic acid (MES) solution (pH 6.8)) was flowed at 1.25 mL/min and 3 CV thereof was further flowed at 5 mL/min. Thereafter, elution was performed with solution A and solution B (5 mM phosphate buffer/50 mM morpholinoethanesulfonic acid (MES) solution (pH 6.8), 2 M sodium chloride solution). The elution conditions were solution A: solution B=100:0 to 0:100 (15 CV). Further, 5 CV of washing solution (500 mM phosphate buffer (pH 6.5)) was flowed.

Fractions containing the desired compound were subjected to buffer exchange by using common operation C to afford a 6.08 mg/mL (Fucα1,6) GlcNAc-Trastuzumab variant solution (50 mM phosphate buffer (pH 6.0)) (6.10 mL).

Step 2: Preparation of Trastuzumab Variant-[MSG1-$N_3$]$_2$

To the 6.08 mg/mL (Fucα1,6) GlcNAc-Trastuzumab variant solution (50 mM phosphate buffer (pH 6.0)) obtained in Step 1 (6.10 mL), a solution (0.200 mL) of the compound synthesized in Step 4 of Example 3 (9.78 mg) in 50 mM phosphate buffer (pH 6.0) and 5.80 mg/mL EndoS D233Q/Q303L solution (PBS) (0.128 mL) were added, and the resultant was incubated at 30° C. for 3 hours. The progress of the reaction was checked by using an Experion electrophoresis station (produced by Bio-Rad Laboratories, Inc.). After the completion of the reaction, purification by affinity chromatography and purification by hydroxyapatite chromatography were performed as in Step 1, and fractions containing the desired compound were then subjected to buffer exchange to phosphate buffered saline (pH 6.0) by using common operation C to afford a 10.2 mg/mL Trastuzumab variant-[MSG-N3] 2 solution (phosphate buffered saline (pH 6.0)) (3.65 mL).

The operations same as in Steps 1 and 2 of Example 38 were performed using Trastuzumab variant 2 (light chain: SEQ ID NO: 76, heavy chain: 77) to afford Trastuzumab variant 2-[MSG1-$N_3$]$_2$.

Example 39: ADC6

Step 1: Conjugation of Antibody and Drug-Linker

To a phosphate buffered saline (pH 6.0) solution of Trastuzumab variant-[MSG1-$N_3$]$_2$ obtained in Step 2 of Example 38 (10.0 mg/mL, 0.40 mL), 1,2-propanediol (0.767 mL) and a 10 mM dimethyl sulfoxide solution of compound (3-14) obtained in Step 13 of Example 2-1 (0.033 mL; 12 equivalents per antibody molecule) were added at room temperature, and the reaction was carried out using a tube rotator (MTR-103, AS ONE Corporation) at room temperature for 48 hours.

Purification operation: The solution was purified by using common operation D described later to afford 7.00 mL of a solution of the desired compound.

Characterization: The following characteristic values were obtained by using common operations E and F.

Antibody concentration: 0.48 mg/mL, antibody yield: 3.39 mg (85%), average number of conjugated drug molecules per antibody molecule (n): 1.7

Example 40: ADC7

Step 1-1: Conjugation of Antibody and Drug-Linker (ADC7)

To a phosphate buffered saline (pH 6.0) solution of Trastuzumab variant 2-[MSG1-$N_3$]$_2$ obtained in Example 38 (10.0 mg/mL, 0.50 mL), 1,2-propanediol (0.486 mL) and a 10 mM dimethyl sulfoxide solution of compound (3-14) obtained in Step 13 of Example 2-1 (0.014 mL; 4 equivalents per antibody molecule) were added at room temperature, and the reaction was carried out using a tube rotator (MTR-103, AS ONE Corporation) at room temperature for 40 hours.

Purification operation: The solution was purified by using common operation D described later to afford 2.50 mL of a solution of the desired compound.

Characterization: The following characteristic values were obtained by using common operations E and F.

Antibody concentration: 1.12 mg/mL, antibody yield: 2.80 mg (56%), average number of conjugated drug molecules per antibody molecule (n): 1.8

INDUSTRIAL APPLICABILITY

Use of the antibody-drug conjugate, antibody and/or PBD derivative, and so on of the present invention enables treatment or prevention of various cancers.

Free Text of Sequence Listing

SEQ ID NO: 1—Amino acid sequence of human CLDN6
SEQ ID NO: 2—Nucleotide sequence of cDNA encoding amino acid sequence of human CLDN6
SEQ ID NO: 3—Amino acid sequence of human CLDN9
SEQ ID NO: 4—Nucleotide sequence of cDNA encoding amino acid sequence of human CLDN9
SEQ ID NO: 5—Amino acid sequence of CDRL1 of B1 antibody light chain
SEQ ID NO: 6—Amino acid sequence of CDRL2 of B1 antibody light chain
SEQ ID NO: 7—Amino acid sequence of CDRL3 of B1 antibody light chain
SEQ ID NO: 8—Amino acid sequence of CDRL3 of humanized B1 antibody light chain L4
SEQ ID NO: 9—Amino acid sequence of CDRH1 of B1 antibody heavy chain
SEQ ID NO: 10—Amino acid sequence of CDRH2 of B1 antibody heavy chain
SEQ ID NO: 11—Amino acid sequence of CDRH3 of B1 antibody heavy chain
SEQ ID NO: 12—Amino acid sequence of CDRL1 of C7 antibody light chain
SEQ ID NO: 13—Amino acid sequence of CDRL2 of C7 antibody light chain
SEQ ID NO: 14—Amino acid sequence of CDRL3 of C7 antibody light chain
SEQ ID NO: 15—Amino acid sequence of CDRH1 of C7 antibody heavy chain
SEQ ID NO: 16—Amino acid sequence of CDRH2 of C7 antibody heavy chain
SEQ ID NO: 17—Amino acid sequence of CDRH3 of C7 antibody heavy chain
SEQ ID NO: 18—Nucleotide sequence of cDNA encoding variable region of B1 antibody light chain
SEQ ID NO: 19—Amino acid sequence of variable region of B1 antibody light chain
SEQ ID NO: 20—Nucleotide sequence of cDNA encoding variable region of B1 antibody heavy chain
SEQ ID NO: 21—Amino acid sequence of variable region of B1 antibody heavy chain
SEQ ID NO: 22—Nucleotide sequence of cDNA encoding variable region of C7 antibody light chain
SEQ ID NO: 23—Amino acid sequence of variable region of C7 antibody light chain
SEQ ID NO: 24—Nucleotide sequence of cDNA encoding variable region of C7 antibody heavy chain
SEQ ID NO: 25—Amino acid sequence of variable region of C7 antibody heavy chain
SEQ ID NO: 26—DNA fragment including DNA sequence encoding human light chain signal sequence and human K chain constant region
SEQ ID NO: 27—DNA fragment including DNA sequence encoding human heavy chain signal sequence and human IgG1 LALA constant region
SEQ ID NO: 28—Amino acid sequence of chB1 light chain
SEQ ID NO: 29—DNA fragment including DNA sequence encoding amino acid sequence of chB1 light chain
SEQ ID NO: 30—Amino acid sequence of variable region of chB1 light chain
SEQ ID NO: 31—Nucleotide sequence encoding chB1 light chain variable region
SEQ ID NO: 32—Amino acid sequence of chB1 heavy chain
SEQ ID NO: 33—Nucleotide sequence encoding chB1 heavy chain
SEQ ID NO: 34—Amino acid sequence of variable region of chB1 heavy chain
SEQ ID NO: 35—Nucleotide sequence encoding variable region of chB1 heavy chain
SEQ ID NO: 36—Amino acid sequence of humanized antibody light chain hL1
SEQ ID NO: 37—Nucleotide sequence encoding humanized antibody light chain hL1
SEQ ID NO: 38—Amino acid sequence of variable region of humanized antibody light chain hL1
SEQ ID NO: 39—Nucleotide sequence encoding variable region of humanized antibody light chain hL1
SEQ ID NO: 40—Amino acid sequence of humanized antibody light chain hL2
SEQ ID NO: 41—Nucleotide sequence encoding humanized antibody light chain hL2
SEQ ID NO: 42—Amino acid sequence of variable region of humanized antibody light chain hL2
SEQ ID NO: 43—Nucleotide sequence encoding variable region of humanized antibody light chain hL2
SEQ ID NO: 44—Amino acid sequence of humanized antibody light chain hL3
SEQ ID NO: 45—Nucleotide sequence encoding humanized antibody light chain hL3
SEQ ID NO: 46—Amino acid sequence of variable region of humanized antibody light chain hL3
SEQ ID NO: 47—Nucleotide sequence encoding variable region of humanized antibody light chain hL3

SEQ ID NO: 48—Amino acid sequence of humanized antibody light chain hL4
SEQ ID NO: 49—Nucleotide sequence encoding humanized antibody light chain hL4
SEQ ID NO: 50—Amino acid sequence of variable region of humanized antibody light chain hL4
SEQ ID NO: 51—Nucleotide sequence encoding variable region of humanized antibody light chain hL4
SEQ ID NO: 52—Amino acid sequence of humanized antibody heavy chain hH1
SEQ ID NO: 53—Nucleotide sequence encoding humanized antibody heavy chain hH1
SEQ ID NO: 54—Amino acid sequence of variable region of humanized antibody heavy chain hH1
SEQ ID NO: 55—Nucleotide sequence encoding variable region of humanized antibody heavy chain hH1
SEQ ID NO: 56—Amino acid sequence of humanized antibody heavy chain hH2
SEQ ID NO: 57—Nucleotide sequence encoding humanized antibody heavy chain hH2
SEQ ID NO: 58—Amino acid sequence of variable region of humanized antibody heavy chain hH2
SEQ ID NO: 59—Nucleotide sequence encoding variable region of humanized antibody heavy chain hH2
SEQ ID NO: 60—Amino acid sequence of humanized antibody heavy chain hH3
SEQ ID NO: 61—Nucleotide sequence encoding humanized antibody heavy chain hH3
SEQ ID NO: 62—Amino acid sequence of variable region of humanized antibody heavy chain hH3
SEQ ID NO: 63—Nucleotide sequence encoding variable region of humanized antibody heavy chain hH3
SEQ ID NO: 64—Amino acid sequence of Trastuzumab light chain
SEQ ID NO: 65—Amino acid sequence of Trastuzumab heavy chain
SEQ ID NO: 66—Amino acid sequence of anti-LPS antibody (h #1G5-H1L1) light chain
SEQ ID NO: 67—Amino acid sequence of anti-LPS antibody (h #1G5-H1L1) heavy chain
SEQ ID NO: 68—Amino acid sequence of anti-TROP2 antibody (hRS7) light chain
SEQ ID NO: 69—Amino acid sequence of anti-TROP2 antibody (hRS7) heavy chain
SEQ ID NO: 70—Amino acid sequence of anti-CD98 antibody (hM23-H1L1) light chain
SEQ ID NO: 71—Amino acid sequence of anti-CD98 antibody (hM23-H1L1) heavy chain
SEQ ID NO: 72—Nucleotide sequence encoding Trastuzumab variant light chain
SEQ ID NO: 73—Amino acid sequence of Trastuzumab variant light chain
SEQ ID NO: 74—Nucleotide sequence encoding Trastuzumab variant heavy chain
SEQ ID NO: 75—Amino acid sequence of Trastuzumab variant heavy chain
SEQ ID NO: 76—Amino acid sequence of Trastuzumab variant 2 light chain
SEQ ID NO: 77—Amino acid sequence of Trastuzumab variant 2 heavy chain

The invention claimed is:

1. A pharmaceutical composition for treatment of cancer, the pharmaceutical composition comprising an antibody-pyrrolobenzodiazepine derivative conjugate and a PARP inhibitor, wherein the antibody-pyrrolobenzodiazepine derivative conjugate and the PARP inhibitor are administered in combination, and the conjugate has the following formula:

[Formula 1]

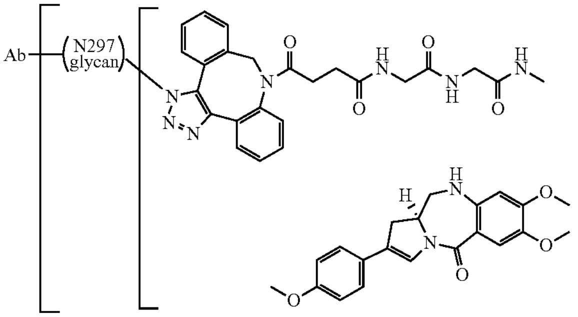

-continued

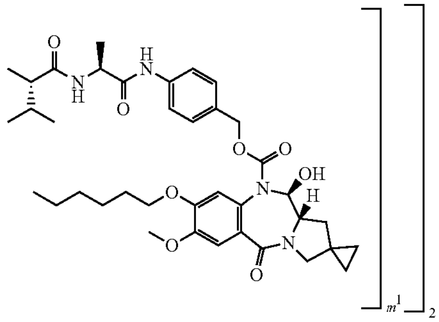

or

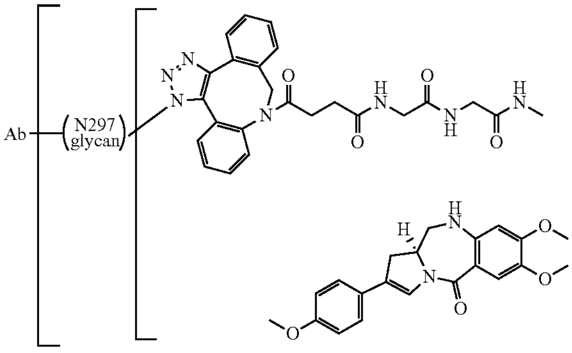

-continued
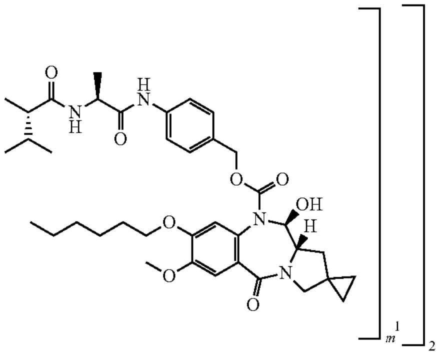
[Formula 2]
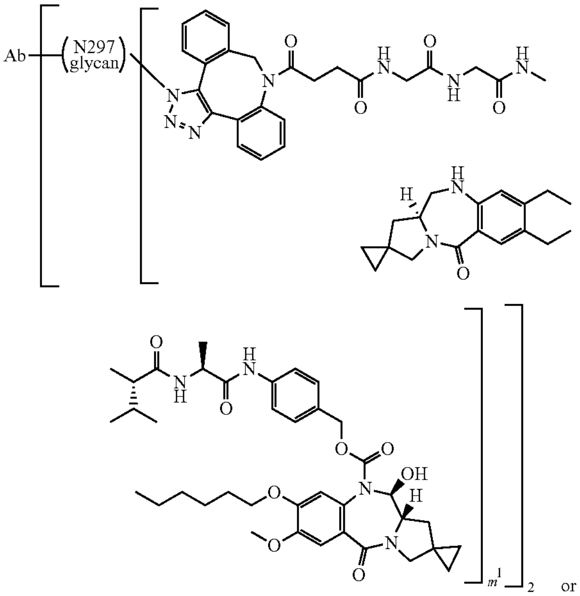
or
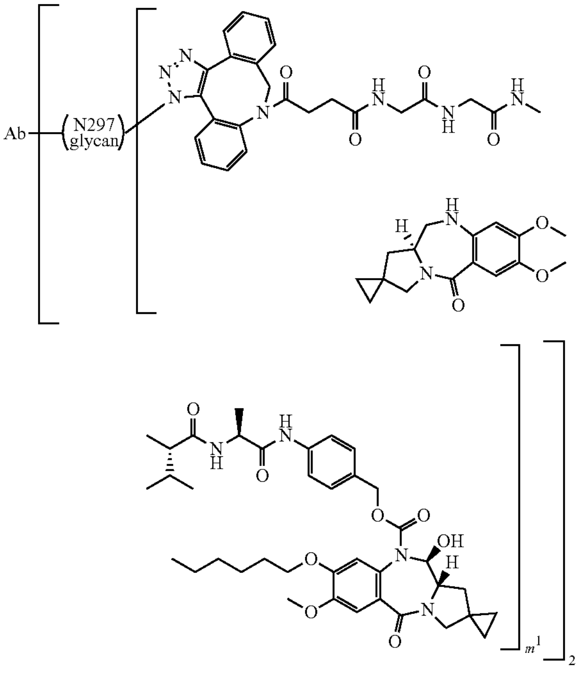
-continued
[Formula 3]
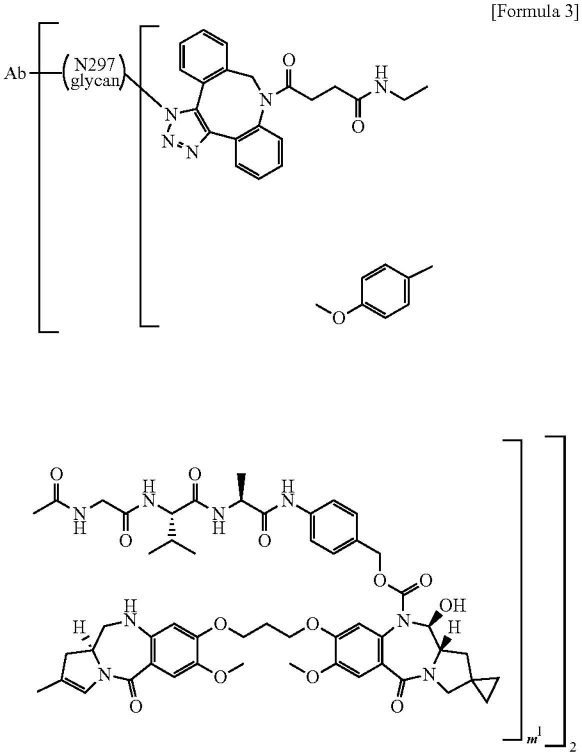
or
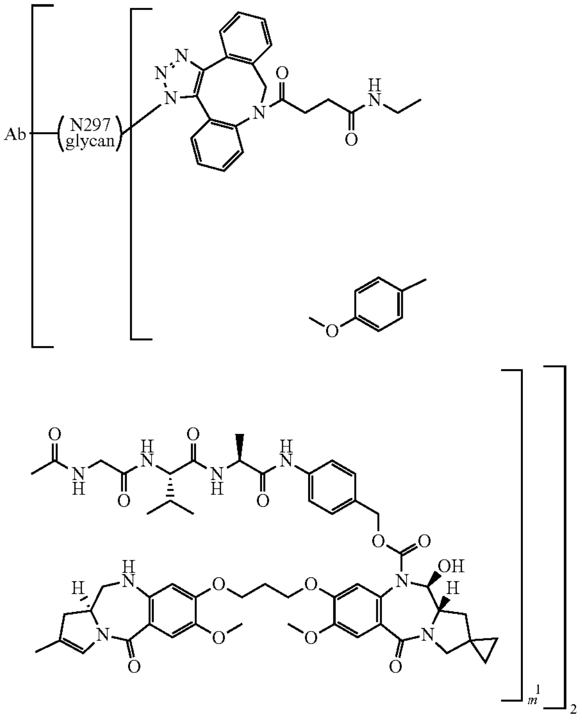
or, -continued

[Formula 4]

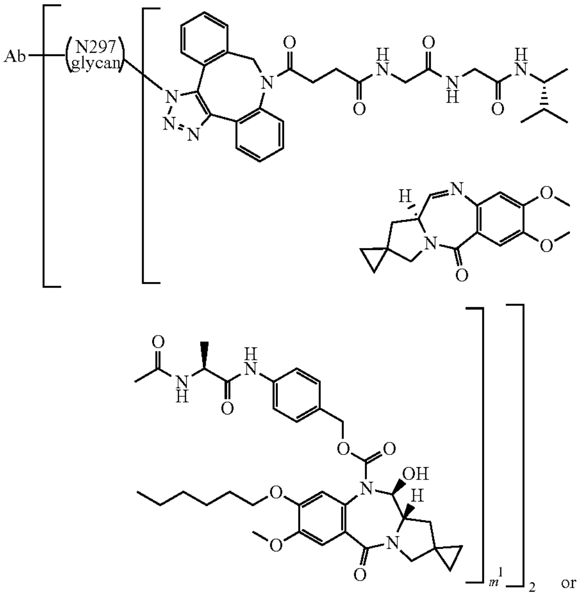

or

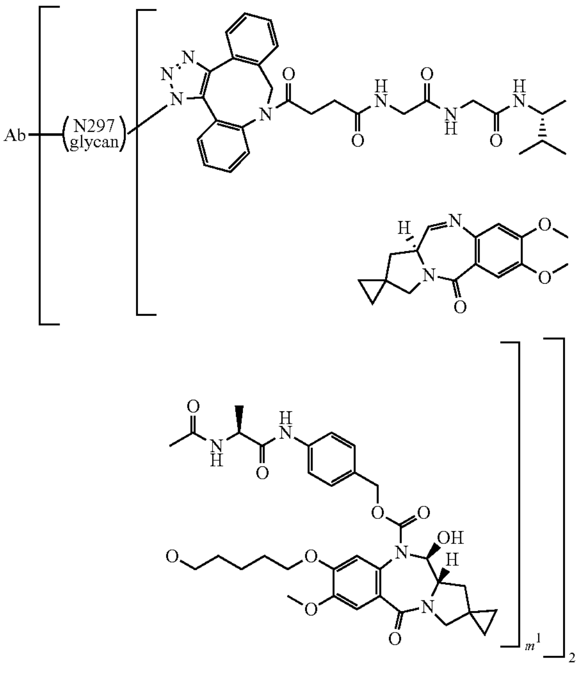

wherein, in each structural formula shown above, $m^1$ is an integer of 1 or 2;

Ab is an antibody or a functional fragment of the antibody;

the N297 glycan is any one of N297-(Fuc)MSG1, N297-(Fuc)MSG2, and a mixture thereof, and N297-(Fuc)SG, with N297-(Fuc)MSG1, N297-(Fuc)MSG2, and N297-(Fuc)SG having structures represented by the following formulas:

[Formula 5]

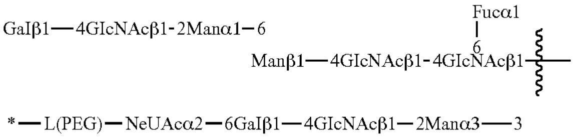

[N297-(Fuc)MSG1]

[Formula 6]

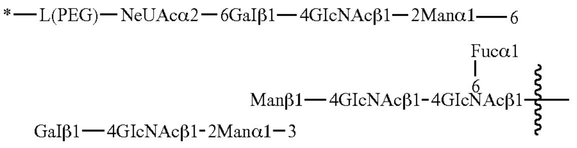

[N297-(Fuc)MSG2]

[Formula 7]

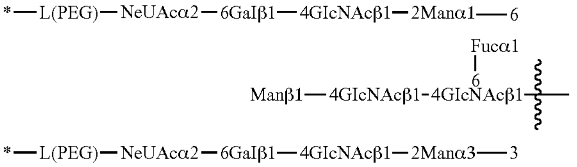

[N297-(Fuc)SG]

wherein each wavy line represents bonding to Asn297 of the antibody,

L(PEG) in the N297 glycan represents *—$(CH_2CH_2—O)_3—CH_2CH_2—NH—$, wherein the amino group at the right end is bound via an amide bond to carboxylic acid at the 2-position of a sialic acid at the non-reducing terminal in each or either one of the 1-3 and 1-6 branched chains of β-Man in the N297 glycan, and the asterisk * at the left end represents bonding to a nitrogen atom at the 1- or 3-position of the triazole ring in the corresponding structural formula.

2. The pharmaceutical composition according to claim 1, wherein the antibody is an anti-CLDN6 antibody, an anti-CLDN9 antibody, an anti-CLDN6/CLDN9 antibody, an anti-HER2 antibody, an anti-HER3 antibody, an anti-DLL3 antibody, an anti-FAP antibody, an anti-CDH11 antibody, an anti-A33 antibody, an anti-CanAg antibody, an anti-CD19 antibody, an anti-CD20 antibody, an anti-CD22 antibody, an anti-CD25 antibody, an anti-CD30 antibody, an anti-CD33 antibody, an anti-CD37 antibody, an anti-CD56 antibody, an anti-CD70 antibody, an anti-CD98 antibody, an anti-B7-H3 antibody, an anti-TROP2 antibody, an anti-CEA antibody, an anti-Cripto antibody, an anti-EphA2 antibody, an anti-FGFR2 antibody, an anti-G250 antibody, an anti-MUC1 antibody, an anti-GPNMB antibody, an anti-Integrin antibody, an anti-PSMA antibody, an anti-Tenascin-C antibody, an anti-SLC44A4 antibody, an anti-Mesothelin antibody, an anti-EGFR antibody, an anti-5T4 antibody, an anti-LRRC15 antibody, an anti-DR5 antibody, an anti-CDH3 antibody, an anti-PDPN antibody, or an anti-CD123 antibody.

3. The pharmaceutical composition according to claim 1, wherein the antibody specifically binds to CLDN6 and/or CLDN9.

4. The pharmaceutical composition according to claim 3, the antibody comprising a heavy chain comprising CDRH1, CDRH2, and CDRH3 and a light chain comprising CDRL1, CDRL2, and CDRL3 as described in any one of the following (a) and (b):

(a) CDRH1 consisting of the amino acid sequence of SEQ ID NO: 9, CDRH2 consisting of the amino acid sequence of SEQ ID NO: 10, and CDRH3 consisting of the amino acid sequence of SEQ ID NO: 11, and CDRL1 consisting of the amino acid sequence of SEQ ID NO: 5, CDRL2 consisting of the amino acid sequence of SEQ ID NO: 6, and CDRL3 consisting of the amino acid sequence of SEQ ID NO: 7 or an amino acid sequence having one or two amino acid substitutions in the amino acid sequence represented by SEQ ID NO: 7; and (b) CDRH1 consisting of the amino acid sequence of SEQ ID NO: 15, CDRH2 consisting of the amino acid sequence of SEQ ID NO: 16, and CDRH3 consisting of the amino acid sequence of SEQ ID NO: 17, and CDRL1 consisting of the amino acid sequence of SEQ ID NO: 12, CDRL2 consisting of the amino acid sequence of SEQ ID NO: 13, and CDRL3 consisting of the amino acid sequence of SEQ ID NO: 14.

5. The pharmaceutical composition according to claim 4, the antibody comprising a heavy chain comprising CDRH1, CDRH2, and CDRH3 and a light chain comprising CDRL1, CDRL2, and CDRL3 as described in any one of the following (a) and (b):

(a) CDRH1 consisting of the amino acid sequence of SEQ ID NO: 9, CDRH2 consisting of the amino acid sequence of SEQ ID NO: 10, and CDRH3 consisting of the amino acid sequence of SEQ ID NO: 11, and CDRL1 consisting of the amino acid sequence of SEQ ID NO: 5, CDRL2 consisting of the amino acid sequence of SEQ ID NO: 6, and CDRL3 consisting of the amino acid sequence of SEQ ID NO: 7 or the amino acid sequence of SEQ ID NO: 8; and (b) CDRH1 consisting of the amino acid sequence of SEQ ID NO: 15, CDRH2 consisting of the amino acid sequence of SEQ ID NO: 16, and CDRH3 consisting of the amino acid sequence of SEQ ID NO: 17, and CDRL1 consisting of the amino acid sequence of SEQ ID NO: 12, CDRL2 consisting of the amino acid sequence of SEQ ID NO: 13, and CDRL3 consisting of the amino acid sequence of SEQ ID NO: 14.

6. The pharmaceutical composition according to claim 3, the antibody comprising a heavy chain variable region and a light chain variable region as described in any one of the following (a) and (b):

(a) a heavy chain variable region consisting of the amino acid sequence of SEQ ID NO: 21 and a light chain variable region consisting of the amino acid sequence of SEQ ID NO: 19; and (b) a heavy chain variable region consisting of the amino acid sequence of SEQ ID NO: 25 and a light chain variable region consisting of the amino acid sequence of SEQ ID NO: 23.

7. The pharmaceutical composition according to claim 3, the antibody comprising a heavy chain variable region consisting of an amino acid sequence selected from the group consisting of the following (a) to (e) and a light chain variable region consisting of an amino acid sequence selected from the group consisting of the following (f) to (k):

(a) the amino acid sequence of SEQ ID NO: 54;

(b) the amino acid sequence of SEQ ID NO: 58

(c) the amino acid sequence of SEQ ID NO: 62;

(d) an amino acid sequence with a homology of at least 95% or higher to a sequence of a framework region excluding CDR sequences in any of the sequences (a) to (c);

(e) an amino acid sequence having one to several amino acid deletions, substitutions, or additions in a sequence of a framework region excluding CDR sequences in any of the sequences (a) to (c);

(f) the amino acid sequence of SEQ ID NO: 38;

(g) the amino acid sequence of SEQ ID NO: 42;

(h) the amino acid sequence of SEQ ID NO: 46;

(i) the amino acid sequence of SEQ ID NO: 50;

(j) an amino acid sequence with a homology of at least 95% or higher to a sequence of a framework region excluding CDR sequences in any of the sequences (f) to (i); and (k) an amino acid sequence having one to several amino acid deletions, substitutions, or additions in a sequence of a framework region excluding CDR sequences in any of the sequences (f) to (i).

8. The pharmaceutical composition according to claim 7, the antibody comprising a heavy chain variable region and a light chain variable region selected from the group consisting of the following (a) to (e):

(a) a heavy chain variable region consisting of the amino acid sequence of SEQ ID NO: 54 and a light chain variable region consisting of the amino acid sequence of SEQ ID NO: 38;

(b) a heavy chain variable region consisting of the amino acid sequence of SEQ ID NO: 58 and a light chain variable region consisting of the amino acid sequence of SEQ ID NO: 42;

(c) a heavy chain variable region consisting of the amino acid sequence of SEQ ID NO: 54 and a light chain variable region consisting of the amino acid sequence of SEQ ID NO: 46;

(d) a heavy chain variable region consisting of the amino acid sequence of SEQ ID NO: 58 and a light chain variable region consisting of a light chain variable region consisting of the amino acid sequence of SEQ ID NO: 50; and (e) a heavy chain variable region consisting of the amino acid sequence of SEQ ID NO: 62 and a light chain variable region consisting of the amino acid sequence of SEQ ID NO: 46.

9. The pharmaceutical composition according to claim 3, wherein the antibody is a chimeric antibody.

10. The pharmaceutical composition according to claim 3, wherein the antibody is a humanized antibody.

11. The pharmaceutical composition according to claim 10, comprising a heavy chain and a light chain selected from the group consisting of the following (a) to (e):

(a) a heavy chain consisting of an amino acid sequence consisting of amino acid residues 20 to 471 of SEQ ID NO: 52 and a light chain consisting of an amino acid sequence consisting of amino acid residues 21 to 234 of SEQ ID NO: 36;

(b) a heavy chain consisting of an amino acid sequence consisting of amino acid residues 20 to 471 of SEQ ID NO: 56 and a light chain consisting of an amino acid sequence consisting of amino acid residues 21 to 234 of SEQ ID NO: 40;

(c) a heavy chain consisting of an amino acid sequence consisting of amino acid residues 20 to 471 of SEQ ID NO: 52 and a light chain consisting of an amino acid sequence consisting of amino acid residues 21 to 234 of SEQ ID NO: 44;

(d) a heavy chain consisting of an amino acid sequence consisting of amino acid residues 20 to 471 of SEQ ID NO: 56 and a light chain consisting of an amino acid sequence consisting of amino acid residues 21 to 234 of SEQ ID NO: 48; and (e) a heavy chain consisting of an amino acid sequence consisting of amino acid residues 20 to 471 of SEQ ID NO: 60 and a light chain consisting of an amino acid sequence consisting of amino acid residues 21 to 234 of SEQ ID NO: 44.

12. The pharmaceutical composition according to claim 3, wherein the antibody comprises a heavy chain constant region of human IgG1, human IgG2, or human IgG4.

13. The pharmaceutical composition according to claim 3, wherein the antibody competes with the antibody comprising a heavy chain comprising CDRH1, CDRH2, and CDRH3 and a light chain comprising CDRL1, CDRL2, and CDRL3 as described in any one of the following (a) and (b):

(a) CDRH1 consisting of the amino acid sequence of SEQ ID NO: 9, CDRH2 consisting of the amino acid sequence of SEQ ID NO: 10, and CDRH3 consisting of the amino acid sequence of SEQ ID NO: 11, and CDRL1 consisting of the amino acid sequence of SEQ ID NO: 5, CDRL2 consisting of the amino acid sequence of SEQ ID NO: 6, and CDRL3 consisting of the amino acid sequence of SEQ ID NO: 7 or an amino acid sequence having one or two amino acid substitutions in the amino acid sequence represented by SEQ ID NO: 7; and (b) CDRH1 consisting of the amino acid sequence of SEQ ID NO: 15, CDRH2 consisting of the amino acid sequence of SEQ ID NO: 16, and CDRH3 consisting of the amino acid sequence of SEQ ID NO: 17, and CDRL1 consisting of the amino acid sequence of SEQ ID NO: 12, CDRL2 consisting of the amino acid sequence of SEQ ID NO: 13, and CDRL3 consisting of the amino acid sequence of SEQ ID NO: 14 for binding to CLDN6 and/or CLDN9, or binds to a site of CLDN6 and/or CLDN9 recognizable to the antibody.

14. The pharmaceutical composition according to claim 3, wherein the antibody comprises one or two or more modifications selected from the group consisting of N-linked glycosylation, O-linked glycosylation, N-terminal processing, C-terminal processing, deamidation, isomerization of aspartic acid, oxidation of methionine, addition of a methionine residue at an N terminus, amidation of a proline residue, and deletion of one or two amino acid residues at the carboxyl terminus of a heavy chain.

15. The pharmaceutical composition according to claim 14, wherein one or several amino acid residues are deleted at the carboxyl terminus of a heavy chain of the antibody.

16. The pharmaceutical composition according to claim 14, wherein one amino acid residue is deleted at the carboxyl terminus of each of the two heavy chains of the antibody.

17. The pharmaceutical composition according to claim 14, wherein a proline residue at the carboxyl terminus of a heavy chain of the antibody is further amidated.

18. The pharmaceutical composition according to claim 1, wherein the antibody specifically binds to HER2.

19. The pharmaceutical composition according to claim 18, having activities or activity of antibody-dependent cellular cytotoxicity (ADCC) and/or complement-dependent cytotoxicity (CDC).

20. The pharmaceutical composition according to claim 18, wherein the heavy chain constant region of the antibody is a heavy chain constant region of human IgG1, and comprises a mutation that causes lowering of activities or activity of ADCC and/or CDC.

21. The pharmaceutical composition according to claim 20, wherein the heavy chain constant region of the antibody is a heavy chain constant region of human IgG1, and leucine at the 234- and 235-positions specified by EU Index numbering in the heavy chain constant region is substituted with alanine.

22. The pharmaceutical composition according to claim 18, being an antibody comprising a heavy chain consisting of the amino acid sequence of SEQ ID NO: 65 and a light chain consisting of the amino acid sequence of SEQ ID NO: 64.

23. The pharmaceutical composition according to claim 18, being an antibody comprising a heavy chain variable region consisting of an amino acid sequence consisting of amino acid residues 20 to 139 of SEQ ID NO: 75 and a light chain variable region consisting of an amino acid sequence consisting of amino acid residues 21 to 127 of SEQ ID NO: 73.

24. The pharmaceutical composition according to claim 18, wherein the antibody comprises a heavy chain consisting of an amino acid sequence consisting of amino acid residues 20 to 469 of SEQ ID NO: 75 and a light chain consisting of an amino acid sequence consisting of amino acid residues 21 to 234 of SEQ ID NO: 73.

25. The pharmaceutical composition according to claim 18, wherein the antibody comprises a heavy chain consisting of an amino acid sequence consisting of amino acid residues 20 to 469 of SEQ ID NO: 77 and a light chain consisting of an amino acid sequence consisting of amino acid residues 21 to 234 of SEQ ID NO: 76.

26. The pharmaceutical composition according to claim 1, wherein the N297 glycan is N297-(Fuc)MSG1.

27. The pharmaceutical composition according to claim 1, wherein $m^1$ is an integer of 1.

28. The pharmaceutical composition according to claim 1, wherein the average number of conjugated drug molecules per antibody molecule in the antibody-pyrrolobenzodiazepine derivative conjugate is 1 to 3 or 3 to 5.

29. The pharmaceutical composition according to claim 1, wherein the PARP inhibitor is olaparib, rucaparib, niraparib, or talazoparib, or a pharmacologically acceptable salt thereof.

30. The pharmaceutical composition according to claim 1, wherein the antibody-drug conjugate and the PARP inhibitor are individually contained as an active ingredient in separate formulations and administered simultaneously or at different times.

31. The pharmaceutical composition according to claim 1, for treatment of at least one cancer selected from the group consisting of lung cancer (e.g., non-small cell lung cancer, small cell lung cancer), kidney cancer, urothelial cancer, colorectal cancer, prostate cancer, glioblastoma multiforme, ovarian cancer (e.g., surface epithelial tumor, stromal tumor, germ cell tumor), pancreatic cancer, breast cancer, melanoma, liver cancer, bladder cancer, gastric cancer, esophageal cancer, endometrial cancer, testicular cancer (seminoma, non-seminoma), uterine cervix cancer, placental choriocarcinoma, brain tumor, and head-and-neck cancer, and metastatic forms of them.

32. The pharmaceutical composition according to claim 1, wherein the average number of conjugated drug molecules per antibody molecule is 1 to 3, and wherein the PARP inhibitor is olaparib, rucaparib, niraparib, or talazoparib, or a pharmacologically acceptable salt thereof.

33. The pharmaceutical composition according to claim 1, wherein the average number of conjugated drug molecules per antibody molecule is 3 to 5, and wherein the PARP inhibitor is olaparib, rucaparib, niraparib, or talazoparib, or a pharmacologically acceptable salt thereof.

34. A method for treating a cancer that expresses CLDN6 and/or CLDN9, wherein an antibody-pyrrolobenzodiazepine derivative conjugate and a PARP inhibitor are administered in combination, and the conjugate has the following formula:

[Formula 8]

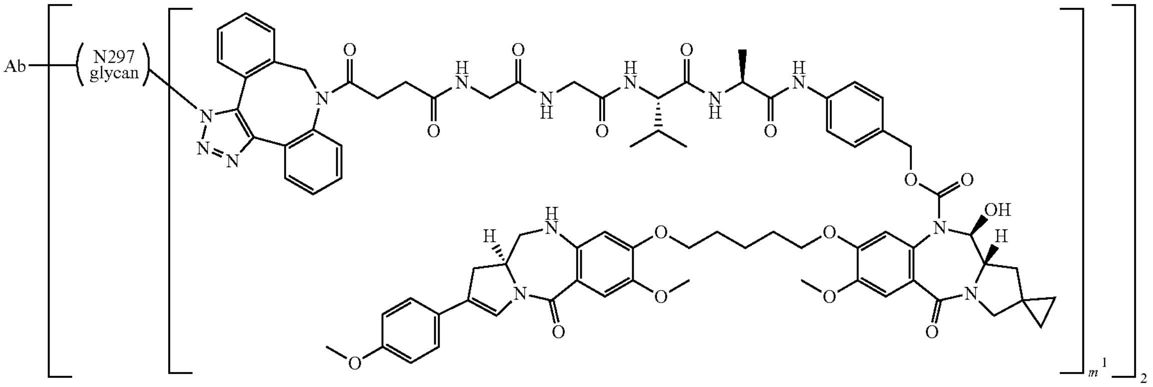

or

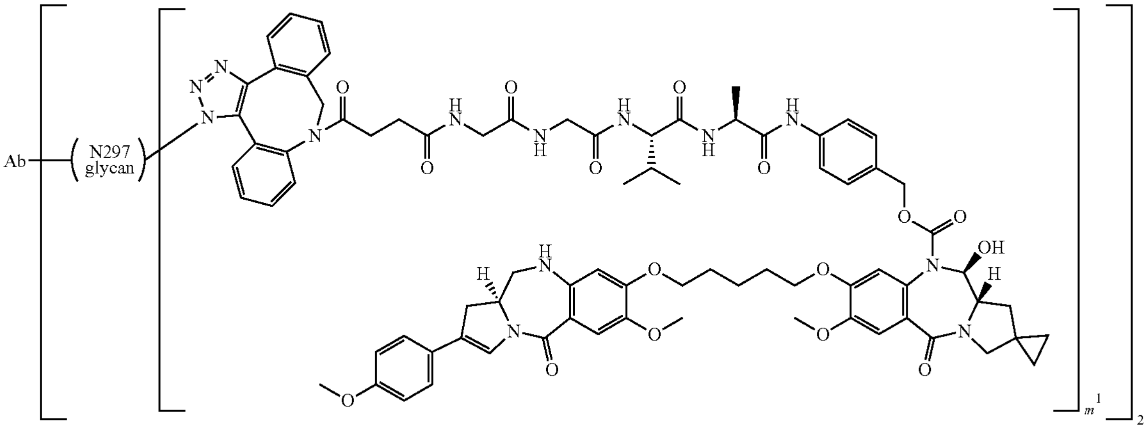

[Formula 9]

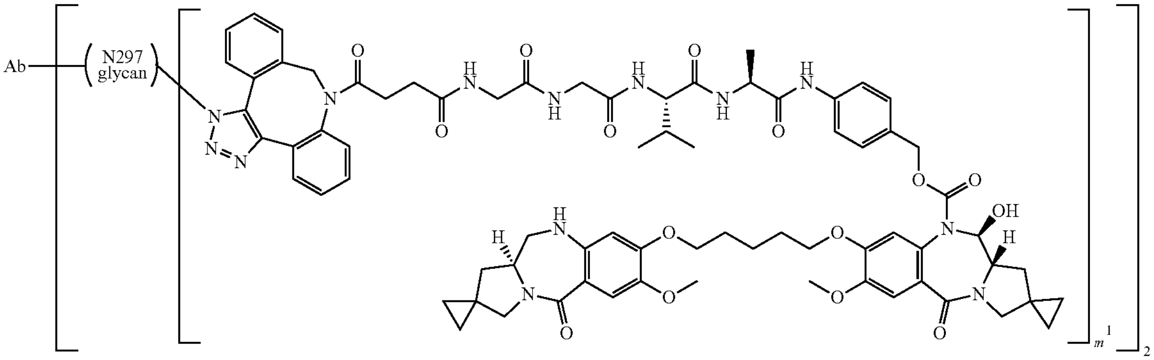

or

-continued
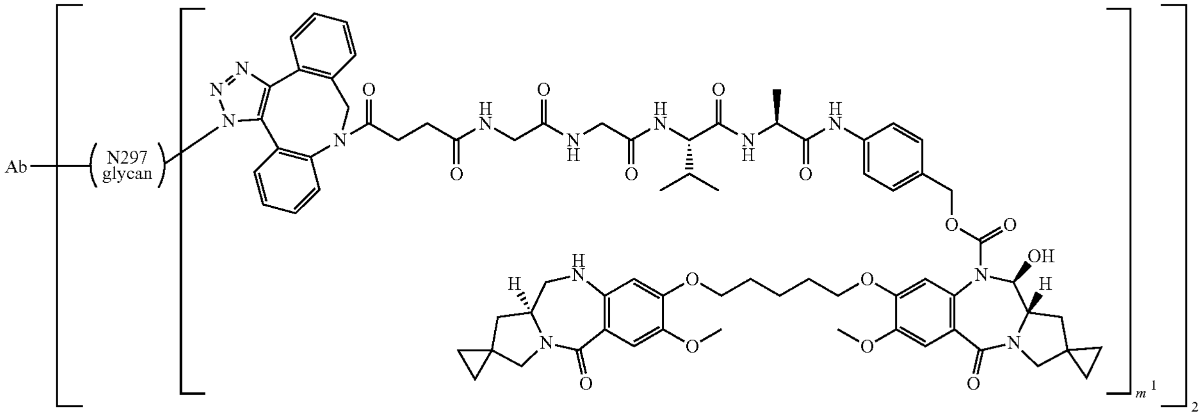
[Formula 10]
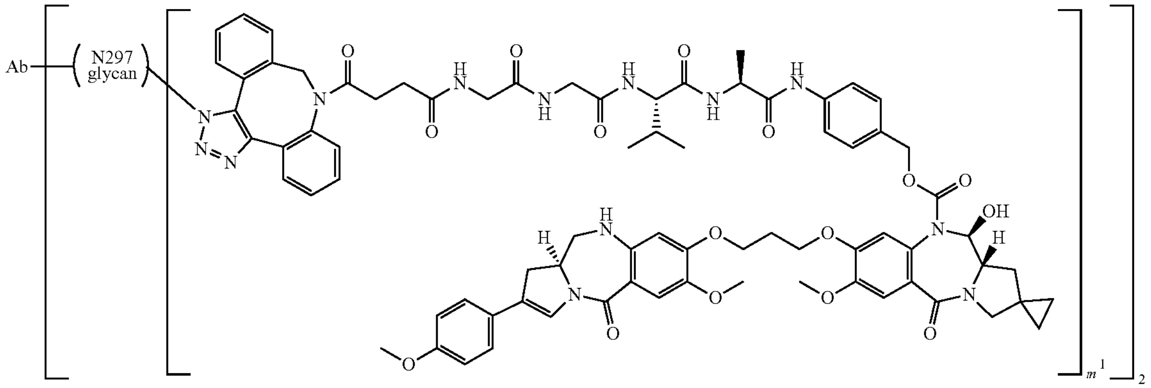
or
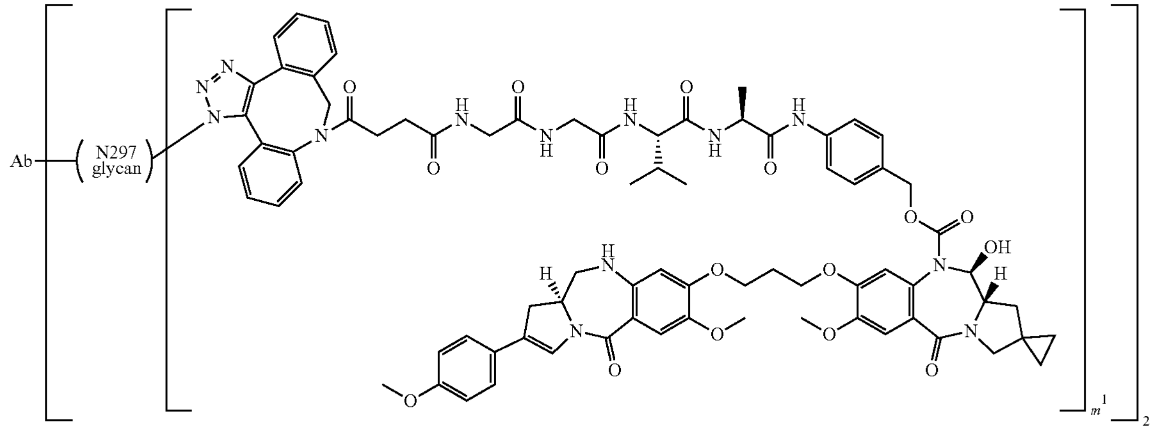
or,
[Formula 11]
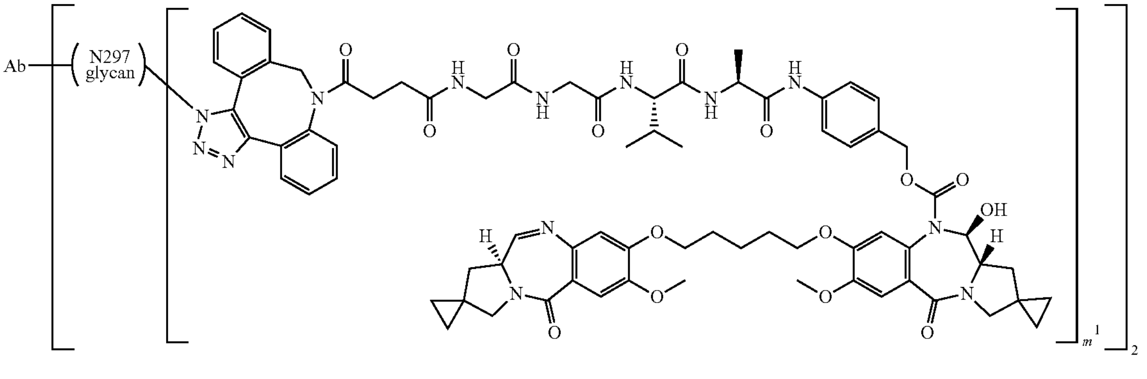
or -continued

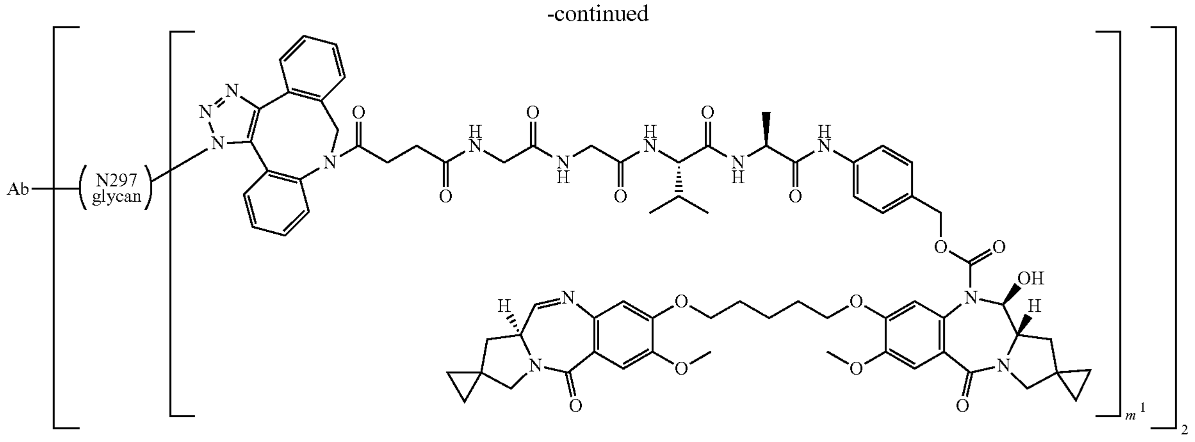

wherein, in each structural formula shown above, $m^1$ is an integer of 1 or 2;

Ab is an antibody or a functional fragment of the antibody;

the N297 glycan is N297-(Fuc)MSG1, N297-(Fuc)MSG2, or a mixture thereof, or N297-(Fuc)SG, with N297-(Fuc)MSG1, N297-(Fuc)MSG2, and N297-(Fuc)SG having structures represented by the following formulas:

[Formula 12]

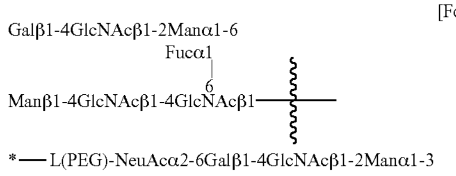

[N297-(Fuc)MSG1]

[Formula 13]

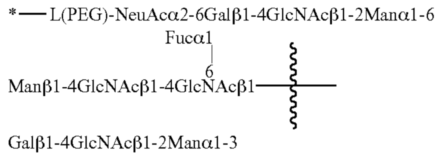

[N297-(Fuc)MSG2]

[Formula 14]

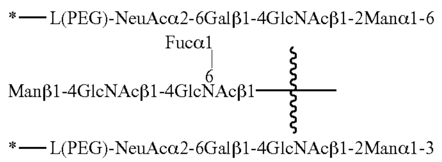

[N297-(Fuc)SG]

wherein each wavy line represents bonding to Asn297 of the antibody,

L(PEG) in the N297 glycan represents *—$(CH_2CH_2—O)_3—CH_2CH_2—NH$—, wherein the amino group at the right end is bound via an amide bond to carboxylic acid at the 2-position of a sialic acid at the non-reducing terminal in each or either one of the 1-3 and 1-6 branched chains of β-Man in the N297 glycan, and the asterisk * at the left end represents bonding to a nitrogen atom at the 1- or 3-position of the triazole ring in the corresponding structural formula.

35. The method according to claim 34, wherein the antibody binds to an antigen expressed on a tumor cell and is incorporated and internalized in the tumor cell.

36. The method according to claim 34, wherein the antibody has antitumor effect.

37. The method according to claim 34, wherein the antibody is an anti-CLDN6 antibody, an anti-CLDN9 antibody, or an anti-CLDN6/CLDN9 antibody.

38. The method according to claim 34, wherein the antibody specifically binds to CLDN6 and/or CLDN9.

39. The method according to claim 38, the antibody comprising a heavy chain comprising CDRH1, CDRH2, and CDRH3 and a light chain comprising CDRL1, CDRL2, and CDRL3 as described in any one of the following (a) and (b):

(a) CDRH1 consisting of the amino acid sequence of SEQ ID NO: 9, CDRH2 consisting of the amino acid sequence of SEQ ID NO: 10, and CDRH3 consisting of the amino acid sequence of SEQ ID NO: 11, and CDRL1 consisting of the amino acid sequence of SEQ ID NO: 5, CDRL2 consisting of the amino acid sequence of SEQ ID NO: 6, and CDRL3 consisting of the amino acid sequence of SEQ ID NO: 7 or an amino acid sequence having one or two amino acid substitutions in the amino acid sequence represented by SEQ ID NO: 7; and (b) CDRH1 consisting of the amino acid sequence of SEQ ID NO: 15, CDRH2 consisting of the amino acid sequence of SEQ ID NO: 16, and CDRH3 consisting of the amino acid sequence of SEQ ID NO: 17, and CDRL1 consisting of the amino acid sequence of SEQ ID NO: 12, CDRL2 consisting of the amino acid sequence of SEQ ID NO: 13, and CDRL3 consisting of the amino acid sequence of SEQ ID NO: 14.

40. The method according to claim 39, wherein the antibody comprises a heavy chain comprising CDRH1, CDRH2, and CDRH3 and a light chain comprising CDRL1, CDRL2, and CDRL3 as described in any one of the following (a) and (b):

(a) CDRH1 consisting of the amino acid sequence of SEQ ID NO: 9, CDRH2 consisting of the amino acid sequence of SEQ ID NO: 10, and CDRH3 consisting of the amino acid sequence of SEQ ID NO: 11, and CDRL1 consisting of the amino acid sequence of SEQ ID NO: 5, CDRL2 consisting of the amino acid sequence of SEQ ID NO: 6, and CDRL3 consisting of the amino acid sequence of SEQ ID NO: 7 or the amino acid sequence of SEQ ID NO: 8; and (b) CDRH1 consisting of the amino acid sequence of SEQ ID NO: 15, CDRH2 consisting of the amino acid sequence of SEQ ID NO: 16, and CDRH3 consisting of the amino acid sequence of SEQ ID NO: 17, and CDRL1 consisting of the amino acid sequence of SEQ ID NO: 12, CDRL2 consisting of the amino acid sequence of SEQ ID NO: 13, and CDRL3 consisting of the amino acid sequence of SEQ ID NO: 14.

41. The method according to claim 38, wherein the antibody comprises a heavy chain variable region and a light chain variable region as described in any one of the following (a) and (b):

(a) a heavy chain variable region consisting of the amino acid sequence of SEQ ID NO: 21 and a light chain variable region consisting of the amino acid sequence of SEQ ID NO: 19; and (b) a heavy chain variable region consisting of the amino acid sequence of SEQ ID NO: 25 and a light chain variable region consisting of the amino acid sequence of SEQ ID NO: 23.

42. The method according to claim 38, the antibody comprising a heavy chain variable region consisting of an amino acid sequence selected from the group consisting of the following (a) to (e) and a light chain variable region consisting of an amino acid sequence selected from the group consisting of the following (f) to (k):

(a) the amino acid sequence of SEQ ID NO: 54;

(b) the amino acid sequence of SEQ ID NO: 58;

(c) the amino acid sequence of SEQ ID NO: 62;

(d) an amino acid sequence with at least 95% sequence identity or higher to a sequence of a framework region excluding CDR sequences in any of the sequences (a) to (c);

(e) an amino acid sequence having one to several amino acid deletions, substitutions, or additions in a sequence of a framework region excluding CDR sequences in any of the sequences (a) to (c);

(f) the amino acid sequence of SEQ ID NO: 38;

(g) the amino acid sequence of SEQ ID NO: 42;

(h) the amino acid sequence of SEQ ID NO: 46;

(i) the amino acid sequence of SEQ ID NO: 50;

(j) an amino acid sequence with at least 95% sequence identity or higher to a sequence of a framework region excluding CDR sequences in any of the sequences (f) to (i); and (k) an amino acid sequence having one to several amino acid deletions, substitutions, or additions in a sequence of a framework region excluding CDR sequences in any of the sequences (f) to (i).

43. The method according to claim 42, the antibody comprising a heavy chain variable region and a light chain variable region selected from the group consisting of the following (a) to (e):

(a) a heavy chain variable region consisting of the amino acid sequence of SEQ ID NO: 54 and a light chain variable region consisting of the amino acid sequence of SEQ ID NO: 38;

(b) a heavy chain variable region consisting of the amino acid sequence of SEQ ID NO: 58 and a light chain variable region consisting of the amino acid sequence of SEQ ID NO: 42;

(c) a heavy chain variable region consisting of the amino acid sequence of SEQ ID NO: 54 and a light chain variable region consisting of the amino acid sequence of SEQ ID NO: 46;

(d) a heavy chain variable region consisting of the amino acid sequence of SEQ ID NO: 58 and a light chain variable region consisting of a light chain variable region consisting of the amino acid sequence of SEQ ID NO: 50; and (e) a heavy chain variable region consisting of the amino acid sequence of SEQ ID NO: 62 and a light chain variable region consisting of the amino acid sequence of SEQ ID NO: 46.

44. The method according to claim 38, wherein the antibody is a chimeric antibody.

45. The method according to claim 38, wherein the antibody is a humanized antibody.

46. The method according to claim 45, comprising a heavy chain and a light chain selected from the group consisting of the following (a) to (e):

(a) a heavy chain consisting of an amino acid sequence consisting of amino acid residues 20 to 471 of SEQ ID NO: 52 and a light chain consisting of an amino acid sequence consisting of amino acid residues 21 to 234 of SEQ ID NO: 36;

(b) a heavy chain consisting of an amino acid sequence consisting of amino acid residues 20 to 471 of SEQ ID NO: 56 and a light chain consisting of an amino acid sequence consisting of amino acid residues 21 to 234 of SEQ ID NO: 40;

(c) a heavy chain consisting of an amino acid sequence consisting of amino acid residues 20 to 471 of SEQ ID NO: 52 and a light chain consisting of an amino acid sequence consisting of amino acid residues 21 to 234 of SEQ ID NO: 44;

(d) a heavy chain consisting of an amino acid sequence consisting of amino acid residues 20 to 471 of SEQ ID NO: 56 and a light chain consisting of an amino acid sequence consisting of amino acid residues 21 to 234 of SEQ ID NO: 48; and (e) a heavy chain consisting of an amino acid sequence consisting of amino acid residues 20 to 471 of SEQ ID NO: 60 and a light chain consisting of an amino acid sequence consisting of amino acid residues 21 to 234 of SEQ ID NO: 44.

47. The method according to claim 38, wherein the antibody comprises a heavy chain constant region of human IgG1, human IgG2, or human IgG4.

48. The method according to claim 38, wherein the antibody comprises a heavy chain comprising CDRH1, CDRH2, and CDRH3 and a light chain comprising CDRL1, CDRL2, and CDRL3 as described in any one of the following (a) and (b):

(a) CDRH1 consisting of the amino acid sequence of SEQ ID NO: 9, CDRH2 consisting of the amino acid sequence of SEQ ID NO: 10, and CDRH3 consisting of the amino acid sequence of SEQ ID NO: 11, and CDRL1 consisting of the amino acid sequence of SEQ ID NO: 5, CDRL2 consisting of the amino acid sequence of SEQ ID NO: 6, and CDRL3 consisting of the amino acid sequence of SEQ ID NO: 7 or an amino acid sequence having one or two amino acid substitutions in the amino acid sequence represented by SEQ ID NO: 7; and (b) CDRH1 consisting of the amino acid sequence of SEQ ID NO: 15, CDRH2 consisting of the amino acid sequence of SEQ ID NO: 16, and CDRH3 consisting of the amino acid sequence of SEQ ID NO: 17, and CDRL1 consisting of the amino acid sequence of SEQ ID NO: 12, CDRL2 consisting of the amino acid sequence of SEQ ID NO: 13, and CDRL3 consisting of the amino acid sequence of SEQ ID NO: 14.

49. The method according to claim 38, wherein the antibody comprises one or two or more modifications selected from the group consisting of N-linked glycosylation, O-linked glycosylation, N-terminal processing, C-terminal processing, deamidation, isomerization of aspartic acid, oxidation of methionine, addition of a methionine residue at an N terminus, amidation of a proline residue, and deletion of one or two amino acid residues at the carboxyl terminus of a heavy chain.

50. The method according to claim 49, wherein one or several amino acid residues are deleted at the carboxyl terminus of a heavy chain of the antibody.

51. The method according to claim 49, wherein one amino acid residue is deleted at the carboxyl terminus of each of the two heavy chains of the antibody.

52. The method according to claim 49, wherein a proline residue at the carboxyl terminus of a heavy chain of the antibody is further amidated.

53. The method according to claim 34, wherein the N297 glycan is N297-(Fuc)MSG1.

54. The method according to claim 34, wherein $m^1$ is an integer of 1.

55. The method according to claim 34, wherein the average number of conjugated drug molecules per antibody molecule in the antibody-pyrrolobenzodiazepine derivative conjugate is 1 to 3 or 3 to 5.

56. The method according to claim 34, wherein the PARP inhibitor is olaparib, rucaparib, niraparib, or talazoparib, or a pharmacologically acceptable salt thereof.

57. The method according to claim 34, for treatment of at least one cancer selected from the group consisting of lung cancer non-small cell lung cancer, small cell lung cancer, kidney cancer, urothelial cancer, colorectal cancer, prostate cancer, glioblastoma multiforme, ovarian cancer, ovarian surface epithelial tumor, ovarian stromal tumor, ovarian germ cell tumor, pancreatic cancer, breast cancer, melanoma, liver cancer, bladder cancer, gastric cancer, esophageal cancer, endometrial cancer, testicular cancer, seminoma testicular cancer, non-seminoma testicular cancer, uterine cervix cancer, placental choriocarcinoma, brain tumor, and head-and-neck cancer, and metastatic forms of them.

58. A method for treating a cancer that expresses CLDN6 and/or CLDN9, wherein an antibody-pyrrolobenzodiazepine derivative conjugate and a PARP inhibitor are administered in combination, and the conjugate has the following formula:

[Formula 8]

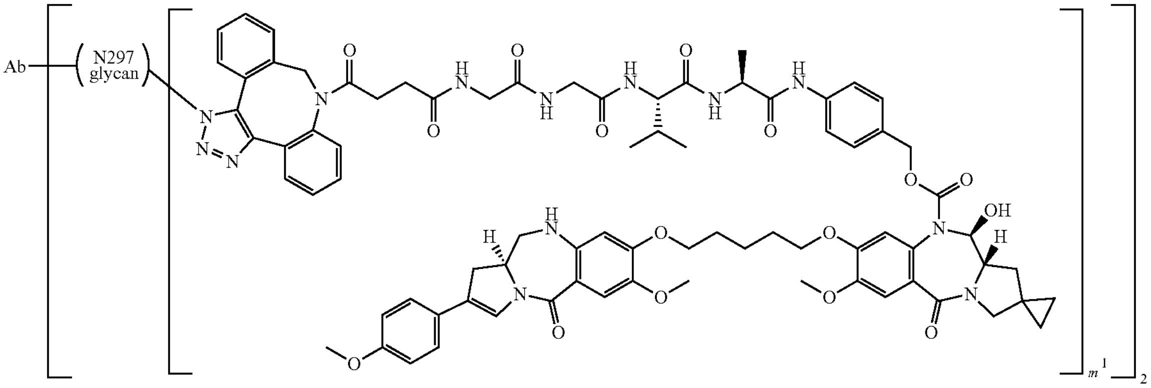

or

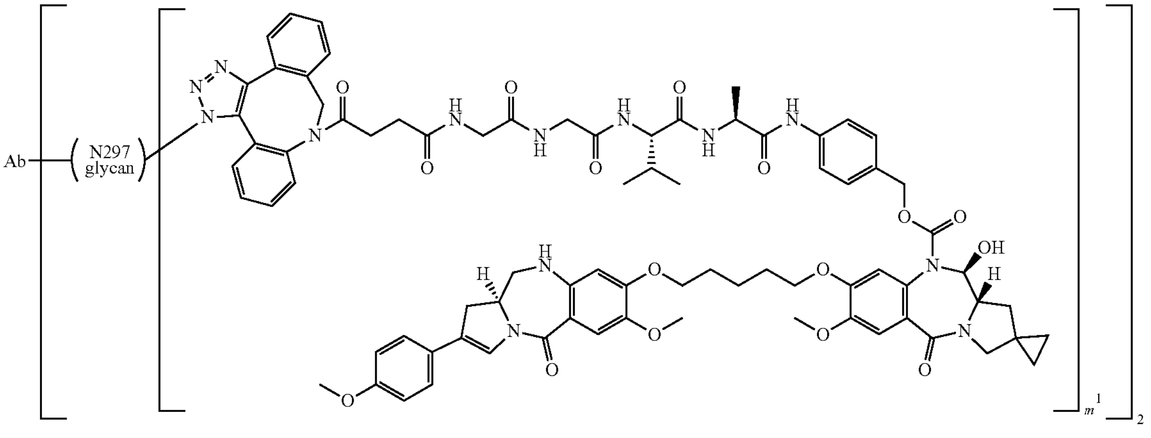

-continued
[Formula 9]
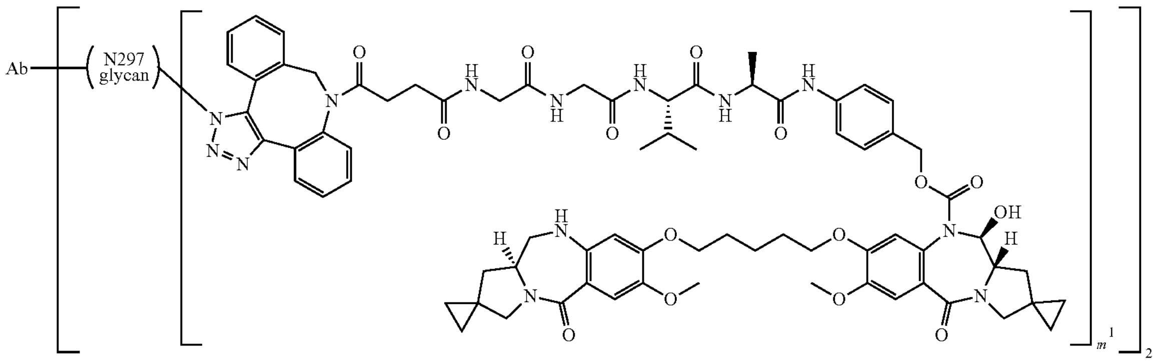
or
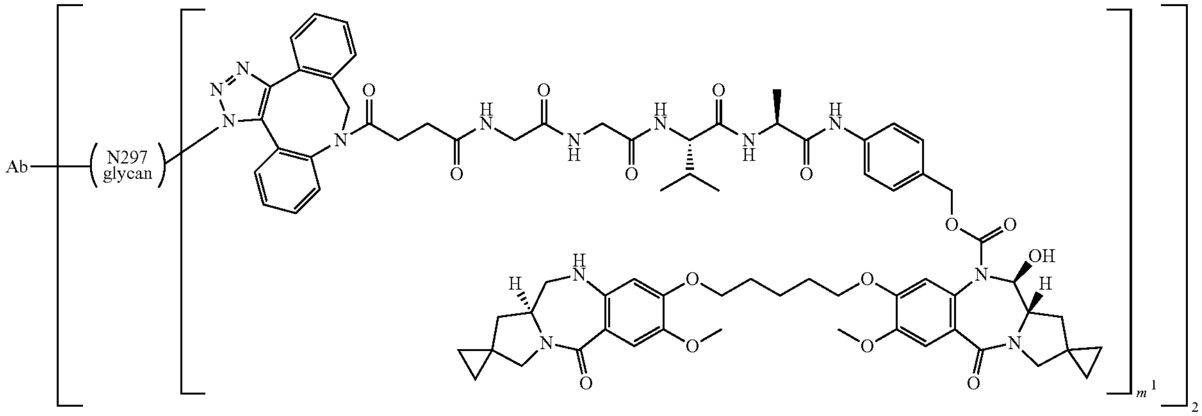
[Formula 10]
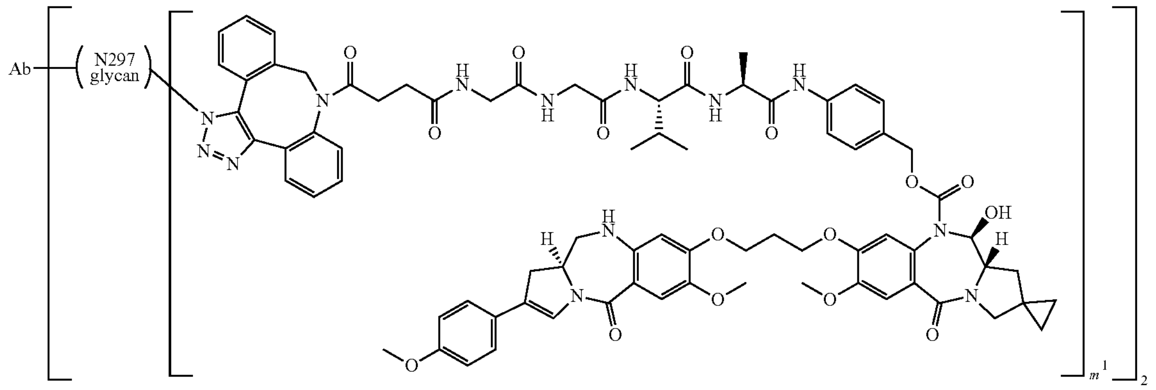
or
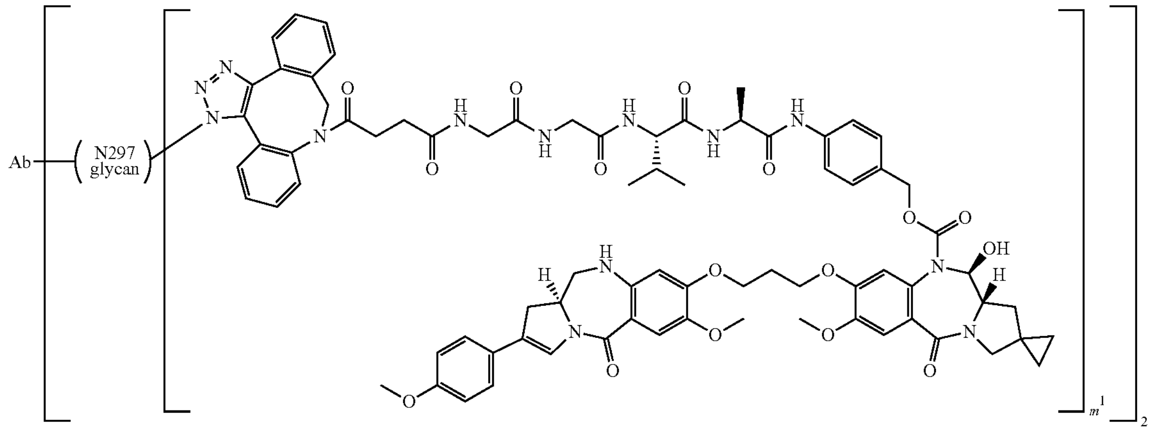
or, -continued

[Formula 11]

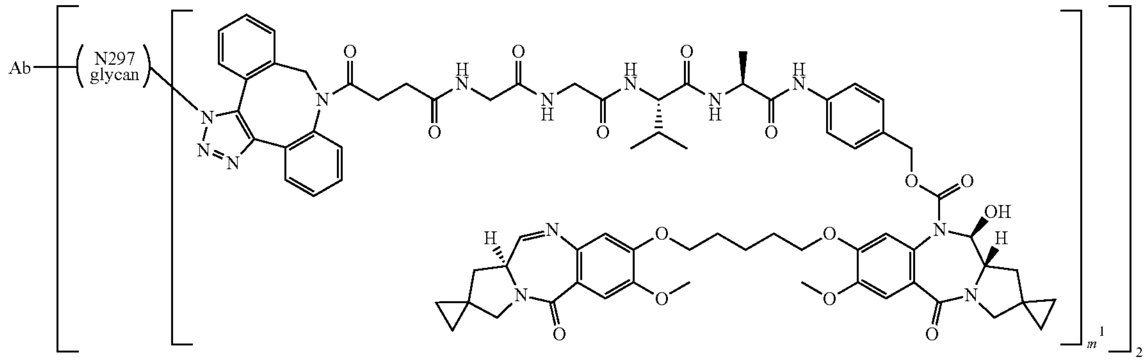

or

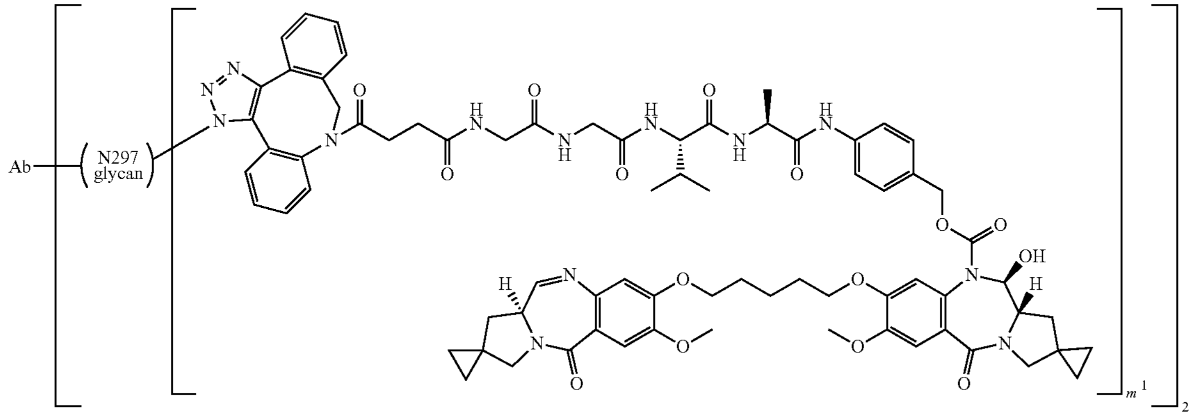

wherein, in each structural formula shown above, $m^1$ is an integer of 1 or 2;

Ab is an antibody or a functional fragment of the antibody;

the N297 glycan is N297-(Fuc)MSG1, N297-(Fuc)MSG2, or a mixture thereof, or N297-(Fuc)SG, with N297-(Fuc)MSG1, N297-(Fuc)MSG2, and N297-(Fuc)SG having structures represented by the following formulas:

[Formula 12]

Fucα1

6

Galβ1-4GlcNAcβ1-2Manα1-6

Manβ1-4GlcNAcβ1-4GlcNAcβ1

*—L(PEG)-NeuAcα2-6Galβ1-4GlcNAcβ1-2Manα1-3

[N297-(Fuc)MSG1]

[Formula 13]

Fucα1

6

*—L(PEG)-NeuAcα2-6Galβ1-4GlcNAcβ1-2Manα1-6

Manβ1-4GlcNAcβ1-4GlcNAcβ1

Galβ1-4GlcNAcβ1-2Manα1-3

[N297-(Fuc)MSG2]

-continued

[Formula 14]

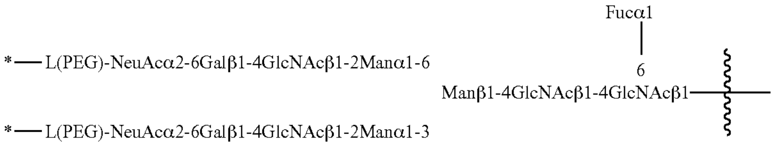

[N297-(Fuc)SG]

wherein each wavy line represents bonding to Asn297 of the antibody,

L(PEG) in the N297 glycan represents *—($CH_2CH_2$—O)$_3$—$CH_2CH_2$—NH—, wherein the amino group at the right end is bound via an amide bond to carboxylic acid at the 2-position of a sialic acid at the non-reducing terminal in each or either one of the 1-3 and 1-6 branched chains of β-Man in the N297 glycan, and the asterisk * at the left end represents bonding to a nitrogen atom at the 1- or 3-position of the triazole ring in the corresponding structural formula, wherein the antibody-drug conjugate and PARP inhibitor according to claim 1 are individually contained as an active ingredient in separate formulations and administered simultaneously or at different times.

* * * * *

SEQUENCE LISTING

```
<160> NUMBER OF SEQ ID NOS: 77

<210> SEQ ID NO 1
<211> LENGTH: 220
<212> TYPE: PRT
<213> ORGANISM: Homo sapiens
<220> FEATURE:
<221> NAME/KEY: MISC_FEATURE
<223> OTHER INFORMATION: amino acid sequence of human CLDN6

<400> SEQUENCE: 1

Met Ala Ser Ala Gly Met Gln Ile Leu Gly Val Val Leu Thr Leu Leu
1               5                   10                  15

Gly Trp Val Asn Gly Leu Val Ser Cys Ala Leu Pro Met Trp Lys Val
            20                  25                  30

Thr Ala Phe Ile Gly Asn Ser Ile Val Val Ala Gln Val Val Trp Glu
        35                  40                  45

Gly Leu Trp Met Ser Cys Val Val Gln Ser Thr Gly Gln Met Gln Cys
    50                  55                  60

Lys Val Tyr Asp Ser Leu Leu Ala Leu Pro Gln Asp Leu Gln Ala Ala
65                  70                  75                  80

Arg Ala Leu Cys Val Ile Ala Leu Leu Val Ala Leu Phe Gly Leu Leu
                85                  90                  95

Val Tyr Leu Ala Gly Ala Lys Cys Thr Thr Cys Val Glu Glu Lys Asp
            100                 105                 110

Ser Lys Ala Arg Leu Val Leu Thr Ser Gly Ile Val Phe Val Ile Ser
        115                 120                 125

Gly Val Leu Thr Leu Ile Pro Val Cys Trp Thr Ala His Ala Ile Ile
    130                 135                 140

Arg Asp Phe Tyr Asn Pro Leu Val Ala Glu Ala Gln Lys Arg Glu Leu
```

-continued

```
145                 150                 155                 160

Gly Ala Ser Leu Tyr Leu Gly Trp Ala Ala Ser Gly Leu Leu Leu Leu
                165                 170                 175

Gly Gly Gly Leu Leu Cys Cys Thr Cys Pro Ser Gly Gly Ser Gln Gly
            180                 185                 190

Pro Ser His Tyr Met Ala Arg Tyr Ser Thr Ser Ala Pro Ala Ile Ser
        195                 200                 205

Arg Gly Pro Ser Glu Tyr Pro Thr Lys Asn Tyr Val
    210                 215                 220


<210> SEQ ID NO 2
<211> LENGTH: 663
<212> TYPE: DNA
<213> ORGANISM: Homo sapiens
<220> FEATURE:
<221> NAME/KEY: misc_feature
<223> OTHER INFORMATION: nucleotide sequence of cDNA encoding amino acid
      sequence of human CLDN6

<400> SEQUENCE: 2

atggcctctg ccggaatgca gatcctggga gtcgtcctga cactgctggg ctgggtgaat      60

ggcctggtct cctgtgccct gcccatgtgg aaggtgaccg ctttcatcgg caacagcatc     120

gtggtggccc aggtggtgtg ggagggcctg tggatgtcct gcgtggtgca gagcaccggc     180

cagatgcagt gcaaggtgta cgactcactg ctggcgctgc cacaggacct gcaggctgca     240

cgtgccctct gtgtcatcgc cctccttgtg gccctgttcg gcttgctggt ctaccttgct     300

ggggccaagt gtaccacctg tgtggaggag aaggattcca aggcccgcct ggtgctcacc     360

tctgggattg tctttgtcat ctcaggggtc ctgacgctaa tccccgtgtg ctggacggcg     420

catgccatca tccgggactt ctataacccc ctggtggctg aggcccaaaa gcgggagctg     480

ggggcctccc tctacttggg ctgggcggcc tcaggccttt tgttgctggg tggggggttg     540

ctgtgctgca cttgcccctc ggggggggtcc cagggcccca gccattacat ggcccgctac     600

tcaacatctg cccctgccat ctctcggggg ccctctgagt accctaccaa gaattacgtc     660

tga                                                                   663


<210> SEQ ID NO 3
<211> LENGTH: 217
<212> TYPE: PRT
<213> ORGANISM: Homo sapiens
<220> FEATURE:
<221> NAME/KEY: MISC_FEATURE
<223> OTHER INFORMATION: amino acid sequence of human CLDN9

<400> SEQUENCE: 3

Met Ala Ser Thr Gly Leu Glu Leu Leu Gly Met Thr Leu Ala Val Leu
1               5                   10                  15

Gly Trp Leu Gly Thr Leu Val Ser Cys Ala Leu Pro Leu Trp Lys Val
            20                  25                  30

Thr Ala Phe Ile Gly Asn Ser Ile Val Val Ala Gln Val Val Trp Glu
        35                  40                  45

Gly Leu Trp Met Ser Cys Val Val Gln Ser Thr Gly Gln Met Gln Cys
    50                  55                  60

Lys Val Tyr Asp Ser Leu Leu Ala Leu Pro Gln Asp Leu Gln Ala Ala
65                  70                  75                  80

Arg Ala Leu Cys Val Ile Ala Leu Leu Leu Ala Leu Leu Gly Leu Leu
                85                  90                  95
```

```
Val Ala Ile Thr Gly Ala Gln Cys Thr Thr Cys Val Glu Asp Glu Gly
            100                 105                 110

Ala Lys Ala Arg Ile Val Leu Thr Ala Gly Val Ile Leu Leu Leu Ala
        115                 120                 125

Gly Ile Leu Val Leu Ile Pro Val Cys Trp Thr Ala His Ala Ile Ile
    130                 135                 140

Gln Asp Phe Tyr Asn Pro Leu Val Ala Glu Ala Leu Lys Arg Glu Leu
145                 150                 155                 160

Gly Ala Ser Leu Tyr Leu Gly Trp Ala Ala Ala Ala Leu Leu Met Leu
                165                 170                 175

Gly Gly Gly Leu Leu Cys Cys Thr Cys Pro Pro Pro Gln Val Glu Arg
            180                 185                 190

Pro Arg Gly Pro Arg Leu Gly Tyr Ser Ile Pro Ser Arg Ser Gly Ala
        195                 200                 205

Ser Gly Leu Asp Lys Arg Asp Tyr Val
    210                 215


<210> SEQ ID NO 4
<211> LENGTH: 654
<212> TYPE: DNA
<213> ORGANISM: Homo sapiens
<220> FEATURE:
<221> NAME/KEY: misc_feature
<223> OTHER INFORMATION: nucleotide sequence of cDNA encoding amino acid
      sequence of human CLDN9

<400> SEQUENCE: 4

atggcttcga ccggcttaga actgctgggc atgaccctgg ctgtgctggg ctggctgggg      60

accctggtgt cctgcgccct gcccctgtgg aaggtgaccg ccttcatcgg caacagcatc     120

gtggtggccc aggtggtgtg ggagggcctg tggatgtcct gcgtggtgca gagcacgggc     180

cagatgcagt gcaaggtgta cgactcactg ctggctctgc cgcaggacct gcaggccgca     240

cgtgccctct gtgtcattgc cctcctgctg gccctgcttg gcctcctggt ggccatcaca     300

ggtgcccagt gtaccacgtg tgtggaggac gaaggtgcca aggcccgtat cgtgctcacc     360

gcgggggtca tcctcctcct cgccggcatc ctggtgctca tccctgtgtg ctggacggcg     420

cacgccatca tccaggactt ctacaacccc ctggtggctg aggccctcaa gcgggagctg     480

ggggcctccc tctacctggg ctgggcggcg gctgcactgc ttatgctggg cggggggctc     540

ctctgctgca cgtgcccccc gccccaggtc gagcggcccc gcggacctcg gctgggctac     600

tccatcccct cccgctcggg tgcatctgga ctggacaaga gggactacgt gtga           654


<210> SEQ ID NO 5
<211> LENGTH: 11
<212> TYPE: PRT
<213> ORGANISM: Mus musculus
<220> FEATURE:
<221> NAME/KEY: MISC_FEATURE
<223> OTHER INFORMATION: amino acid sequence of CDRL1 of B1 antibody
      light chain

<400> SEQUENCE: 5

Arg Ala Ser Gln Asp Ile Asn Asn Tyr Leu Asn
1               5                   10


<210> SEQ ID NO 6
<211> LENGTH: 7
<212> TYPE: PRT
<213> ORGANISM: Mus musculus
<220> FEATURE:
```

<221> NAME/KEY: MISC_FEATURE
<223> OTHER INFORMATION: amino acid sequence of CDRL2 of B1 antibody
      light chain

<400> SEQUENCE: 6

Phe Thr Ser Arg Leu His Ser
1               5

<210> SEQ ID NO 7
<211> LENGTH: 9
<212> TYPE: PRT
<213> ORGANISM: Mus musculus
<220> FEATURE:
<221> NAME/KEY: MISC_FEATURE
<223> OTHER INFORMATION: amino acid sequence of CDRL3 of B1 antibody
      light chain

<400> SEQUENCE: 7

Gln Gln Gly Tyr Pro Leu Pro Trp Thr
1               5

<210> SEQ ID NO 8
<211> LENGTH: 9
<212> TYPE: PRT
<213> ORGANISM: Artificial Sequence
<220> FEATURE:
<223> OTHER INFORMATION: humanized antibody
<220> FEATURE:
<221> NAME/KEY: MISC_FEATURE
<223> OTHER INFORMATION: amino acid sequence of CDRL3 of humanized B1
      antibody light chain L4

<400> SEQUENCE: 8

Gln Gln Gly Asn Thr Leu Pro Trp Thr
1               5

<210> SEQ ID NO 9
<211> LENGTH: 10
<212> TYPE: PRT
<213> ORGANISM: Mus musculus
<220> FEATURE:
<221> NAME/KEY: MISC_FEATURE
<223> OTHER INFORMATION: amino acid sequence of CDRH1 of B1 antibody
      heavy chain

<400> SEQUENCE: 9

Gly Tyr Thr Phe Thr Glu Tyr Thr Met His
1               5                   10

<210> SEQ ID NO 10
<211> LENGTH: 10
<212> TYPE: PRT
<213> ORGANISM: Mus musculus
<220> FEATURE:
<221> NAME/KEY: MISC_FEATURE
<223> OTHER INFORMATION: amino acid sequence of CDRH2 of B1 antibody
      heavy chain

<400> SEQUENCE: 10

Gly Val Asn Pro Asn Ser Gly Asp Thr Ser
1               5                   10

<210> SEQ ID NO 11
<211> LENGTH: 13
<212> TYPE: PRT
<213> ORGANISM: Mus musculus
<220> FEATURE:
<221> NAME/KEY: MISC_FEATURE
<223> OTHER INFORMATION: amino acid sequence of CDRH3 of B1 antibody heavy chain

<400> SEQUENCE: 11

Pro Gly Gly Tyr Asp Val Gly Tyr Tyr Ala Met Asp Tyr
1 5 10

<210> SEQ ID NO 12
<211> LENGTH: 11
<212> TYPE: PRT
<213> ORGANISM: Mus musculus
<220> FEATURE:
<221> NAME/KEY: MISC_FEATURE
<223> OTHER INFORMATION: amino acid sequence of CDRL1 of C7 antibody light chain

<400> SEQUENCE: 12

Arg Ala Ser Gln Asp Ile Asn Asn Tyr Leu Asn
1 5 10

<210> SEQ ID NO 13
<211> LENGTH: 7
<212> TYPE: PRT
<213> ORGANISM: Mus musculus
<220> FEATURE:
<221> NAME/KEY: MISC_FEATURE
<223> OTHER INFORMATION: amino acid sequence of CDRL2 of C7 antibody light chain

<400> SEQUENCE: 13

Ser Thr Ser Arg Leu His Ser
1 5

<210> SEQ ID NO 14
<211> LENGTH: 9
<212> TYPE: PRT
<213> ORGANISM: Mus musculus
<220> FEATURE:
<221> NAME/KEY: MISC_FEATURE
<223> OTHER INFORMATION: amino acid sequence of CDRL3 of C7 antibody light chain

<400> SEQUENCE: 14

Gln Gln Gly Tyr Pro Leu Pro Trp Thr
1 5

<210> SEQ ID NO 15
<211> LENGTH: 10
<212> TYPE: PRT
<213> ORGANISM: Mus musculus
<220> FEATURE:
<221> NAME/KEY: MISC_FEATURE
<223> OTHER INFORMATION: amino acid sequence of CDRH1 of C7 antibody heavy chain

<400> SEQUENCE: 15

Gly Tyr Thr Phe Thr Glu Tyr Thr Met His
1 5 10

<210> SEQ ID NO 16
<211> LENGTH: 10
<212> TYPE: PRT
<213> ORGANISM: Mus musculus
<220> FEATURE:
<221> NAME/KEY: MISC_FEATURE
<223> OTHER INFORMATION: amino acid sequence of CDRH2 of C7 antibody heavy chain

<400> SEQUENCE: 16

Gly Val Asn Pro Asn Ser Gly Asp Thr Ser
1 5 10

<210> SEQ ID NO 17
<211> LENGTH: 13
<212> TYPE: PRT
<213> ORGANISM: Mus musculus
<220> FEATURE:
<221> NAME/KEY: MISC_FEATURE
<223> OTHER INFORMATION: amino acid sequence of CDRH3 of C7 antibody heavy chain

<400> SEQUENCE: 17

Pro Gly Gly Tyr Asp Val Gly Tyr Tyr Ala Met Asp Tyr
1 5 10

<210> SEQ ID NO 18
<211> LENGTH: 321
<212> TYPE: DNA
<213> ORGANISM: Mus musculus
<220> FEATURE:
<221> NAME/KEY: misc_feature
<223> OTHER INFORMATION: nucleotide sequence of cDNA encoding variable region of B1 antibody light chain

<400> SEQUENCE: 18
gatatccaga tgacacagac tgcatcctcc ctgtctgcct ctcttggaga cagagtcacc 60
atcagttgca gggcaagtca ggacattaac aattatttaa actggtatca gcagaaacca 120
gatggaactg ttaaactcct gatctacttc acatcaagat tacactcagg agtcccatca 180
aggttcagtg gcagtgggtc tggaacacat tattctctca ccattactaa cctggaacaa 240
gaagatattg ccacttactt ttgccaacag ggttatccgc ttccgtggac gttcggtgga 300
ggcaccaaac tggaaatcaa a 321

<210> SEQ ID NO 19
<211> LENGTH: 107
<212> TYPE: PRT
<213> ORGANISM: Mus musculus
<220> FEATURE:
<221> NAME/KEY: MISC_FEATURE
<223> OTHER INFORMATION: amino acid sequence of variable region of B1 antibody light chain

<400> SEQUENCE: 19

Asp Ile Gln Met Thr Gln Thr Ala Ser Ser Leu Ser Ala Ser Leu Gly
1 5 10 15

Asp Arg Val Thr Ile Ser Cys Arg Ala Ser Gln Asp Ile Asn Asn Tyr
20 25 30

Leu Asn Trp Tyr Gln Gln Lys Pro Asp Gly Thr Val Lys Leu Leu Ile
35 40 45

Tyr Phe Thr Ser Arg Leu His Ser Gly Val Pro Ser Arg Phe Ser Gly
50 55 60

Ser Gly Ser Gly Thr His Tyr Ser Leu Thr Ile Thr Asn Leu Glu Gln
65 70 75 80

Glu Asp Ile Ala Thr Tyr Phe Cys Gln Gln Gly Tyr Pro Leu Pro Trp
85 90 95

Thr Phe Gly Gly Gly Thr Lys Leu Glu Ile Lys
100 105

<210> SEQ ID NO 20
<211> LENGTH: 366
<212> TYPE: DNA

<213> ORGANISM: Mus musculus
<220> FEATURE:
<221> NAME/KEY: misc_feature
<223> OTHER INFORMATION: nucleotide sequence of cDNA encoding variable region of B1 antibody heavy chain

<400> SEQUENCE: 20
gaggtccagc ttcaacagtc tggacctgaa ctggtgaagc ctggggcttc agtgaagata 60
tcctgcaaga cttctggata cacattcact gaatacacca tgcactgggt gcagcagagc 120
catggaaaga gccttgagtg gattggaggt gttaatccta atagtggtga tactagctac 180
aaccagaagt tcaagggcaa ggccacattg actgttgaca agtcctccag cacagcctac 240
atggagctcc gcagcctgac atctgaggat tctgcagtct attactgtgc aagacccggg 300
gggtacgacg tgggttacta tgctatggac tactggggtc aaggaacctc agtcaccgtc 360
tcctca 366

<210> SEQ ID NO 21
<211> LENGTH: 122
<212> TYPE: PRT
<213> ORGANISM: Mus musculus
<220> FEATURE:
<221> NAME/KEY: MISC_FEATURE
<223> OTHER INFORMATION: amino acid sequence of variable region of B1 antibody heavy chain

<400> SEQUENCE: 21

Glu Val Gln Leu Gln Gln Ser Gly Pro Glu Leu Val Lys Pro Gly Ala
1 5 10 15

Ser Val Lys Ile Ser Cys Lys Thr Ser Gly Tyr Thr Phe Thr Glu Tyr
20 25 30

Thr Met His Trp Val Gln Gln Ser His Gly Lys Ser Leu Glu Trp Ile
35 40 45

Gly Gly Val Asn Pro Asn Ser Gly Asp Thr Ser Tyr Asn Gln Lys Phe
50 55 60

Lys Gly Lys Ala Thr Leu Thr Val Asp Lys Ser Ser Ser Thr Ala Tyr
65 70 75 80

Met Glu Leu Arg Ser Leu Thr Ser Glu Asp Ser Ala Val Tyr Tyr Cys
85 90 95

Ala Arg Pro Gly Gly Tyr Asp Val Gly Tyr Tyr Ala Met Asp Tyr Trp
100 105 110

Gly Gln Gly Thr Ser Val Thr Val Ser Ser
115 120

<210> SEQ ID NO 22
<211> LENGTH: 321
<212> TYPE: DNA
<213> ORGANISM: Mus musculus
<220> FEATURE:
<221> NAME/KEY: misc_feature
<223> OTHER INFORMATION: nucleotide sequence of cDNA encoding variable region of C7 antibody light chain

<400> SEQUENCE: 22
gatatccaga tgacacagac tgcatcctcc ctgtctgcct ctcttggaga cagagtcacc 60
atcagttgca gggcaagtca ggacattaac aattatttaa actggtatca gcagaaacca 120
gatggaactg ttaaactcct gatctactcc acatcaagat tacactcagg agtcccatca 180
aggttcagtg gcagtgggtc tggaacacat tattctctca ccattactca cctggaacaa 240
gaagatattg ccacttactt ttgccaacag ggttatccgc ttccgtggac gttcggtgga 300

```
ggcaccaaac tggaaatcaa a                                          321


<210> SEQ ID NO 23
<211> LENGTH: 107
<212> TYPE: PRT
<213> ORGANISM: Mus musculus
<220> FEATURE:
<221> NAME/KEY: MISC_FEATURE
<223> OTHER INFORMATION: amino acid sequence of variable region of C7
      antibody light chain

<400> SEQUENCE: 23

Asp Ile Gln Met Thr Gln Thr Ala Ser Ser Leu Ser Ala Ser Leu Gly
1               5                   10                  15

Asp Arg Val Thr Ile Ser Cys Arg Ala Ser Gln Asp Ile Asn Asn Tyr
            20                  25                  30

Leu Asn Trp Tyr Gln Gln Lys Pro Asp Gly Thr Val Lys Leu Leu Ile
        35                  40                  45

Tyr Ser Thr Ser Arg Leu His Ser Gly Val Pro Ser Arg Phe Ser Gly
    50                  55                  60

Ser Gly Ser Gly Thr His Tyr Ser Leu Thr Ile Thr His Leu Glu Gln
65                  70                  75                  80

Glu Asp Ile Ala Thr Tyr Phe Cys Gln Gln Gly Tyr Pro Leu Pro Trp
                85                  90                  95

Thr Phe Gly Gly Gly Thr Lys Leu Glu Ile Lys
            100                 105


<210> SEQ ID NO 24
<211> LENGTH: 366
<212> TYPE: DNA
<213> ORGANISM: Mus musculus
<220> FEATURE:
<221> NAME/KEY: misc_feature
<223> OTHER INFORMATION: nucleotide sequence of cDNA encoding variable
      region of C7 antibody heavy chain

<400> SEQUENCE: 24

gaggtccagc ttcaacagtc tggacctgaa ctggtgaagc ctggggcttc agtgaagata     60

tcctgcaaga cttctggata cacattcact gaatacacca tgcactgggt gcagcagagc    120

catggaaaga gccttgagtg gattggaggt gttaatccta atagtggtga tactagctac    180

aaccagaagt tcaagggcaa ggccacattg actgttgaca agtcctccag cacagcctac    240

atggagctcc gcagcctgac atctgaggat tctgcagtct attactgtgc aagacccggg    300

gggtacgacg tgggttacta tgctatggac tactggggtc aaggaacctc agtcaccgtc    360

tcctca                                                               366


<210> SEQ ID NO 25
<211> LENGTH: 122
<212> TYPE: PRT
<213> ORGANISM: Mus musculus
<220> FEATURE:
<221> NAME/KEY: MISC_FEATURE
<223> OTHER INFORMATION: amino acid sequence of variable region of C7
      antibody heavy chain

<400> SEQUENCE: 25

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Glu Tyr
            20                  25                  30
```

```
Thr Met His Trp Val Gln Gln Ser His Gly Lys Ser Leu Glu Trp Ile
        35                  40                  45

Gly Gly Val Asn Pro Asn Ser Gly Asp Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Pro Gly Gly Tyr Asp Val Gly Tyr Tyr Ala Met Asp Tyr Trp
            100                 105                 110

Gly Gln Gly Thr Ser Val Thr Val Ser Ser
        115                 120
```

<210> SEQ ID NO 26
<211> LENGTH: 449
<212> TYPE: DNA
<213> ORGANISM: Homo sapiens
<220> FEATURE:
<221> NAME/KEY: misc_feature
<223> OTHER INFORMATION: DNA fragment comprising DNA sequence encoding human light chain signal sequence and human ƒÈ chain constant region

<400> SEQUENCE: 26

```
gcctccggac tctagagcca ccatggtgct gcagacccag gtgttcatct ccctgctgct     60

gtggatctcc ggcgcgtacg gcgatatcgt gatgattaaa cgtacggtgg ccgccccctc    120

cgtgttcatc ttcccccct ccgacgagca gctgaagtcc ggcaccgcct ccgtggtgtg    180

cctgctgaat aacttctacc ccagagaggc caaggtgcag tggaaggtgg acaacgccct    240

gcagtccggg aactcccagg agagcgtgac cgagcaggac agcaaggaca gcacctacag    300

cctgagcagc accctgaccc tgagcaaagc cgactacgag aagcacaagg tgtacgcctg    360

cgaggtgacc caccagggcc tgagctcccc cgtcaccaag agcttcaaca ggggggagtg    420

ttaggggccc gtttaaacgg gggaggcta                                      449
```

<210> SEQ ID NO 27
<211> LENGTH: 1137
<212> TYPE: DNA
<213> ORGANISM: Homo sapiens
<220> FEATURE:
<221> NAME/KEY: misc_feature
<223> OTHER INFORMATION: DNA fragment comprising DNA sequence encoding human heavy chain signal sequence and human IgG1 LALA constant region

<400> SEQUENCE: 27

```
ccagcctccg gactctagag ccaccatgaa acacctgtgg ttcttcctcc tgctggtggc     60

agctcccaga tgggtgctga gccaggtgca attgtgcagg cggttagctc agcctccacc    120

aagggcccaa gcgtcttccc cctggcaccc tcctccaaga gcacctctgg cggcacagcc    180

gccctgggct gcctggtcaa ggactacttc cccgaacccg tgaccgtgag ctggaactca    240

ggcgccctga ccagcggcgt gcacaccttc cccgctgtcc tgcagtcctc aggactctac    300

tccctcagca gcgtggtgac cgtgccctcc agcagcttgg gcacccagac ctacatctgc    360

aacgtgaatc acaagcccag caacaccaag gtggacaaga gagttgagcc caaatcttgt    420

gacaaaactc acacatgccc accctgccca gcacctgaag ccgcgggggg accctcagtc    480

ttcctcttcc ccccaaaacc caaggacacc ctcatgatct cccggacccc tgaggtcaca    540
```

```
tgcgtggtgg tggacgtgag ccacgaagac cctgaggtca agttcaactg gtacgtggac    600

ggcgtggagg tgcataatgc caagacaaag ccccgggagg agcagtacaa cagcacgtac    660

cgggtggtca gcgtcctcac cgtcctgcac caggactggc tgaatggcaa ggagtacaag    720

tgcaaggtct ccaacaaagc cctcccagcc cccatcgaga aaaccatctc caaagccaaa    780

ggccagcccc gggaaccaca ggtgtacacc ctgcccccat cccgggagga gatgaccaag    840

aaccaggtca gcctgacctg cctggtcaaa ggcttctatc ccagcgacat cgccgtggag    900

tgggagagca atggccagcc cgagaacaac tacaagacca cccctcccgt gctggactcc    960

gacggctcct tcttcctcta cagcaagctc accgtggaca agagcaggtg gcagcagggc   1020

aacgtcttct catgctccgt gatgcatgag gctctgcaca accactacac ccagaagagc   1080

ctctccctgt ctcccggcaa atgagatatc gggcccgttt aaacgggga ggctaac       1137
```

```
<210> SEQ ID NO 28
<211> LENGTH: 234
<212> TYPE: PRT
<213> ORGANISM: Artificial Sequence
<220> FEATURE:
<223> OTHER INFORMATION: chimeric antibody
<220> FEATURE:
<221> NAME/KEY: MISC_FEATURE
<223> OTHER INFORMATION: amino acid sequence of chB1 light chain

<400> SEQUENCE: 28

Met Val Leu Gln Thr Gln Val Phe Ile Ser Leu Leu Leu Trp Ile Ser
1               5                   10                  15

Gly Ala Tyr Gly Asp Ile Gln Met Thr Gln Thr Ala Ser Ser Leu Ser
            20                  25                  30

Ala Ser Leu Gly Asp Arg Val Thr Ile Ser Cys Arg Ala Ser Gln Asp
        35                  40                  45

Ile Asn Asn Tyr Leu Asn Trp Tyr Gln Gln Lys Pro Asp Gly Thr Val
    50                  55                  60

Lys Leu Leu Ile Tyr Phe Thr Ser Arg Leu His Ser Gly Val Pro Ser
65                  70                  75                  80

Arg Phe Ser Gly Ser Gly Ser Gly Thr His Tyr Ser Leu Thr Ile Thr
                85                  90                  95

Asn Leu Glu Gln Glu Asp Ile Ala Thr Tyr Phe Cys Gln Gln Gly Tyr
            100                 105                 110

Pro Leu Pro Trp Thr Phe Gly Gly Gly Thr Lys Leu Glu Ile Lys Arg
        115                 120                 125

Ala Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

<210> SEQ ID NO 29
<211> LENGTH: 752
<212> TYPE: DNA
<213> ORGANISM: Artificial Sequence
<220> FEATURE:
<223> OTHER INFORMATION: chimeric antibody
<220> FEATURE:
<221> NAME/KEY: misc_feature
<223> OTHER INFORMATION: DNA fragment comprising DNA sequence encoding
amino acid sequence of chB1 light chain

<400> SEQUENCE: 29

```
ccagcctccg gactctagag ccaccatggt gctgcagacc caggtgttca tcagcctgct     60

gctgtggatc agcggcgcct acggcgacat ccagatgacc cagacagcca gcagcctgag    120

cgccagcctg ggcgatagag tgaccatcag ctgcagagcc agccaggaca tcaacaacta    180

cctgaactgg tatcagcaga aacccgacgg caccgtgaag ctgctgatct acttcaccag    240

cagactgcac agcggcgtgc ccagcagatt ttctggcagc ggctctggca cccactacag    300

cctgaccatc accaacctgg aacaggaaga tatcgctacc tacttctgtc agcaaggcta    360

ccccctgccc tggacctttg gcggcggaac aaagctggaa atcaagcggg ccgtggccgc    420

tccctccgtg ttcatctttc cacccagcga cgagcagctg aagtccggca cagctagcgt    480

cgtgtgcctg ctgaacaact tctacccccg cgaggccaag gtgcagtgga aggtggacaa    540

tgccctgcag agcggcaaca gccaggaaag cgtgaccgag caggacagca aggactccac    600

ctactccctg agcagcaccc tgaccctgag caaggccgac tacgagaagc acaaggtgta    660

cgcctgcgaa gtgacccacc agggcctgtc tagccccgtg accaagagct tcaaccgggg    720

cgagtgttga gtttaaacgg gggaggctaa ct                                  752
```

<210> SEQ ID NO 30
<211> LENGTH: 107
<212> TYPE: PRT
<213> ORGANISM: Artificial Sequence
<220> FEATURE:
<223> OTHER INFORMATION: chimeric antibody
<220> FEATURE:
<221> NAME/KEY: MISC_FEATURE
<223> OTHER INFORMATION: amino acid sequence of variable region of chB1
light chain

<400> SEQUENCE: 30

```
Asp Ile Gln Met Thr Gln Thr Ala Ser Ser Leu Ser Ala Ser Leu Gly
1               5                   10                  15

Asp Arg Val Thr Ile Ser Cys Arg Ala Ser Gln Asp Ile Asn Asn Tyr
            20                  25                  30

Leu Asn Trp Tyr Gln Gln Lys Pro Asp Gly Thr Val Lys Leu Leu Ile
        35                  40                  45

Tyr Phe Thr Ser Arg Leu His Ser Gly Val Pro Ser Arg Phe Ser Gly
    50                  55                  60

Ser Gly Ser Gly Thr His Tyr Ser Leu Thr Ile Thr Asn Leu Glu Gln
65                  70                  75                  80

Glu Asp Ile Ala Thr Tyr Phe Cys Gln Gln Gly Tyr Pro Leu Pro Trp
                85                  90                  95

Thr Phe Gly Gly Gly Thr Lys Leu Glu Ile Lys
            100                 105
```

<210> SEQ ID NO 31
<211> LENGTH: 321
<212> TYPE: DNA
<213> ORGANISM: Artificial Sequence
<220> FEATURE:
<223> OTHER INFORMATION: chimeric antibody
<220> FEATURE:
<221> NAME/KEY: misc_feature
<223> OTHER INFORMATION: nucleotide sequence encoding amino acid sequence of variable region of chB1 light chain

<400> SEQUENCE: 31
gacatccaga tgacccagac agccagcagc ctgagcgcca gcctgggcga tagagtgacc 60
atcagctgca gagccagcca ggacatcaac aactacctga actggtatca gcagaaaccc 120
gacggcaccg tgaagctgct gatctacttc accagcagac tgcacagcgg cgtgcccagc 180
agattttctg gcagcggctc tggcacccac tacagcctga ccatcaccaa cctggaacag 240
gaagatatcg ctacctactt ctgtcagcaa ggctaccccc tgccctggac ctttggcggc 300
ggaacaaagc tggaaatcaa g 321

<210> SEQ ID NO 32
<211> LENGTH: 471
<212> TYPE: PRT
<213> ORGANISM: Artificial Sequence
<220> FEATURE:
<223> OTHER INFORMATION: chimeric antibody
<220> FEATURE:
<221> NAME/KEY: MISC_FEATURE
<223> OTHER INFORMATION: amino acid sequence of chB1 heavy chain

<400> SEQUENCE: 32

Met Lys His Leu Trp Phe Phe Leu Leu Leu Val Ala Ala Pro Arg Trp
1 5 10 15

Val Leu Ser Glu Val Gln Leu Gln Gln Ser Gly Pro Glu Leu Val Lys
20 25 30

Pro Gly Ala Ser Val Lys Ile Ser Cys Lys Thr Ser Gly Tyr Thr Phe
35 40 45

Thr Glu Tyr Thr Met His Trp Val Gln Gln Ser His Gly Lys Ser Leu
50 55 60

Glu Trp Ile Gly Gly Val Asn Pro Asn Ser Gly Asp Thr Ser Tyr Asn
65 70 75 80

Gln Lys Phe Lys Gly Lys Ala Thr Leu Thr Val Asp Lys Ser Ser Ser
85 90 95

Thr Ala Tyr Met Glu Leu Arg Ser Leu Thr Ser Glu Asp Ser Ala Val
100 105 110

Tyr Tyr Cys Ala Arg Pro Gly Gly Tyr Asp Val Gly Tyr Tyr Ala Met
115 120 125

Asp Tyr Trp Gly Gln Gly Thr Ser Val Thr Val Ser Ser Ala Ser Thr
130 135 140

Lys Gly Pro Ser Val Phe Pro Leu Ala Pro Ser Ser Lys Ser Thr Ser
145 150 155 160

Gly Gly Thr Ala Ala Leu Gly Cys Leu Val Lys Asp Tyr Phe Pro Glu
165 170 175

Pro Val Thr Val Ser Trp Asn Ser Gly Ala Leu Thr Ser Gly Val His
180 185 190

Thr Phe Pro Ala Val Leu Gln Ser Ser Gly Leu Tyr Ser Leu Ser Ser
195 200 205

Val Val Thr Val Pro Ser Ser Ser Leu Gly Thr Gln Thr Tyr Ile Cys
210 215 220

Asn Val Asn His Lys Pro Ser Asn Thr Lys Val Asp Lys Arg Val Glu
225 230 235 240

```
Pro Lys Ser Cys Asp Lys Thr His Thr Cys Pro Pro Cys Pro Ala Pro
                245                 250                 255

Glu Ala Ala Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Glu Glu Met Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly Lys
465                 470
```

<210> SEQ ID NO 33
<211> LENGTH: 1413
<212> TYPE: DNA
<213> ORGANISM: Artificial Sequence
<220> FEATURE:
<223> OTHER INFORMATION: chimeric antibody
<220> FEATURE:
<221> NAME/KEY: misc_feature
<223> OTHER INFORMATION: nucleotide sequence encoding chB1 heavy chain

<400> SEQUENCE: 33

```
atgaaacacc tgtggttctt cctcctgctg gtggcagctc ccagatgggt gctgagcgaa     60

gtgcagctgc agcagtctgg ccccgagctc gtgaaacctg gcgcctccgt gaagatcagc    120

tgcaagacca gcggctacac cttcaccgag tacaccatgc actgggtgca gcagagccac    180

ggcaagagcc tggaatggat cggcggcgtg aaccccaaca gcggcgacac cagctacaac    240

cagaagttca agggcaaggc caccctgacc gtggacaaga gcagcagcac cgcctacatg    300

gaactgcgga gcctgaccag cgaggacagc gccgtgtact actgtgccag acctggcggc    360

tacgacgtgg gctactacgc catggattac tggggccagg gcaccagcgt gaccgtcagc    420

tcagcctcca ccaagggccc aagcgtcttc cccctggcac cctcctccaa gagcacctct    480

ggcggcacag ccgccctggg ctgcctggtc aaggactact tccccgaacc cgtgaccgtg    540

agctggaact caggcgccct gaccagcggc gtgcacacct tccccgctgt cctgcagtcc    600

tcaggactct actccctcag cagcgtggtg accgtgccct ccagcagctt gggcacccag    660
```

```
acctacatct gcaacgtgaa tcacaagccc agcaacacca aggtggacaa gagagttgag    720

cccaaatctt gtgacaaaac tcacacatgc ccaccctgcc cagcacctga agccgcgggg    780

ggaccctcag tcttcctctt ccccccaaaa cccaaggaca ccctcatgat ctcccggacc    840

cctgaggtca catgcgtggt ggtggacgtg agccacgaag accctgaggt caagttcaac    900

tggtacgtgg acggcgtgga ggtgcataat gccaagacaa agccccggga ggagcagtac    960

aacagcacgt accgggtggt cagcgtcctc accgtcctgc accaggactg gctgaatggc   1020

aaggagtaca agtgcaaggt ctccaacaaa gccctcccag cccccatcga gaaaaccatc   1080

tccaaagcca aaggccagcc ccgggaacca caggtgtaca ccctgccccc atcccgggag   1140

gagatgacca agaaccaggt cagcctgacc tgcctggtca aaggcttcta tcccagcgac   1200

atcgccgtgg agtgggagag caatggccag cccgagaaca actacaagac cacccctccc   1260

gtgctggact ccgacggctc cttcttcctc tacagcaagc tcaccgtgga caagagcagg   1320

tggcagcagg gcaacgtctt ctcatgctcc gtgatgcatg aggctctgca caaccactac   1380

acccagaaga gcctctccct gtctcccggc aaa                                1413
```

```
<210> SEQ ID NO 34
<211> LENGTH: 122
<212> TYPE: PRT
<213> ORGANISM: Artificial Sequence
<220> FEATURE:
<223> OTHER INFORMATION: chimeric antibody
<220> FEATURE:
<221> NAME/KEY: MISC_FEATURE
<223> OTHER INFORMATION: amino acid sequence of variable region of chB1
      heavy chain

<400> SEQUENCE: 34

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Glu Tyr
            20                  25                  30

Thr Met His Trp Val Gln Gln Ser His Gly Lys Ser Leu Glu Trp Ile
        35                  40                  45

Gly Gly Val Asn Pro Asn Ser Gly Asp Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Pro Gly Gly Tyr Asp Val Gly Tyr Tyr Ala Met Asp Tyr Trp
            100                 105                 110

Gly Gln Gly Thr Ser Val Thr Val Ser Ser
        115                 120


<210> SEQ ID NO 35
<211> LENGTH: 366
<212> TYPE: DNA
<213> ORGANISM: Artificial Sequence
<220> FEATURE:
<223> OTHER INFORMATION: chimeric antibody
<220> FEATURE:
<221> NAME/KEY: misc_feature
<223> OTHER INFORMATION: nucleotide sequence encoding variable region of
      chB1 heavy chain

<400> SEQUENCE: 35
```

-continued

```
gaagtgcagc tgcagcagtc tggccccgag ctcgtgaaac ctggcgcctc cgtgaagatc     60

agctgcaaga ccagcggcta caccttcacc gagtacacca tgcactgggt gcagcagagc    120

cacggcaaga gcctggaatg gatcggcggc gtgaacccca acagcggcga caccagctac    180

aaccagaagt tcaagggcaa ggccaccctg accgtggaca agagcagcag caccgcctac    240

atggaactgc ggagcctgac cagcgaggac agcgccgtgt actactgtgc cagacctggc    300

ggctacgacg tgggctacta cgccatggat tactggggcc agggcaccag cgtgaccgtc    360

agctca                                                               366
```

```
<210> SEQ ID NO 36
<211> LENGTH: 234
<212> TYPE: PRT
<213> ORGANISM: Artificial Sequence
<220> FEATURE:
<223> OTHER INFORMATION: humanized antibody
<220> FEATURE:
<221> NAME/KEY: MISC_FEATURE
<223> OTHER INFORMATION: amino acid sequence of humanized antibody light
      chain hL1

<400> SEQUENCE: 36

Met Val Leu Gln Thr Gln Val Phe Ile Ser Leu Leu Leu Trp Ile Ser
1               5                   10                  15

Gly Ala Tyr Gly Asp Ile Gln Met Thr Gln Ser Pro Ser Ser Leu Ser
            20                  25                  30

Ala Ser Val Gly Asp Arg Val Thr Ile Thr Cys Arg Ala Ser Gln Asp
        35                  40                  45

Ile Asn Asn Tyr Leu Asn Trp Tyr Gln Gln Lys Pro Gly Lys Ala Pro
    50                  55                  60

Lys Leu Leu Ile Tyr Phe Thr Ser Arg Leu His Ser Gly Val Pro Ser
65                  70                  75                  80

Arg Phe Ser Gly Ser Gly Ser Gly Thr Asp Tyr Thr Leu Thr Ile Ser
                85                  90                  95

Ser Leu Gln Pro Glu Asp Phe Ala Thr Tyr Tyr Cys Gln Gln Gly Tyr
            100                 105                 110

Pro Leu Pro Trp Thr Phe Gly Gln Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230


<210> SEQ ID NO 37
<211> LENGTH: 702
<212> TYPE: DNA
<213> ORGANISM: Artificial Sequence
<220> FEATURE:
```

<223> OTHER INFORMATION: humanized antibody
<220> FEATURE:
<221> NAME/KEY: misc_feature
<223> OTHER INFORMATION: nucleotide sequence encoding humanized antibody
light chain hL1

<400> SEQUENCE: 37
atggtgctgc agacccaggt gttcatctcc ctgctgctgt ggatctccgg cgcgtacggc 60
gacatccaga tgacccagag ccctagcagc ctgagcgcca gcgtgggcga cagagtgacc 120
atcacctgta gagccagcca ggacatcaac aactacctga actggtatca gcagaagccc 180
ggcaaggccc ccaagctgct gatctacttc accagcagac tgcacagcgg cgtgcccagc 240
agattttctg gcagcggctc cggcaccgac tacaccctga caatcagcag cctgcagccc 300
gaggacttcg ccacctacta ctgccagcag ggctaccccc tgccttggac atttggccag 360
ggcaccaagg tggaaatcaa gcgtacggtg gccgcccccct ccgtgttcat cttccccccc 420
tccgacgagc agctgaagtc cggcaccgcc tccgtggtgt gcctgctgaa taacttctac 480
cccagagagg ccaaggtgca gtggaaggtg gacaacgccc tgcagtccgg gaactcccag 540
gagagcgtga ccgagcagga cagcaaggac agcacctaca gcctgagcag caccctgacc 600
ctgagcaaag ccgactacga gaagcacaag gtgtacgcct gcgaggtgac ccaccagggc 660
ctgagctccc ccgtcaccaa gagcttcaac aggggggagt gt 702

<210> SEQ ID NO 38
<211> LENGTH: 107
<212> TYPE: PRT
<213> ORGANISM: Artificial Sequence
<220> FEATURE:
<223> OTHER INFORMATION: humanized antibody
<220> FEATURE:
<221> NAME/KEY: MISC_FEATURE
<223> OTHER INFORMATION: amino acid sequence of variable region of
humanized antibody light chain hL1

<400> SEQUENCE: 38

Asp Ile Gln Met Thr Gln Ser Pro Ser Ser Leu Ser Ala Ser Val Gly
1 5 10 15

Asp Arg Val Thr Ile Thr Cys Arg Ala Ser Gln Asp Ile Asn Asn Tyr
20 25 30

Leu Asn Trp Tyr Gln Gln Lys Pro Gly Lys Ala Pro Lys Leu Leu Ile
35 40 45

Tyr Phe Thr Ser Arg Leu His Ser Gly Val Pro Ser Arg Phe Ser Gly
50 55 60

Ser Gly Ser Gly Thr Asp Tyr Thr Leu Thr Ile Ser Ser Leu Gln Pro
65 70 75 80

Glu Asp Phe Ala Thr Tyr Tyr Cys Gln Gln Gly Tyr Pro Leu Pro Trp
85 90 95

Thr Phe Gly Gln Gly Thr Lys Val Glu Ile Lys
100 105

<210> SEQ ID NO 39
<211> LENGTH: 321
<212> TYPE: DNA
<213> ORGANISM: Artificial Sequence
<220> FEATURE:
<223> OTHER INFORMATION: humanized antibody
<220> FEATURE:
<221> NAME/KEY: misc_feature
<223> OTHER INFORMATION: nucleotide sequence encoding variable region of
humanized antibody light chain hL1

<400> SEQUENCE: 39

```
gacatccaga tgacccagag ccctagcagc ctgagcgcca gcgtgggcga cagagtgacc     60

atcacctgta gagccagcca ggacatcaac aactacctga actggtatca gcagaagccc    120

ggcaaggccc ccaagctgct gatctacttc accagcagac tgcacagcgg cgtgcccagc    180

agattttctg gcagcggctc cggcaccgac tacaccctga caatcagcag cctgcagccc    240

gaggacttcg ccacctacta ctgccagcag ggctaccccc tgccttggac atttggccag    300

ggcaccaagg tggaaatcaa g                                              321
```

<210> SEQ ID NO 40
<211> LENGTH: 234
<212> TYPE: PRT
<213> ORGANISM: Artificial Sequence
<220> FEATURE:
<223> OTHER INFORMATION: humanized antibody
<220> FEATURE:
<221> NAME/KEY: MISC_FEATURE
<223> OTHER INFORMATION: amino acid sequence of humanized antibody light chain hL2

<400> SEQUENCE: 40

```
Met Val Leu Gln Thr Gln Val Phe Ile Ser Leu Leu Leu Trp Ile Ser
1               5                   10                  15

Gly Ala Tyr Gly Asp Ile Gln Met Thr Gln Ser Pro Ser Ser Leu Ser
            20                  25                  30

Ala Ser Val Gly Asp Arg Val Thr Ile Thr Cys Arg Ala Ser Gln Asp
        35                  40                  45

Ile Asn Asn Tyr Leu Asn Trp Tyr Gln Gln Lys Pro Gly Lys Ala Val
    50                  55                  60

Lys Leu Leu Ile Tyr Phe Thr Ser Arg Leu His Ser Gly Val Pro Ser
65                  70                  75                  80

Arg Phe Ser Gly Ser Gly Ser Gly Thr His Tyr Thr Leu Thr Ile Ser
                85                  90                  95

Ser Leu Gln Pro Glu Asp Phe Ala Thr Tyr Tyr Cys Gln Gln Gly Tyr
            100                 105                 110

Pro Leu Pro Trp Thr Phe Gly Gln Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

<210> SEQ ID NO 41
<211> LENGTH: 702
<212> TYPE: DNA
<213> ORGANISM: Artificial Sequence
<220> FEATURE:

```
<223> OTHER INFORMATION: humanized antibody
<220> FEATURE:
<221> NAME/KEY: misc_feature
<223> OTHER INFORMATION: nucleotide sequence encoding humanized antibody
      light chain hL2

<400> SEQUENCE: 41

atggtgctgc agacccaggt gttcatctcc ctgctgctgt ggatctccgg cgcgtacggc     60

gacatccaga tgacccagag ccctagcagc ctgagcgcca gcgtgggcga cagagtgacc    120

atcacctgta gagccagcca ggacatcaac aactacctga actggtatca gcagaaaccc    180

ggcaaggccg tgaagctgct gatctacttc accagcagac tgcacagcgg cgtgcccagc    240

agattttctg gcagcggctc tggcacccac tacaccctga caatcagcag cctgcagccc    300

gaggacttcg ccacctacta ctgccagcag ggctaccccc tgccttggac atttggccag    360

ggcaccaagg tggaaatcaa gcgtacggtg gccgccccct ccgtgttcat cttccccccc    420

tccgacgagc agctgaagtc cggcaccgcc tccgtggtgt gcctgctgaa taacttctac    480

cccagagagg ccaaggtgca gtggaaggtg gacaacgccc tgcagtccgg gaactcccag    540

gagagcgtga ccgagcagga cagcaaggac agcacctaca gcctgagcag caccctgacc    600

ctgagcaaag ccgactacga gaagcacaag gtgtacgcct gcgaggtgac ccaccagggc    660

ctgagctccc ccgtcaccaa gagcttcaac aggggggagt gt                        702


<210> SEQ ID NO 42
<211> LENGTH: 107
<212> TYPE: PRT
<213> ORGANISM: Artificial Sequence
<220> FEATURE:
<223> OTHER INFORMATION: humanized antibody
<220> FEATURE:
<221> NAME/KEY: MISC_FEATURE
<223> OTHER INFORMATION: amino acid sequence of variable region of
      humanized antibody light chain hL2

<400> SEQUENCE: 42

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Asn Tyr
            20                  25                  30

Leu Asn Trp Tyr Gln Gln Lys Pro Gly Lys Ala Val Lys Leu Leu Ile
        35                  40                  45

Tyr Phe Thr Ser Arg Leu His Ser Gly Val Pro Ser Arg Phe Ser Gly
    50                  55                  60

Ser Gly Ser Gly Thr His Tyr Thr Leu Thr Ile Ser Ser Leu Gln Pro
65                  70                  75                  80

Glu Asp Phe Ala Thr Tyr Tyr Cys Gln Gln Gly Tyr Pro Leu Pro Trp
                85                  90                  95

Thr Phe Gly Gln Gly Thr Lys Val Glu Ile Lys
            100                 105


<210> SEQ ID NO 43
<211> LENGTH: 321
<212> TYPE: DNA
<213> ORGANISM: Artificial Sequence
<220> FEATURE:
<223> OTHER INFORMATION: humanized antibody
<220> FEATURE:
<221> NAME/KEY: misc_feature
<223> OTHER INFORMATION: nucleotide sequence encoding variable region of
      humanized antibody light chain hL2
```

<400> SEQUENCE: 43

```
gacatccaga tgacccagag ccctagcagc ctgagcgcca gcgtgggcga cagagtgacc      60

atcacctgta gagccagcca ggacatcaac aactacctga actggtatca gcagaaaccc     120

ggcaaggccg tgaagctgct gatctacttc accagcagac tgcacagcgg cgtgcccagc     180

agattttctg gcagcggctc tggcacccac tacaccctga caatcagcag cctgcagccc     240

gaggacttcg ccacctacta ctgccagcag ggctaccccc tgccttggac atttggccag     300

ggcaccaagg tggaaatcaa g                                               321
```

<210> SEQ ID NO 44
<211> LENGTH: 234
<212> TYPE: PRT
<213> ORGANISM: Artificial Sequence
<220> FEATURE:
<223> OTHER INFORMATION: humanized antibody
<220> FEATURE:
<221> NAME/KEY: MISC_FEATURE
<223> OTHER INFORMATION: amino acid sequence of humanized antibody light chain hL3

<400> SEQUENCE: 44

```
Met Val Leu Gln Thr Gln Val Phe Ile Ser Leu Leu Leu Trp Ile Ser
1               5                   10                  15

Gly Ala Tyr Gly Asp Ile Gln Met Thr Gln Ser Pro Ser Ser Leu Ser
            20                  25                  30

Ala Ser Val Gly Asp Arg Val Thr Ile Thr Cys Arg Ala Ser Gln Asp
        35                  40                  45

Ile Asn Asn Tyr Leu Asn Trp Tyr Gln Gln Lys Pro Gly Gly Ala Val
    50                  55                  60

Lys Leu Leu Ile Tyr Phe Thr Ser Arg Leu His Ser Gly Val Pro Ser
65                  70                  75                  80

Arg Phe Ser Gly Ser Gly Ser Gly Thr Asp Tyr Thr Leu Thr Ile Ser
                85                  90                  95

Ser Leu Gln Pro Glu Asp Phe Ala Thr Tyr Tyr Cys Gln Gln Gly Tyr
            100                 105                 110

Pro Leu Pro Trp Thr Phe Gly Gly Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

<210> SEQ ID NO 45
<211> LENGTH: 702
<212> TYPE: DNA
<213> ORGANISM: Artificial Sequence
<220> FEATURE:

-continued

<223> OTHER INFORMATION: humanized antibody
<220> FEATURE:
<221> NAME/KEY: misc_feature
<223> OTHER INFORMATION: nucleotide sequence encoding humanized antibody
light chain hL3

<400> SEQUENCE: 45
atggtgctgc agacccaggt gttcatctcc ctgctgctgt ggatctccgg cgcgtacggc 60
gacatccaga tgacccagag ccctagcagc ctgagcgcca gcgtgggcga cagagtgacc 120
atcacctgta gagccagcca ggacatcaac aactacctga actggtatca gcagaaaccc 180
ggcggagccg tgaagctgct gatctacttc accagcagac tgcacagcgg cgtgcccagc 240
agattttctg gcagcggctc cggcaccgac tacaccctga caatcagcag cctgcagccc 300
gaggacttcg ccacctacta ctgccagcag ggctaccccc tgccctggac atttggcggc 360
ggaacaaagg tggaaatcaa gcgtacggtg gccgccccct ccgtgttcat cttccccccc 420
tccgacgagc agctgaagtc cggcaccgcc tccgtggtgt gcctgctgaa taacttctac 480
cccagagagg ccaaggtgca gtggaaggtg gacaacgccc tgcagtccgg gaactcccag 540
gagagcgtga ccgagcagga cagcaaggac agcacctaca gcctgagcag caccctgacc 600
ctgagcaaag ccgactacga gaagcacaag gtgtacgcct gcgaggtgac ccaccagggc 660
ctgagctccc ccgtcaccaa gagcttcaac aggggggagt gt 702

<210> SEQ ID NO 46
<211> LENGTH: 107
<212> TYPE: PRT
<213> ORGANISM: Artificial Sequence
<220> FEATURE:
<223> OTHER INFORMATION: humanized antibody
<220> FEATURE:
<221> NAME/KEY: MISC_FEATURE
<223> OTHER INFORMATION: amino acid sequence of variable region of
humanized antibody light chain hL3

<400> SEQUENCE: 46

Asp Ile Gln Met Thr Gln Ser Pro Ser Ser Leu Ser Ala Ser Val Gly
1 5 10 15

Asp Arg Val Thr Ile Thr Cys Arg Ala Ser Gln Asp Ile Asn Asn Tyr
20 25 30

Leu Asn Trp Tyr Gln Gln Lys Pro Gly Gly Ala Val Lys Leu Leu Ile
35 40 45

Tyr Phe Thr Ser Arg Leu His Ser Gly Val Pro Ser Arg Phe Ser Gly
50 55 60

Ser Gly Ser Gly Thr Asp Tyr Thr Leu Thr Ile Ser Ser Leu Gln Pro
65 70 75 80

Glu Asp Phe Ala Thr Tyr Tyr Cys Gln Gln Gly Tyr Pro Leu Pro Trp
85 90 95

Thr Phe Gly Gly Gly Thr Lys Val Glu Ile Lys
100 105

<210> SEQ ID NO 47
<211> LENGTH: 321
<212> TYPE: DNA
<213> ORGANISM: Artificial Sequence
<220> FEATURE:
<223> OTHER INFORMATION: humanized antibody
<220> FEATURE:
<221> NAME/KEY: misc_feature
<223> OTHER INFORMATION: nucleotide sequence encoding variable region of
humanized antibody light chain hL3

<400> SEQUENCE: 47
gacatccaga tgacccagag ccctagcagc ctgagcgcca gcgtgggcga cagagtgacc 60
atcacctgta gagccagcca ggacatcaac aactacctga actggtatca gcagaaaccc 120
ggcggagccg tgaagctgct gatctacttc accagcagac tgcacagcgg cgtgcccagc 180
agattttctg gcagcggctc cggcaccgac tacaccctga caatcagcag cctgcagccc 240
gaggacttcg ccacctacta ctgccagcag ggctaccccc tgccctggac atttggcggc 300
ggaacaaagg tggaaatcaa g 321

<210> SEQ ID NO 48
<211> LENGTH: 234
<212> TYPE: PRT
<213> ORGANISM: Artificial Sequence
<220> FEATURE:
<223> OTHER INFORMATION: humanized antibody
<220> FEATURE:
<221> NAME/KEY: MISC_FEATURE
<223> OTHER INFORMATION: amino acid sequence of humanized antibody light chain hL4

<400> SEQUENCE: 48

Met Val Leu Gln Thr Gln Val Phe Ile Ser Leu Leu Leu Trp Ile Ser
1 5 10 15

Gly Ala Tyr Gly Asp Ile Gln Met Thr Gln Ser Pro Ser Ser Leu Ser
20 25 30

Ala Ser Val Gly Asp Arg Val Thr Ile Thr Cys Arg Ala Ser Gln Asp
35 40 45

Ile Asn Asn Tyr Leu Asn Trp Tyr Gln Gln Lys Pro Gly Gly Ala Val
50 55 60

Lys Leu Leu Ile Tyr Phe Thr Ser Arg Leu His Ser Gly Val Pro Ser
65 70 75 80

Arg Phe Ser Gly Ser Gly Ser Gly Thr Asp Tyr Thr Leu Thr Ile Ser
85 90 95

Ser Leu Gln Pro Glu Asp Phe Ala Thr Tyr Tyr Cys Gln Gln Gly Asn
100 105 110

Thr Leu Pro Trp Thr Phe Gly Gly Gly Thr Lys Val Glu Ile Lys Arg
115 120 125

Thr Val Ala Ala Pro Ser Val Phe Ile Phe Pro Pro Ser Asp Glu Gln
130 135 140

Leu Lys Ser Gly Thr Ala Ser Val Val Cys Leu Leu Asn Asn Phe Tyr
145 150 155 160

Pro Arg Glu Ala Lys Val Gln Trp Lys Val Asp Asn Ala Leu Gln Ser
165 170 175

Gly Asn Ser Gln Glu Ser Val Thr Glu Gln Asp Ser Lys Asp Ser Thr
180 185 190

Tyr Ser Leu Ser Ser Thr Leu Thr Leu Ser Lys Ala Asp Tyr Glu Lys
195 200 205

His Lys Val Tyr Ala Cys Glu Val Thr His Gln Gly Leu Ser Ser Pro
210 215 220

Val Thr Lys Ser Phe Asn Arg Gly Glu Cys
225 230

<210> SEQ ID NO 49
<211> LENGTH: 702
<212> TYPE: DNA
<213> ORGANISM: Artificial Sequence
<220> FEATURE:

<223> OTHER INFORMATION: humanized antibody
<220> FEATURE:
<221> NAME/KEY: misc_feature
<223> OTHER INFORMATION: nucleotide sequence encoding humanized antibody
light chain hL4

<400> SEQUENCE: 49
atggtgctgc agacccaggt gttcatctcc ctgctgctgt ggatctccgg cgcgtacggc 60
gacatccaga tgacccagag ccctagcagc ctgagcgcca gcgtgggcga cagagtgacc 120
atcacctgta gagccagcca ggacatcaac aactacctga actggtatca gcagaaaccc 180
ggcggagccg tgaagctgct gatctacttc accagcagac tgcacagcgg cgtgcccagc 240
agattttctg gcagcggctc cggcaccgac tacaccctga caatcagcag cctgcagccc 300
gaggacttcg ccacctacta ctgccagcag ggcaacaccc tgccctggac atttggcgga 360
ggcaccaagg tggaaatcaa gcgtacggtg gccgcccct ccgtgttcat cttcccccc 420 tccgacgagc agctgaagtc cggcaccgcc tccgtggtgt gcctgctgaa taacttctac 480
cccagagagg ccaaggtgca gtggaaggtg gacaacgccc tgcagtccgg gaactcccag 540
gagagcgtga ccgagcagga cagcaaggac agcacctaca gcctgagcag caccctgacc 600
ctgagcaaag ccgactacga gaagcacaag gtgtacgcct gcgaggtgac ccaccagggc 660
ctgagctccc ccgtcaccaa gagcttcaac aggggggagt gt 702

<210> SEQ ID NO 50
<211> LENGTH: 107
<212> TYPE: PRT
<213> ORGANISM: Artificial Sequence
<220> FEATURE:
<223> OTHER INFORMATION: humanized antibody
<220> FEATURE:
<221> NAME/KEY: MISC_FEATURE
<223> OTHER INFORMATION: amino acid sequence of variable region of
humanized antibody light chain hL4

<400> SEQUENCE: 50

Asp Ile Gln Met Thr Gln Ser Pro Ser Ser Leu Ser Ala Ser Val Gly
1 5 10 15

Asp Arg Val Thr Ile Thr Cys Arg Ala Ser Gln Asp Ile Asn Asn Tyr
20 25 30

Leu Asn Trp Tyr Gln Gln Lys Pro Gly Gly Ala Val Lys Leu Leu Ile
35 40 45

Tyr Phe Thr Ser Arg Leu His Ser Gly Val Pro Ser Arg Phe Ser Gly
50 55 60

Ser Gly Ser Gly Thr Asp Tyr Thr Leu Thr Ile Ser Ser Leu Gln Pro
65 70 75 80

Glu Asp Phe Ala Thr Tyr Tyr Cys Gln Gln Gly Asn Thr Leu Pro Trp
85 90 95

Thr Phe Gly Gly Gly Thr Lys Val Glu Ile Lys
100 105

<210> SEQ ID NO 51
<211> LENGTH: 321
<212> TYPE: DNA
<213> ORGANISM: Artificial Sequence
<220> FEATURE:
<223> OTHER INFORMATION: humanized antibody
<220> FEATURE:
<221> NAME/KEY: misc_feature
<223> OTHER INFORMATION: nucleotide sequence encoding variable region of
humanized antibody light chain hL4

<400> SEQUENCE: 51
gacatccaga tgacccagag ccctagcagc ctgagcgcca gcgtgggcga cagagtgacc 60
atcacctgta gagccagcca ggacatcaac aactacctga actggtatca gcagaaaccc 120
ggcggagccg tgaagctgct gatctacttc accagcagac tgcacagcgg cgtgcccagc 180
agattttctg gcagcggctc cggcaccgac tacaccctga caatcagcag cctgcagccc 240
gaggacttcg ccacctacta ctgccagcag ggcaacaccc tgccctggac atttggcgga 300
ggcaccaagg tggaaatcaa g 321

<210> SEQ ID NO 52
<211> LENGTH: 471
<212> TYPE: PRT
<213> ORGANISM: Artificial Sequence
<220> FEATURE:
<223> OTHER INFORMATION: humanized antibody
<220> FEATURE:
<221> NAME/KEY: MISC_FEATURE
<223> OTHER INFORMATION: amino acid sequence of humanized antibody heavy chain hH1

<400> SEQUENCE: 52

Met Lys His Leu Trp Phe Phe Leu Leu Leu Val Ala Ala Pro Arg Trp
1 5 10 15

Val Leu Ser Gln Val Gln Leu Val Gln Ser Gly Ala Glu Val Lys Lys
20 25 30

Pro Gly Ala Ser Val Lys Val Ser Cys Lys Ala Ser Gly Tyr Thr Phe
35 40 45

Thr Glu Tyr Thr Met His Trp Val Arg Gln Ala Pro Gly Gln Gly Leu
50 55 60

Glu Trp Met Gly Gly Val Asn Pro Asn Ser Gly Asp Thr Ser Tyr Ala
65 70 75 80

Gln Lys Phe Gln Gly Arg Val Thr Ile Thr Ala Asp Thr Ser Thr Ser
85 90 95

Thr Ala Tyr Met Glu Leu Ser Ser Leu Arg Ser Glu Asp Thr Ala Val
100 105 110

Tyr Tyr Cys Ala Arg Pro Gly Gly Tyr Asp Val Gly Tyr Tyr Ala Met
115 120 125

Asp Tyr Trp Gly Gln Gly Thr Leu Val Thr Val Ser Ser Ala Ser Thr
130 135 140

Lys Gly Pro Ser Val Phe Pro Leu Ala Pro Ser Ser Lys Ser Thr Ser
145 150 155 160

Gly Gly Thr Ala Ala Leu Gly Cys Leu Val Lys Asp Tyr Phe Pro Glu
165 170 175

Pro Val Thr Val Ser Trp Asn Ser Gly Ala Leu Thr Ser Gly Val His
180 185 190

Thr Phe Pro Ala Val Leu Gln Ser Ser Gly Leu Tyr Ser Leu Ser Ser
195 200 205

Val Val Thr Val Pro Ser Ser Ser Leu Gly Thr Gln Thr Tyr Ile Cys
210 215 220

Asn Val Asn His Lys Pro Ser Asn Thr Lys Val Asp Lys Arg Val Glu
225 230 235 240

Pro Lys Ser Cys Asp Lys Thr His Thr Cys Pro Pro Cys Pro Ala Pro
245 250 255

Glu Ala Ala Gly Gly Pro Ser Val Phe Leu Phe Pro Pro Lys Pro Lys
260 265 270

```
Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Glu Glu Met Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly Lys
465                 470
```

<210> SEQ ID NO 53
<211> LENGTH: 1413
<212> TYPE: DNA
<213> ORGANISM: Artificial Sequence
<220> FEATURE:
<223> OTHER INFORMATION: humanized antibody
<220> FEATURE:
<221> NAME/KEY: misc_feature
<223> OTHER INFORMATION: nucleotide sequence encoding humanized antibody
heavy chain hH1

<400> SEQUENCE: 53

```
atgaaacacc tgtggttctt cctcctgctg gtggcagctc ccagatgggt gctgagccag     60

gtgcagctgg tgcagtctgg cgccgaagtg aagaaaccag gcgccagcgt gaaggtgtcc    120

tgcaaggcca gcggctacac ctttaccgag tacaccatgc actgggtgcg ccaggctcca    180

ggccagggac tggaatggat gggcggcgtg aaccccaaca gcggcgatac aagctacgcc    240

cagaaattcc agggcagagt gaccatcacc gccgacacca gcacctccac cgcctacatg    300

gaactgagca gcctgcggag cgaggacacc gccgtgtact actgtgctag acctggcggc    360

tacgacgtgg gctactacgc catggattac tggggccagg gcaccctcgt gaccgtcagc    420

tcagcctcca ccaagggccc aagcgtcttc cccctggcac cctcctccaa gagcacctct    480

ggcggcacag ccgccctggg ctgcctggtc aaggactact tccccgaacc cgtgaccgtg    540

agctggaact caggcgccct gaccagcggc gtgcacacct tccccgctgt cctgcagtcc    600

tcaggactct actccctcag cagcgtggtg accgtgccct ccagcagctt gggcacccag    660

acctacatct gcaacgtgaa tcacaagccc agcaacacca aggtggacaa gagagttgag    720

cccaaatctt gtgacaaaac tcacacatgc ccaccctgcc cagcacctga agccgcgggg    780
```

```
ggaccctcag tcttcctctt ccccccaaaa cccaaggaca ccctcatgat ctcccggacc    840

cctgaggtca catgcgtggt ggtggacgtg agccacgaag accctgaggt caagttcaac    900

tggtacgtgg acggcgtgga ggtgcataat gccaagacaa agccccggga ggagcagtac    960

aacagcacgt accgggtggt cagcgtcctc accgtcctgc accaggactg gctgaatggc   1020

aaggagtaca agtgcaaggt ctccaacaaa gccctcccag cccccatcga gaaaaccatc   1080

tccaaagcca aaggccagcc ccgggaacca caggtgtaca ccctgccccc atcccgggag   1140

gagatgacca agaaccaggt cagcctgacc tgcctggtca aaggcttcta tcccagcgac   1200

atcgccgtgg agtgggagag caatggccag cccgagaaca actacaagac cacccctccc   1260

gtgctggact ccgacggctc cttcttcctc tacagcaagc tcaccgtgga caagagcagg   1320

tggcagcagg gcaacgtctt ctcatgctcc gtgatgcatg aggctctgca caaccactac   1380

acccagaaga gcctctccct gtctcccggc aaa                                1413
```

<210> SEQ ID NO 54
<211> LENGTH: 122
<212> TYPE: PRT
<213> ORGANISM: Artificial Sequence
<220> FEATURE:
<223> OTHER INFORMATION: humanized antibody
<220> FEATURE:
<221> NAME/KEY: MISC_FEATURE
<223> OTHER INFORMATION: amino acid sequence of variable region of humanized antibody heavy chain hH1

<400> SEQUENCE: 54

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30

Thr Met His Trp Val Arg Gln Ala Pro Gly Gln Gly Leu Glu Trp Met
        35                  40                  45

Gly Gly Val Asn Pro Asn Ser Gly Asp Thr Ser Tyr Ala Gln Lys Phe
    50                  55                  60

Gln Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Pro Gly Gly Tyr Asp Val Gly Tyr Tyr Ala Met Asp Tyr Trp
            100                 105                 110

Gly Gln Gly Thr Leu Val Thr Val Ser Ser
        115                 120
```

<210> SEQ ID NO 55
<211> LENGTH: 366
<212> TYPE: DNA
<213> ORGANISM: Artificial Sequence
<220> FEATURE:
<223> OTHER INFORMATION: humanized antibody
<220> FEATURE:
<221> NAME/KEY: misc_feature
<223> OTHER INFORMATION: nucleotide sequence encoding variable region of humanized antibody heavy chain hH1

<400> SEQUENCE: 55

```
caggtgcagc tggtgcagtc tggcgccgaa gtgaagaaac caggcgccag cgtgaaggtg     60

tcctgcaagg ccagcggcta cacctttacc gagtacacca tgcactgggt gcgccaggct    120

ccaggccagg gactggaatg gatgggcggc gtgaacccca acagcggcga tacaagctac    180
```

```
gcccagaaat tccagggcag agtgaccatc accgccgaca ccagcacctc caccgcctac    240

atggaactga gcagcctgcg gagcgaggac accgccgtgt actactgtgc tagacctggc    300

ggctacgacg tgggctacta cgccatggat tactggggcc agggcaccct cgtgaccgtc    360

agctca                                                               366


<210> SEQ ID NO 56
<211> LENGTH: 471
<212> TYPE: PRT
<213> ORGANISM: Artificial Sequence
<220> FEATURE:
<223> OTHER INFORMATION: humanized antibody
<220> FEATURE:
<221> NAME/KEY: MISC_FEATURE
<223> OTHER INFORMATION: amino acid sequence of humanized antibody heavy
      chain hH2

<400> SEQUENCE: 56

Met Lys His Leu Trp Phe Phe Leu Leu Leu Val Ala Ala Pro Arg Trp
1               5                   10                  15

Val Leu Ser Glu Val Gln Leu Val Gln Ser Gly Ala Glu Val Lys Lys
            20                  25                  30

Pro Gly Ala Ser Val Lys Val Ser Cys Lys Thr Ser Gly Tyr Thr Phe
        35                  40                  45

Thr Glu Tyr Thr Met His Trp Val Arg Gln Ala Pro Gly Lys Ser Leu
    50                  55                  60

Glu Trp Met Gly Gly Val Asn Pro Asn Ser Gly Asp Thr Ser Tyr Ala
65                  70                  75                  80

Gln Lys Phe Gln Gly Arg Val Thr Ile Thr Ala Asp Thr Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Pro Gly Gly Tyr Asp Val Gly Tyr Tyr Ala Met
        115                 120                 125

Asp Tyr Trp Gly Gln Gly Thr Leu Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Arg Val Glu
225                 230                 235                 240

Pro Lys Ser Cys Asp Lys Thr His Thr Cys Pro Pro Cys Pro Ala Pro
                245                 250                 255

Glu Ala Ala Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300
```

```
Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Glu Glu Met Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly Lys
465                 470


<210> SEQ ID NO 57
<211> LENGTH: 1413
<212> TYPE: DNA
<213> ORGANISM: Artificial Sequence
<220> FEATURE:
<223> OTHER INFORMATION: humanized antibody
<220> FEATURE:
<221> NAME/KEY: misc_feature
<223> OTHER INFORMATION: nucleotide sequence encoding humanized antibody
      heavy chain hH2

<400> SEQUENCE: 57

atgaaacacc tgtggttctt cctcctgctg gtggcagctc ccagatgggt gctgagcgaa     60

gtgcagctgg tgcagtctgg cgccgaagtg aagaaaccag gcgccagcgt gaaggtgtcc    120

tgcaagacca gcggctacac ctttaccgag tacaccatgc actgggtgcg ccaggcccct    180

ggcaagagcc tggaatggat gggcggcgtg aaccccaaca gcggcgatac aagctacgcc    240

cagaaattcc agggcagagt gaccatcacc gccgacacca gcacctccac cgcctacatg    300

gaactgagca gcctgcggag cgaggacacc gccgtgtact actgtgctag acctggcggc    360

tacgacgtgg gctactacgc catggattac tggggccagg gcaccctcgt gaccgtcagc    420

tcagcctcca ccaagggccc aagcgtcttc cccctggcac cctcctccaa gagcacctct    480

ggcggcacag ccgccctggg ctgcctggtc aaggactact tccccgaacc cgtgaccgtg    540

agctggaact caggcgccct gaccagcggc gtgcacacct tccccgctgt cctgcagtcc    600

tcaggactct actccctcag cagcgtggtg accgtgccct ccagcagctt gggcacccag    660

acctacatct gcaacgtgaa tcacaagccc agcaacacca aggtggacaa gagagttgag    720

cccaaatctt gtgacaaaac tcacacatgc ccaccctgcc cagcacctga agccgcgggg    780

ggaccctcag tcttcctctt ccccccaaaa cccaaggaca ccctcatgat ctcccggacc    840

cctgaggtca catgcgtggt ggtggacgtg agccacgaag accctgaggt caagttcaac    900

tggtacgtgg acggcgtgga ggtgcataat gccaagacaa agccccggga ggagcagtac    960
```

aacagcacgt accgggtggt cagcgtcctc accgtcctgc accaggactg gctgaatggc 1020
aaggagtaca agtgcaaggt ctccaacaaa gccctcccag cccccatcga gaaaaccatc 1080
tccaaagcca aaggccagcc ccgggaacca caggtgtaca ccctgccccc atcccgggag 1140
gagatgacca agaaccaggt cagcctgacc tgcctggtca aaggcttcta tcccagcgac 1200
atcgccgtgg agtgggagag caatggccag cccgagaaca actacaagac caccccctccc 1260 gtgctggact ccgacggctc cttcttcctc tacagcaagc tcaccgtgga caagagcagg 1320
tggcagcagg gcaacgtctt ctcatgctcc gtgatgcatg aggctctgca caaccactac 1380
acccagaaga gcctctccct gtctcccggc aaa 1413

<210> SEQ ID NO 58
<211> LENGTH: 122
<212> TYPE: PRT
<213> ORGANISM: Artificial Sequence
<220> FEATURE:
<223> OTHER INFORMATION: humanized antibody
<220> FEATURE:
<221> NAME/KEY: MISC_FEATURE
<223> OTHER INFORMATION: amino acid sequence of variable region of humanized antibody heavy chain hH2

<400> SEQUENCE: 58

Glu Val Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Thr Glu Tyr
            20                  25                  30

Thr Met His Trp Val Arg Gln Ala Pro Gly Lys Ser Leu Glu Trp Met
        35                  40                  45

Gly Gly Val Asn Pro Asn Ser Gly Asp Thr Ser Tyr Ala Gln Lys Phe
    50                  55                  60

Gln Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Pro Gly Gly Tyr Asp Val Gly Tyr Tyr Ala Met Asp Tyr Trp
            100                 105                 110

Gly Gln Gly Thr Leu Val Thr Val Ser Ser
        115                 120

<210> SEQ ID NO 59
<211> LENGTH: 366
<212> TYPE: DNA
<213> ORGANISM: Artificial Sequence
<220> FEATURE:
<223> OTHER INFORMATION: humanized antibody
<220> FEATURE:
<221> NAME/KEY: misc_feature
<223> OTHER INFORMATION: nucleotide sequence encoding variable region of humanized antibody heavy chain hH2

<400> SEQUENCE: 59
gaagtgcagc tggtgcagtc tggcgccgaa gtgaagaaac caggcgccag cgtgaaggtg 60
tcctgcaaga ccagcggcta cacctttacc gagtacacca tgcactgggt gcgccaggcc 120
cctggcaaga gcctggaatg gatgggcggc gtgaacccca acagcggcga tacaagctac 180
gcccagaaat tccagggcag agtgaccatc accgccgaca ccagcacctc caccgcctac 240
atggaactga gcagcctgcg gagcgaggac accgccgtgt actactgtgc tagacctggc 300

-continued ggctacgacg tgggctacta cgccatggat tactggggcc agggcaccct cgtgaccgtc 360
agctca 366

<210> SEQ ID NO 60
<211> LENGTH: 471
<212> TYPE: PRT
<213> ORGANISM: Artificial Sequence
<220> FEATURE:
<223> OTHER INFORMATION: humanized antibody
<220> FEATURE:
<221> NAME/KEY: MISC_FEATURE
<223> OTHER INFORMATION: amino acid sequence of humanized antibody heavy chain hH3

<400> SEQUENCE: 60

Met Lys His Leu Trp Phe Phe Leu Leu Leu Val Ala Ala Pro Arg Trp
1 5 10 15

Val Leu Ser Glu Val Gln Leu Val Gln Ser Gly Ala Glu Val Lys Lys
20 25 30

Pro Gly Ala Ser Val Lys Val Ser Cys Lys Thr Ser Gly Tyr Thr Phe
35 40 45

Thr Glu Tyr Thr Met His Trp Val Arg Gln Ala Pro Gly Gln Gly Leu
50 55 60

Glu Trp Met Gly Gly Val Asn Pro Asn Ser Gly Asp Thr Ser Tyr Ala
65 70 75 80

Gln Lys Phe Gln Gly Arg Val Thr Leu Thr Val Asp Lys Ser Thr Ser
85 90 95

Thr Ala Tyr Met Glu Leu Ser Ser Leu Arg Ser Glu Asp Thr Ala Val
100 105 110

Tyr Tyr Cys Ala Arg Pro Gly Gly Tyr Asp Val Gly Tyr Tyr Ala Met
115 120 125

Asp Tyr Trp Gly Gln Gly Thr Leu Val Thr Val Ser Ser Ala Ser Thr
130 135 140

Lys Gly Pro Ser Val Phe Pro Leu Ala Pro Ser Ser Lys Ser Thr Ser
145 150 155 160

Gly Gly Thr Ala Ala Leu Gly Cys Leu Val Lys Asp Tyr Phe Pro Glu
165 170 175

Pro Val Thr Val Ser Trp Asn Ser Gly Ala Leu Thr Ser Gly Val His
180 185 190

Thr Phe Pro Ala Val Leu Gln Ser Ser Gly Leu Tyr Ser Leu Ser Ser
195 200 205

Val Val Thr Val Pro Ser Ser Ser Leu Gly Thr Gln Thr Tyr Ile Cys
210 215 220

Asn Val Asn His Lys Pro Ser Asn Thr Lys Val Asp Lys Arg Val Glu
225 230 235 240

Pro Lys Ser Cys Asp Lys Thr His Thr Cys Pro Pro Cys Pro Ala Pro
245 250 255

Glu Ala Ala Gly Gly Pro Ser Val Phe Leu Phe Pro Pro Lys Pro Lys
260 265 270

Asp Thr Leu Met Ile Ser Arg Thr Pro Glu Val Thr Cys Val Val Val
275 280 285

Asp Val Ser His Glu Asp Pro Glu Val Lys Phe Asn Trp Tyr Val Asp
290 295 300

Gly Val Glu Val His Asn Ala Lys Thr Lys Pro Arg Glu Glu Gln Tyr
305 310 315 320

Asn Ser Thr Tyr Arg Val Val Ser Val Leu Thr Val Leu His Gln Asp

-continued

```
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Glu Glu Met Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly Lys
465                 470


<210> SEQ ID NO 61
<211> LENGTH: 1413
<212> TYPE: DNA
<213> ORGANISM: Artificial Sequence
<220> FEATURE:
<223> OTHER INFORMATION: humanized antibody
<220> FEATURE:
<221> NAME/KEY: misc_feature
<223> OTHER INFORMATION: nucleotide sequence encoding humanized antibody
      heavy chain hH3

<400> SEQUENCE: 61

atgaaacacc tgtggttctt cctcctgctg gtggcagctc ccagatgggt gctgagcgaa      60

gtgcagctgg tgcagtctgg cgccgaagtg aagaaaccag gcgccagcgt gaaggtgtcc     120

tgcaagacca gcggctacac ctttaccgag tacaccatgc actgggtgcg ccaggctcca     180

ggccagggac tggaatggat gggcggcgtg aaccccaaca gcggcgatac aagctacgcc     240

cagaaattcc agggcagagt gaccctgacc gtggacaaga gcaccagcac cgcctacatg     300

gaactgagca gcctgcggag cgaggacacc gccgtgtact actgtgctag acctggcggc     360

tacgacgtgg gctactacgc catggattac tggggccagg gcaccctcgt gaccgtcagc     420

tcagcctcca ccaagggccc aagcgtcttc cccctggcac cctcctccaa gagcacctct     480

ggcggcacag ccgccctggg ctgcctggtc aaggactact tccccgaacc cgtgaccgtg     540

agctggaact caggcgccct gaccagcggc gtgcacacct tccccgctgt cctgcagtcc     600

tcaggactct actccctcag cagcgtggtg accgtgccct ccagcagctt gggcacccag     660

acctacatct gcaacgtgaa tcacaagccc agcaacacca aggtggacaa gagagttgag     720

cccaaatctt gtgacaaaac tcacacatgc ccaccctgcc cagcacctga agccgcgggg     780

ggaccctcag tcttcctctt ccccccaaaa cccaaggaca ccctcatgat ctcccggacc     840

cctgaggtca catgcgtggt ggtggacgtg agccacgaag accctgaggt caagttcaac     900

tggtacgtgg acggcgtgga ggtgcataat gccaagacaa agccccggga ggagcagtac     960

aacagcacgt accgggtggt cagcgtcctc accgtcctgc accaggactg gctgaatggc    1020

aaggagtaca agtgcaaggt ctccaacaaa gccctcccag cccccatcga gaaaaccatc    1080
```

```
tccaaagcca aaggccagcc ccgggaacca caggtgtaca ccctgccccc atcccgggag   1140

gagatgacca agaaccaggt cagcctgacc tgcctggtca aaggcttcta tcccagcgac   1200

atcgccgtgg agtgggagag caatggccag cccgagaaca actacaagac cacccctccc   1260

gtgctggact ccgacggctc cttcttcctc tacagcaagc tcaccgtgga caagagcagg   1320

tggcagcagg gcaacgtctt ctcatgctcc gtgatgcatg aggctctgca caaccactac   1380

acccagaaga gcctctccct gtctcccggc aaa                                1413


<210> SEQ ID NO 62
<211> LENGTH: 122
<212> TYPE: PRT
<213> ORGANISM: Artificial Sequence
<220> FEATURE:
<223> OTHER INFORMATION: humanized antibody
<220> FEATURE:
<221> NAME/KEY: MISC_FEATURE
<223> OTHER INFORMATION: amino acid sequence of variable region of
      humanized antibody heavy chain hH3

<400> SEQUENCE: 62

Glu Val Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Thr Glu Tyr
            20                  25                  30

Thr Met His Trp Val Arg Gln Ala Pro Gly Gln Gly Leu Glu Trp Met
        35                  40                  45

Gly Gly Val Asn Pro Asn Ser Gly Asp Thr Ser Tyr Ala Gln Lys Phe
    50                  55                  60

Gln Gly Arg Val Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Pro Gly Gly Tyr Asp Val Gly Tyr Tyr Ala Met Asp Tyr Trp
            100                 105                 110

Gly Gln Gly Thr Leu Val Thr Val Ser Ser
        115                 120


<210> SEQ ID NO 63
<211> LENGTH: 366
<212> TYPE: DNA
<213> ORGANISM: Artificial Sequence
<220> FEATURE:
<223> OTHER INFORMATION: humanized antibody
<220> FEATURE:
<221> NAME/KEY: misc_feature
<223> OTHER INFORMATION: nucleotide sequence encoding variable region of
      humanized antibody heavy chain hH3

<400> SEQUENCE: 63

gaagtgcagc tggtgcagtc tggcgccgaa gtgaagaaac caggcgccag cgtgaaggtg     60

tcctgcaaga ccagcggcta cacctttacc gagtacacca tgcactgggt gcgccaggct    120

ccaggccagg gactggaatg gatgggcggc gtgaacccca acagcggcga tacaagctac    180

gcccagaaat tccagggcag agtgaccctg accgtggaca agagcaccag caccgcctac    240

atggaactga gcagcctgcg gagcgaggac accgccgtgt actactgtgc tagacctggc    300

ggctacgacg tgggctacta cgccatggat tactggggcc agggcaccct cgtgaccgtc    360

agctca                                                               366
```

<210> SEQ ID NO 64
<211> LENGTH: 214
<212> TYPE: PRT
<213> ORGANISM: Artificial Sequence
<220> FEATURE:
<223> OTHER INFORMATION: humanized antibody
<220> FEATURE:
<221> NAME/KEY: MISC_FEATURE
<223> OTHER INFORMATION: amino acid sequence of Trastuzumab light chain

<400> SEQUENCE: 64

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 65
<211> LENGTH: 450
<212> TYPE: PRT
<213> ORGANISM: Artificial Sequence
<220> FEATURE:
<223> OTHER INFORMATION: humanized antibody
<220> FEATURE:
<221> NAME/KEY: MISC_FEATURE
<223> OTHER INFORMATION: amino acid sequence of Trastuzumab heavy chain

<400> SEQUENCE: 65

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60
```

-continued

```
Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450
```

<210> SEQ ID NO 66
<211> LENGTH: 234
<212> TYPE: PRT

<213> ORGANISM: Artificial Sequence
<220> FEATURE:
<223> OTHER INFORMATION: humanized antibody
<220> FEATURE:
<221> NAME/KEY: MISC_FEATURE
<223> OTHER INFORMATION: amino acid sequence of anti-LPS antibody
(h#1G5-H1L1) light chain

<400> SEQUENCE: 66

Met Val Leu Gln Thr Gln Val Phe Ile Ser Leu Leu Leu Trp Ile Ser
1 5 10 15

Gly Ala Tyr Gly Asp Ile Val Met Thr Gln Ser Pro Asp Ser Leu Ala
20 25 30

Val Ser Leu Gly Glu Arg Ala Thr Ile Asn Cys Lys Ala Ser Glu Asn
35 40 45

Val Gly Asn Ser Val Ser Trp Tyr Gln Gln Lys Pro Gly Gln Pro Pro
50 55 60

Lys Leu Leu Ile Tyr Gly Ala Ser Asn Arg Tyr Thr Gly Val Pro Asp
65 70 75 80

Arg Phe Ser Gly Ser Gly Ser Gly Thr Asp Phe Thr Leu Thr Ile Ser
85 90 95

Ser Leu Gln Ala Glu Asp Val Ala Val Tyr Tyr Cys Gly Gln Ser Tyr
100 105 110

Ser Tyr Pro Tyr Thr Phe Gly Gln Gly Thr Lys Val Glu Ile Lys Arg
115 120 125

Thr Val Ala Ala Pro Ser Val Phe Ile Phe Pro Pro Ser Asp Glu Gln
130 135 140

Leu Lys Ser Gly Thr Ala Ser Val Val Cys Leu Leu Asn Asn Phe Tyr
145 150 155 160

Pro Arg Glu Ala Lys Val Gln Trp Lys Val Asp Asn Ala Leu Gln Ser
165 170 175

Gly Asn Ser Gln Glu Ser Val Thr Glu Gln Asp Ser Lys Asp Ser Thr
180 185 190

Tyr Ser Leu Ser Ser Thr Leu Thr Leu Ser Lys Ala Asp Tyr Glu Lys
195 200 205

His Lys Val Tyr Ala Cys Glu Val Thr His Gln Gly Leu Ser Ser Pro
210 215 220

Val Thr Lys Ser Phe Asn Arg Gly Glu Cys
225 230

<210> SEQ ID NO 67
<211> LENGTH: 474
<212> TYPE: PRT
<213> ORGANISM: Artificial Sequence
<220> FEATURE:
<223> OTHER INFORMATION: humanized antibody
<220> FEATURE:
<221> NAME/KEY: MISC_FEATURE
<223> OTHER INFORMATION: amino acid sequence of anti-LPS antibody
(h#1G5-H1L1) heavy chain

<400> SEQUENCE: 67

Met Lys His Leu Trp Phe Phe Leu Leu Leu Val Ala Ala Pro Arg Trp
1 5 10 15

Val Leu Ser Gln Val Gln Leu Val Gln Ser Gly Ala Glu Val Lys Lys
20 25 30

Pro Gly Ala Ser Val Lys Val Ser Cys Lys Ala Ser Gly Tyr Thr Phe
35 40 45

Thr Ser Tyr Trp Ile Asn Trp Val Arg Gln Ala Pro Gly Gln Gly Leu

-continued

```
    50                  55                  60

Glu Trp Met Gly Asn Ile Tyr Pro Gly Ser Ser Ser Ile Asn Tyr Asn
65                  70                  75                  80

Glu Lys Phe Lys Ser Arg Val Thr Ile Thr Ala Asp Thr Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Thr Ile Tyr Asn Tyr Gly Ser Ser Gly Tyr Asn
        115                 120                 125

Tyr Ala Met Asp Tyr Trp Gly Gln Gly Thr Leu Val Thr Val Ser Ser
    130                 135                 140

Ala Ser Thr Lys Gly Pro Ser Val Phe Pro Leu Ala Pro Ser Ser Lys
145                 150                 155                 160

Ser Thr Ser Gly Gly Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Ser Leu Gly Thr Gln Thr
    210                 215                 220

Tyr Ile Cys Asn Val Asn His Lys Pro Ser Asn Thr Lys Val Asp Lys
225                 230                 235                 240

Arg Val Glu Pro Lys Ser Cys Asp Lys Thr His Thr Cys Pro Pro Cys
                245                 250                 255

Pro Ala Pro Glu Leu Leu Gly Gly Pro Ser Val Phe Leu Phe Pro Pro
            260                 265                 270

Lys Pro Lys Asp Thr Leu Met Ile Ser Arg Thr Pro Glu Val Thr Cys
        275                 280                 285

Val Val Val Asp Val Ser His Glu Asp Pro Glu Val Lys Phe Asn Trp
    290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

Lys Ala Leu Pro Ala Pro Ile Glu Lys Thr Ile Ser Lys Ala Lys Gly
        355                 360                 365

Gln Pro Arg Glu Pro Gln Val Tyr Thr Leu Pro Pro Ser Arg Glu Glu
    370                 375                 380

Met Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Asp Ser Asp Gly Ser Phe Phe
            420                 425                 430

Leu Tyr Ser Lys Leu Thr Val Asp Lys Ser Arg Trp Gln Gln Gly Asn
        435                 440                 445

Val Phe Ser Cys Ser Val Met His Glu Ala Leu His Asn His Tyr Thr
    450                 455                 460

Gln Lys Ser Leu Ser Leu Ser Pro Gly Lys
465                 470
```

<210> SEQ ID NO 68
<211> LENGTH: 234
<212> TYPE: PRT
<213> ORGANISM: Artificial Sequence
<220> FEATURE:
<223> OTHER INFORMATION: humanized antibody
<220> FEATURE:
<221> NAME/KEY: MISC_FEATURE
<223> OTHER INFORMATION: amino acid sequence of anti-TROP2 antibody
      (hRS7) light chain

<400> SEQUENCE: 68

```
Met Val Leu Gln Thr Gln Val Phe Ile Ser Leu Leu Leu Trp Ile Ser
1               5                   10                  15

Gly Ala Tyr Gly Asp Ile Gln Leu Thr Gln Ser Pro Ser Ser Leu Ser
            20                  25                  30

Ala Ser Val Gly Asp Arg Val Ser Ile Thr Cys Lys Ala Ser Gln Asp
        35                  40                  45

Val Ser Ile Ala Val Ala Trp Tyr Gln Gln Lys Pro Gly Lys Ala Pro
    50                  55                  60

Lys Leu Leu Ile Tyr Ser Ala Ser Tyr Arg Tyr Thr Gly Val Pro Asp
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Val Tyr Tyr Cys Gln Gln His Tyr
            100                 105                 110

Ile Thr Pro Leu Thr Phe Gly Ala Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

<210> SEQ ID NO 69
<211> LENGTH: 470
<212> TYPE: PRT
<213> ORGANISM: Artificial Sequence
<220> FEATURE:
<223> OTHER INFORMATION: humanized antibody
<220> FEATURE:
<221> NAME/KEY: MISC_FEATURE
<223> OTHER INFORMATION: amino acid sequence of anti-TROP2 antibody
      (hRS7) heavy chain

<400> SEQUENCE: 69

```
Met Lys His Leu Trp Phe Phe Leu Leu Leu Val Ala Ala Pro Arg Trp
1               5                   10                  15

Val Leu Ser Gln Val Gln Leu Gln Gln Ser Gly Ser Glu Leu Lys Lys
            20                  25                  30
```

-continued

```
Pro Gly Ala Ser Val Lys Val Ser Cys Lys Ala Ser Gly Tyr Thr Phe
        35                  40                  45

Thr Asn Tyr Gly Met Asn Trp Val Lys Gln Ala Pro Gly Gln Gly Leu
    50                  55                  60

Lys Trp Met Gly Trp Ile Asn Thr Tyr Thr Gly Glu Pro Thr Tyr Thr
65                  70                  75                  80

Asp Asp Phe Lys Gly Arg Phe Ala Phe Ser Leu Asp Thr Ser Val Ser
                85                  90                  95

Thr Ala Tyr Leu Gln Ile Ser Ser Leu Lys Ala Asp Asp Thr Ala Val
            100                 105                 110

Tyr Phe Cys Ala Arg Gly Gly Phe Gly Ser Ser Tyr Trp Tyr Phe Asp
        115                 120                 125

Val Trp Gly Gln Gly Ser Leu Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Arg Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Glu Glu Met Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445
```

```
Ser Val Met His Glu Ala Leu His Asn His Tyr Thr Gln Lys Ser Leu
    450                 455                 460

Ser Leu Ser Pro Gly Lys
465                 470


<210> SEQ ID NO 70
<211> LENGTH: 240
<212> TYPE: PRT
<213> ORGANISM: Artificial Sequence
<220> FEATURE:
<223> OTHER INFORMATION: humanized antibody
<220> FEATURE:
<221> NAME/KEY: MISC_FEATURE
<223> OTHER INFORMATION: amino acid sequence of anti-CD98 antibody
      (hM23-H1L1) light chain

<400> SEQUENCE: 70

Met Val Leu Gln Thr Gln Val Phe Ile Ser Leu Leu Leu Trp Ile Ser
1               5                   10                  15

Gly Ala Tyr Gly Asp Ile Val Met Thr Gln Ser Pro Asp Ser Leu Ala
            20                  25                  30

Val Ser Leu Gly Glu Arg Ala Thr Ile Asn Cys Lys Ser Ser Gln Ser
        35                  40                  45

Leu Leu Tyr Ser Ser Asn Gln Lys Asn Tyr Leu Ala Trp Tyr Gln Gln
    50                  55                  60

Lys Pro Gly Gln Pro Pro Lys Leu Leu Ile Tyr Trp Ala Ser Thr Arg
65                  70                  75                  80

Glu Ser Gly Val Pro Asp Arg Phe Ser Gly Ser Gly Ser Gly Thr Asp
                85                  90                  95

Phe Thr Leu Thr Ile Ser Ser Leu Gln Ala Glu Asp Val Ala Val Tyr
            100                 105                 110

Tyr Cys Gln Arg Tyr Tyr Gly Tyr Pro Trp Thr Phe Gly Gln Gly Thr
        115                 120                 125

Lys Val Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240


<210> SEQ ID NO 71
<211> LENGTH: 465
<212> TYPE: PRT
<213> ORGANISM: Artificial Sequence
<220> FEATURE:
<223> OTHER INFORMATION: humanized antibody
<220> FEATURE:
<221> NAME/KEY: MISC_FEATURE
<223> OTHER INFORMATION: amino acid sequence of anti-CD98 antibody
      (hM23-H1L1) heavy chain

<400> SEQUENCE: 71
```

-continued

```
Met Lys His Leu Trp Phe Phe Leu Leu Leu Val Ala Ala Pro Arg Trp
1               5                   10                  15

Val Leu Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Ala Phe
        35                  40                  45

Ser Asn Tyr Leu Ile Glu Trp Val Arg Gln Ala Pro Gly Gln Gly Leu
    50                  55                  60

Glu Trp Met Gly Val Ile Asn Pro Gly Ser Gly Val Thr Asn Tyr Asn
65                  70                  75                  80

Glu Lys Phe Lys Gly Arg Val Thr Ile Thr Ala Asp Thr Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Ala Glu Ala Trp Phe Ala Tyr Trp Gly Gln Gly
        115                 120                 125

Thr Leu Val Thr Val Ser Ser Ala Ser Thr Lys Gly Pro Ser Val Phe
    130                 135                 140

Pro Leu Ala Pro Ser Ser Lys Ser Thr Ser Gly Gly Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Ser Leu Gly Thr Gln Thr Tyr Ile Cys Asn Val Asn His Lys Pro
    210                 215                 220

Ser Asn Thr Lys Val Asp Lys Arg Val Glu Pro Lys Ser Cys Asp Lys
225                 230                 235                 240

Thr His Thr Cys Pro Pro Cys Pro Ala Pro Glu Leu Leu Gly Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
        275                 280                 285

Pro Glu Val Lys Phe Asn Trp Tyr Val Asp Gly Val Glu Val His Asn
    290                 295                 300

Ala Lys Thr Lys Pro Arg Glu Glu Gln Tyr Asn Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Ala Leu Pro Ala Pro Ile Glu Lys
            340                 345                 350

Thr Ile Ser Lys Ala Lys Gly Gln Pro Arg Glu Pro Gln Val Tyr Thr
        355                 360                 365

Leu Pro Pro Ser Arg Glu Glu Met Thr Lys Asn Gln Val Ser Leu Thr
    370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Lys Leu Thr Val Asp Lys
```

```
            420                 425                 430

Ser Arg Trp Gln Gln Gly Asn Val Phe Ser Cys Ser Val Met His Glu
        435                 440                 445

Ala Leu His Asn His Tyr Thr Gln Lys Ser Leu Ser Leu Ser Pro Gly
    450                 455                 460

Lys
465


<210> SEQ ID NO 72
<211> LENGTH: 702
<212> TYPE: DNA
<213> ORGANISM: Artificial Sequence
<220> FEATURE:
<223> OTHER INFORMATION: humanized antibody
<220> FEATURE:
<221> NAME/KEY: misc_feature
<223> OTHER INFORMATION: nucleotide sequence encoding Trastuzumab mutant
      light chain

<400> SEQUENCE: 72

atggtgctgc agacccaggt gttcatctcc ctgctgctgt ggatctccgg cgcgtacggc      60

gacatccaga tgacacagag ccctagcagc ctgtctgcca gcgtgggaga cagagtgacc     120

atcacctgta gagccagcca ggacgtgaac acagccgtgg cttggtatca gcagaagcct     180

ggcaaggccc ctaagctgct gatctacagc gccagctttc tgtacagcgg cgtgcccagc     240

agattcagcg gctctagaag cggcaccgac ttcaccctga ccataagcag tctgcagccc     300

gaggacttcg ccacctacta ctgtcagcag cactacacca cacctccaac ctttggccag     360

ggcaccaagg tggaaatcaa gcgtacggtg gccgccccct ccgtgttcat cttccccccc     420

tccgacgagc agctgaagtc cggcaccgcc tccgtggtgt gcctgctgaa taacttctac     480

cccagagagg ccaaggtgca gtggaaggtg gacaacgccc tgcagtccgg gaactcccag     540

gagagcgtga ccgagcagga cagcaaggac agcacctaca gcctgagcag caccctgacc     600

ctgagcaaag ccgactacga gaagcacaag gtgtacgcct gcgaggtgac ccaccagggc     660

ctgagctccc ccgtcaccaa gagcttcaac aggggggagt gt                        702


<210> SEQ ID NO 73
<211> LENGTH: 234
<212> TYPE: PRT
<213> ORGANISM: Artificial Sequence
<220> FEATURE:
<223> OTHER INFORMATION: humanized antibody
<220> FEATURE:
<221> NAME/KEY: MISC_FEATURE
<223> OTHER INFORMATION: amino acid sequence of Trastuzumab mutant light
      chain

<400> SEQUENCE: 73

Met Val Leu Gln Thr Gln Val Phe Ile Ser Leu Leu Leu Trp Ile Ser
1               5                   10                  15

Gly Ala Tyr Gly Asp Ile Gln Met Thr Gln Ser Pro Ser Ser Leu Ser
            20                  25                  30

Ala Ser Val Gly Asp Arg Val Thr Ile Thr Cys Arg Ala Ser Gln Asp
        35                  40                  45

Val Asn Thr Ala Val Ala Trp Tyr Gln Gln Lys Pro Gly Lys Ala Pro
    50                  55                  60

Lys Leu Leu Ile Tyr Ser Ala Ser Phe Leu Tyr Ser Gly Val Pro Ser
65                  70                  75                  80

Arg Phe Ser Gly Ser Arg Ser Gly Thr Asp Phe Thr Leu Thr Ile Ser
```

```
                85                  90                  95

Ser Leu Gln Pro Glu Asp Phe Ala Thr Tyr Tyr Cys Gln Gln His Tyr
            100                 105                 110

Thr Thr Pro Pro Thr Phe Gly Gln Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230


<210> SEQ ID NO 74
<211> LENGTH: 1407
<212> TYPE: DNA
<213> ORGANISM: Artificial Sequence
<220> FEATURE:
<223> OTHER INFORMATION: humanized antibody
<220> FEATURE:
<221> NAME/KEY: misc_feature
<223> OTHER INFORMATION: nucleotide sequence encoding Trastuzumab mutant
      heavy chain

<400> SEQUENCE: 74

atgaaacacc tgtggttctt cctcctgctg gtggcagctc ccagatgggt gctgagcgag     60

gtgcagctgg ttgaatctgg cggaggactg gttcagcctg gcggatctct gagactgtct    120

tgtgccgcca gcggcttcaa catcaaggac acctacatcc actgggtccg acaggcccct    180

ggcaaaggac ttgaatgggt cgccagaatc taccccacca acggctacac cagatacgcc    240

gactctgtga agggcagatt caccatcagc gccgacacca gcaagaacac cgcctacctg    300

cagatgaaca gcctgagagc cgaggacacc gccgtgtact actgttctag atggggaggc    360

gacggcttct acgccatgga ttattggggc cagggcaccc tggttaccgt tagctcagcc    420

tccaccaagg gcccaagcgt cttcccctg gcaccctcct ccaagagcac ctctggcggc    480

acagccgccc tgggctgcct ggtcaaggac tacttccccg aacccgtgac cgtgagctgg    540

aactcaggcg ccctgaccag cggcgtgcac accttccccg ctgtcctgca gtcctcagga    600

ctctactccc tcagcagcgt ggtgaccgtg ccctccagca gcttgggcac ccagacctac    660

atctgcaacg tgaatcacaa gcccagcaac accaaggtgg acaagagagt tgagcccaaa    720

tcttgtgaca aaactcacac atgcccaccc tgcccagcac ctgaagccgc gggggggaccc    780

tcagtcttcc tcttcccccc aaaacccaag gacaccctca tgatctcccg gacccctgag    840

gtcacatgcg tggtggtgga cgtgagccac gaagaccctg aggtcaagtt caactggtac    900

gtggacggcg tggaggtgca taatgccaag acaaagcccc gggaggagca gtacaacagc    960

acgtaccggg tggtcagcgt cctcaccgtc ctgcaccagg actggctgaa tggcaaggag   1020

tacaagtgca aggtctccaa caaagccctc ccagccccca tcgagaaaac catctccaaa   1080
```

-continued gccaaaggcc agccccggga accacaggtg tacaccctgc ccccatcccg ggaggagatg 1140
accaagaacc aggtcagcct gacctgcctg gtcaaaggct tctatcccag cgacatcgcc 1200
gtggagtggg agagcaatgg ccagcccgag aacaactaca agaccacccc tcccgtgctg 1260
gactccgacg gctccttctt cctctacagc aagctcaccg tggacaagag caggtggcag 1320
cagggcaacg tcttctcatg ctccgtgatg catgaggctc tgcacaacca ctacacccag 1380
aagagcctct ccctgtctcc cggcaaa 1407

<210> SEQ ID NO 75
<211> LENGTH: 469
<212> TYPE: PRT
<213> ORGANISM: Artificial Sequence
<220> FEATURE:
<223> OTHER INFORMATION: humanized antibody
<220> FEATURE:
<221> NAME/KEY: MISC_FEATURE
<223> OTHER INFORMATION: amino acid sequence of Trastuzumab mutant heavy chain

<400> SEQUENCE: 75

Met Lys His Leu Trp Phe Phe Leu Leu Leu Val Ala Ala Pro Arg Trp
1 5 10 15

Val Leu Ser Glu Val Gln Leu Val Glu Ser Gly Gly Gly Leu Val Gln
20 25 30

Pro Gly Gly Ser Leu Arg Leu Ser Cys Ala Ala Ser Gly Phe Asn Ile
35 40 45

Lys Asp Thr Tyr Ile His Trp Val Arg Gln Ala Pro Gly Lys Gly Leu
50 55 60

Glu Trp Val Ala Arg Ile Tyr Pro Thr Asn Gly Tyr Thr Arg Tyr Ala
65 70 75 80

Asp Ser Val Lys Gly Arg Phe Thr Ile Ser Ala Asp Thr Ser Lys Asn
85 90 95

Thr Ala Tyr Leu Gln Met Asn Ser Leu Arg Ala Glu Asp Thr Ala Val
100 105 110

Tyr Tyr Cys Ser Arg Trp Gly Gly Asp Gly Phe Tyr Ala Met Asp Tyr
115 120 125

Trp Gly Gln Gly Thr Leu Val Thr Val Ser Ser Ala Ser Thr Lys Gly
130 135 140

Pro Ser Val Phe Pro Leu Ala Pro Ser Ser Lys Ser Thr Ser Gly Gly
145 150 155 160

Thr Ala Ala Leu Gly Cys Leu Val Lys Asp Tyr Phe Pro Glu Pro Val
165 170 175

Thr Val Ser Trp Asn Ser Gly Ala Leu Thr Ser Gly Val His Thr Phe
180 185 190

Pro Ala Val Leu Gln Ser Ser Gly Leu Tyr Ser Leu Ser Ser Val Val
195 200 205

Thr Val Pro Ser Ser Ser Leu Gly Thr Gln Thr Tyr Ile Cys Asn Val
210 215 220

Asn His Lys Pro Ser Asn Thr Lys Val Asp Lys Arg Val Glu Pro Lys
225 230 235 240

Ser Cys Asp Lys Thr His Thr Cys Pro Pro Cys Pro Ala Pro Glu Ala
245 250 255

Ala Gly Gly Pro Ser Val Phe Leu Phe Pro Pro Lys Pro Lys Asp Thr
260 265 270

Leu Met Ile Ser Arg Thr Pro Glu Val Thr Cys Val Val Val Asp Val
275 280 285

```
Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Glu Glu Met Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
    450                 455                 460

Leu Ser Pro Gly Lys
465


<210> SEQ ID NO 76
<211> LENGTH: 234
<212> TYPE: PRT
<213> ORGANISM: Artificial Sequence
<220> FEATURE:
<223> OTHER INFORMATION: humanized antibody
<220> FEATURE:
<221> NAME/KEY: MISC_FEATURE
<223> OTHER INFORMATION: amino acid sequence of Trastuzumab mutant 2
      light chain

<400> SEQUENCE: 76

Met Val Leu Gln Thr Gln Val Phe Ile Ser Leu Leu Leu Trp Ile Ser
1               5                   10                  15

Gly Ala Tyr Gly Asp Ile Gln Met Thr Gln Ser Pro Ser Ser Leu Ser
            20                  25                  30

Ala Ser Val Gly Asp Arg Val Thr Ile Thr Cys Arg Ala Ser Gln Asp
        35                  40                  45

Val Asn Thr Ala Val Ala Trp Tyr Gln Gln Lys Pro Gly Lys Ala Pro
    50                  55                  60

Lys Leu Leu Ile Tyr Ser Ala Ser Phe Leu Tyr Ser Gly Val Pro Ser
65                  70                  75                  80

Arg Phe Ser Gly Ser Arg Ser Gly Thr Asp Phe Thr Leu Thr Ile Ser
                85                  90                  95

Ser Leu Gln Pro Glu Asp Phe Ala Thr Tyr Tyr Cys Gln Gln His Tyr
            100                 105                 110

Thr Thr Pro Pro Thr Phe Gly Gln Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
```

145 150 155 160

Pro Arg Glu Ala Lys Val Gln Trp Lys Val Asp Asn Ala Leu Gln Ser
165 170 175

Gly Asn Ser Gln Glu Ser Val Thr Glu Gln Asp Ser Lys Asp Ser Thr
180 185 190

Tyr Ser Leu Ser Ser Thr Leu Thr Leu Ser Lys Ala Asp Tyr Glu Lys
195 200 205

His Lys Val Tyr Ala Cys Glu Val Thr His Gln Gly Leu Ser Ser Pro
210 215 220

Val Thr Lys Ser Phe Asn Arg Gly Glu Cys
225 230

<210> SEQ ID NO 77
<211> LENGTH: 469
<212> TYPE: PRT
<213> ORGANISM: Artificial Sequence
<220> FEATURE:
<223> OTHER INFORMATION: humanized antibody
<220> FEATURE:
<221> NAME/KEY: MISC_FEATURE
<223> OTHER INFORMATION: amino acid sequence of Trastuzumab mutant 2 heavy chain

<400> SEQUENCE: 77

Met Lys His Leu Trp Phe Phe Leu Leu Leu Val Ala Ala Pro Arg Trp
1 5 10 15

Val Leu Ser Glu Val Gln Leu Val Glu Ser Gly Gly Gly Leu Val Gln
20 25 30

Pro Gly Gly Ser Leu Arg Leu Ser Cys Ala Ala Ser Gly Phe Asn Ile
35 40 45

Lys Asp Thr Tyr Ile His Trp Val Arg Gln Ala Pro Gly Lys Gly Leu
50 55 60

Glu Trp Val Ala Arg Ile Tyr Pro Thr Asn Gly Tyr Thr Arg Tyr Ala
65 70 75 80

Asp Ser Val Lys Gly Arg Phe Thr Ile Ser Ala Asp Thr Ser Lys Asn
85 90 95

Thr Ala Tyr Leu Gln Met Asn Ser Leu Arg Ala Glu Asp Thr Ala Val
100 105 110

Tyr Tyr Cys Ser Arg Trp Gly Gly Asp Gly Phe Tyr Ala Met Asp Tyr
115 120 125

Trp Gly Gln Gly Thr Leu Val Thr Val Ser Ser Ala Ser Thr Lys Gly
130 135 140

Pro Ser Val Phe Pro Leu Ala Pro Ser Ser Lys Ser Thr Ser Gly Gly
145 150 155 160

Thr Ala Ala Leu Gly Cys Leu Val Lys Asp Tyr Phe Pro Glu Pro Val
165 170 175

Thr Val Ser Trp Asn Ser Gly Ala Leu Thr Ser Gly Val His Thr Phe
180 185 190

Pro Ala Val Leu Gln Ser Ser Gly Leu Tyr Ser Leu Ser Ser Val Val
195 200 205

Thr Val Pro Ser Ser Ser Leu Gly Thr Gln Thr Tyr Ile Cys Asn Val
210 215 220

Asn His Lys Pro Ser Asn Thr Lys Val Asp Lys Lys Val Glu Pro Lys
225 230 235 240

Ser Cys Asp Lys Thr His Thr Cys Pro Pro Cys Pro Ala Pro Glu Ala
245 250 255

-continued

```
Ala Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Glu Glu Met Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
    450                 455                 460

Leu Ser Pro Gly Lys
465
```